US012778121B2

(12) United States Patent
Tamashima

(10) Patent No.: US 12,778,121 B2
(45) Date of Patent: Nov. 3, 2026

(54) ACRYLATE DERIVATIVE, USE AND PRODUCTION INTERMEDIATE COMPOUND OF THE SAME

(71) Applicant: SUMITOMO CHEMICAL COMPANY, LIMITED, Chuo-ku (JP)

(72) Inventor: Hiroto Tamashima, Takarazuka (JP)

(73) Assignee: SUMITOMO CHEMICAL COMPANY, LIMITED, Chuo-ku (JP)

( * ) Notice: Subject to any disclaimer, the term of this patent is extended or adjusted under 35 U.S.C. 154(b) by 194 days.

(21) Appl. No.: 18/794,040

(22) Filed: Aug. 5, 2024

(65) Prior Publication Data

US 2024/0389583 A1 Nov. 28, 2024

Related U.S. Application Data

(62) Division of application No. 17/623,129, filed as application No. PCT/JP2020/025341 on Jun. 26, 2020, now Pat. No. 12,082,581.

(30) Foreign Application Priority Data

Jun. 28, 2019 (JP) ................................ 2019-120901
Jan. 31, 2020 (JP) ................................ 2020-015184

(51) Int. Cl.

| | |
|---|---|
| *A01N 37/50* | (2006.01) |
| *A01N 37/10* | (2006.01) |
| *A01N 37/36* | (2006.01) |
| *A01N 37/38* | (2006.01) |
| *A01N 41/04* | (2006.01) |
| *A01N 41/06* | (2006.01) |
| *A01N 43/08* | (2006.01) |
| *A01N 43/10* | (2006.01) |
| *A01N 43/20* | (2006.01) |
| *A01N 43/40* | (2006.01) |
| *A01N 43/60* | (2006.01) |
| *A01N 43/78* | (2006.01) |
| *A01N 43/80* | (2006.01) |
| *A01N 47/10* | (2006.01) |
| *A01N 47/16* | (2006.01) |
| *A01N 47/22* | (2006.01) |
| *A01N 55/00* | (2006.01) |
| *A61P 1/00* | (2006.01) |
| *A61P 3/00* | (2006.01) |
| *A61P 7/00* | (2006.01) |
| *C07C 69/712* | (2006.01) |
| *C07C 69/734* | (2006.01) |
| *C07C 69/736* | (2006.01) |
| *C07C 251/40* | (2006.01) |

(Continued)

(52) U.S. Cl.

CPC ............. *A01N 37/38* (2013.01); *A01N 37/50* (2013.01); *A01N 43/08* (2013.01); *A01N 43/10* (2013.01); *A01N 43/20* (2013.01); *A01N 43/40* (2013.01); *A01N 43/60* (2013.01); *A01N 43/78* (2013.01); *A01N 43/80* (2013.01); *A01N 55/00* (2013.01); *C07C 69/736* (2013.01); *C07C 251/40* (2013.01); *C07D 213/61* (2013.01); *C07D 241/16* (2013.01); *C07D 261/18* (2013.01); *C07D 277/24* (2013.01); *C07D 295/088* (2013.01); *C07D 303/23* (2013.01); *C07D 307/12* (2013.01); *C07D 333/16* (2013.01); *C07F 7/081* (2013.01)

(58) Field of Classification Search

None

See application file for complete search history.

(56) References Cited

U.S. PATENT DOCUMENTS

| | | |
|---|---|---|
| 4,802,913 A | 2/1989 | Clough et al. |
| 2001/0029239 A1 | 10/2001 | Cramp et al. |
| 2003/0225158 A1 | 12/2003 | Auerbach et al. |

FOREIGN PATENT DOCUMENTS

| | | |
|---|---|---|
| EP | 0 212 859 A2 | 3/1987 |
| JP | 62-48649 A | 3/1987 |

(Continued)

OTHER PUBLICATIONS

Li et al., registry database compound, 2007, caplus an 2007:554803.*

(Continued)

*Primary Examiner* — Sun Jae Yoo

(74) *Attorney, Agent, or Firm* — Oblon, McClelland, Maier & Neustadt, L.L.P.

(57) ABSTRACT

The present invention provides a compound represented by formula (I) [wherein L represents an oxygen atom or $CH_2$, E represents a C2-C10 chain hydrocarbon group or the like, $R^1$ represents a C1-C3 chain hydrocarbon group or the like, $R^2$ represents a C1-C3 chain hydrocarbon group or the like, and n is 0, 1, 2 or 3.] or its N oxide or agriculturally acceptable salt, which is a compound that have excellent pests controlling effects.

(I)

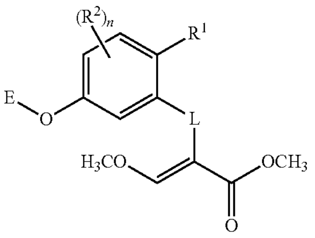

1 Claim, No Drawings

(51) Int. Cl.

| | |
|---|---|
| ***C07C 255/54*** | (2006.01) |
| ***C07C 271/40*** | (2006.01) |
| ***C07C 271/44*** | (2006.01) |
| ***C07C 271/56*** | (2006.01) |
| ***C07C 271/58*** | (2006.01) |
| ***C07C 309/65*** | (2006.01) |
| ***C07C 309/66*** | (2006.01) |
| ***C07C 309/73*** | (2006.01) |
| ***C07C 333/04*** | (2006.01) |
| ***C07D 207/08*** | (2006.01) |
| ***C07D 213/30*** | (2006.01) |
| ***C07D 213/61*** | (2006.01) |
| ***C07D 241/16*** | (2006.01) |
| ***C07D 261/18*** | (2006.01) |
| ***C07D 277/24*** | (2006.01) |
| ***C07D 295/088*** | (2006.01) |
| ***C07D 295/205*** | (2006.01) |
| ***C07D 303/23*** | (2006.01) |
| ***C07D 307/12*** | (2006.01) |
| ***C07D 307/42*** | (2006.01) |
| ***C07D 333/16*** | (2006.01) |
| ***C07F 7/08*** | (2006.01) |

(56) References Cited

FOREIGN PATENT DOCUMENTS

| | | |
|---|---|---|
| JP | 2001-64237 A | 3/2001 |
| JP | 2002-520384 A | 7/2002 |
| JP | 2005-521741 A | 7/2005 |
| WO | WO 00/03975 A2 | 1/2000 |
| WO | WO 00/41999 A1 | 7/2000 |
| WO | WO 01/00562 A1 | 1/2001 |

OTHER PUBLICATIONS

Godoy, C.V.et al., "Asian Soybean rust in Brazil: past, present, and future", Pesquisa Agropecuária Brasileira, vol. 51. No. 5, May 2016, pp. 407-421.

Extended European Search Report issued on Aug. 31, 2023 in European Patent Application No. 20833402.9, 10 pages.

Bolivian Office Action issued on Aug. 17, 2023 in Bolivian Patent Application No. SP-000093-2020 (with English translation), 27 pages.

International Search Report issued Aug. 18, 2020 in PCT/JP2020/025341 filed Jun. 26, 2020, 4 pages.

English translation of International Preliminary Report on Patentability and Written Opinion issued Dec. 28, 2021 in PCT/JP2020/025341, 6 pages.

Hideo Ishii, "Current Status of Qol-Resistant Bacteria," Plant Protection, vol. 69, No. 8, 2015, 10 pages (with partial English language translation).

Indian Office Action issued Nov. 24, 2023 in Indian Patent Application No. 202247003497, 7 pages.

RN2369626-33-3, registry database compound, 2019.

RN2239284-23-0, registry database compound, 2018.

First Office Action with Search Report issued Jun. 7, 2024 in corresponding Chinese Patent Application No. 202080046220.1 (with English-language Translation), 16 pages.

Office Action issued Jul. 9, 2024 in corresponding Japanese Patent Application No. 2021-527794 (with machine English translation), 10 pages.

* cited by examiner

ACRYLATE DERIVATIVE, USE AND PRODUCTION INTERMEDIATE COMPOUND OF THE SAME

CROSS-REFERENCE TO RELATED APPLICATIONS

The present application is a divisional application of U.S. application Ser. No. 17/623,129, filed Dec. 27, 2021, which is a 35 U.S.C. § 371 national stage patent application of International patent application PCT/JP2020/025341, filed on Jun. 26, 2020, which is based on and claims the benefits of priority to Japanese Application No. 2020-015184, filed on Jan. 31, 2020, and Japanese Application No. 2019-120901, filed on Jun. 28, 2019. The entire contents of all of the above applications are incorporated herein by reference.

TECHNICAL FIELD

This application claims priority to and the benefit of Japanese Patent Application Nos. 2019-120901 filed Jun. 28, 2019 and 2020-015184 filed Jan. 31, 2020, the entire contents of which are incorporated herein by reference.

The present invention is related to an acrylate derivative, a use and a production intermediate compound of the same.

BACKGROUND ART

Patent document 1 describes an acrylate derivative.

CITATION LIST

Patent Document

Patent Document 1: EP patent publication No. 212859

SUMMARY OF THE INVENTION

Problems to be Solved by Invention

An object of the present invention is to provide a compound having an excellent efficacy for controlling pests.

Means to Solve Problems

The present inventors have intensively studied to find compounds having an excellent efficacy for controlling pests, and as a result, found that a compound represented by the following formula (I) has an excellent efficacy for controlling pests.

That is, the present invention includes the followings.

[1] A compound represented by formula (I):

(I)

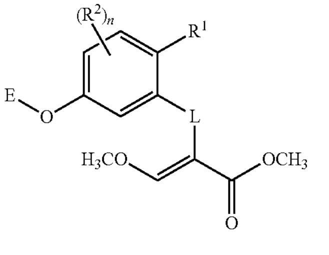

[wherein,

L represents an oxygen atom or $CH_2$,

E represents a methyl group which is substituted with one or more substituents selected from Group A, a C2-C10 chain hydrocarbon group which may be optionally substituted with one or more substituents selected from Group A, $R^6C(O)$—, $R^4OC(O)$—, $R^3R^5NC(O)$—, $R^3R^5NC(S)$—, $R^4S(O)_2$—, or $R^3R^5NS(O)_2$—, $R^1$ represents a C1-C3 chain hydrocarbon group which may be optionally substituted with one or more halogen atoms, a cyclopropyl group, or a halogen atom, n is 0, 1, 2 or 3, when n is 2 or 3, a plurality of $R^2$ are identical to or different from each other, $R^2$ represents a C1-C3 chain hydrocarbon group which may be optionally substituted with one or more halogen atoms, a cyclopropyl group, or a halogen atom, $R^3$ represents a C1-C6 chain hydrocarbon group which may be optionally substituted with one or more substituents selected from Group A, a C3-C6 cycloalkyl group which may be optionally substituted with one or more substituents selected from Group B, a C6-C10 aryl group, a five- to ten-membered aromatic heterocyclic group {the C6-C10 aryl group, and the five- to ten-membered aromatic heterocyclic group may be optionally substituted with one or more substituents selected from Group C} or a hydrogen atom, $R^4$ represents a C1-C6 chain hydrocarbon group which may be optionally substituted with one or more substituents selected from Group A, a C3-C6 cycloalkyl group which may be optionally substituted with one or more substituents selected from Group B, a C6-C10 aryl group, or a five- to ten-membered aromatic heterocyclic group {the C6-C10 aryl group, and the five- to ten-membered aromatic heterocyclic group may be optionally substituted with one or more substituents selected from Group C}, $R^5$ represents a C1-C3 chain hydrocarbon group which may be optionally substituted with one or more halogen atoms, a C1-C3 alkoxy group which may be optionally substituted with one or more halogen atoms, or a hydrogen atom, $R^6$ represents a C1-C6 chain hydrocarbon group which may be optionally substituted with one or more substituents selected from Group A, a C3-C6 cycloalkyl group which may be optionally substituted with one or more substituents selected from Group B, a C6-C10 aryl group, a five- to ten-membered aromatic heterocyclic group {the C6-C10 aryl group, and the five- to ten-membered aromatic heterocyclic group may be optionally substituted with one or more substituents selected from Group C} or a hydrogen atom, $R^3$ and $R^5$ may be combined together with the nitrogen atom to which they are attached to form a four- to seven-membered non-aromatic heterocyclic group {the four- to seven-membered non-aromatic heterocyclic group may have optionally one or more substituents selected from Group B}, Group A: a group consisting of $OR^{11}$, $S(O)_mR^{13}$, $OS(O)_2R^{13}$, $C(O)R^{11}$, $C(O)\ OR^{11}$, $OC(O)R^{11}$, $OC(O)OR^{11}$, $OC(O)NR^{11}R^{12}$, $NR^{11}C(O)NR^{12}R^{13}$, $NR^{11}R^{12}$, $C(O)NR^{11}R^{12}$, $S(O)_2NR^{11}R^{12}$, $NR^{12}C(O)R^{11}$, $NR^{12}C(O)\ OR^{13}$, $NR^{12}S(O)_2R^{13}$, $C(R^{12})$═N—$OR^{11}$, O—N═$CR^{11}R^{13}$, $SiR^{14}R^{15}R^{16}$, a C3-C6 cycloalkyl group, a phenyl group, a naphthyl group, a five- to six-membered aromatic heterocyclic group, a three- to eight-membered non-aromatic heterocyclic group {the C3-C6 cycloalkyl group, the phenyl group, the naphthyl group, the five- to six-membered aromatic heterocyclic group, and the three- to eight-membered non-aromatic heterocyclic group may be optionally substituted with one or more substituents selected from Group E}, a halogen atom, a cyano group, and a nitro group.

$R^{11}$ and $R^{12}$ are identical to or different from each other, and each represents a C1-C6 chain hydrocarbon group which may be optionally substituted with one or more substituents selected from Group D, a C3-C6 cycloalkyl group which may be optionally substituted with one or more substituents selected from Group E, a phenyl group, a naphthyl group, a five- to six-membered aromatic heterocyclic group, a three—to eight-membered non-aromatic heterocyclic group {the phenyl group, the naphthyl group, the five- to six-membered aromatic heterocyclic group, and the three- to eight-membered non-aromatic heterocyclic group may be optionally substituted with one or more substituents selected from Group F} or a hydrogen atom, $R^{13}$ represents a C1-C6 chain hydrocarbon group which may be optionally substituted with one or more substituents selected from Group D, a C3-C6 cycloalkyl group which may be optionally substituted with one or more substituents selected from Group E, a phenyl group, a naphthyl group, a five- to six-membered aromatic heterocyclic group, or a three- to eight-membered non-aromatic heterocyclic group {the phenyl group, the naphthyl group, the five- to six-membered aromatic heterocyclic group, and the three- to eight-membered non-aromatic heterocyclic group may be optionally substituted with one or more substituents selected from Group F}, $R^{14}$, $R^{15}$ and $R^{16}$ are identical to or different from each other, and each represents a C1-C6 chain hydrocarbon group or a phenyl group, m is 0, 1 or 2, Group B: a group consisting of a C1-C6 chain hydrocarbon group which may be optionally substituted with one or more substituents selected from Group D, $OR^{11}$, $S(O)_mR^{13}$, $OS(O)_2R^{13}$, $C(O)R^{11}$, $C(O)OR^{11}$, $OC(O)R^{11}$, $OC(O)OR^{11}$, $OC(O)NR^{11}R^{12}$, $NR^{11}C(O)NR^{12}R^{13}$, $NR^{11}R^{12}$, $C(O)NR^{11}R^{12}$, $S(O)_2NR^{11}R^{12}$, $NR^{12}C(O)R^{11}$, $NR^{12}C(O)OR^{13}$, $NR^{12}S(O)_2R^{13}$, $C(R^{12}){=}N{-}OR^{11}$, $O{-}N{=}CR^{11}R^{13}$, $SiR^{14}R^{15}R^{16}$, a C3-C6 cycloalkyl group, a phenyl group, a naphthyl group, a five- to six-membered aromatic heterocyclic group, a three- to eight-membered non-aromatic heterocyclic group {the C3-C6 cycloalkyl group, the phenyl group, the naphthyl group, the five- to six-membered aromatic heterocyclic group, and the three- to eight-membered non-aromatic heterocyclic group may be optionally substituted with one or more substituents selected from Group E}, an oxo group, a thioxo group, a halogen atom, a cyano group, and a nitro group.

Group C: a group consisting of a C1-C6 chain hydrocarbon group which may be optionally substituted with one or more substituents selected from Group D, $OR^{11}$, $S(O)_mR^{13}$, $OS(O)_2R^{13}$, $C(O)R^{11}$, $C(O)OR^{11}$, $OC(O)R^{11}$, $OC(O)OR^{11}$, $OC(O)NR^{11}R^{12}$, $NR^{11}C(O)NR^{12}R^{13}$, $NR^{11}R^{12}$, $C(O)NR^{11}R^{12}$, $S(O)_2NR^{11}R^{12}$, $NR^{12}C(O)R^{11}$, $NR^{12}C(O)OR^{13}$, $NR^{12}S(O)_2R^{13}$, $C(R^{12}){=}N{-}OR^{11}$, $O{-}N{=}CR^{11}R^{13}$, $SiR^{14}R^{15}R^{16}$, a C3-C6 cycloalkyl group, a phenyl group, a naphthyl group, a five- to six-membered aromatic heterocyclic group, a three- to eight-membered non-aromatic heterocyclic group {the C3-C6 cycloalkyl group, the phenyl group, the naphthyl group, the five- to six-membered aromatic heterocyclic group, and the three- to eight-membered non-aromatic heterocyclic group may be optionally substituted with one or more substituents selected from Group E}, a halogen atom, a cyano group, and a nitro group.

Group D: a group consisting of a C3-C6 cycloalkyl group {the C3-C6 cycloalkyl group may be optionally substituted with one or more substituents selected from a group consisting of a halogen atom, a cyano group, and a C1-C3 alkoxy group}, $OR^{17}$, $S(O)_mR^{19}$, $OS(O)_2R^{19}$, $C(O)R^{17}$, $C(O)OR^{17}$, $OC(O)R^{17}$, $OC(O)OR^{17}$, $OC(O)NR^{17}R^{18}$, $NR^{17}C(O)NR^{18}R^{19}$, $NR^{17}R^{18}$, $C(O)NR^{17}R^{18}$, $S(O)_2NR^{17}R^{18}$, $NR^{18}C(O)R^{17}$, $NR^{18}C(O)OR^{19}$, $NR^{18}S(O)_2R^{19}$, $C(R^{18}){=}N{-}OR^{17}$, $O{-}N{=}CR^{17}R^{19}$, $SiR^{14}R^{15}R^{16}$, a halogen atom, a cyano group, a nitro group, a hydroxy group, a phenoxy group, a phenyl group, a naphthyl group, a five- to six-membered aromatic heterocyclic group and a three- to eight-membered non-aromatic heterocyclic group {the phenoxy group, the phenyl group, the naphthyl group, the five- to six-membered aromatic heterocyclic group, and the three- to eight-membered non-aromatic heterocyclic group may be optionally substituted with one or more substituents selected from Group F}.

$R^{17}$ and $R^{18}$ are identical to or different from each other, and each represents a C1-C6 chain hydrocarbon group, a C3-C6 cycloalkyl group, a phenyl group, a naphthyl group, a five- to six-membered aromatic heterocyclic group, a three—to eight-membered non-aromatic heterocyclic group {the C1-C6 chain hydrocarbon group, the C3-C6 cycloalkyl group, the phenyl group, the naphthyl group, the five- to six-membered aromatic heterocyclic group, and the three- to eight-membered non-aromatic heterocyclic group may be optionally substituted with one or more substituents selected from a group consisting of a halogen atom, a cyano group, and a C1-C3 alkoxy group} or a hydrogen atom, $R^{19}$ represents a C1-C6 chain hydrocarbon group, a C3-C6 cycloalkyl group, a phenyl group, a naphthyl group, a five—to six-membered aromatic heterocyclic group, or a three- to eight-membered non-aromatic heterocyclic group {the C1-C6 chain hydrocarbon group, the C3-C6 cycloalkyl group, the phenyl group, the naphthyl group, the five- to six-membered aromatic heterocyclic group, and the three- to eight-membered non-aromatic heterocyclic group may be optionally substituted with one or more substituents selected from a group consisting of a halogen atom, a cyano group, and a C1-C3 alkoxy group}, Group E: a group consisting of a C1-C6 chain hydrocarbon group, a C3-C6 cycloalkyl group {the C1-C6 chain hydrocarbon group, and the C3-C6 cycloalkyl group may be optionally substituted with one or more substituents selected from a group consisting of a halogen atom, a cyano group and a C1-C3 alkoxy group}, $OR^{17}$, $S(O)_mR^{19}$, $OS(O)_2R^{19}$, $C(O)R^{17}$, $C(O)OR^{17}$, $OC(O)R^{17}$, $OC(O)OR^{17}$, $OC(O)NR^{17}R^{18}$, $NR^{17}C(O)NR^{18}R^{19}$, $NR^{17}R^{18}$, $C(O)NR^{17}R^{18}$, $S(O)_2NR^{17}R^{18}$, $NR^{18}C(O)R^{17}$, $NR^{18}C(O)OR^{19}$, $NR^{18}S(O)_2R^{19}$, $C(R^{18}){=}N{-}OR^{17}$, $O{-}N{=}CR^{17}R^{19}$, $SiR^{14}R^{15}R^{16}$, a halogen atom, a cyano group, a nitro group, a hydroxy group, a phenoxy group, a phenyl group, a naphthyl group, a five- to six-membered aromatic heterocyclic group, and a three- to eight-membered non-aromatic heterocyclic group {the phenoxy group, the phenyl group, the naphthyl group, the five- to six-membered aromatic heterocyclic group, and the three- to eight-membered non-aromatic heterocyclic group may be optionally substituted with one or more substituents selected from Group F}.

Group F: a group consisting of a C1-C6 chain hydrocarbon group, a C3-C6 cycloalkyl group, a C1-C6 alkoxy group, and a C1-C6 alkylthio group {the C1-C6 chain hydrocarbon group, the C3-C6 cycloalkyl group, the C1-C6 alkoxy group, and the C1-C6 alkylthio group may be optionally substituted with one or more substituents selected from a group consisting of a halogen atom and a cyano group}, a halogen atom, a cyano group, a nitro group, and a hydroxy group.]

(hereinafter, referred to as "Present compound N" or "Compound N of the present invention"), or its N-oxide or agriculturally acceptable salt (hereinafter, the compound, its N-oxide or agriculturally acceptable salts are referred to as "Present compound" or "Compound of the present invention").

[2] The compound according to [1] wherein E represents a methyl group which is substituted with one or more substituents selected from Group A, or a C2-C10 chain hydrocarbon group which may be optionally substituted with one or more substituents selected from Group A, or its N-oxide compound or agriculturally acceptable salt.

[3] The compound according to [1] wherein E represents $R^6C(O)$—, $R^4OC(O)$—, $R^3R^5NC(O)$—, $R^3R^5NC(S)$—, $R^4S(O)_2$—, or $R^3R^5NS(O)_2$—, or its N-oxide compound or agriculturally acceptable salt.

[4] The compound according to [1] wherein E represents $R^3R^5NC(O)$—, or its N-oxide compound or agriculturally acceptable salt.

[5] The compound according to any one of [1] to [4] wherein $R^1$ represents a methyl group or a chlorine atom, n is 0, and L represents an oxygen atom, or its N-oxide compound or agriculturally acceptable salt.

[6] A composition for controlling pests which comprises the compound according to any one of [1] to [5] or its N-oxide compound or agriculturally acceptable salt and an inert carrier (hereinafter, referred to as "Present Composition" or "Composition of the present invention").

[7] A composition comprising one or more ingredients selected from the group consisting of the following Groups (a), (b), (c) and (d) and the compound according to any one of [1] to [5] or its N-oxide compound or agriculturally acceptable salt:

Group (a): a group consisting of insecticidal ingredients, miticidal ingredients, and nematicidal ingredients;

Group (b): fungicidal ingredients:

Group (c): plant growth modulating ingredients; and

Group (d): repellent ingredients.

[8] A method for controlling a pest which comprises applying an effective amount of the compound according to any one of [1] to [5], or its N-oxide or agriculturally acceptable salt or the composition according to [7] to a plant or soil.

[9] A method for controlling soybean rust fungus with an amino acid replacement at the F129L position in a mitochondrial cytochrome b protein, which comprises applying an effective amount of the compound according to any one of [1] to [5], or its N-oxide or agriculturally acceptable salt or the composition according to [7].

[10] Use of the compound according to any one of [1] to [5]or its N-oxide or agriculturally acceptable salt or the composition according to [7] for controlling a pest.

[11] A seed or vegetative reproductive organ carrying an effective amount of the compound according to any one of [1]to [5] or its N-oxide or agriculturally acceptable salt or the composition according to [7].

[12] A compound represented by formula (II):

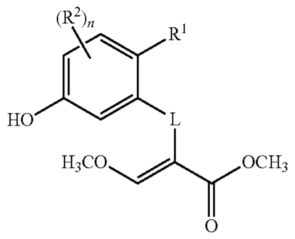

(II)

[wherein

L represents an oxygen atom or $CH_2$, $R^1$ represents a C1-C3 chain hydrocarbon group which may be optionally substituted with one or more halogen atoms, a cyclopropyl group, or a halogen atom, n is 0, 1, 2 or 3, when n is 2 or 3, a plurality of $R^2$ are identical to or different from each other, $R^2$ represents a C1-C3 chain hydrocarbon group which may be optionally substituted with one or more halogen atoms, a cyclopropyl group, or a halogen atom.]

(hereinafter, referred to as "Intermediate compound A").

[13] The compound according to [12] wherein $R^1$ represents a methyl group or a chlorine atom, and n is 0.

[14] A compound represented by formula (III):

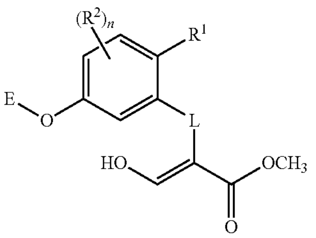

(III)

[wherein

L represents an oxygen atom or $CH_2$,

E represents a methyl group which is substituted with one or more substituents selected from Group A, a C2-C10 chain hydrocarbon group which may be optionally substituted with one or more substituents selected from Group A, $R^6C(O)$—, $R^4OC(O)$—, $R^3R^5NC(O)$—, $R^3R^5NC(S)$—, $R^4S(O)_2$—, or $R^3R^5NS(O)_2$—, $R^1$ represents a C1-C3 chain hydrocarbon group which may be optionally substituted with one or more halogen atoms, a cyclopropyl group or a halogen atom, n is 0, 1, 2 or 3, when n is 2 or 3, a plurality of $R^2$ are identical to or different from each other, $R^2$ represents a C1-C3 chain hydrocarbon group which may be optionally substituted with one or more halogen atoms, a cyclopropyl group, or a halogen atom, $R^3$ represents a C1-C6 chain hydrocarbon group which may be optionally substituted with one or more substituents selected from Group A, a C3-C6 cycloalkyl group which may be optionally substituted with one or more substituents selected from Group B, a C6-C10 aryl group, a five- to ten-membered aromatic heterocyclic group {the C6-C10 aryl group and the five- to ten-membered aromatic heterocyclic group may be optionally substituted with one or more substituents selected from Group C} or a hydrogen atom, $R^4$ represents a C1-C6 chain hydrocarbon group which may be optionally substituted with one or more substituents selected from Group A, a C3-C6 cycloalkyl group which may be optionally substituted with one or more substituents selected from Group B, a C6-C10 aryl group, or a five- to ten-membered aromatic heterocyclic group {the C6-C10 aryl group and the five- to ten-membered aromatic heterocyclic group may be optionally substituted with one or more substituents selected from Group C}, $R^5$ represents a C1-C3 chain hydrocarbon group which may be optionally substituted with one or more halogen atoms, a C1-C3 alkoxy group which may be optionally substituted with one or more halogen atoms, or a hydrogen atom, $R^6$ represents a C1-C6 chain hydrocarbon group which may be optionally substituted with one or more substituents selected from Group A, a C3-C6 cycloalkyl group which may be optionally substituted with one or more substituents selected from Group B, a C6-C10 aryl group, a five- to ten-membered aromatic heterocyclic group {the C6-C10 aryl group, and the five- to ten-membered aromatic heterocyclic group may be optionally substituted with one or more substituents selected from Group C} or a hydrogen atom, $R^3$ and $R^5$ may be combined together with the nitrogen atom to which they are attached to form a four- to seven-membered non-aromatic heterocyclic group {the four- to seven-non-aromatic heterocyclic group may have optionally one or more substituents selected from Group B}.

Group A: a group consisting of $OR^{11}$, $S(O)_mR^{13}$, $OS(O)_2R^{13}$, $C(O)R^{11}$, $C(O)\ OR^{11}$, $OC(O)R^{11}$, $OC(O)OR^{11}$, $OC(O)NR^{11}R^{12}$, $NR^{11}C(O)NR^{12}R^{13}$, $NR^{11}R^{12}$, $C(O)NR^{11}R^{12}$, $S(O)_2NR^{11}R^{12}$, $NR^{12}C(O)R^{11}$, $NR^{12}C(O)\ OR^{13}$, $NR^{12}S(O)_2R^{13}$, $C(R^{12})=N-OR^{11}$, $O-N=CR^{11}R^{13}$, $SiR^{14}R^{15}R^{16}$, a C3-C6 cycloalkyl group, a phenyl group, a naphthyl group, a five- to six-membered aromatic heterocyclic group, a three- to eight-membered non-aromatic heterocyclic group {the C3-C6 cycloalkyl group, the phenyl group, the naphthyl group, the five- to six-membered aromatic heterocyclic group and the three- to eight-membered non-aromatic heterocyclic group may be optionally substituted with one or more substituents selected from Group E}, a halogen atom, a cyano group, and a nitro group.

$R^{11}$ and $R^{12}$ are identical to or different from each other, and each represents a C1-C6 chain hydrocarbon group which may be optionally substituted with one or more substituents selected from Group D, a C3-C6 cycloalkyl group which may be optionally substituted with one or more substituents selected from Group E, a phenyl group, a naphthyl group, a five- to six-membered aromatic heterocyclic group, a three—to eight-membered non-aromatic heterocyclic group {the phenyl group, the naphthyl group, the five- to six-membered aromatic heterocyclic group and the three- to eight-membered non-aromatic heterocyclic group may be optionally substituted with one or more substituents selected from Group F} or a hydrogen atom, $R^{13}$ represents a C1-C6 chain hydrocarbon group which may be optionally substituted with one or more substituents selected from Group D, a C3-C6 cycloalkyl group which may be optionally substituted with one or more substituents selected from Group E, a phenyl group, a naphthyl group, a five- to six-membered aromatic heterocyclic group, or a three- to eight-membered non-aromatic heterocyclic group {the phenyl group, the naphthyl group, the five- to six-membered aromatic heterocyclic group, and the three- to eight-membered non-aromatic heterocyclic group may be optionally substituted with one or more substituents selected from Group F}, $R^{14}$, $R^{15}$ and $R^{16}$ are identical to or different from each other, and each represents a C1-C6 chain hydrocarbon group, or a phenyl group, m is 0, 1 or 2, Group B: a group consisting of a C1-C6 chain hydrocarbon group which may be optionally substituted with one or more substituents selected from Group D, $OR^{11}$, $S(O)_mR^{13}$, $OS(O)_2R^{13}$, $C(O)R^{11}$, $C(O)\ OR^{11}$, $OC(O)R^{11}$, $OC(O)\ OR^{11}$, $OC(O)NR^{11}R^{12}$, $NR^{11}C(O)NR^{12}R^{13}$, $NR^{11}R^{12}$, $C(O)NR^{11}R^{12}$, $S(O)_2NR^{11}R^{12}$, $NR^{12}C(O)R^{11}$, $NR^{12}C(O)\ OR^{13}$, $NR^{12}S(O)_2R^{13}$, $C(R^{12})=N-OR^{11}$, $O-N=CR^{11}R^{13}$, $SiR^{14}R^{15}R^{16}$, a C3-C6 cycloalkyl group, a phenyl group, a naphthyl group, a five- to six-membered aromatic heterocyclic group, a three- to eight-membered non-aromatic heterocyclic group {the C3-C6 cycloalkyl group, the phenyl group, the naphthyl group, the five- to six-membered aromatic heterocyclic group, and the three- to eight-membered non-aromatic heterocyclic group may be optionally substituted with one or more substituents selected from Group E}, an oxo group, a thioxo group, a halogen atom, a cyano group, and a nitro group.

Group C: a group consisting of a C1-C6 chain hydrocarbon group which may be optionally substituted with one or more substituents selected from Group D, $OR^{11}$, $S(O)_mR^{13}$, $OS(O)_2R^{13}$, $C(O)R^{11}$, $C(O)\ OR^{11}$, $OC(O)R^{11}$, $OC(O)\ OR^{11}$, $OC(O)NR^{11}R^{12}$, $NR^{11}C(O)NR^{12}R^{13}$, $NR^{11}R^{12}$, $C(O)NR^{11}R^{12}$, $S(O)_2NR^{11}R^{12}$, $NR^{12}C(O)R^1$, $NR^{12}C(O)\ OR^{13}$, $NR^{12}S(O)_2R^{13}$, $C(R^{12})=N-OR^{11}$, $O-N=CR^{11}R^{13}$, $SiR^{14}R^{15}R^{16}$, a C3-C6 cycloalkyl group, a phenyl group, a naphthyl group, a five- to six-membered aromatic heterocyclic group, a three- to eight-membered non-aromatic heterocyclic group {the C3-C6 cycloalkyl group, the phenyl group, the naphthyl group, the five- to six-membered aromatic heterocyclic group, and the three- to eight-membered non-aromatic heterocyclic group may be optionally substituted with one or more substituents selected from Group E}, a halogen atom, a cyano group and a nitro group.

Group D: a group consisting of C3-C6 cycloalkyl group {the C3-C6 cycloalkyl group may be optionally substituted with one or more substituents selected from a group consisting of a halogen atom, a cyano group and a C1-C3 alkoxy group}, $OR^{17}$, $S(O)_mR^{19}$, $OS(O)_2R^{19}$, $C(O)R^{17}$, $C(O)\ OR^{17}$, $OC(O)R^{17}$, $OC(O)\ OR^{17}$, $OC(O)NR^{17}R^{18}$, $NR^{17}C(O)NR^{18}R^{19}$, $NR^{17}R^{18}$, $C(O)NR^{17}R^{18}$, $S(O)_2NR^{17}R^{18}$, $NR^{18}C(O)R^{17}$, $NR^{18}C(O)OR^{19}$, $NR^{18}S(O)_2R^{19}$, $C(R^{18})=N-OR^{17}$, $O-N=CR^{17}R^{19}$, $SiR^{14}R^{15}R^{16}$, a halogen atom, a cyano group, a nitro group, a hydroxy group, a phenoxy group, a phenyl group, a naphthyl group, a five- to six-membered aromatic heterocyclic group and a three- to eight-membered non-aromatic heterocyclic group {the phenoxy group, the phenyl group, the naphthyl group, the five- to six-membered aromatic heterocyclic group, and the three- to eight-membered non-aromatic heterocyclic group may be optionally substituted with one or more substituents selected from Group F}, $R^{17}$ and $R^{18}$ are identical to or different from each other, and each represents a C1-C6 chain hydrocarbon group, a C3-C6 cycloalkyl group, a phenyl group, a naphthyl group, a five- to six-membered aromatic heterocyclic group, a three—to eight-membered non-aromatic heterocyclic group {the C1-C6 chain hydrocarbon group, the C3-C6 cycloalkyl group, the phenyl group, the naphthyl group, the five- to six-membered aromatic heterocyclic group, and the three- to eight-membered non-aromatic heterocyclic group may be optionally substituted with one or more substituents selected from a group consisting of a halogen atom, a cyano group and a C1-C3 alkoxy group} or a hydrogen atom, $R^{19}$ represents a C1-C6 chain hydrocarbon group, a C3-C6 cycloalkyl group, a phenyl group, a naphthyl group, a five—to six-membered aromatic heterocyclic group, or a three- to eight-membered non-aromatic heterocyclic group {the C1-C6 chain hydrocarbon group, the C3-C6 cycloalkyl group, the phenyl group, the naphthyl group, the five- to six-membered aromatic heterocyclic group, and the three- to eight-membered non-aromatic heterocyclic group may be optionally substituted with one or more substituents selected from a group consisting of a halogen atom, a cyano group and a C1-C3 alkoxy group}, Group E: a group consisting of a C1-C6 chain hydrocarbon group, a C3-C6 cycloalkyl group {the C1-C6 chain hydrocarbon group and the C3-C6 cycloalkyl group may be optionally substituted with one or more substituents selected from a group consisting of a halogen atom, a cyano group and a C1-C3 alkoxy group} $OR^{17}$, $S(O)_mR^{19}$, $OS(O)_2R^{19}$, $C(O)R^{17}$, C(O) $OR^{17}$, OC(O) $R^{17}$, OC(O) $OR^{17}$, $OC(O)NR^{17}R^{18}$, $NR^{17}C(O)$ $NR^{18}$Rig, $NR^{17}R^{18}$, $C(O)NR^{17}R^{18}$, $S(O)_2NR^{17}R^{18}$, $NR^{18}C(O)R^{17}$, $NR^{18}C(O)$ $OR^{19}$, $NR^{18}S(O)_2R^{19}$, $C(R^{18})$=N—$OR^{17}$, O—N=$CR^{17}R^{19}$, $SiR^{14}R^{15}R^{16}$, a halogen atom, a cyano group, a nitro group, a hydroxy group, a phenoxy group, a phenyl group, a naphthyl group, a five- to six-membered aromatic heterocyclic group and a three- to eight-membered non-aromatic heterocyclic group {the phenoxy group, the phenyl group, the naphthyl group, the five- to six-membered aromatic heterocyclic group, and the three- to eight-membered non-aromatic heterocyclic group may be optionally substituted with one or more substituents selected from Group F}.

Group F: a group consisting of a C1-C6 chain hydrocarbon group, a C3-C6 cycloalkyl group, a C1-C6 alkoxy group and a C1-C6 alkylthio group {the C1-C6 chain hydrocarbon group, the C3-C6 cycloalkyl group, the C1-C6 an alkoxy group and the C1-C6 alkylthio group may be optionally substituted with one or more substituents selected from a group consisting of a halogen atom and a cyano group}, a halogen atom, a cyano group, a nitro group and a hydroxy group.]

(hereinafter, referred to as "Intermediate compound B").

[15] The compound according to [14] wherein E represents a methyl group which is substituted with one or more substituents selected from Group A, or a C2-C10 chain hydrocarbon group which may be optionally substituted with one or more substituents selected from Group A.

[16] The compound according to [14] wherein E represents $R^6C(O)$—, $R^4OC(O)$—, $R^3R^5NC(O)$—, $R^3R^5NC$ (S)—, $R^4S(O)_2$—, or $R^3R^5NS(O)_2$—.

[17] The compound according to [14] wherein E represents $R^3R^5NC(O)$ —.

[18] The compound according to any one of [14] to [17]wherein $R^1$ represents a methyl group or a chlorine atom, n is 0, and L represents an oxygen atom.

[19] A compound represented by formula (IV):

(IV)

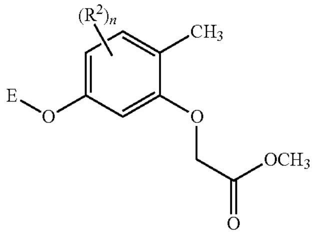

[wherein

E represents a methyl group which is substituted with one or more substituents selected from Group A, a C2-C10 chain hydrocarbon group which may be optionally substituted with one or more substituents selected from Group A, $R^6C(O)$—, $R^4OC(O)$—, $R^3R^5NC(O)$—, $R^3R^5NC(S)$—, $R^4S(O)_2$—, or $R^3R^5NS(O)_2$—, n is 0, 1, 2 or 3, when n is 2 or 3, a plurality of $R^2$ are identical to or different from each other, $R^2$ represents a C1-C3 chain hydrocarbon group which may be optionally substituted with one or more halogen atoms, a cyclopropyl group or a halogen atom, $R^3$ represents a C1-C6 chain hydrocarbon group which may be optionally substituted with one or more substituents selected from Group A, a C3-C6 cycloalkyl group which may be optionally substituted with one or more substituents selected from Group B, a C6-C10 aryl group, a five- to ten-membered aromatic heterocyclic group {the C6-C10 aryl group and the five- to ten-membered aromatic heterocyclic group may be optionally substituted with one or more substituents selected from Group C} or a hydrogen atom, $R^4$ represents a C1-C6 chain hydrocarbon group which may be optionally substituted with one or more substituents selected from Group A, a C3-C6 cycloalkyl group which may be optionally substituted with one or more substituents selected from Group B, a C6-C10 aryl group, or a five- to ten-membered aromatic heterocyclic group {the C6-C10 aryl group and the five- to ten-membered aromatic heterocyclic group may be optionally substituted with one or more substituents selected from Group C}, $R^5$ represents a C1-C3 chain hydrocarbon group which may be optionally substituted with one or more halogen atoms, a C1-C3 alkoxy group which may be optionally substituted with one or more halogen atoms, or a hydrogen atom, $R^6$ represents a C1-C6 chain hydrocarbon group which may be optionally substituted with one or more substituents selected from Group A, a C3-C6 cycloalkyl group which may be optionally substituted with one or more substituents selected from Group B, a C6-C10 aryl group, a five- to ten-membered aromatic heterocyclic group {the C6-C10 aryl group and the five- to ten-membered aromatic heterocyclic group may be optionally substituted with one or more substituents selected from Group C} or a hydrogen atom, $R^3$ and $R^5$ may be combined together with the nitrogen atom to which they are attached to form a four- to seven-membered non-aromatic heterocyclic group {the four- to seven-membered non-aromatic heterocyclic group may have optionally one or more substituents selected from Group B}.

Group A: a group consisting of $OR^{11}$, $S(O)_mR^{13}$, $OS(O)_2R^{13}$, $C(O)R^{11}$, C(O) $OR^{11}$, $OC(O)R^{11}$, OC(O) $OR^{11}$, $OC(O)NR^{11}R^{12}$, $NR^{11}C(O)NR^{12}R^{13}$, $NR^{11}R^{12}$, $C(O)NR^{11}R^{12}$, $S(O)_2NR^{11}R^{12}$, $NR^{12}C(O)R^{11}$, $NR^{12}C$ (O) $OR^{13}$, $NR^{12}S(O)_2R^{13}$, $C(R^{12})$=N—$OR^{11}$, O—N=$CR^{11}R^{13}$, $SiR^{14}R^{15}R^{16}$, a C3-C6 cycloalkyl group, a phenyl group, a naphthyl group, a five- to six-membered aromatic heterocyclic group, a three- to eight-membered non-aromatic heterocyclic group {the C3-C6 cycloalkyl group, the phenyl group, the naphthyl group, the five- to six-membered aromatic heterocyclic group, and the three- to eight-membered non-aromatic heterocyclic group may be optionally substituted with one or more substituents selected from Group E}, a halogen atom, a cyano group, and a nitro group.

$R^{11}$ and $R^{12}$ are identical to or different from each other, and each represents a C1-C6 chain hydrocarbon group which may be optionally substituted with one or more substituents selected from Group D, a C3-C6 cycloalkyl group which may be optionally substituted with one or more substituents selected from Group E, a phenyl group, a naphthyl group, a five- to six-membered aromatic heterocyclic group, a three—to eight-membered non-aromatic heterocyclic group {the phenyl group, the naphthyl group, the five- to six-membered aromatic heterocyclic group, and the three- to eight-membered non-aromatic heterocyclic group may be optionally substituted with one or more substituents selected from Group F} or a hydrogen atom, $R^{13}$ represents a C1-C6 chain hydrocarbon group which may be optionally substituted with one or more substituents selected from Group D, a C3-C6 cycloalkyl group which may be optionally substituted with one or more substituents selected from Group E, a phenyl group, a naphthyl group, a five- to six-membered aromatic heterocyclic group or a three- to eight-membered non-aromatic heterocyclic group {the phenyl group, the naphthyl group, the five- to six-membered aromatic heterocyclic group and the three- to eight-membered non-aromatic heterocyclic group may be optionally substituted with one or more substituents selected from Group F}, $R^{14}$, $R^{15}$ and $R^{16}$ are identical to or different from each other, and each represents a C1-C6 chain hydrocarbon group or a phenyl group, m is 0, 1 or 2, Group B: a group consisting of a C1-C6 chain hydrocarbon group which may be optionally substituted with one or more substituents selected from Group D, $OR^{11}$, $S(O)_mR^{13}$, $OS(O)_2R^{13}$, $C(O)R^{11}$, C(O) $OR^{11}$, OC(O) $R^{11}$, OC(O) $OR^{11}$, $OC(O)NR^{11}R^{12}$, $NR^{11}C(O)$ $NR^{12}R^{13}$, $NR^{11}R^{12}$, $C(O)NR^{11}R^{12}$, $S(O)_2NR^{11}R^{12}$, $NR^{12}C(O)R^{11}$, $NR^{12}C(O)$ $OR^{13}$, $NR^{12}S(O)_2R^{13}$, $C(R^{12})$=N—$OR^{11}$, O—N=$CR^{11}R^{13}$, $SiR^{14}R^{15}R^{16}$, a C3-C6 cycloalkyl group, a phenyl group, a naphthyl group, a five- to six-membered aromatic heterocyclic group, a three- to eight-membered non-aromatic heterocyclic group {the C3-C6 cycloalkyl group, the phenyl group, the naphthyl group, the five- to six-membered aromatic heterocyclic group and the three- to eight-membered non-aromatic heterocyclic group may be optionally substituted with one or more substituents selected from Group E}, an oxo group, a thioxo group, a halogen atom, a cyano group and a nitro group.

Group C: a group consisting of a C1-C6 chain hydrocarbon group which may be optionally substituted with one or more substituents selected from Group D, $OR^{11}$, $S(O)_mR^{13}$, $OS(O)_2R^{13}$, $C(O)R^{11}$, C(O) $OR^{11}$, OC(O) $R^{11}$, OC(O) $OR^{11}$, $OC(O)NR^{11}R^{12}$, $NR^{11}C(O)$ $NR^{12}R^{13}$, $NR^{11}R^{12}$, $C(O)NR^{11}R^{12}$, $S(O)_2NR^{11}R^{12}$, $NR^{12}C(O)R^{11}$, $NR^{12}C(O)$ $OR^{13}$, $NR^{12}S(O)_2R^{13}$, $C(R^{12})$=N—$OR^{11}$, O—N=$CR^{11}R^{13}$, $SiR^{14}R^{15}R^{16}$, a C3-C6 cycloalkyl group, a phenyl group, a naphthyl group, a five- to six-membered aromatic heterocyclic group, a three- to eight-membered non-aromatic heterocyclic group {the C3-C6 cycloalkyl group, the phenyl group, the naphthyl group, the five- to six-membered aromatic heterocyclic group and the three- to eight-membered non-aromatic heterocyclic group may be optionally substituted with one or more substituents selected from Group E}, a halogen atom, a cyano group and a nitro group.

Group D: a group consisting of a C3-C6 cycloalkyl group {the C3-C6 cycloalkyl group may be optionally substituted with one or more substituents selected from a group consisting of a halogen atom, a cyano group and a C1-C3 alkoxy group}, $OR^{17}$, $S(O)_mR^{19}$, $OS(O)_2R'^{9}$, $C(O)R^{17}$, C(O) $OR^{17}$, $OC(O)R^{17}$, OC(O) $OR^{17}$, OC(O) $NR^{17}R^{18}$, $NR^{17}C(O)NR^{18}R^{19}$, $NR^{17}R^{18}$, C(O) $NR^{17}R^{18}$, $S(O)_2NR^{17}R^{18}$, $NR^{18}C(O)R^{17}$, $NR^{18}C(O)$ $OR^{19}$, $NR^{18}S(O)_2R^{19}$, $C(R^{18})$=N—$OR^{17}$, O—N=$CR^{17}R^{19}$, $SiR^{14}R^{15}R^{16}$, a halogen atom, a cyano group, a nitro group, a hydroxy group, a phenoxy group, a phenyl group, a naphthyl group, a five- to six-membered aromatic heterocyclic group and a three- to eight-membered non-aromatic heterocyclic group {the phenoxy group, the phenyl group, the naphthyl group, the five- to six-membered aromatic heterocyclic group and the three- to eight-membered non-aromatic heterocyclic group may be optionally substituted with one or more substituents selected from Group F}.

$R^{17}$ and $R^{18}$ are identical to or different from each other, and each represents a C1-C6 chain hydrocarbon group, a C3-C6 cycloalkyl group, a phenyl group, a naphthyl group, a five- to six-membered aromatic heterocyclic group, a three—to eight-membered non-aromatic heterocyclic group {the C1-C6 chain hydrocarbon group, the C3-C6 cycloalkyl group, the phenyl group, the naphthyl group, the five- to six-membered aromatic heterocyclic group and the three- to eight-membered non-aromatic heterocyclic group may be optionally substituted with one or more substituents selected from a group consisting of a halogen atom, a cyano group and a C1-C3 alkoxy group} or a hydrogen atom, $R^{19}$ represents a C1-C6 chain hydrocarbon group, a C3-C6 cycloalkyl group, a phenyl group, a naphthyl group, a five—to six-membered aromatic heterocyclic group or a three- to eight-membered non-aromatic heterocyclic group {the C1-C6 chain hydrocarbon group, the C3-C6 cycloalkyl group, the phenyl group, the naphthyl group, the five- to six-membered aromatic heterocyclic group and the three- to eight-membered non-aromatic heterocyclic group may be optionally substituted with one or more substituents selected from a group consisting of a halogen atom, a cyano group and a C1-C3 alkoxy group}, Group E: a group consisting of a C1-C6 chain hydrocarbon group, a C3-C6 cycloalkyl group {the C1-C6 chain hydrocarbon group and the C3-C6 cycloalkyl group may be optionally substituted with one or more substituents selected from a group consisting of a halogen atom, a cyano group and a C1-C3 alkoxy group}, $OR^{17}$, $S(O)_mR^{19}$, $OS(O)_2R^{19}$, $C(O)R^{17}$, $C(O)\ OR^{17}$, $OC(O)R^{17}$, $OC(O)\ OR^{17}$, $OC(O)NR^{17}R^{18}$, $NR^{17}C(O)NR^{18}R^{19}$, $NR^{17}R^{18}$, $C(O)NR^{17}R^{18}$, $S(O)_2NR^{17}R^{18}$, $NR^{18}C(O)R^{17}$, $NR^{18}C(O)\ OR^{19}$, $NR^{18}S(O)_2R^{19}$, $C(R^{18})$=N—$OR^{17}$, O—N=$CR^{17}R^{19}$, $SiR^{14}R^{15}R^{16}$, a halogen atom, a cyano group, a nitro group, a hydroxy group, a phenoxy group, a phenyl group, a naphthyl group, a five- to six-membered aromatic heterocyclic group and a three- to eight-membered non-aromatic heterocyclic group {the phenoxy group, the phenyl group, the naphthyl group, the five- to six-membered aromatic heterocyclic group and the three- to eight-membered non-aromatic heterocyclic group may be optionally substituted with one or more substituents selected from Group F}.

Group F: a group consisting of a C1-C6 chain hydrocarbon group, a C3-C6 cycloalkyl group, a C1-C6 alkoxy group and a C1-C6 alkylthio group {the C1-C6 chain hydrocarbon group, the C3-C6 cycloalkyl group, the C1-C6 alkoxy group and the C1-C6 alkylthio group may be optionally substituted with one or more substituents selected from a group consisting of a halogen atom and a cyano group}, a halogen atom, a cyano group, a nitro group and a hydroxy group.]

(hereinafter, referred to as "Intermediate compound C").

[20] The compound according to [19] wherein n is 0, and E represents a methyl group which is substituted with one or more substituents selected from Group A, or a C2-C10 chain hydrocarbon group which may be optionally substituted with one or more substituents selected from Group A.

[21] The compound according to [19] wherein n is 0, and E represents $R^6C(O)$—, $R^4OC(O)$—, $R^3R^5NC(O)$—, $R^3R^5NC(S)$—, $R^4S(O)_2$—, or $R^3R^5NS(O)_2$—.

[22] The compound according to [19] wherein n is 0, and E represents $R^3R^5NC(O)$ —.

[23] A compound represented by formula (VI):

(VI)

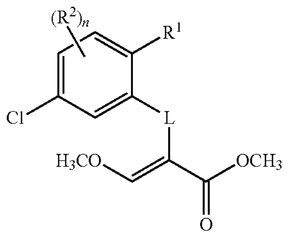

[wherein

L represents an oxygen atom or $CH_2$, $R^1$ represents a C1-C3 chain hydrocarbon group which may be optionally substituted with one or more halogen atoms, a cyclopropyl group or a halogen atom, $R^2$ represents a C1-C3 chain hydrocarbon group which may be optionally substituted with one or more halogen atoms, a cyclopropyl group or a halogen atom, n is 0, 1, 2 or 3, when n is 2 or 3, a plurality of $R^2$ are identical to or different from each other.]

(hereinafter, referred to as Intermediate compound D").

[24] The compound according to [23] wherein $R^1$ represents a methyl group or a chlorine atom, and n is 0.

Effect of Invention

The present invention can control pests.

MODE FOR CARRYING OUT THE INVENTION

The substituents as used herein are explained as follows.

The term "halogen atom" represents a fluorine atom, a chlorine atom, a bromine atom, or an iodine atom.

When a substituent has two or more halogen atoms, the halogen atoms are identical to or different from each other.

The expression "CX-CY" as used herein represents that the number of carbon atoms is from X to Y. For example, the expression "C1-C6" represents that the number of carbon atoms is from 1 to 6.

The term "chain hydrocarbon group" represents an alkyl group, an alkenyl group, or an alkynyl group.

Examples of the "alkyl group" include methyl group, ethyl group, propyl group, isopropyl group, 1,1-dimethylpropyl group, 1,2-dimethylpropyl group, butyl group, sec-butyl group, tert-butyl group, pentyl group, hexyl group, and decyl group.

Examples of the "alkenyl group" include vinyl group, 1-propenyl group, 2-propenyl group, 1-methyl-1-propenyl group, 1-methyl-2-propenyl group, 1,2-dimethyl-1-propenyl group, 3-butenyl group, 4-pentenyl group, 5-hexenyl group, and 9-decenyl group.

Examples of the "alkynyl group" include ethynyl group, 1-propynyl group, 2-propynyl group, 1-methyl-2-propynyl group, 1,1-dimethyl-2-propynyl group, 2-butynyl group, 4-pentynyl group, 5-hexynyl group, and 9-decynyl group.

Examples of the "alkoxy group" include methoxy group, ethoxy group, propoxy group, isopropoxy group, butoxy group, tert-butoxy group, pentyloxy group, and hexyloxy group.

Examples of the "alkylthio group" includes methylthio group, ethylthio group, propylthio group, isopropylthio group, butylthio group, tert-butylthio group, pentylthio group, and hexylthio group.

Examples of the "cycloalkyl group" include cyclopropyl group, cyclobutyl group, cyclopentyl group, and cyclohexyl group.

Examples of the "aryl group" include phenyl group, indenyl group, indanyl group, naphthyl group, and tetrahydronaphthyl group.

Examples of the "aromatic heterocyclic group" include pyrrolyl group, furyl group, thienyl group, pyrazolyl group, imidazolyl group, triazolyl group, tetrazolyl group, oxazolyl group, isoxazolyl group, thiazolyl group, isothiazolyl group, oxadiazolyl group, thiadiazolyl group, pyridyl group, pyridazinyl group, pyrimidinyl group, pyrazinyl group, triazinyl group, tetrazinyl group, indolyl group, indazolyl group, benzimidazolyl group, imidazopyridyl group, benzothiophenyl group, benzofuranyl group, quinolyl group, isoquinolyl group, quinazolinyl group, and quinoxalinyl group.

Examples of the "Non-aromatic heterocyclic group" include aziridinyl group, oxiranyl group, thiranyl group, azetidinyl group, oxetanyl group, thietanyl group, pyrrolidinyl group, tetrahydrofuranyl group, tetrahydrothienyl group, piperidyl group, pyranyl group, tetrahydropyranyl group, tetrahydrothiopyranyl group, azepanyl group, oxepanyl group, thiepanyl group, pyrazolynyl group, pyrazolidinyl group, imidazolinyl group, imidazolidinyl group, oxazolinyl group, thiazolinyl group, oxazolidinyl group, thiazolidinyl group, isoxazolinyl group, isoxazolidinyl group, isothiazolynyl group, isothiazolidinyl group, morpholinyl group, thiomorpholinyl group, and piperazinyl group.

The term(s) as described herein is/are explained.

The term of "soybean rust fungus having an amino acid substitution of F129L on mitochondrial cytochrome b protein" represents soybean rust fungus (scientific name: *Phakopsora pachyrhizi*) which shows a resistance against QoI fungicide by having a mutation in the mitochondrial cytochrome b gene encoding mitochondrial cytochrome protein and as a result of the mutation, causing amino acid substitution of F129L.

The present compound, the intermediate compound A, the intermediate compound B, the intermediate compound C, and the intermediate compound D may be existed as one or more stereoisomers. Examples of the stereoisomer include enantiomer, diastereoisomer, atropisomer, and geometric isomer. Each stereoisomer, and stereoisomer mixture(s) in an arbitrary ratio thereof are included in the present invention.

The present compound N or its N oxide may form an acid additional salts thereof such as hydrochloride salt, sulfate, nitrate, phosphate, acetate, and benzoate by mixing it with an acid such as hydrochloric acid, sulfuric acid, nitric acid, phosphoric acid, acetic acid, and benzoic acid.

Embodiments of the compound N of the present invention include the following compounds.

[Embodiment 1] The compound N of the present invention wherein n is 0.

[Embodiment 2] The compound according to the Embodiment 1 wherein $R^1$ represents a methyl group or a chlorine atom.

[Embodiment 3] The compound according to the Embodiment 1 wherein $R^1$ represents a methyl group.

[Embodiment 4] The compound according to the Embodiment 1 wherein L represents an oxygen atom.

[Embodiment 5] The compound according to the Embodiment 2 wherein L represents an oxygen atom.

[Embodiment 6] The compound according to the Embodiment 3 wherein L represents an oxygen atom.

[Embodiment 7] The compound according to the Embodiment 1 wherein $R^1$ represents a chlorine atom.

[Embodiment 8] The compound according to the Embodiment 1 wherein L represents $CH_2$.

[Embodiment 9] The compound according to the Embodiment 2 wherein L represents $CH_2$.

[Embodiment 10] The compound according to the Embodiment 3 wherein L represents $CH_2$.

[Embodiment 11] The compound according to any one of the Embodiment 1 to Embodiment 10 or the compound N of the present invention wherein E represents a methyl group which is substituted with one or more substituents selected from Group A, or a C2-C10 chain hydrocarbon group which may be optionally substituted with one or more substituents selected from Group A.

[Embodiment 12] The compound according to any one of Embodiment 1 to Embodiment 10 or the compound N of the present invention wherein E represents a methyl group which is substituted with one or more substituents selected from Group A.

[Embodiment 13] The compound according to any one of Embodiment 1 to Embodiment 10 or the compound N of the present invention wherein E represents a C2-C10 chain hydrocarbon group which may be optionally substituted with one or more substituents selected from Group A.

[Embodiment 14] The compound according to any one of Embodiment 1 to Embodiment 10 or the compound N of the present invention wherein E represents $R^6C(O)$—, $R^4OC(O)$—, $R^3R^5NC(O)$—, $R^3R^5NC(S)$—, $R^4S(O)_2$—, or $R^3R^5NS(O)_2$—.

[Embodiment 15] The compound according to any one of Embodiment 1 to Embodiment 10 or the compound N of the present invention wherein E represents $R^3R^5NC(O)$—.

[Embodiment 16] The compound according to any one of Embodiment 1 to Embodiment 10 or the compound N of the present invention wherein E represents a methyl group which is substituted with one or more substituents selected from Group J, a C2-C6 chain hydrocarbon group which may be optionally substituted with one or more substituents selected from Group J, or $R^3R^5NC(O)$—, $R^3$ represents a C1-C5 chain hydrocarbon group which may be optionally substituted with one or more halogen atoms, or a phenyl group which may be optionally substituted with one or more halogen atoms, $R^5$ represents a methyl group, a methoxy group, or a hydrogen atom, and $R^3$ and $R^5$ may be combined together the nitrogen atom to which they are attached to form a five- to six-membered non-aromatic heterocyclic group.

Group J: a group consisting of $OCH_3$, $Si(CH_3)_3$, a C3-C6 cycloalkyl group, a cyano group, a halogen atom, a phenyl group, and a five- to six-membered aromatic heterocyclic group {the phenyl group and the five- to six-membered aromatic heterocyclic group may be optionally substituted with one or more substituents selected from a group consisting of a trifluoromethyl group, a halogen atom and a cyano group}.

[Embodiment 17] The compound according to the Embodiment 16 wherein E represents a methyl group which is substituted with one or more substituents selected from Group J, or a C2-C6 chain hydrocarbon group which may be optionally substituted with one or more substituents selected from Group J.

[Embodiment 18] The compound according to the Embodiment 16 wherein E represents $R^3R^5NC(O)$—, $R^3$ represents a C1-C5 chain hydrocarbon group which may be optionally substituted with one or more halogen atoms, or a phenyl group which may be optionally substituted with one or more halogen atoms, and $R^5$ represents a methyl group, a methoxy group, or a hydrogen atom.

[Embodiment 19] The compound according to the Embodiment 16 wherein E represents $R^3R^5NC(O)$—, $R^3$ and $R^5$ may be combined together with the nitrogen atom to which they are attached to form a five- to six-membered non-aromatic heterocyclic group.

[Embodiment 20] The compound according to any one of the Embodiment 1 to the Embodiment 10 or the compound N of the present invention, wherein E represents a methyl group which is substituted with one or more substituents selected from Group K, a C2-C6 chain hydrocarbon group which may be optionally substituted with one or more substituents selected from Group K, or $R^3R^5NC(O)$—, $R^3$ represents a C1-C3 chain hydrocarbon group which may be optionally substituted with one or more halogen atoms, a C3-C6 cycloalkyl group which may be substituted with one or more halogen atoms, or a phenyl group which may be optionally substituted with one or more halogen atoms, $R^5$ represents a methyl group, a methoxy group, or a hydrogen atom, and $R^3$ and $R^5$ may be combined together with the nitrogen atom to which they are attached to form a five- to six-membered non-aromatic heterocyclic group.

Group K: a group consisting of $OCH_3$, $Si(CH_3)_3$, a C3-C6 cycloalkyl group, a cyano group, a halogen atom, a three- to six-membered non-aromatic heterocyclic group, a phenyl group, and a five- to six-membered aromatic heterocyclic group {the C3-C6 cycloalkyl group, the three- to six-membered non-aromatic heterocyclic group, the phenyl group and the five- to six-membered aromatic heterocyclic group may be optionally substituted with one or more substituents selected from a group consisting of a trifluoromethyl group, a halogen atom and a cyano group}.

[Embodiment 21] The compound according to any one of Embodiment 1 to Embodiment 10 or the compound N of the present invention, wherein E represents a methyl group which is substituted with one or more substituents selected from Group K, or a C2-C6 chain hydrocarbon group which may be optionally substituted with one or more substituents selected from Group K.

[Embodiment 22] The compound according to any one of Embodiment 1 to Embodiment 10 or the compound N of the present invention, wherein E represents a methyl group which is substituted with one or more substituents selected from Group K.

[Embodiment 23] The compound according to any one of Embodiment 1 to Embodiment 10 or the compound N of the present invention, wherein E represents a C2-C6 chain hydrocarbon group which may be substituted with one or more substituents selected from Group K.

[Embodiment 24] The compound according to any one of Embodiment 1 to Embodiment 10 or the compound N of the present invention, wherein E represents a C2-C6 chain hydrocarbon group which may be optionally substituted with one or more halogen atoms.

[Embodiment 25] The compound according to any one of Embodiment 1 to Embodiment 10 or the compound N of the present invention, wherein E represents $R^3R^5NC(O)$—, $R^3$ represents a C1-C3 chain hydrocarbon group which may be optionally substituted with one or more halogen atoms, a C3-C6 cycloalkyl group which may be substituted with one or more halogen atoms, or a phenyl group which may be optionally substituted with one or more halogen atoms, $R^5$ represents a methyl group, a methoxy group, or a hydrogen atom, and $R^3$ and $R^5$ may be combined together with the nitrogen atom to which they are attached to form a five- to six-membered non-aromatic heterocyclic group.

[Embodiment 26] The compound according to any one of Embodiment 1 to Embodiment 10 or the compound N of the present invention, wherein E represents $R^3R^5NC(O)$—, and $R^3$ and $R^5$ may be combined together with the nitrogen atom to which the $R^3$ and the $R^5$ are attached to form a five- to six-membered non-aromatic heterocyclic group.

Embodiments of the intermediate compound A include the following compounds.

[Embodiment A1] The intermediate compound A wherein n is 0.

[Embodiment A2] The compound according to Embodiment A1 wherein $R^1$ represents a methyl group or a chlorine atom.

[Embodiment A3] The compound according to Embodiment A1 wherein $R^1$ represents a methyl group.

[Embodiment A4] The compound according to Embodiment A1 wherein L represents an oxygen atom.

[Embodiment A5] The compound according to Embodiment A2 wherein L represents an oxygen atom.

[Embodiment A6] The compound according to Embodiment A3 wherein L represents an oxygen atom.

[Embodiment A7] The compound according to Embodiment A1 wherein $R^1$ represents a chlorine atom.

[Embodiment A8] The compound according to Embodiment A7 wherein L represents an oxygen atom.

[Embodiment A9] The compound according to Embodiment A1 wherein L represents $CH_2$.

[Embodiment A10] The compound according to Embodiment A2 wherein L represents $CH_2$. [Embodiment A11] The compound according to Embodiment A3 wherein L represents $CH_2$.

[Embodiment A12] The compound according to Embodiment A7 wherein L represents $CH_2$.

Embodiments of the intermediate compound B include the following compounds.

[Embodiment B1] The intermediate compound B wherein n is 0.

[Embodiment B2] The compound according to Embodiment B1 wherein $R^1$ represents a methyl group or a chlorine atom.

[Embodiment B3] The compound according to Embodiment B1 wherein $R^1$ represents a methyl group.

[Embodiment B4] The compound according to Embodiment B1 wherein L represents an oxygen atom.

[Embodiment B5] The compound according to Embodiment B2 wherein L represents an oxygen atom.

[Embodiment B6] The compound according to Embodiment B3 wherein L represents an oxygen atom.

[Embodiment B7] The compound according to any one of Embodiment B1 to Embodiment B6 or the intermediate compound B, wherein E represents a methyl group which is substituted with one or more substituents selected from Group A, or a C2-C10 chain hydrocarbon group which may be optionally substituted with one or more substituents selected from Group A.

[Embodiment B8] The compound according to any one of Embodiment B1 to Embodiment B6 or the intermediate compound B, wherein E represents a methyl group which is substituted with one or more substituents selected from Group A.

[Embodiment B9] The compound according to any one of Embodiment B1 to Embodiment B6 or the intermediate compound B, wherein E represents a C2-C10 chain hydrocarbon group which may be optionally substituted with one or more substituents selected from Group A.

[Embodiment B10] The compound according to any one of Embodiment B1 to Embodiment B6 or the intermediate compound B, wherein E represents $R^6C(O)$—, $R^4OC(O)$—, $R^3R^5NC(O)$—, $R^3R^5NC(S)$—, $R^4S(O)_2$—, or $R^3R^5NS(O)_2$—.

[Embodiment B11] The compound according to any one of Embodiment B1 to Embodiment B6 or the intermediate compound B, wherein E represents $R^3R^5NC(O)$—.

[Embodiment B12] The compound according to any one of Embodiment B1 to Embodiment B6 or the intermediate compound B, wherein E represents a benzyl group or a (C3-C6 cycloalkyl)methyl group.

Embodiments of the intermediate compound C include the following compounds.

[Embodiment C1] The intermediate compound C wherein n is 0.

[Embodiment C2] The compound according Embodiment C1 or the intermediate compound C, wherein E represents a methyl group which is substituted with one or more substituents selected from Group A, or a C2-C10 chain hydrocarbon group which may be optionally substituted with one or more substituents selected from Group A.

[Embodiment C3] The compound according to Embodiment C1 or the intermediate compound C, wherein E represents a methyl group which is substituted with one or more substituents selected from Group A.

[Embodiment C4] The compound according to Embodiment C1 or the intermediate compound C, wherein E represents a C2-C10 chain hydrocarbon group which may be optionally substituted with one or more substituents selected from Group A.

[Embodiment C5] The compound according to Embodiment C1 or the intermediate compound C, wherein E represents $R^6C(O)$—, $R^4OC(O)$—, $R^3R^5NC(O)$—, $R^3R^5NC(S)$—, $R^4S(O)_2$—, or $R^3R^5NS(O)_2$—.

[Embodiment C6] The compound according to Embodiment C1 or the intermediate compound C, wherein E represents $R^3R^5NC(O)$ —.

[Embodiment C7] The compound according to Embodiment C1 or the intermediate compound C, wherein E represents a benzyl group or a (C3-C6 cycloalkyl) methyl group.

Embodiments of the intermediate compound D include the following compounds.

[Embodiment D1] The intermediate compound D wherein n is 0.

[Embodiment D2] The compound according to Embodiment D1 wherein $R^1$ represents a methyl group or a chlorine atom.

[Embodiment D3] The compound according to Embodiment D1 wherein $R^1$ represents a methyl group.

[Embodiment D4] The compound according to Embodiment D1 wherein L represents an oxygen atom.

[Embodiment D5] The compound according to Embodiment D2 wherein L represents an oxygen atom.

[Embodiment D6] The compound according to Embodiment D3 wherein L represents an oxygen atom.

[Embodiment D7] The compound according to Embodiment D1 wherein $R^1$ represents a chlorine atom.

[Embodiment D8] The compound according to Embodiment D7 wherein L represents an oxygen atom.

[Embodiment D9] The compound according to Embodiment D1 wherein L represents $CH_2$.

[Embodiment D10] The compound according to Embodiment D2 wherein L represents $CH_2$.

[Embodiment D11] The compound according to Embodiment D3 wherein L represents $CH_2$.

[Embodiment D12] The compound according to Embodiment D7 wherein L represents $CH_2$.

Next, a process for preparing a compound of the present invention is explained.

Process A

A compound represented by formula (I-E1)(hereinafter, referred to as Compound (I-E1)) can be prepared by reacting the intermediate compound A represented by formula (II) with a compound represented by formula (R1)(hereinafter, referred to as Compound (R1)) in the presence of phosphines and azodiesters.

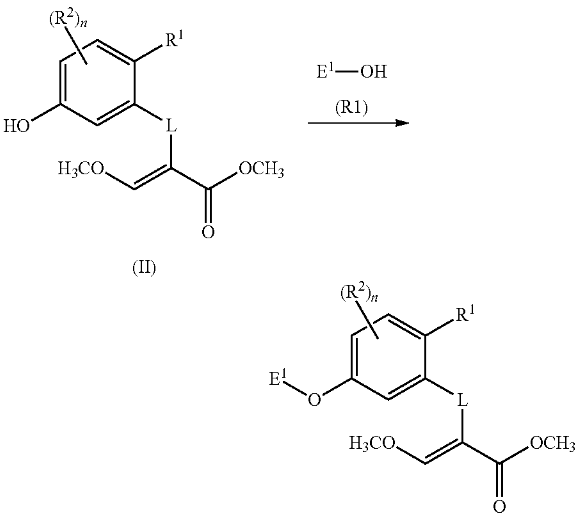

(II)

(I-E1)

[wherein $E^1$ represents a methyl group which is substituted with one or more substituents selected from Group A, or a C2-C10 chain hydrocarbon group which may be optionally substituted with one or more substituents selected from Group A, and other symbols are the same as defined above.]

The reaction is usually carried out in a solvent.

Examples of the solvent to be used in the reaction include hydrocarbons such as hexane, toluene, and xylene (hereinafter, collectively referred to as hydrocarbons); ethers such as methyl tert-butyl ether (hereinafter, referred to as MTBE), tetrahydrofuran (hereinafter, referred to as THF), dimethoxyethane (hereinafter, collectively referred to as ethers); halogenated hydrocarbons such as chloroform and chlorobenzene)(hereinafter, collectively referred to as halogenated hydrocarbons); amides such as dimethylformamide (hereinafter, referred to as DMF) and N-methyl pyrrolidone (hereinafter, collectively referred to as amides); esters such as methyl acetate and ethyl acetate (hereinafter, collectively referred to as esters); nitriles such as acetonitrile and propionitrile (hereinafter, referred to as nitriles); and mixed solvents of two or more kinds of the solvents.

Examples of phosphines include triphenylphosphine and trimethylphosphine.

Examples of azodiesters include diethyl azodicarboxylate, diisopropyl azodicarboxylate, and bis(2-methoxyethyl) azodicarboxylate.

In the reaction, the compound (R1) is usually used within a range of 1 to 10 molar ratio(s), the phosphines is usually used within a range of 1 to 10 molar ratio(s), and the azodiesters is usually used within a range of 1 to 10 molar ratio(s), as opposed to 1 mole of the intermediate compound A.

The reaction temperature for the reaction is usually with a range of 0 to 150° C. The reaction period in the reaction is usually within a range of 0.1 to 48 hours.

When the reaction is completed, water is added to reaction mixture, and the reaction mixture is extracted with organic solvent(s), and the organic layer is worked up (for example, drying and concentration) to isolate the compound (I-E1).

The compound (R1) is commercially available, or can be prepared according to a publicly known method.

Process B The compound (I-E1) can be prepared by the intermediate compound represented by formula (II) with a compound represented by formula (R2)(hereinafter, referred to as Compound ($R^2$)) in the presence of a base.

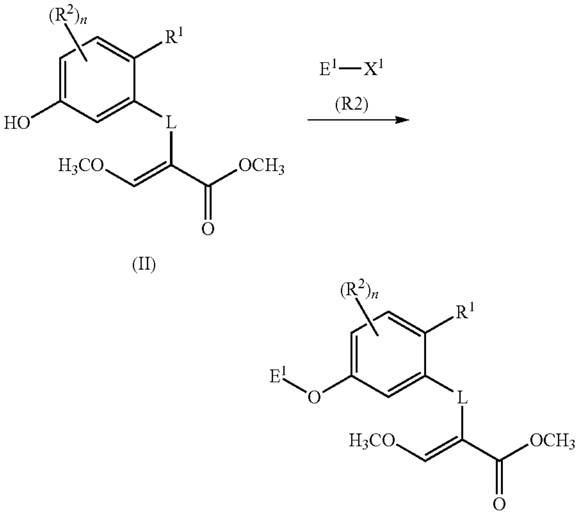

(II)

(I-E1)

[wherein $X^1$ represents a leaving group such as a chlorine atom, a bromine atom, an iodine atom, a methansulfonyl group, a p-toluenesulfonyl group, and the other symbols are the same as defined above.]The reaction is usually carried out in a solvent.

Examples of the solvent to be used in the reaction include hydrocarbons, ethers, halogenated hydrocarbons, amides, esters, nitriles, and mixed solvents of two or more of these solvents.

Examples of the bases include organic bases such as triethylamine and pyridine (hereinafter, referred to as organic bases); alkali metal carbonates such as sodium carbonate and potassium carbonate (hereinafter, referred to as alkali metal carbonates); alkali metal hydrocarbonates (such as sodium hydrocarbonates and potassium hydrocarbonates)(hereinafter, referred to as alkali metal hydrocarbonates); sodium hydride and tripotassium phosphate.

In the reaction, the compound (R2) is usually used within a range of 1 to 10 molar ratio(s), and the base is usually used within a range of 1 to 10 molar ratio(s), as opposed to 1 mole of the intermediate compound A.

The reaction mixture is usually within a range of −20 to 150° C. The reaction period in the reaction is usually within a range of 0.1 to 48 hours.

When the reaction is completed, the reaction mixtures are worked up (such as concentration and drying) to isolate the compound (I-E1).

The compound (R2) is publicly known or can be prepared according to a publicly known method.

Process C

A compound represented by formula (I-E2)(hereinafter, referred to as Compound (I-E2)) can be prepared by reacting an intermediate compound A represented by formula (II) and a compound represented by formula (R3)(hereinafter, referred to as Compound ($R^3$)) in the presence of a base.

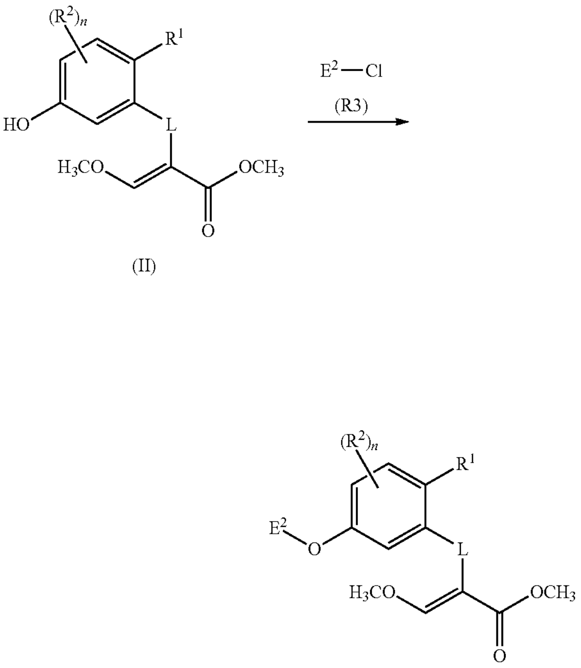

(II)

(I-E2)

[wherein $E^2$ represents $R^6C(O)$—, $R^4OC(O)$—, $R^3R^5NC(O)$—, $R^3R^5NC(S)$—, $R^4S(O)_2$—, or $R^3R^5NS(O)_2$—, and the other symbols are the same as defined above.]

The reaction is usually carried out in a solvent. Examples of the solvents to be used in the reaction include hydrocarbons, ethers, halogenated hydrocarbons, amides, esters, nitriles and mixed solvents of two or more these solvents.

Examples of the base include organic bases, alkali metal carbonates, alkali metal hydrocarbonates, sodium hydride, and tripotassium phosphate.

In the reaction, the compound (R3) is usually used within a range of 1 to 10 molar ratio(s), and the base is usually used within a range of 1 to 10 molar ratio(s), as opposed to 1 mole of the intermediate compound A.

The reaction temperature of the reaction is usually within a range of −78 to 100° C. The reaction period in the reaction is usually within a range of 0.1 to 48 hours.

When the reaction is completed, water is added to the reaction mixtures, and the resulting mixtures are extracted with organic solvent, and the organic layers are worked up (such as drying and concentration) to isolate the compound (I-E2).

The compound (R3) is publicly known, or can be prepared according to a publicly known method.

Process D

A compound represented by formula (I-E3)(hereinafter, referred to Compound (I-E3)) can be prepared by reacting the intermediate compound A represented by formula (II) and triphosgene in the presence of a base, followed by reacting with a compound represented by formula (R4) (hereinafter, referred to as Compound (R4)). Also the reaction can be conducted in one pot.

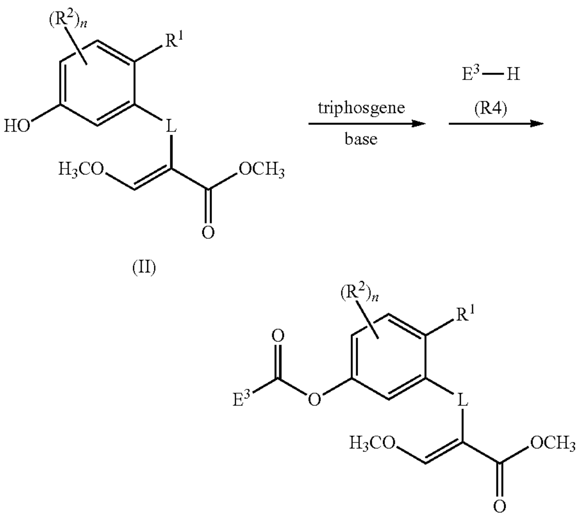

(II)

(I-E3)

[wherein $E^3$ represents $R^4O$—, or $R^3R5N$—, and the other symbols are the same as defined.]

The reaction is usually carried out in a solvent. Examples of the solvents to be used in the reaction include hydrocarbons, ethers, halogenated hydrocarbons, amides, esters, nitriles, and mixed solvents of two or more of these solvents.

Examples of the base include organic bases.

In the reaction, triphosgene is usually used within a range of 0.3 to 3 molar ratios, the base is usually used within a range of 1 to 10 molar ration(s), and the compound (R4) is usually used within a range of 1 to 10 molar ratio(s), as opposed to 1 mole of the intermediate compound A.

The reaction temperature of the reaction of the intermediate compound A and triphosgene is usually within a range of −78 to 100° C., and the reaction period in the reaction is usually within a range of 0.1 to 48 hours. The reaction temperature of the subsequent reaction with the compound (R4) is within a range of −78 to 100° C., and the reaction period in the reaction is usually within a range of 0.1 to 48 hours.

When the reaction is completed, water is added to the reaction mixtures, and the reaction mixtures are extracted with organic solvent(s), and the organic layers are worked up (such as drying and concentration) to isolate the compound (I-E3).

The compound (R4) is publicly known, or can be prepared according to a publicly known method.

Process E

The compound N of the present invention can be prepared by reacting the intermediate compound B represented by formula (III) and iodomethane in the presence of a base.

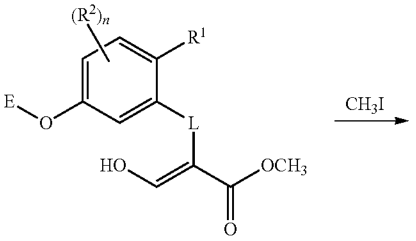

(III)

-continued

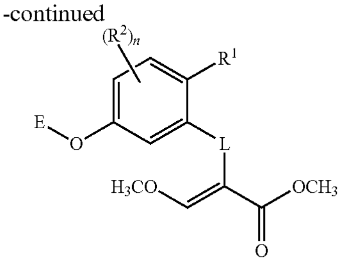

(I)

[wherein the symbols are the same as defined above.]

The reaction is usually carried out in a solvent. Examples of the solvents to be used in the reaction include hydrocarbons, ethers, halogenated hydrocarbons, amides, esters, nitriles, and mixed solvents of two or more of these solvents.

Examples of the base to be used in the reaction include organic bases, alkali metal carbonates, alkali metal hydrocarbonates, sodium hydride, and mixtures thereof.

In the reaction, iodomethane is usually used within a range of 1 to 10 molar ratio(s), and the base is usually used within a range of 1 to 20 molar ratio(s).

The reaction temperature for the reaction is usually within a range of −20 to 100° C. The reaction period in the reaction is usually within a range of 0.1 to 48 hours.

When the reaction is completed, water is added to the reaction mixtures, and the reaction mixtures are extracted with organic solvent(s), and the organic layers are worked up (such as drying and concentration) to isolate the compound N of the present invention.

Process F

The compound (I-E1) can be prepared by reacting the intermediate compound D represented by formula (VI) and the compound (R1) in the presence of a palladium catalyst.

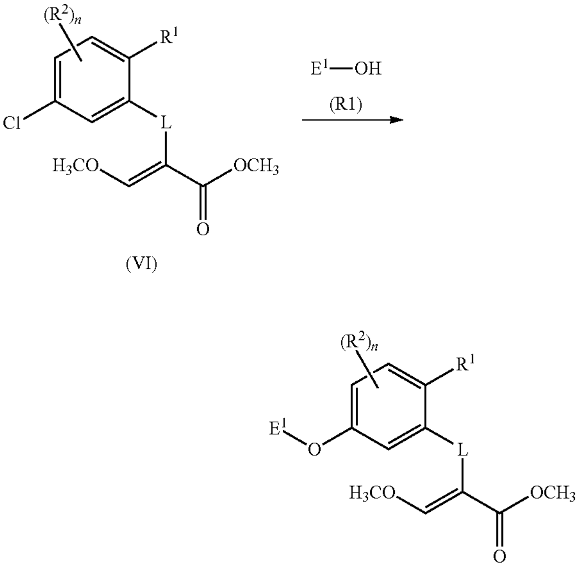

(VI)

(I-E1)

[wherein the symbols are the same as defined above.]

The reaction is usually carried out in a solvent. Examples of the solvents to be used in the reaction include hydrocarbons, ethers, halogenated hydrocarbons, amides, esters, nitriles, water, and mixed solvents of two or more of these solvents.

Examples of the palladium catalyst to be used in the reaction include palladium (II) acetate, {1,1'-bis(diphenylphosphino)ferrocene} dichloropalladium (II), Xphos Pd G3, BrettPhos Pd G3, tBuBrettPhos Pd G3, XantPhos Pd G3, and RockPhos Pd G3.

A ligand, a base or an additive may be added to the reaction as needed.

Examples of the ligand to be used in the reaction include 2-(di-t-butylphosphino)-1,1'-binaphthyl, BrettPhos, tBuBrettPhos, RockPhos, AdBrettPhos, tBuXPhos, and 5-(di-t-butylphosphino)-1,3',5'-triphenyl-1'H-[1,4']-bipyrazol.

When a ligand is used in the reaction, the ligand is usually used within a range of 0.01 to 1 molar ratio(s) as opposed to 1 mole of the intermediate compound D.

Examples of the base to be used in the reaction include organic bases; alkali metal carbonates: alkali metal alkoxides such as potassium t-butoxide, and sodium t-butoxide; and tripotassium phosphate.

When the reaction is completed, water is added to reaction mixtures, and the reaction mixtures are extracted with organic solvent(s), and the organic layers are worked up (for example, drying and concentration) to isolate the compound (I-E1).

The compound (R1) is publicly known, or can be prepared according to a publicly known method.

Process G

The N oxide of the compound N of the present invention can be prepared by reacting the compound N of the present invention and an oxidizing agent. The reaction can be conducted according the method described in U.S. patent publication No. 2018/0009778 or WO 2016/121970 A1.

Reference Process A

The intermediate compound A represented by formula (II) can be prepared by reacting a compound represented by formula (II-A)(hereinafter, referred to as Compound (II-A)) and bis(pinacolato)diboron in the presence of a base and a palladium catalyst to obtain a compound represented by formula (II-B)(hereinafter, referred to as compound (II-B)), followed by oxidizing the compound (II-B).

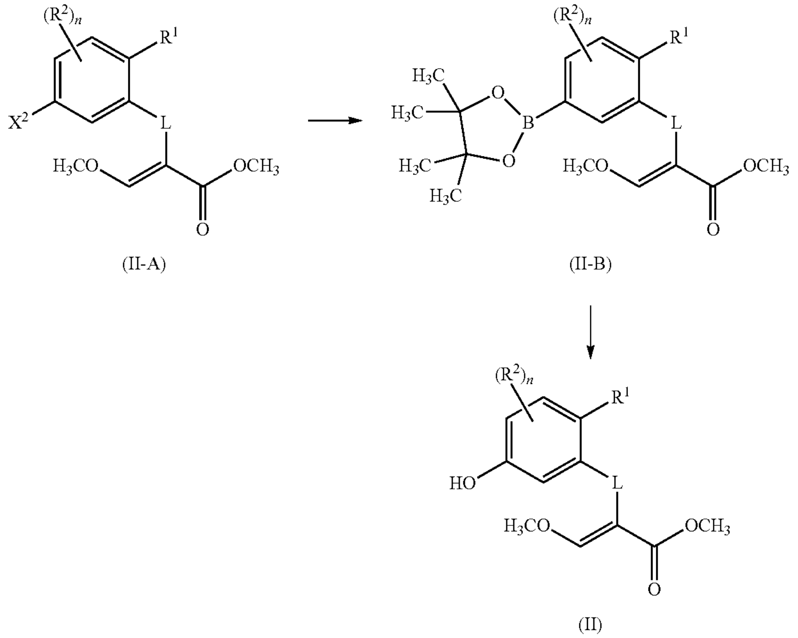

(II-A) (II-B) (II)

When the base is used in the reaction, the base is usually used within a range of 1 to 10 molar ratio(s), as opposed to 1 mole of the intermediate compound D.

Examples of the additive to be used in the reaction include sodium iodide, and potassium iodide.

When the additive is used in the reaction, the additive is usually used within a range of 0.1 to 10 molar ratios as opposed to 1 mole of the intermediate compound D.

In the reaction, the compound (R1) is usually used within a range of 1 to 10 molar ratio(s), and palladium catalyst is used within a range of 0.01 to 1 molar ratio(s), as opposed to 1 mole of the intermediate compound D.

The reaction temperature for the reaction is usually within a range of 0 to 150° C. The reaction period in the reaction is usually within a range of 0.1 to 120 hours.

[wherein X2 represents a bromine atom, an iodine atom, or a trifluoromethansulfonyl group, and the other symbols are the same as defined above.]

First, a process for preparing the compound (II-B) from the compound (II-A) is described.

The reaction is usually carried out in a solvent. Examples of the solvents to be used in the reaction include hydrocarbons, ethers, halogenated hydrocarbons, amides, esters, sulfoxides such as dimethyl sulfoxide (hereinafter, which is referred to as "DMSO")(hereinafter, which is collectively referred to as "sulfoxides"), nitriles, and mixed solvents of two or more of these solvents.

Examples of the bases to be used in the reaction include organic bases, alkali metal carbonates, alkali metal hydrocarbonates, and tripotassium phosphate.

Examples of the palladium include [1,1'-bis(diphenylphosphino)ferrocene] palladium (II) dichloride.

In the reaction, bis(pinacolato)diboron is usually used within a range of 1 to 5 molar ratio(s), the base is usually used within a range of 1 to 5 molar ratios, and the palladium catalyst is usually used within a range of 0.01 to 0.5 molar ratios, as opposed to 1 mole of the compound (II-A).

The reaction temperature for the reaction is usually within a range of 0 to 150° C., and the reaction period in the reaction is usually within a range of 0.1 to 48 hours.

When the reaction is completed, water is added to reaction mixtures, and the reaction mixtures are extracted with organic solvent(s), and the organic layers are worked up (for example, drying and concentration) to isolate the compound (II-B).

Next, a process for preparing the intermediate compound A from the compound (II-B) is described.

The reaction is usually carried out in a solvent. Examples of the solvents to be used in the reaction include hydrocarbons; ethers; halogenated hydrocarbons; amides; esters; nitriles; alcohols such as methanol, ethanol, propanol and butanol (hereinafter, collectively referred to as alcohols), water; and mixed solvents of two or more of these solvents.

Examples of the oxidizing agent to be used in the reaction include meta-chloroperoxybenzoic and hydrogen peroxide water.

When hydrogen peroxide is used as an oxidizing agent, a base may be added as needed.

Examples of the base include sodium hydroxide and potassium hydroxide.

In the reaction, the oxidizing agent is usually used within a range of 1 to 5 molar ratio(s) as opposed to 1 mole of the compound (II-B).

When a base is usually used, the base is usually used within a range of 0.1 to 5 molar ratios as opposed to 1 mole of the compound (II-B).

The reaction temperature of the reaction is usually within a range of −20 to 120° C., and the reaction period in the reaction is usually within a range of 0.1 to 48 hours.

When the reaction is completed, water and a reducing agent such as sodium thiosulfate are added to reaction mixtures, and the reaction mixtures are extracted with organic solvent(s), and the organic layers are worked up (for example, drying and concentration) to isolate the intermediate compound A.

The compound (II-A) is publicly known, or can be prepared according to a publicly known method.

Reference Process B

The intermediate compound B represented by formula (III) can be prepared by reacting a compound represented by formula (V)(hereinafter, referred to as compound (V)) and methyl formate in the presence of a base.

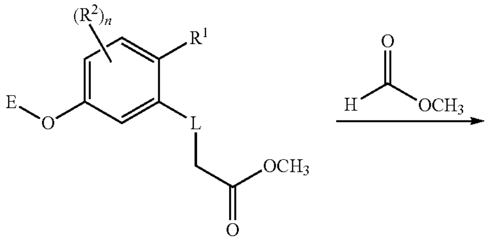

(V)

-continued

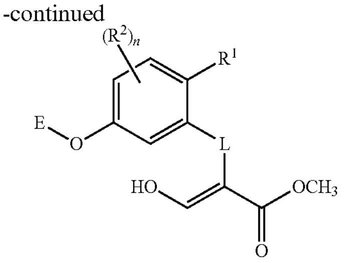

(III)

[wherein the symbols are the same defined above.]

The reaction is usually carried out in a solvent. Examples of the solvents to be used in the reaction include hydrocarbons, ethers, halogenated hydrocarbons, amides, nitriles, and mixed solvents of two or more of these solvents.

Examples of the base include alkali metal hydrides such as sodium hydride and potassium hydride; alkali metal alkoxides such as sodium methoxide, sodium ethoxide and potassium tert-butoxide; alkali metal amides such as sodium amide, lithium amide, lithium diisopropylamide, sodium hexamethyldisilazide, and lithium hexamethyldisilazide; and mixtures thereof.

In the reaction, methyl formate is usually used within a range of 1 to 100 molar ratio(s), and the base is usually used within a range of 1 to 10 molar ratio(s), as opposed to 1 mole of the compound (V).

The reaction temperature for the reaction is usually within a range of −20 to 80° C. The reaction period in the reaction is usually within a range of 0.1 to 48 hours.

When the reaction is completed, acidic aqueous solution such as dilute hydrochloric acid is added to reaction mixtures, and the reaction mixtures are extracted with organic solvent(s), and the organic layers are worked up (for example, drying and concentration) to isolate the intermediate compound B.

Reference Process C

A compound represented by formula (V-E1)(hereinafter, referred to as Compound (V-E1)) can be prepared by reacting a compound represented by formula (V-A)(hereinafter referred to as Compound (V-A)) and the compound (R1) in the presence of phosphines and azo diesters.

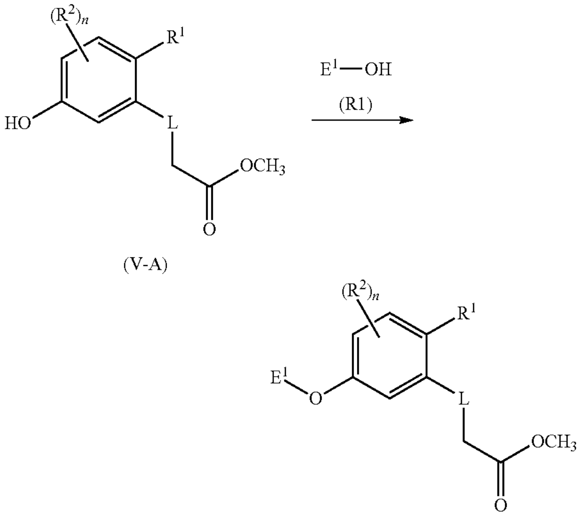

(V-A)

(V-E1)

[wherein the symbols are the same as defined above.]

The reaction can be conducted by using the compound (V-A) in the place of the intermediate compound A according to the process A.

The compound (V-A) is publicly known, or can be prepared according to a publicly known method.

Reference Process D

A compound represented by formula (V-E2)(hereinafter, referred to as "Compound (V-E2)") can be prepared by reacting the compound (V-A) and the compound (R3) in the presence of a base.

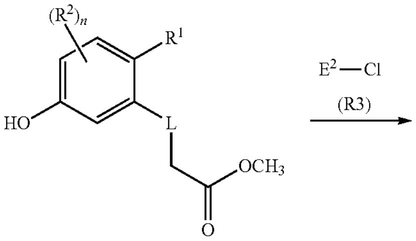

(V-A)

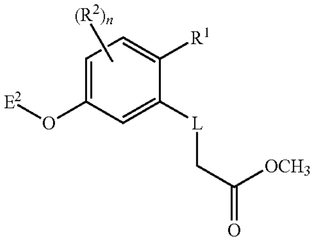

(V-E2)

[wherein the symbols are the same as defined above.]

The reaction can be conducted by using the compound (V-A) in the place of the intermediate compound A according to the process C.

Reference Process E

The intermediate compound D can be prepared by reacting a compound represented by formula (VI-A)(hereinafter, referred to as "Compound (VI-A)" and iodomethane in the presence of a base.

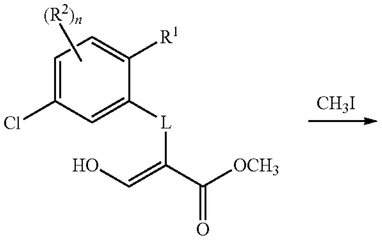

(VI-A)

-continued

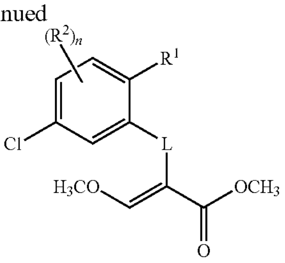

(VI)

[wherein the symbols are the same as defined above.]

The reaction can be conducted by using the compound (VI-A) in the place of the intermediate compound B according to the process E.

Reference Process F

The compound (VI-A) can be prepared by reacting a compound represented by formula (VI-B)(hereinafter, referred to as "Compound (VI-B)" and methyl formate in the presence of a base.

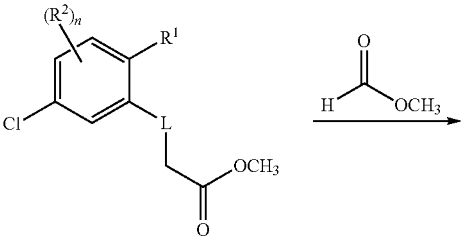

(VI-B)

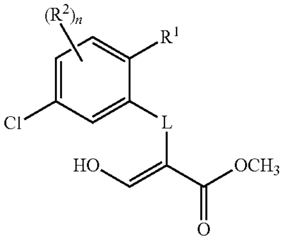

(VI-A)

[wherein the symbols are the same as defined above.]

The reaction can be conducted by using the compound (VI-B) in the place of the compound (V) according to the Reference process B.

The compound (VI-B) is publicly known, or can be prepared according to a publicly known method.

The present compound can be mixed or combined with one or more ingredients selected from the group consisting of the following Group (a), Group (b), Group (c), and Group (d) (hereinafter, referred to as "present ingredient").

The mixing or combining represents that the present compound and the present ingredient are used concurrently, separately, or at an interval.

When the present compound and the present ingredient are concurrently used, the present compound and the present ingredient may be incorporated as a separate formulation or one formulation.

One aspect of the present invention relates to a composition comprising one or more ingredients selected from the group consisting of the Group (a), the Group (b), the Group (c), and the Group (d), and the present compound (hereinafter, the composition is referred to as “Composition A”).

The Group (a) represents insecticidal ingredients, miticidal ingredients and nematicidal ingredients that are a group consisting of acetylcholinesterase inhibitors (for example, carbamate insecticides and organophosphate insecticides), GABA-gated chloride ion channel antagonists (for example, phenylpyrazole insecticides), sodium channel modulators (for example, pyrethroid insecticides), nicotinic acetylcholine receptor antagonist modulators (for example, neonicotinoid insecticides), nicotinic acetylcholine receptor allosteric modulators, glutamate-gated chloride ion channel allosteric modulators (for example, macrolide insecticides), juvenile hormone mimics, multisite inhibitors, chordotonal organ TRPV channel modulators, mites growth regulators, mitochondrial ATP synthase inhibitors, uncouplers of oxidative phosphorylation, nicotinic acetylcholine receptor channel blockers (for example, nereistoxin insecticides), inhibitors of chitin biosynthesis, moulting disruptors, ecdysone receptor agonists, octopamine receptor agonists, Inhibitors of mitochondrial electron transport chain complex I, II, III, and IV, voltage-dependent sodium channel blockers, Inhibitors of acetyl CoA carboxylase, ryanodine receptor modulators (for example, diamide insecticides), chordotonal organ modulators, each active ingredient of microbial fungicides, and other insecticidal ingredients, miticidal ingredients and nematicidal ingredients. These agents are described in the classification based on the IRAC mode of action.

The Group (b) represents fungicidal ingredients that are a group consisting of nucleic acid synthesis inhibitors (for example, phenylamide fungicides and acylamino acid fungicides), cytostatic and cytoskeletal inhibitors (for example, MBC fungicides), respiration inhibitors (for example, QoI fungicides and QiI fungicides), amino-acid synthesis and protein synthesis inhibitors (for example, anilinopyridine fungicides), signal-transduction inhibitors, lipid synthesis and membrane synthesis inhibitors, sterol biosynthesis inhibitors (for example, DMI fungicides such as triazoles), cell wall synthesis inhibitors, melanin synthesis inhibitors, plant defense inducer, multisite fungicides, microbial fungicides, and other fungicidal ingredients. These agents are described in the classification based on the FRAC mode of action.

The Group (c) represents a group of plant growth modulating ingredients including mycorrhizal fungus and *rhizobia*.

The Group (d) represents a group of repellent ingredients.

Examples of combinations of the present ingredient and the present compound are recited as follows. For example, the “alanycarb+SX” indicates a combination of alanycarb and SX.

The abbreviation “SX” means to any one of the present compounds X selected from the compound classes SX1 to SX80 described in Examples. Further, any of the present ingredients as described below are a known ingredient, and can be obtained as a commercially available drug or prepared according to a known method. When the present ingredient represents a microorganism, the present ingredient can be obtained from a microorganism depositary authority. The number in parentheses represents CAS RN (registered trademark).

A combination of the present ingredient in the above-mentioned Group (a) and the present compound:

abamectin+SX, acephate+SX, acequinocyl+SX, acetamiprid+SX, acetoprole+SX, acrinathrin+SX, acynonapyr+SX, afidopyropen+SX, afoxolaner+SX, alanycarb+SX, aldicarb+SX, allethrin+SX, alpha-cypermethrin+SX, alpha-endosulfan+SX, aluminium phosphide+SX, amitraz+SX, azadirachtin+SX, azamethiphos+SX, azinphos-ethyl+SX, azinphos-methyl+SX, azocyclotin+SX, bark of *Celastrus angulatus*+SX, bendiocarb+SX, benfluthrin+SX, benfuracarb+SX, bensultap+SX, benzoximate+SX, benzpyrimoxan+SX, beta-cyfluthrin+SX, beta-cypermethrin+SX, bifenazate+SX, bifenthrin+SX, bioallethrin+SX, bioresmethrin+SX, bistrifluron+SX, borax+SX, boric acid+SX, broflanilide+SX, bromopropylate+SX, buprofezin+SX, butocarboxim+SX, butoxycarboxim+SX, cadusafos+SX, calcium phosphide+SX, carbaryl+SX, carbofuran+SX, carbosulfan+SX, cartap hydrochloride+SX, cartap+SX, chinomethionat+SX, chlorantraniliprole+SX, chlordane+SX, chlorethoxyfos+SX, chlorfenapyr+SX, chlorfenvinphos+SX, chlorfluazuron+SX, chlormephos+SX, chloropicrin+SX, chlorpyrifos+SX, chlorpyrifos-methyl+SX, chromafenozide+SX, clofentezine+SX, clothianidin+SX, concanamycin A+SX, coumaphos+SX, cryolite+SX, cyanophos+SX, cyantraniliprole+SX, cycloniliprole+SX, cycloprothrin+SX, cycloxaprid+SX, cyenopyrafen+SX, cyflumetofen+SX, cyfluthrin+SX, cyhalodiamide+SX, cyhalothrin+SX, cyhexatin+SX, cypermethrin+SX, cyphenothrin+SX, cyromazine+SX, dazomet+SX, deltamethrin+SX, demeton-S-methyl+SX, diafenthiuron+SX, diazinon+SX, dichlorvos+SX, dicloromezotiaz+SX, dicofol+SX, dicrotophos+SX, diflovidazin+SX, diflubenzuron+SX, dimefluthrin+SX, dimethoate+SX, dimethylvinphos+SX, dimpropyridaz+SX, dinotefuran+SX, disodium octaborate+SX, disulfoton+SX, DNOC (2-methyl-4,6-dinitrophenol)+SX, doramectin+SX, dried leaves of Dryopteris filix-mas+SX, emamectin-benzoate+SX, empenthrin+SX, endosulfan+SX, EPN (O-ethyl 0-(4-nitrophenyl)phenylphosphonothioate+SX, epsilon-metofluthrin+SX, epsilon-momfluorothrin+SX, esfenvalerate+SX, ethiofencarb+SX, ethion+SX, ethiprole+SX, ethoprophos+SX, etofenprox+SX, etoxazole+SX, extract of *Artemisia absinthium*+SX, extract of *Cassia nigricans*+SX, extract of clitoria ternatea+SX, extract of Symphytum *officinale*+SX, extracts or simulated blend of *Chenopodium ambrosioides*+SX, extract of *Tanacetum vulgare*+SX, extract of *Urtica dioica*+SX, extract of Viscum album+SX, famphur+SX, fenamiphos+SX, fenazaquin+SX, fenbutatin oxide+SX, fenitrothion+SX, fenobucarb+SX, fenoxycarb+SX, fenpropathrin+SX, fenpyroximate+SX, fenthion+SX, fenvalerate+SX, fipronil+SX, flometoquin+SX, flonicamid+SX, fluacrypyrim+SX, fluazaindolizine+SX, fluazuron+SX, flubendiamide+SX, flucycloxuron+SX, flucythrinate+SX, fluensulfone+SX, flufenoprox+SX, flufenoxuron+SX, flufiprole+SX, flumethrin+SX, flupyradifurone+SX, flupyrimin+SX, fluralaner+SX, fluvalinate+SX, fluxametamide+SX, formetanate+SX, fosthiazate+SX, furamethrin+SX, furathiocarb+SX, gamma-cyhalothrin+SX, GS-omega/kappa HXTX-Hvla peptide+SX, halfenprox+SX, halofenozide+SX, heptafluthrin+SX, heptenophos+SX, hexaflumuron+SX, hexythiazox+SX, potassium salt of hop beta acid+SX, hydramethylnon+SX, hydroprene+SX, imicyafos+SX, imidacloprid+SX, imidaclothiz+SX, imiprothrin+SX, indoxacarb+SX, isocycloseram+SX, isofenphos+SX, isoprocarb+SX, isopropyl-O-(methoxyaminothiophosphoryl) salicylate+SX, isoxathion+SX, ivermectin+SX, kadethrin+SX, kappa-tefluthrin+SX, kappa-bifenthrin+SX, kinoprene+SX, lambda-cyhalothrin+SX, lenoremycin+SX, lepimectin+SX, lime sulfur+SX, lotilaner+SX, lufenuron+SX, machine oil+SX, malathion+SX, mecarbam+SX, meperfluthrin+SX, metaflumizone+SX, metam+SX, methamidophos+SX, methidathion+SX, methiocarb+SX, methomyl+SX, methoprene+SX, methoxychlor+SX, methoxyfenozide+SX, methyl bromide+SX, metofluthrin+SX, metolcarb+SX, metoxadiazone+SX, mevinphos+SX, milbemectin+SX, milbemycin oxime+SX, momfluorothrin+SX, monocrotophos+SX, moxidectin+SX, naled+SX, neem oil+SX, nicotine+SX, nicotine-sulfate+SX, nitenpyram+SX, novaluron+SX, noviflumuron+SX, oil of the seeds of *Chenopodium* anthelminticum+SX, omethoate+SX, oxamyl+SX, oxazosulfyl+SX, oxydemeton-methyl+SX, parathion+SX, parathion-methyl+SX, permethrin+SX, phenothrin+SX, phenthoate+SX, phorate+SX, phosalone+SX, phosmet+SX, phosphamidon+SX, phosphine+SX, phoxim+SX, pirimicarb+SX, pirimiphos-methyl+SX, prallethrin+SX, profenofos+SX, profluthrin+SX, propargite+SX, propetamphos+SX, propoxur+SX, propylene glycol alginate+SX, prothiofos+SX, pyflubumide+SX, pymetrozine+SX, pyraclofos+SX, pyrethrins+SX, pyridaben+SX, pyridalyl+SX, pyridaphenthion+SX, pyrifluquinazone+SX, pyrimidifen+SX, pyriminostrobin+SX, pyriprole+SX, pyriproxyfen+SX, quinalphos+SX, resmethrin+SX, rotenone+SX, ryanodine+SX, sarolaner+SX, selamectin+SX, sigma-cypermethrin+SX, silafluofen+SX, sodium borate+SX, sodium metaborate+SX, spinetoram+SX, spinosad+SX, spirodiclofen+SX, spiromesifen+SX, spiropidion+SX, spirotetramat+SX, sulfluramid+SX, sulfotep+SX, sulfoxaflor+SX, sulfur+SX, sulfuryl fluoride+SX, tartar emetic+SX, tau-fluvalinate+SX, tebufenozide+SX, tebufenpyrad+SX, tebupirimfos+SX, teflubenzuron+SX, tefluthrin+SX, temephos+SX, terbufos+SX, terpene constituents of the extract of *chenopodium ambrosioides* near *ambrosioides*+SX, tetrachlorantraniliprole+SX, tetrachlorvinphos+SX, tetradifon+SX, tetramethrin+SX, tetramethylfluthrin+SX, tetraniliprole+SX, theta-cypermethrin+SX, thiacloprid+SX, thiamethoxam+SX, thiocyclam+SX, thiodicarb+SX, thiofanox+SX, thiometon+SX, thiosultap-disodium+SX, thiosultap-monosodium+SX, tioxazafen+SX, tolfenpyrad+SX, tralomethrin+SX, transfluthrin+SX, triazamate+SX, triazophos+SX, trichlorfon+SX, triflumezopyrim+SX, triflumuron+SX, trimethacarb+SX, tyclopyrazoflor+SX, vamidothion+SX, wood extract of Quassia *amara*+SX, XMC (3,5-dimethylphenyl N-methylcarbamate)+SX, xylylcarb+SX, zeta-cypermethrin+SX, zinc phosphide+SX, N-[3-chloro-1-(pyridin-3-yl)-1H-pyrazol-4-yl]-N-ethyl-3-(3,3,3-trifluoropropanesulfinyl)propanamide (1477923-37-7)+SX, 4-[5-(3,5-dichlorophenyl)-5-(trifluoromethyl)-4,5-dihydro-1,2-oxazol-3-yl]-2-methyl-N-(1-oxothietan-3-yl)benzamide (1241050-20-3)+SX, 3-methoxy-N-(5—{5-(trifluoromethyl)-5-[3-(trifluoromethyl)phenyl]-4,5-dihydro-1,2-oxazol-3-yl}indan-1-yl)propanamide (1118626-57-5)+SX, N-[2-bromo-6-chloro-4-(1,1,1,2,3,3,3-heptafluoropropan-2-yl) phenyl]-3-{ethyl[(pyridin-4-yl)carbonyl]amino}-2-methoxybenzamide (1429513-53-0)+SX, N-[2-bromo-6-chloro-4-(1,1,1,2,3,3,3-heptafluoropropan-2-yl) phenyl]-3-[ethyl(4-cyanobenzoyl)amino]-2-methoxybenzamide (1609007-65-9)+SX, N-[2-bromo-6-(difluoromethoxy)-4-(1,1,1,2,3,3,3-heptafluoropropan-2-yl)phenyl]-3-{methyl[(pyridin-4-yl)carbonyl]amino}-2-methoxybenzamide (1630969-78-6)+SX, 1-{2-fluoro-4-methyl-5-[(2,2,2-trifluoroethyl)sulfanyl]phenyl}-3-(trifluoromethyl)-1H-1,2,4-triazol-5-amine (885026-50-6)+SX, (1Z)-2-(4-tert-butylphenyl)-2-cyano-1-(1-ethyl-3-methyl-1H-pyrazol-5-yl)ethenyl 2,2-dimethylpropanoate (1253429-01-4)+SX, N-[(1S,2S)-2-(2,4-dichlorophenyl)cyclobutyl]-2-(trifluoromethyl)pyridine-3-carboxamide+SX, BT crop protein CrylAb+SX, BT crop protein CrylAc+SX, BT crop protein CrylFa)+SX, BT crop protein CrylA.105+SX, BT crop protein Cry2Ab+SX, BT crop protein Vip3A+SX, BT crop protein Cry3A+SX, BT crop protein Cry3Ab+SX, BT crop protein Cry3Bb+SX, BT crop protein Cry34Abl/Cry35Abl+SX, *Adoxophyes orana* granulosis virus strain BV-0001+SX, *Anticarsia gemmatalis* mNPV+SX, *Autographa californica* mNPV+SX, *Cydia pomonella* GV strain V15+SX, *Cydia pomonella* GV strain V22+SX, Cryptophlebia leucotreta GV+SX, *Dendrolimus* punctatus cypovirus+SX, *Helicoverpa armigera* NPV strain BV-0003+SX, *Helicoverpa zea* NPV+SX, *Lymantria dispar* NPV+SX, *Mamestra brassicae* NPV+SX, *Mamestra* configurata NPV+SX, Neodiprion *abietis* NPV+SX, Neodiprion *lecontei* NPV+SX, Neodiprion sertifer NPV+SX, *Nosema* locustae+SX, *Orgyia pseudotsugata* NPV+SX, *Pieris rapae* GV+SX, Plodia interpunctella GV+SX, *Spodoptera exigua* mNPV+SX, *Spodoptera littoralis* mNPV+SX, *Spodoptera litura* NPV+SX, Arthrobotrys *dactyloides*+SX, *Bacillus firmus* strain GB-126+SX, *Bacillus firmus* strain I-1582+SX, *Bacillus megaterium*+SX, *Bacillus* sp. strain AQ175+SX, *Bacillus* sp. strain AQ177+SX, *Bacillus* sp. strain AQ178+SX, *Bacillus sphaericus* strain 2362+SX, *Bacillus sphaericus* strain ABTS1743+SX, *Bacillus sphaericus* Serotype strain H5a5b+SX, *Bacillus thuringiensis* strain AQ52+SX, *Bacillus thuringiensis* strain BD #32+SX, *Bacillus thuringiensis* strain CR-371+SX, *Bacillus thuringiensis* subsp. Aizawai strain ABTS-1857+SX, *Bacillus thuringiensis* subsp. Aizawai strain AM65-52+SX, *Bacillus thuringiensis* subsp. Aizawai strain GC-91+SX, *Bacillus thuringiensis* subsp. Aizawai Serotype strain H-7+SX, *Bacillus thuringiensis* subsp. Kurstaki strain ABTS351+SX, *Bacillus thuringiensis* subsp. Kurstaki strain BMP123+SX, *Bacillus thuringiensis* subsp. Kurstaki strain EG234+SX, *Bacillus thuringiensis* subsp. Kurstaki strain EG7841+SX, *Bacillus thuringiensis* subsp. Kurstaki strain EVB113-19+SX, *Bacillus thuringiensis* subsp. Kurstaki strain F810+SX, *Bacillus thuringiensis* subsp. Kurstaki strain HD-1+SX, *Bacillus thuringiensis* subsp. Kurstaki strain PB54+SX, *Bacillus thuringiensis* subsp. Kurstaki strain SA-11+SX, *Bacillus thuringiensis* subsp. Kurstaki strain SA-12+SX, *Bacillus thuringiensis* subsp. Tenebriosis strain NB176+SX, *Bacillus thuringiensis* subsp. *Thuringiensis* strain MPPL002+SX, *Bacillus thuringiensis* subsp.morrisoni+SX, *Bacillus thuringiensis* var. colmeri+SX, *Bacillus thuringiensis* var. darmstadiensis strain 24-91+SX, *Bacillus thuringiensis* var. *dendrolimus*+SX, *Bacillus thuringiensis* var. galleriae+SX, *Bacillus thuringiensis* var. *israelensis* strain BMP144+SX, *Bacillus thuringiensis* var. *israelensis* serotype strain H-14+SX, *Bacillus thuringiensis* var. japonensis strain buibui+SX, *Bacillus thuringiensis* var. san diego strain M-7+SX, *Bacillus thuringiensis* var.7216+SX, *Bacillus thuringiensis* var.*aegypti*+SX, *Bacillus thuringiensis* var. T36+SX, *Beauveria bassiana* strain ANT-03+SX, *Beauveria bassiana* strain ATCC74040+SX, *Beauveria bassiana* strain GHA+SX, *Beauveria brongniartii*+SX, *Burkholderia* rinojensis strain A396+SX, Chromobacterium subtsugae strain PPAA4-1T+SX, Dactyllela ellipsospora+SX, Dectylaria thaumasia+SX, Hirsutella minnesotensis+SX, Hirsutella rhossiliensis+SX, Hirsutella thompsonii+SX, Lagenidium *giganteum*+SX, Lecanicillium lecanii strain KV01+SX, Lecanicillium lecanii conidia of strain DAOM198499+SX, Lecanicillium lecanii conidia of strain DAOM216596+SX, Lecanicillium muscarium strain Ve6+SX, Metarhizium anisopliae strain F52+SX, Metarhizium anisopliae var. acridum+SX, Metarhizium anisopliae var. anisopliae BIPESCO 5/F52+SX, Metarhizium flavoviride+SX, Monacrosporium phymatopagum+SX, *Paecilomyces* fumosoroseus Apopka strain 97+SX, *Paecilomyces lilacinus* strain 251+SX, *Paecilomyces tenuipes* strain T1+SX, *Paenibacillus popilliae*+SX, Pasteuria nishizawae strain Pnl+SX, Pasteuria *penetrans*+SX, Pasteuria usgae+SX, Pasteuria thoynei+SX, *Serratia entomophila*+SX, *Verticillium* chlamydosporium+SX, *Verticillium* lecani strain NCIM1312+SX, 2-chloro-4-fluoro-5-{[5-(trifluoromethylthio)pentyl]oxy} phenyl 2,2,2-trifluoroethyl sulfoxide (1472050-04-6)+SX, 4-chloro-5-[2,2-difluoro-2-(3,4,5-trifluorophenyl)ethoxy]-2-methylphenyl 2,2,2-trifluoroethyl sulfoxide (1632218-00-8)+SX, 4-fluoro-5-[2,2-difluoro-2-(3,4,5-trifluorophenyl) ethoxy]-2-methylphenyl 2,2,2-trifluoroethyl sulfoxide (1632217-98-1)+SX, 2-({2-fluoro-4-methyl-5-[(2,2,2-trifluoroethyl)sulfinyl]phenyl} imino)-3-(2,2,2-trifluoroethyl)-1,3-thiazolidin-4-one (1445683-71-5)+SX, (3R)-3-(2-chlorothiazol-5-yl)-8-methyl-7-oxo-6-phenyl-2,3-dihydrothiazolo[3,2-a]pyrimidin-4-ium-5-olate (2249718-27-0)+SX, N—{4-chloro-3-[(1-cyanocyclopropyl)carbamoyl]phenyl}-1-methyl-4-(methanesulfonyl)-3-(1,1,2,2,2-pentafluoroethyl)-1H-pyrazole-3-carboxamide (1400768-21-9)+SX, 11-(4-chloro-2,6-dimethylphenyl)-12-hydroxy-1,4-dioxa-9-azadispiro [4.2.4.2]tetradec-11-en-10-one (907187-07-9)+SX, 3-(4'-fluoro-2,4-dimethyl[1,1'-biphenyl]-3-yl)-4-hydroxy-8-oxa-1-azaspiro[4.5]dec-3-en-2-one (1031385-91-7)+SX, N-[3-chloro-1-(pyridin-3-yl)-1H-pyrazol-4-yl]-2-(methanesulfonyl)propanamide (2396747-83-2)+SX, 2-isopropyl-5-[(3,4,4-trifluoro-3-buten-1-yl) sulfonyl]-1,3,4-thiadiazole (2058052-95-0)+SX, nicofluprole+SX, 1,4-dimethyl-2-[2-(3-pyridinyl)-2H-indazol-5-yl]-1,2,4-triazolidine-3,5-dione (2171099-09-3)+SX.

A combination of the present ingredient in the above-mentioned Group (b) and the present compound:

acibenzolar-S-methyl+SX, aldimorph+SX, ametoctradin+SX, aminopyrifen+SX, amisulbrom+SX, anilazine+SX, azaconazole+SX, azoxystrobin+SX, basic copper sulfate+SX, benalaxyl+SX, benalaxyl-M+SX, benodanil+SX, benomyl+SX, benthiavalicarb+SX, benthivalicarb-isopropyl+SX, benzovindiflupyr+SX, binapacryl+SX, biphenyl+SX, bitertanol+SX, bixafen+SX, blasticidin-S+SX, Bordeaux mixture+SX, boscalid+SX, bromothalonil+SX, bromuconazole+SX, bupirimate+SX, captafol+SX, captan+SX, carbendazim+SX, carboxin+SX, carpropamid+SX, chinomethionat+SX, chitin+SX, chloroneb+SX, chlorothalonil+SX, chlozolinate+SX, colletochlorin B+SX, copper(II) acetate+SX, copper(II) hydroxide+SX, copper oxychloride+SX, copper(II) sulfate+SX, coumoxystrobin+SX, cyazofamid+SX, cyflufenamid+SX, cymoxanil+SX, cyproconazole+SX, cyprodinil+SX, dichlobentiazox+SX, dichlofluanid+SX, diclocymet+SX, diclomezine+SX, dicloran+SX, diethofencarb+SX, difenoconazole+SX, diflumetorim+SX, dimethachlone+SX, dimethirimol+SX, dimethomorph+SX, dimoxystrobin+SX, diniconazole+SX, diniconazole-M+SX, dinocap+SX, dipotassium hydrogenphosphite+SX, dipymetitrone+SX, dithianon+SX, dodecylbenzenesulphonic acid bisethylenediamine copper(II) salt+SX, dodemorph+SX, dodine+SX, edifenphos+SX, enoxastrobin+SX, epoxiconazole+SX, etaconazole+SX, ethaboxam+SX, ethirimol+SX, etridiazole+SX, extract from *Melaleuca* alternifolia+SX, extract from *Reynoutria sachalinensis*+SX, extract from the cotyledons of lupine plantlets("BLAD")+SX, extract of *Allium sativum*+SX, extract of Equisetum *arvense*+SX, extract of *Tropaeolum majus*+SX, famoxadone+SX, fenamidone+SX, fenaminstrobin+SX, fenarimol+SX, fenbuconazole+SX, fenfuram+SX, fenhexamid+SX, fenoxanil+SX, fenpiclonil+SX, fenpicoxamid+SX, fenpropidin+SX, fenpropimorph+SX, fenpyrazamine+SX, fentin acetate+SX, fentin chloride+SX, fentin hydroxide+SX, ferbam+SX, ferimzone+SX, florylpicoxamid+SX, fluazinam+SX, fludioxonil+SX, flufenoxystrobin+SX, fluindapyr+SX, flumorph+SX, fluopicolide+SX, fluopyram+SX, fluopimomide+SX, fluoroimide+SX, fluoxapiprolin+SX, fluoxastrobin+SX, fluquinconazole+SX, flusilazole+SX, flusulfamide+SX, flutianil+SX, flutolanil+SX, flutriafol+SX, fluxapyroxad+SX, folpet+SX, fosetyl+SX, fosetyl-aluminium+SX, fuberidazole+SX, furalaxyl+SX, furametpyr+SX, guazatine+SX, hexaconazole+SX, hymexazole+SX, imazalil+SX, imibenconazole+SX, iminoctadine+SX, iminoctadine triacetate+SX, inpyrfluxam+SX, iodocarb+SX, ipconazole+SX, ipfentrifluconazole+SX, ipflufenoquin+SX, iprobenfos+SX, iprodione+SX, iprovalicarb+SX, isofetamid+SX, isoflucypram+SX, isoprothiolane+SX, isopyrazam+SX, isotianil+SX, kasugamycin+SX, kresoxim-methyl+SX, laminarin+SX, leaves and bark of *Quercus*+SX, mancozeb+SX, mandestrobin+SX, mandipropamid+SX, maneb+SX, mefentrifluconazole+SX, mepanipyrim+SX, mepronil+SX, meptyldinocap+SX, metalaxyl+SX, metalaxyl-M+SX, metconazole+SX, methasulfocarb+SX, metiram+SX, metominostrobin+SX, metrafenone+SX, metyltetraprole+SX, mineral oils+SX, myclobutanil+SX, naftifine+SX, nuarimol+SX, octhilinone+SX, ofurace+SX, orysastrobin+SX, oxadixyl+SX, oxathiapiprolin+SX, oxine-copper+SX, oxolinic acid+SX, oxpoconazole+SX, oxpoconazole fumarate+SX, oxycarboxin+SX, oxytetracycline+SX, pefurazoate+SX, penconazole+SX, pencycuron+SX, penflufen+SX, penthiopyrad+SX, phenamacril+SX, phosphorous acid+SX, phthalide+SX, picarbutrazox+SX, picoxystrobin+SX, piperalin+SX, polyoxins+SX, potassium hydrogencarbonate+SX, potassium dihydrogenphosphite+SX, probenazole+SX, prochloraz+SX, procymidone+SX, propamidine+SX, propamocarb+SX, propiconazole+SX, propineb+SX, proquinazid+SX, prothiocarb+SX, prothioconazole+SX, pydiflumetofen+SX, pyraclostrobin+SX, pyrametostrobin+SX, pyraoxystrobin+SX, pyrapropoyne+SX, pyraziflumid+SX, pyrazophos+SX, pyribencarb+SX, pyributicarb+SX, pyridachlometyl+SX, pyrifenox+SX, pyrimethanil+SX, pyrimorph+SX, pyriofenone+SX, pyrisoxazole+SX, pyroquilon+SX, Quillaja extract+SX, quinconazole+SX, quinofumelin+SX, quinoxyfen+SX, quintozene+SX, Saponins of *Chenopodium quinoa*+SX, sedaxane+SX, silthiofam+SX, simeconazole+SX, sodium hydrogencarbonate+SX, spiroxamine+SX, streptomycin+SX, sulfur+SX, tebuconazole+SX, tebufloquin+SX, teclofthalam+SX, tecnazene+SX, terbinafine+SX, tetraconazole+SX, thiabendazole+SX, thifluzamide+SX, thiophanate+SX, thiophanate-methyl+SX, thiram+SX, thymol+

SX, tiadinil+SX, tolclofos-methyl+SX, tolfenpyrad+SX, tolprocarb+SX, tolylfluanid+SX, triadimefon+SX, triadimenol+SX, triazoxide+SX, triclopyricarb+SX, tricyclazole+SX, tridemorph+SX, trifloxystrobin+SX, triflumizole+SX, triforine+SX, triticonazole+SX, validamycin+SX, valifenalate+SX, vinclozolin+SX, yellow mustard powder+SX, zinc thiazole+SX, zineb+SX, ziram+SX, zoxamide+SX, N'-[4-({3-[(4-chlorophenyl)methyl]-1,2,4-thiadiazol-5-yl}oxy)-2,5-dimethylphenyl]-N-ethyl-N-methylmethanimidamide (1202781-91-6)+SX, N'-{4-[(4,5-dichlorothiazol-2-yl)oxy]-2,5-dimethylphenyl}-N-ethyl-N-methylmethanimidamide (929908-57-6)+SX, N'-(2,5-dimethyl-4-phenoxyphenyl)-N-ethyl-N-methylmethanimidamide (1052688-31-9)+SX, N'-[5-choro-4-(2-fluorophenoxy)-2-methylphenyl)-N-ethyl-N-methylmethanimidamide (2055589-28-9)+SX, N'-[2-choro-4-(2-fluorophenoxy)-5-methylphenyl)-N-ethyl-N-methylmethanimidamide (2055756-21-1)+SX, N'-[4-(1-hydroxy-1-phenyl-2,2,2-trifluoroethyl)-2-methyl-5-methoxyphenyl)-N-isopropyl-N-methylmethanimidamide (2101814-55-3)+SX, N'-[5-bromo-6-(1-methyl-2-propoxyethoxy)-2-methylpyridin-3-yl)-N-ethyl-N-methylmethanimidamide (1817828-69-5)+SX, 4-(2-bromo-4-fluorophenyl)-N-(2-chloro-6-fluorophenyl)-1,3-dimethyl-1H-pyrazol-5-amine (1362477-26-6)+SX, 2-[6-(3-fluoro-4-methoxyphenyl)-5-methylpyridin-2-yl]quinazoline (1257056-97-5)+SX, 5-fluoro-4-imino-3-methyl-1-tosyl-3,4-dihydropyrimidin-2(1H)-one (1616664-98-2)+SX, ethyl (2Z)-3-amino-2-cyano-3-phenylacrylate (39491-78-6)+SX, N-[(2-chlorothiazol-5-yl)methyl]-N-ethyl-6-methoxy-3-nitropyridin-2-amine (1446247-98-8)+SX, 5-(4-chlorobenzyl)-2-(chloromethyl)-2-methyl-1-(1H-1,2,4-triazol-1-ylmethyl)cyclopentan-1-ol (1394057-11-4)+SX, (1R, 2S, 5S)-5-(4-chlorobenzyl)-2-(chloromethyl)-2-methyl-1-(1H-1,2,4-triazol-1-ylmethyl)cyclopentan-1-ol (1801930-06-2)+SX, (1S, 2R, 5R)-5-(4-chlorobenzyl)-2-(chloromethyl)-2-methyl-1-(1H-1,2,4-triazol-1-ylmethyl)cyclopentan-1-ol (1801930-07-3)+SX, 2-(chloromethyl)-5-(4-fluorobenzyl)-2-methyl-1-(1H-1,2,4-triazol-1-ylmethyl)cyclopentan-1-ol (1394057-13-6)+SX, (1R, 2S, 5S)-2-(chloromethyl)-5-(4-fluorobenzyl)-2-methyl-1-(1H-1,2,4-triazol-1-ylmethyl)cyclopentan-1-ol (1801930-08-4)+SX, (1S, 2R, 5R)-2-(chloromethyl)-5-(4-fluorobenzyl)-2-methyl-1-(1H-1,2,4-triazol-1-ylmethyl)cyclopentan-1-ol (1801930-09-5)+SX, methyl 3-[(4-chlorophenyl)methyl]-2-hydroxy-1-methyl-2-(1H-1,2,4-triazol-1-ylmethyl)cyclopentan-1-carboxylate (1791398-02-1)+SX, 1-(2,4-difluorophenyl)-2-(1H-1,2,4-triazol-1-yl)-1-[i-(4-bromo-2,6-difluorophenoxy)cyclopropyl]ethanol (2019215-86-0)+SX, 1-(2,4-difluorophenyl)-2-(1H-1,2,4-triazol-1-yl)-1-[1-(4-chloro-2,6-difluorophenoxy)cyclopropyl]ethanol (2019215-84-8)+SX, 1-[2-(1-chlorocyclopropyl)-3-(2-fluorophenyl)-2-hydroxypropyl]-1H-imidazole-5-carbonitrile (2018316-13-5)+SX, 1-[2-(1-chlorocyclopropyl)-3-(2,3-difluorophenyl)-2-hydroxypropyl]-1H-imidazole-5-carbonitrile (2018317-25-2)+SX, 4-({6-[2-(2,4-difluorophenyl)-1,1-difluoro-2-hydroxy-3-(1H-1,2,4-triazol-1-yl)propyl]pyridin-3-yl}oxy) benzonitrile (2046300-61-0)+SX, 2-[6-(4-bromophenoxy)-2-(trifluoromethyl)pyridin-3-yl]-1-(1H-1,2,4-triazol-1-yl) propan-2-ol (2082661-43-4)+SX, 2-[6-(4-chlorophenoxy)-2-(trifluoromethyl)pyridin-3-yl]-1-(1H-1,2,4-triazol-1-yl) propan-2-ol (2082660-27-1)+SX, methyl({2-methyl-5-[1-(4-methoxy-2-methylphenyl)-1H-pyrazol-3-yl] phenyl}methyl)carbamate (1605879-98-8)+SX, 2-(difluoromethyl)-N-[1,1,3-trimethyl-2,3-dihydro-1H-inden-4-yl]pyridine-3-carboxamide (1616239-21-4)+SX, 2-(difluoromethyl)-N-[3-ethyl-1,1-dimethyl-2,3-dihydro-1H-inden-4-yl]pyridine-3-carboxamide (1847460-02-9)+SX, 2-(difluoromethyl)-N-[3-propyl-1,1-dimethyl-2,3-dihydro-1H-inden-4-yl]pyridine-3-carboxamide (1847460-05-2)+SX, (2E,3Z)-5-{[1-(4-chlorophenyl)-1H-pyrazol-3-yl]oxy}-2-(methoxyimino)-N,3-dimethylpent-3-enamide (1445331-27-0)+SX, (2E,3Z)-5-{[1-(2,4-dichlorophenyl)-1H-pyrazol-3-yl]oxy}-2-(methoxyimino)-N,3-dimethylpent-3-enamide (1445331-54-3)+SX, 5-chloro-4-({2-[6-(4-chlorophenoxy)pyridin-3-yl]ethyl} amino)-6-methylpyrimidine (1605340-92-8)+SX, N-(1-benzyl-1,3-dimethylbutyl)-8-fluoroquinoline-3-carboxamide (2132414-04-9), N-(1-benzyl-3,3,3-trifluoro-1-methylpropyl)-8-fluoroquinoline-3-carboxamide (2132414-00-5)+SX, 4,4-dimethyl-2-({4-[5-(trifluoromethyl)-1,2,4-oxadiazol-3-yl] phenyl} methyl)isoxazolidin-3-one (2098918-25-1)+SX, 5,5-dimethyl-2-({4-[5-(trifluoromethyl)-1,2,4-oxadiazol-3-yl]phenyl} methyl)isoxazolidin-3-one (2098918-26-2)+SX, *Agrobacterium* radiobactor strain K1026+SX, *Agrobacterium* radiobactor strain K84+SX, *Bacillus amyloliquefaciens* (Aveo(registered trademark) EZ Nematicide)+SX, *Bacillus amyloliquefaciens* strain AT332+SX, *Bacillus amyloliquefaciens* strain B3+SX, *Bacillus amyloliquefaciens* strain D747+SX, *Bacillus amyloliquefaciens* strain DB101+SX, *Bacillus amyloliquefaciens* strain DB102+SX, *Bacillus amyloliquefaciens* strain GB03+SX, *Bacillus amyloliquefaciens* strain FZB24+SX, *Bacillus amyloliquefaciens* strain FZB42+SX, *Bacillus amyloliquefaciens* strain IN937a+SX, *Bacillus amyloliquefaciens* strain MBI600+SX, *Bacillus amyloliquefaciens* strain QST713+SX, *Bacillus amyloliquefaciens* isolate strain B246+SX, *Bacillus amyloliquefaciens* strain F727+SX, *Bacillus amyloliquefaciens* subsp. *plantarum* strain D747+SX, *Bacillus licheniformis* strain HB-2+SX, *Bacillus licheniformis* strain SB3086+SX, *Bacillus pumilus* strain AQ717+SX, *Bacillus pumilus* strain BUF-33+SX, *Bacillus pumilus* strain GB34+SX, *Bacillus pumilus* strain QST2808+SX, *Bacillus simplex* strain CGF2856+SX, *Bacillus subtilis* strain AQ153+SX, *Bacillus subtilis* strain AQ743+SX, *Bacillus subtilis* strain BU1814+SX, *Bacillus subtilis* strain D747+SX, *Bacillus subtilis* strain DB101+SX, *Bacillus subtilis* strain FZB24+SX, *Bacillus subtilis* strain GB03+SX, *Bacillus subtilis* strain HAI0404+SX, *Bacillus subtilis* strain IAB/BS03+SX, *Bacillus subtilis* strain MBI600+SX, *Bacillus subtilis* strain QST30002/AQ30002+SX, *Bacillus subtilis* strain QST30004/AQ30004+SX, *Bacillus subtilis* strain QST713+SX, *Bacillus subtilis* strain QST714+SX, *Bacillus subtilis* var. *Amyloliquefaciens* strain FZB24+SX, *Bacillus subtilis* strain Y1336+SX, *Burkholderia cepacia*+SX, *Burkholderia cepacia* type Wisconsin strain J82+SX, *Burkholderia cepacia* type Wisconsin strain M54+SX, *Candida oleophila* strain 0+SX, *Candida saitoana*+SX, *Chaetomium* cupreum+SX, Clonostachys *rosea*+SX, *Coniothyrium minitans* strain CGMCC8325+SX, *Coniothyrium minitans* strain CON/M/91-8+SX, *cryptococcus albidus*+SX, *Erwinia carotovora* subsp.*carotovora* strain CGE234M403+SX, *Fusarium oxysporum* strain Fo47+SX, *Gliocladium catenulatum* strain J1446+SX, *Paenibacillus polymyxa* strain AC-1+SX, *Paenibacillus polymyxa* strain BS-0105+SX, *Pantoea agglomerans* strain E325+SX, *Phlebiopsis gigantea* strain VRA1992+SX, *Pseudomonas aureofaciens* strain TX-1+SX, *Pseudomonas chlororaphis* strain 63-28+SX, *Pseudomonas chlororaphis* strain AFS009+SX, *Pseudomonas chlororaphis* strain MA342+SX, *Pseudomonas fluorescens* strain 1629RS+SX, *Pseudomonas fluorescens* strain A506+SX, *Pseudomonas fluorescens* strain CL145A+SX, *Pseudomonas fluorescens* strain G7090+SX, *Pseudomonas* sp. strain CAB-02+SX, *Pseudomonas syringae* strain 742RS+SX, *Pseudomonas syringae* strain MA-4+SX, Pseudozyma flocculosa strain PF-A22UL+SX, *Pseudomonas rhodesiae* strain HAI-0804+SX, *Pythium oligandrum* strain DV74+SX, *Pythium oligandrum* strain M1+SX, *Streptomyces griseoviridis* strain K61+SX, *Streptomyces lydicus* strain WYCD108US+SX, *Streptomyces lydicus* strain WYEC108+SX, *Talaromyces flavus* strain SAY-Y-94-01+SX, *Talaromyces flavus* strain V117b+SX, *Trichoderma* asperellum strain ICC012+SX, *Trichoderma* asperellum SKT-1+SX, *Trichoderma* asperellum strain T25+SX, *Trichoderma* asperellum strain T34+SX, *Trichoderma* asperellum strain TV1+SX, *Trichoderma* atroviride strain CNCM 1-1237+SX, *Trichoderma* atroviride strain LC52+SX, *Trichoderma* atroviride strain IMI 206040+SX, *Trichoderma* atroviride strain SCl+SX, *Trichoderma* atroviride strain SKT-1+SX, *Trichoderma* atroviride strain T11+SX, *Trichoderma* gamsii strain ICC080+SX, *Trichoderma harzianum* strain 21+SX, *Trichoderma harzianum* strain DB104+SX, *Trichoderma harzianum* strain DSM 14944+SX, *Trichoderma harzianum* strain ESALQ-1303+SX, *Trichoderma harzianum* strain ESALQ-1306+SX, *Trichoderma harzianum* strain IIHR-Th-2+SX, *Trichoderma harzianum* strain ITEM908+SX, *Trichoderma harzianum* strain kd+SX, *Trichoderma harzianum* strain M01+SX, *Trichoderma harzianum* strain SF+SX, *Trichoderma harzianum* strain T22+SX, *Trichoderma harzianum* strain T39+SX, *Trichoderma harzianum* strain T78+SX, *Trichoderma harzianum* strain TH35+SX, *Trichoderma polysporum* strain IMI206039+SX, *trichoderma* stromaticum+SX, *Trichoderma virens* strain G-41+SX, *Trichoderma virens* strain GL-21+SX, *Trichoderma viride*+SX, Variovorax *paradoxus* strain CGF4526+SX, Harpin protein+SX, flubeneteram+SX, N-acetyl-2-(ethanesulfonyl)-N-[2-(methoxycarbonyl)-4-(trifluoromethoxy)phenyl]-4-(trifluoromethyl)benzamide (2043675-28-9)+SX, (2S,3S)-3-(2-methylphenyl)butan-2-yl N-[(3-acetoxy-4-methoxypyridin-2-yl)carbonyl]-L-alaninate (2376210-00-1)+SX, (2S,3S)-3-(4-fluoro-2-methylphenyl)butan-2-yl N-[(3-acetoxy-4-methoxypyridin-2-yl)carbonyl]-L-alaninate+SX, (2S,3S)-3-(4-methoxy-2-methylphenyl)butan-2-yl N-[(3-acetoxy-4-methoxypyridin-2-yl)carbonyl]-L-alaninate+SX, (2S,3S)-3-(2,4-dimethylphenyl)butan-2-yl N-[(3-acetoxy-4-methoxypyridin-2-yl)carbonyl]-L-alaninate (2376209-13-9)+SX, (2S,3S)-3-(2-methylphenyl)butan-2-yl N-({3-[(2-methylpropanoyl)oxy]-4-methoxypyridin-2-yl}carbonyl)-L-alaninate (2376210-02-3)+SX, (2S,3S)-3-(4-fluoro-2-methylphenyl)butan-2-yl N-({3-[(2-methylpropanoyl)oxy]-4-methoxypyridin-2-yl}carbonyl)-L-alaninate+SX, (2S,3S)-3-(4-methoxy-2-methylphenyl)butan-2-yl N-({3-[(2-methylpropanoyl)oxy]-4-methoxypyridin-2-yl}carbonyl)-L-alaninate (2376209-40-2)+SX, (2S,3S)-3-(2,4-dimethylphenyl)butan-2-yl N-({3-[(2-methylpropanoyl)oxy]-4-methoxypyridin-2-yl}carbonyl)-L-alaninate (2376209-15-1)+SX.

A combination of the present ingredient in the above-mentioned Group (c) and the present compound: 1-methylcyclopropene+SX, 1,3-diphenylurea+SX, 2,3,5-triiodobenzoic acid+SX, IAA ((1H-indol-3-yl)acetic acid)+SX, IBA (4-(1H-indol-3-yl)butyric acid)+SX, MCPA (2-(4-chloro-2-methylphenoxy)acetic acid)+SX, MCPB (4-(4-chloro-2-methylphenoxy)butyric acid)+SX, 4-CPA (4-chlorophenoxyacetic acid)+SX, 5-aminolevulinic acid hydrochloride+SX, 6-benzylaminopurine+SX, abscisic acid+SX, AVG (aminoethoxyvinylglycine)+SX, ancymidol+SX, butralin+SX, calcium carbonate+SX, calcium chloride+SX, calcium formate+SX, calcium peroxide+SX, calcium polysulfide+SX, calcium sulfate+SX, chlormequat-chloride+SX, chlorpropham+SX, choline chloride+SX, cloprop+SX, cyanamide+SX, cyclanilide+SX, daminozide+SX, decan-1-ol+SX, dichlorprop+SX, dikegulac+SX, dimethipin+SX, diquat+SX, ethephon+SX, ethychlozate+SX, flumetralin+SX, flurprimidol+SX, forchlorfenuron+SX, formononetin+SX, Gibberellin A+SX, Gibberellin A3+SX, inabenfide+SX, Kinetin+SX, lipochitooligosaccharide SP104+SX, maleic hydrazide+SX, mefluidide+SX, mepiquat-chloride+SX, oxidized glutathione+SX, pacrobutrazol+SX, pendimethalin+SX, prohexandione-calcium+SX, prohydrojasmon+SX, pyraflufen-ethyl+SX, sintofen+SX, sodium 1-naphthaleneacetate+SX, sodium cyanate+SX, streptmycin+SX, thidiazuron+SX, triapenthenol+SX, Tribufos+SX, trinexapac-ethyl+SX, uniconazole-P+SX, 2-(naphthalen-1-yl)acetamide+SX, [4-oxo-4-(2-phenylethyl)amino]butylate+SX, methyl 5-(trifluoromethyl)benzo[b]thiophene-2-carboxylate+SX, 3-[(6-chloro-4-phenylquinazolin-2-yl)amino]-1-propanol+SX, Claroideoglomus *etunicatum*+SX, Claroideoglomus claroideum+SX, Funneliformis *mosseae*+SX, Gigaspora margarita+SX, Gigaspora *rosea*+SX, *Glomus aggregatum*+SX, *Glomus deserticola*+SX, *Glomus monosporum*+SX, Paraglomus brasillianum+SX, Rhizophagus *clarus*+SX, Rhizophagus *intraradices* RTI-801+SX, Rhizophagus *irregularis* DAOM 197198+SX, *Azorhizobium caulinodans*+SX, Azospirillum amazonense+SX, Azospirillum brasilense XOH+SX, Azospirillum brasilense Ab-V5+SX, Azospirillum brasilense Ab-V6+SX, Azospirillum *caulinodans*+SX, Azospirillum halopraeferens+SX, Azospirillum irakense+SX, Azospirillum lipoferum+SX, *Bradyrhizobium elkanii* SEMIA 587+SX, *Bradyrhizobium elkanii* SEMIA 5019+SX, *Bradyrhizobium japonicum* TA-11+SX, *Bradyrhizobium japonicum* USDA 110+SX, *Bradyrhizobium liaoningense*+SX, *Bradyrhizobium lupini*+SX, Delftia *acidovorans* RAY209+SX, *Mesorhizobium* ciceri+SX, *Mesorhizobium* huakii+SX, *Mesorhizobium loti*+SX, *Rhizobium etli*+SX, *Rhizobium galegae*+SX, *Rhizobium leguminosarum* bv. *Phaseoli*+SX, *Rhizobium leguminosarum* bv. *Trifolii*+SX, *Rhizobium leguminosarum* bv. *Viciae*+SX, *Rhizobium trifolii*+SX, *Rhizobium tropici*+SX, *Sinorhizobium fredii*+SX, *Sinorhizobium meliloti*+SX, Zucchini Yellow Mosaik Virus weak strain+SX.

A combination of the present ingredient in the above-mentioned Group (d) and the present compound:

anthraquinone+SX,deet+SX,icaridin+SX.

Examples of a ratio of the present compound to the present ingredient include, but are not particularly limited to 1000:1 to 1:1000, 500:1 to 1:500, 100:1 to 1 100, 50:1, 20:1, 10:1, 9:1, 8:1, 7:1, 6:1, 5 1, 4 1, 3 1, 2:1, 1 1, 1 2, 1 3, 1 4, 1:5, 1 6, 1:7, 1:8, 1:9, 1:10, 1:20, and 1:50 in the weight ratio (the present compound:the present ingredient).

The present compound has an efficacy against pests. Examples of the pests include plant phytopathogenic microorganism, harmful arthropods such as harmful insects and harmful mites, harmful nematicides, and harmful mollusks.

The present compound can be controlled plant diseases caused by phytopathogenic microorganism such as fungi, oomycete, phytomyxea, and bacteria. Examples of the fungi include Ascomycota, Basidiomycota, Blasocladiomycota, Chytridiomycota, Mucoromycota and Olpidiomycota. Specific examples thereof include the followings. Here the descriptions in a parenthesis indicates an academic name of phytopathogenic microorganism that causes each of the disease.

Rice Diseases:

blast (Pyricularia *oryzae*), brown spot (*Cochliobolus miyabeanus*), sheath blight (*Rhizoctonia solani*), bakanae disease (*Gibberella fujikuroi*), downy mildew (Sclerophthora *macrospora*), false blast and head blight (*Epicoccum nigrum*), and seedling blight (*Trichoderma viride, Rhizopus oryzae*);

Wheat Diseases:

powdery mildew (Blumeria *graminis*), *fusarium* blight (*Fusarium* gaminearum, *Fusarium avenaceum, Fusarium culmorum, Microdochium nivale*), stripe rust (*Puccinia striiformis*), stem rust (*Puccinia graminis*), leaf rust (*Puccinia recondita*), snow mould (*Microdochium nivale, Microdochium majus*), typhula snow blight (Typhula *incarnata*, Typhula ishikariensis), loose smut (*Ustilago tritici*), stinking smut (Tilletia caries, Tilletia controversa), eyespot (Pseudocercosporella herpotrichoides), *septoria* leaf blotch (*Septoria tritici*), glume blotch (*Stagonospora nodorum*), tan spot (*Pyrenophora tritici*-repentis), *rhizoctonia* seeding blight (*Rhizoctonia solani*), take-all disease (Gaeumannomyces *graminis*), and blast (Pyricularia *graminis-tritici*);

Barley Diseases:

powdery mildew (Blumeria *graminis*), *fusarium* head blight (*Fusarium* gaminearum, *Fusarium avenaceum, Fusarium culmorum, Microdochium nivale*), stripe rust (*Puccinia striiformis*), stem rust (*Puccinia graminis*), dwarf leaf rust (*Puccinia hordei*), loose smut (*Ustilago nuda*), scald (Rhynchosporium secalis), net blotch (*Pyrenophora teres*), spot blotch (*Cochliobolus sativus*), stripe (*Pyrenophora graminea*), Ramularia disease (Ramularia collo-*cygni*), and *rhizoctonia* seeding blight (*Rhizoctonia solani*);

Corn Diseases:

rust (*Puccinia sorghi*), southern rust (*Puccinia polysora*), northern leaf blight (*Setosphaeria turcica*), tropical rust (Physopella *zeae*), southern leaf blight (*Cochliobolus heterostrophus*), anthracnose (*Colletotrichum graminicola*), gray leaf spot (*Cercospora zeae-maydis*), eyespot (*Kabatiella zeae*), phaeosphaeria leaf spot (Phaeosphaeria *maydis*), *diplodia* rot (*Stenocarpella maydis, Stenocarpella macrospora*), stalk rot (*Fusarium graminearum, Fusarium verticilioides, Colletotrichum graminicola*), smut (*Ustilago maydis*), and Physoderma brown spot and Physoderma stalk rot (Physoderma *maydis*);

Cotton Diseases:

anthracnose (*Colletotrichum gossypii*), grey mildew (Ramularia areola), *alternaria* leaf spot (*Alternaria macrospora, Alternaria gossypii*), and black root rot (*Thielaviopsis basicola*);

Coffee Diseases:

rust (*Hemileia vastatrix*), and leaf spot (*Cercospora coffeicola*);

Rape Seed Diseases:

*sclerotinia* rot (*Sclerotinia sclerotiorum*), gray leaf spot (*Alternaria brassicae*), root rot (*Phoma* lingam), and light leaf spot (Pyrenopeziza *brassicae*);

Sugar Cane Diseases:

rust (*Puccinia* melanocephela, *Puccinia kuehnii*), and smut (*Ustilago* scitaminea);

Sunflower Diseases:

rust (*Puccinia helianthi*), and downy mildew (Plasmopara *halstedii*);

Citrus Diseases:

melanose (*Diaporthe citri*), scab (*Elsinoe* fawcetti), green mold (*Penicillium digitatum*), blue mold (*Penicillium italicum*), *Phytophthora* rot (*Phytophthora parasitica, Phytophthora citrophthora*), and *aspergillus* rot (*Aspergillus niger*);

Apple Diseases:

blossom blight (Monilinia *mali*), valsa canker (Valsa ceratosperma), powdery mildew (*Podosphaera leucotricha*), *alternaria* leaf spot (*Alternaria alternata* apple pathotype), scab (*Venturia inaequalis*), bitter rot (*Glomerella cingulata, Colletotrichum acutatum*), blotch (Diplocarpon *mali*), ring rot (*Botryosphaeria* berengeriana), crown rot (Phytophtora *cactorum*), and rust (*Gymnosporangium juniperi-virginianae, Gymnosporangium* yamadae);

Pear Diseases:

scab (*Venturia* nashicola, *Venturia* pirina), black spot (*Alternaria alternata* Japanese pear pathotype), and rust (*Gymnosporangium* haraeanum);

Peach Diseases:

brown rot (Monilinia fructicola), scab (*Cladosporium carpophilum*), *Phomopsis* rot (*Phomopsis* sp.), and leaf curl (Taphrina deformans);

Grapes Diseases:

anthracnose (*Elsinoe ampelina*), ripe rot (*Glomerella cingulata, Colletotrichum acutatum*), powdery mildew (Uncinula necator), rust (*Phakopsora* ampelopsidis), black rot (*Guignardia* bidwellii), and downy mildew (Plasmopara viticola);

Japanese Persimmon Diseases:

anthracnose (Gloeosporium kaki, *Colletotrichum acutatum*), and leaf spot (*Cercospora* kaki, *Mycosphaerella* nawae);

Fig diseases: rust (*Phakopsora* nishidana);

Diseases of Gourd Family:

anthracnose (*Colletotrichum* lagenarium), powdery mildew (Sphaerotheca *fuliginea*), gummy stem blight (Didymella bryoniae), *Corynespora* leaf spot (*Corynespora cassiicola*), *fusarium* wilt (*Fusarium oxysporum*), downy mildew (*Pseudoperonospora cubensis*), *phytophthora* rot (*Phytophthora capsici*), and damping-off (*Pythium* sp.);

Tomato Diseases:

early blight (*Alternaria solani*), leaf mold (*Cladosporium fulvum*), *Cercospora* leaf mold (*Pseudocercospora* fuligena), late blight (*Phytophthora infestans*), and powdery mildew (Leveillula *taurica*);

Eggplant Diseases:

brown spot (*Phomopsis vexans*), and powdery mildew (*Erysiphe cichoracearum*);

Cruciferous Vegetables Diseases:

*alternaria* leaf spot (*Alternaria japonica*), white spot (Cercosporella *brassicae*), clubroot (Plasmodiophora *brassicae*), downy mildew (*Peronospora parasitica*), and white rust (Albugo *candida*);

Welsh Onion Disease:

rust (*Puccinia allii*);

Soybean Diseases:

purple stain (*Cercospora kikuchii*), *sphaceloma* scab (*Elsinoe* glycines), pod and stem blight (*Diaporthe phaseolorum* var. *sojae*), rust (*Phakopsora pachyrhizi*), target spot (*Corynespora cassiicola*), anthracnose (*Colletotrichum* glycines, *Colletotrichum truncatum*), *Rhizoctonia* rot (*Rhizoctonia solani*), *septoria* brown spot (*Septoria glycines*), *Cercospora* leaf spot (*Cercospora* sojina), stem rot (*Sclerotinia sclerotiorum*), powdery mildew (*Microsphaera diffusa*), *phytophthora* stem and root rot (*Phytophthora sojae*), downy mildew (*Peronospora manshurica*), sudden death syndrome (*Fusarium virguliforme*), red crown rot (Calonectria ilicicola), and *Diaporthe/Phomopsis* complex (*Diaporthe* longicolla);

Kidney Bean Diseases:

stem rot (*Sclerotinia sclerotiorum*), rust (*Uromyces appendiculatus*), angular leaf spot (Phaeoisariopsis griseola), and anthracnose (*Colletotrichum lindemuthianum*), and *Fusarium* root-rot (*Fusarium solani*); Peanut diseases:

leaf spot (*Cercospora personata*), brown leaf spot (*Cercospora arachidicola*), southern blight (*Sclerotium rolfsii*), and Cylindrocladium black rot (Calonectria ilicicola);

Garden Pea Disease:

powdery mildew (*Erysiphe pisi*), and root rot (*Fusarium solani*);

Potato diseases:

early blight (*Alternaria solani*), late blight (*Phytophthora infestans*), Pink rot (*Phytophthora erythroseptica*), powdery scab (Spongospora *subterranea* f. sp. *subterranea*), *verticillium* wilt (*Verticillium albo-atrum, Verticillium dahliae, Verticillium nigrescens*), dry rot (*Fusarium solani*), and potato wart (*Synchytrium* endobioticum);

Strawberry Disease:

powdery mildew (Sphaerotheca *humuli*);

Tea diseases:

net blister blight (Exobasidium *reticulatum*), white scab (*Elsinoe* leucospila), gray blight (*Pestalotiopsis* sp.), and anthracnose (*Colletotrichum* theae-*sinensis*);

Tobacco Diseases:

brown spot (*Alternaria longipes*), anthracnose (*Colletotrichum tabacum*), blue mold (*Peronospora tabacina*), and black shank (*Phytophthora nicotianae*);

Sugar Beet Diseases:

*cercospora* leaf spot (*Cercospora beticola*), leaf blight (*Thanatephorus cucumeris*), root rot (*Thanatephorus cucumeris*), and *aphanomyces* root rot (*Aphanomyces cochlioides*), and rust (*Uromyces betae*);

Rose Diseases:

black spot (Diplocarpon *rosae*), and powdery mildew (Sphaerotheca *pannosa*);

*Chrysanthemum* Diseases:

leaf blight (*Septoria chrysanthemi*-indici), and white rust (*Puccinia* horiana);

Onion Diseases:

*botrytis* leaf blight (*Botrytis cinerea, Botrytis byssoidea, Botrytis squamosa*), gray-mold neck rot (*Botrytis allii*), and small sclerotial neck rot (*Botrytis squamosa*);

Various Crops Diseases:

*Botrytis* rot (*Botrytis cinerea*), *sclerotinia* rot (*Sclerotinia sclerotiorum*), seedling blight (*Pythium aphanidermatum, Pythium irregulare, Pythium ultimum*);

Japanese Radish Disease:

*alternaria* leaf spot (*Alternaria brassicicola*);

Turfgrass Diseases:

dollar spot (*Sclerotinia* homoeocarpa), brown patch and large patch (*Rhizoctonia solani*), and *pythium* bligt (*Pythium aphanidermatum*);

Banana Disease:

Sigatoka disease (*Mycosphaerella fijiensis, Mycosphaerella musicola*);

Lentils Disease:

*ascochyta* blight (*Ascochyta* lentis);

Chickpea Disease:

*ascochyta* blight (*Ascochyta rabiei*);

Green Pepper Disease:

anthracnose (*Colletotrichum* scovillei);

Mango Disease:

anthracnose (*Colletotrichum acutatum*);

Fuit Trees Diseases:

white root rot (Rosellinia necatrix), and violet root rot (Helicobasidium mompa);

Postharvest disease of fruits (for example, apple and pear):

*Mucor* rot diseases (*Mucor piriformis*);

Seed diseases or diseases in the early stages of the growth of various plants caused by *Aspergillus* spp., *Penicillium* spp., *Fusarium* spp., *Gibberella* spp., Tricoderma spp., *Thielaviopsis* spp., *Rhizopus* spp., *Mucor* spp., Corticium spp., *Phoma* spp., *Rhizoctonia* spp. or *Diplodia* spp.; and the like;

Viral Diseases:

Lettuce big-vein disease transmitted by Olpidium *brassicae*, and viral diseases of several crops transmitted by Polymixa spp. (e.g. *Polymyxa betae* and *Polymyxa graminis*);

Diseases caused by bacteria:

bacterial seedling blight of rice (*Burkholderia plantarii*), bacterial spot of cucumber (*Pseudomonas syringae* pv. *Lachrymans*), bacterial wilt of eggplant (*Ralstonia solanacearum*), canker of citrus (*Xanthomonas citri*), bacterial soft rot of Chinese cabbage (*Erwinia carotovora*), scab of potato (*Streptomyces scabiei*), Goss's wilt of corn (*Clavibacter michiganensis*), Pierce's disease of grapes, olive and peach (Xylella fastidiosa), andcrown gall of Rosacead plants such as apple, peach, cherries (*Agrobacterium tumefaciens*).

Examples of harmful arthropods, harmful nematicides and harmful mollusks include the followings.

Hemiptera:

from the family Delphacidae, for example, small brown planthopper (*Laodelphax striatellus*), brown planthopper (*Nilaparvata lugens*), white-backed planthopper (*Sogatella furcifera*), corn planthopper (*Peregrinus maidis*), cereal leafhopper (Javesella pellucida), sugarcane leafhopper (*Perkinsiella saccharicida*), and Tagosodes orizicolus;

from the family Cicadellidae, for example, green rice leafhopper (*Nephotettix cincticeps*), green paddy leafhopper (*Nephotettix virescens*), rice leafhopper (*Nephotettix nigropictus*), zigzag-striped leafhopper (Recilia *dorsalis*), tea green leafhopper (*Empoasca* onukii), potato leafhopper (*Empoasca fabae*), corn leafhopper (Dalbulus *maidis*), rice leafhopper (Cofana spectra), and Amrasca biguttula biguttula;

from the family Aphrophoridae, for example, European spittlebug (Philaenus spumarius);

from the family Cercopidae, for example, Mahanarva posticata and Mahanarva fimbriolata;

from the family Aphididae, for example, bean aphid (*Aphis fabae*), soybean aphid (*Aphis glycines*), cotton aphid (*Aphis gossypii*), green apple aphid (*Aphis pomi*), apple aphid (*Aphis spiraecola*), green peach aphid (*Myzus persicae*), leaf-curling plum aphid (*Brachycaudus helichrysi*), cabbage aphid (*Brevicoryne brassicae*), rosy apple aphid (*Dysaphis plantaginea*), false cabbage aphid (*Lipaphis erysimi*), potato aphid (*Macrosiphum euphorbiae*), foxglove aphid (*Aulacorthum solani*), lettuce aphid (*Nasonovia ribisnigri*), grain aphid (*Rhopalosiphum padi*), corn aphid (*Rhopalosiphum maidis*), brown citrus aphid (*Toxoptera citricida*), mealy plum aphid (*Hyalopterus pruni*), cane aphid (*Melanaphis sacchari*), black rice root aphid (Tetraneura nigriabdominalis), sugarcane cottony aphid (Ceratovacuna *lanigera*), apple woolly aphid (*Eriosoma lanigerum*), and *Sitobion avenae;* from the family Phylloxeridae, for example, grapevine *phylloxera* (Daktulosphaira vitifoliae), Pecan *phylloxera* (*Phylloxera devastatrix*), Pecan leaf *phylloxera* (*Phylloxera notabilis*), and Southern pecan leaf *phylloxera* (*Phylloxera* russellae);

from the family Adelgidae, for example, hemlock woolly aphid (*Adelges tsugae*), *Adelges piceae*, and Aphrastasia pectinatae;

from the family Pentatomidae, for example, black rice bug (*Scotinophara lurida*), Malayan rice black bug (*Scotinophara coarctata*), common green stink bug (*Nezara antennata*), white-spotted spined bug (*Eysarcoris aeneus*), lewis spined bug (*Eysarcoris lewisi*), white-spotted bug (*Eysarcoris ventralis*), *Eysarcoris* annamita, brown marmorated stink bug (*Halyomorpha halys*), green plant bug (*Nezara viridula*), Brown stink bug (*Euschistus heros*), Red banded stink bug (*Piezodorus guildinii*), *Oebalus pugnax*, and *Dichelops melacanthus;* from the family Cydnidae, for example, Burrower brown bug (*Scaptocoris castanea*);

from the family Alydidae, for example, bean bug (Riptortus pedestris), corbett rice bug (Leptocorisa *chinensis*), and rice bug (Leptocorisa *acuta*);

from the family Coreidae, for example, Cletus punctiger and Australian leaf-footed bug (*Leptoglossus australis*); from the family Lygaeidae, for example, oriental chinch bug (Caverelius saccharivorus), seed bug (Togo *hemipterus*), and chinch bug (*Blissus leucopterus*);

from the family Miridae, for example, rice leaf bug (Trigonotylus caelestialium), sorghum plant bug (Stenotus rubrovittatus), wheat leaf bug (Stenodema calcarata), and American tarnished plant bug (*Lygus lineolaris*);

from the family Aleyrodidae, for example, greenhouse whitefly (*Trialeurodes vaporariorum*), tobacco whitefly (*Bemisia tabaci*), citrus whitefly (*Dialeurodes citri*), citrus spiny whitefly (Aleurocanthus spiniferus), tea spiny whitefly (Aleurocanthus *camelliae*), and Pealius euryae;

from the family Diaspididae, for example, Abgrallaspis cyanophylli, red scale (Aonidiella *aurantii*), San Jose scale (Diaspidiotus *perniciosus*), white peach scale (Pseudaulacaspis pentagona), arrowhead scale (Unaspis yanonensis), and citrus snow scale (Unaspis *citri*);

from the family Coccidae, for example, pink wax scale (Ceroplastes *rubens*);

from the family Margarodidae, for example, fluted scale (*Icerya purchasi*) and seychelles fluted scale (*Icerya* seychellarum);

from the family Pseudococcidae, for example, *solanum* mealybug (Phenacoccus *solani*), cotton mealybug (Phenacoccus *solenopsis*), Japanese mealybug (*Planococcus* kraunhiae), white peach scale (Pseudococcus *comstocki*), citrus mealybug (*Planococcus citri*), currant mealybug (Pseudococcus calceolariae), long-tailed mealybug (Pseudococcus *longispinus*), and tuttle mealybug (Brevennia rehi);

from the family Psyllidae, for example, citrus *psylla* (Diaphorina *citri*), two-spotted citrus psyllid (*Trioza erytreae*), pear sucker (*Cacopsylla* pyrisuga), *Cacopsylla chinensis*, potato psyllid (Bactericera cockerelli), and Pear *psylla* (*Cacopsylla pyricola*);

from the family Tingidae, for example, sycamore lace bug (Corythucha *ciliata*), aster tingid (Corythucha marmorata), Japanese pear lace bug (Stephanitis nashi), and azalea lace bug (Stephanitis pyrioides);

from the family Cimicidae, for example, common bed bug (*Cimex lectularius*);

from the family Cicadidae, for example, Giant Cicada (Quesada *gigas*); and from the family Reduviidae, for example, *Triatoma infestans*, large kissing bug (*Triatoma* rubrofasciata), and Rhodonius *prolixus;* and the others.

Lepidoptera:

from the family Crambidae, for example, rice stem borer (*Chilo suppressalis*), Dark-headed stem borer (*Chilo* polychrysus), white stem borer (Scirpophaga innotata), yellow paddy borer (Scirpophaga incertulas), Rupela albina, rice leaf roller (Cnaphalocrocis *medinalis*), Marasmia patnalis, rice leaf roller (Marasmia *exigua*), cotton leaf roller (Notarcha derogata), corn borer (*Ostrinia furnacalis*), European corn borer (*Ostrinia nubilalis*), cabbage webworm (*Hellula undalis*), grape leafroller (*Herpetogramma* luctuosale), bluegrass webworm (Pediasia *teterrellus*), rice case-worm (Nymphula depunctalis), Sugarcane borer (*Diatraea* saccharalis), and eggplant fruit borer (Leucinodes orbonalis);

from the family Pyralidae, for example, lesser cornstalk borer (*Elasmopalpus lignosellus*), mealworm moth (Plodia interpunctella), persimmon bark borer (Euzophera batangensis), and almond moth (Cadra cautella);

from the family Noctuidae, for example, cotton worm (*Spodoptera litura*), beet armyworm (*Spodoptera exigua*), rice armyworm (Mythimna *separata*), cabbage moth (*Mamestra brassicae*), pink borer (Sesamia inferens), grass armyworm (*Spodoptera mauritia*), green rice caterpillar (Naranga aenescens), *Spodoptera frugiperda*, true armyworm (*Spodoptera exempta*), *Spodoptera* cosmioides, semitropical armyworm (*Spodoptera eridania*), black cutworm (*Agrotis ipsilon*), beet worm (*Autographa* nigrisigna), rice looper (Plusia festucae), soybean looper (Chrysodeixis *includens*), *Trichoplusia* spp., *Heliothis* spp. (such as tobacco budworm (*Heliothis virescens*)), *Helicoverpa* spp. (such as tobacco budworm (*Helicoverpa armigera*), corn earworm (*Helicoverpa zea*)), Velvetbean caterpillar (*Anticarsia gemmatalis*), Cotton leafworm (*Alabama argillacea*), and Hop vine borer (Hydraecia immanis);

from the family Pieridae, for example, common cabbage worm (*Pieris rapae*);

from the family Tortricidae, for example, oriental fruit moth (*Grapholita molesta*), *Grapholita* dimorpha, soybean moth (Leguminivora glycinivorella), Matsumuraeses azukivora, summer fruit *tortrix* (*Adoxophyes orana fasciata*), smaller tea *tortrix* (*Adoxophyes* honmai), Japanese tea *tortrix* (Homona magnanima), apple *tortrix* (*Archips* fuscocupreanus), codling moth (*Cydia pomonella*), sugarcane shoot borer (Tetramoera schistaceana), Bean Shoot Borer (Epinotia aporema), Citrus fruit borer (Ecdytolopha aurantiana), and European grape wine moss (*Lobesia botrana*);

from the family Gracillariidae, for example, tea leaf roller (Caloptilia theivora) and Asiatic apple leaf miner (Phyllonorycter ringoniella);

from the family Carposinidae, for example, peach fruit moth (Carposina sasakii); from the family Lyonetiidae, for example, Coffee Leaf miner (*Leucoptera coffeella*), peach leaf miner (*Lyonetia clerkella*), and *Lyonetia* prunifoliella;

from the family Lymantriidae, for example, *Lymantria* spp. (such as gypsy moth (*Lymantria dispar*)) and *Euproctis* spp. (such as tea lymantriid (*Euproctis* pseudoconspersa));

from the family Plutellidae, for example, diamondback moth (*Plutella xylostella*);

from the family Gelechiidae, for example, peach worm (*Anarsia* lineatella), sweetpotato leaf folder (Helcystogramma triannulella), pink bollworm (*Pectinophora gossypiella*), potato moth (*Phthorimaea operculella*), and *Tuta absoluta;* from the family Arctiidae, for example, American white moth (*Hyphantria cunea*); from the family Castniidae, for example, Giant Sugarcane borer (Telchin licus); from the family Cossidae, for example, *Cossus insularis;* from the family Geometridae, for example, Ascotis selenaria;

from the family Limacodidae, for example, blue-striped nettle grub (Parasa lepida);

from the family Stathmopodidae, for example, persimmon fruit moth (Stathmopoda masinissa);

from the family Sphingidae, for example, tobacco hornworm (Acherontia Lachesis);

from the family Sesiidae, for example, Nokona feralis, cherry borer (Synanthedon hector), and Synanthedon *tenuis*: from the family Hesperiidae, for example, rice skipper (Parnara guttata);

from the family Tineidae, for example, casemaking clothes moth (Tinea *translucens*) and common clothes moth (Tineola Bisselliella);

and the others.

Thysanoptera:

from the family Thripidae, for example, western flower *thrips* (*Frankliniella occidentalis*), oriental *thrips* (*Thrips palmi*), yellow tea *thrips* (*Scirtothrips dorsalis*), onion *thrips* (*Thrips tabaci*), eastern flower *thrips* (*Frankliniella intonsa*), rice *thrips* (Stenchaetothrips *biformis*), Echinothrips *americanus*, and *Scirtothrips perseae;* from the family Phlaeothripidae, for example, aculeated rice *thrips* (Haplothrips *aculeatus*);

and the others.

Diptera:

from the family Anthomyiidae, for example, seedcorn maggot (*Delia platura*), onion maggot (*Delia antiqua*), and beet leaf miner (*Pegomya* cunicularia);

from the family Ulidiidae, for example, sugarbeet root maggot (Tetanops myopaeformis);

from the family Agromyzidae, for example, rice leaf miner (Agromyza *oryzae*), tomato leaf miner (*Liriomyza sativae*), *chrysanthemum* leaf miner (*Liriomyza trifolii*), and pea leafminer (Chromatomyia *horticola*);

from the family Chloropidae, for example, rice stem maggot (Chlorops *oryzae*);

from the family Tephritidae, for example, melon fly (Bactrocera cucurbitae), oriental fruit fly (Bactrocera *dorsalis*), Malaysian fruit fly (Bactrocera latifrons), olive fruit fly (Bactrocera *oleae*), Queensland fruit fly (Bactrocera tryoni), Mediterranean fruit fly (*Ceratitis capitata*), apple maggot (*Rhagoletis pomonella*), and Japanese cherry fruit fly (Rhacochlaena *japonica*);

from the family Ephydridae, for example, smaller rice leaf miner (Hydrellia griseola), whorl maggot (Hydrellia philippina), and paddy stem maggot (Hydrellia sasakii); from the family Drosophilidae, for example, cherry *drosophila* (*Drosophila* suzukii) and yellow *drosophila* (*Drosophila melanogaster*);

from the family Phoridae, for example, Megaselia spiracularis;

from the family Psychodidae, for example, Clogmia albipunctata;

from the family Sciaridae, for example, Bradysia *difformis;* from the family Cecidomyiidae, for example, hessian fly (*Mayetiola destructor*) and paddy gall fly (Orseolia *oryzae*); from the family Diopsidae, for example, Diopsis macrophthalma;

from the family Glossinida, for example, *Glossina palpalis*, and *Glossina morsitans;* from the family Simuliidae, for example, *Simulium japonicum*, and *Simulium* damnosum;

from the family Phlebotominae;

from the family Tipulidae, for example, *Tipula* aino, *Tipula oleracea*, and *Tipula paludosa;* from the family Culicidae, for example, *Culex pipiens pallens, Culex tritaeniorhynchus, Culex pipiens* f. molestus, *Culex quinquefasciatus, Culex pipiens, Culex vishnui, Aedes albopictus, Aedes aegypti, Anopheles sinensis, Anopheles gambiae, Anopheles stephensi, Anopheles coluzzii, Anopheles albimanus, Anopheles sundaicus, Anopheles arabiensis, Anopheles funestus, Anopheles darlingi, Anopheles farauti*, and *Anopheles minimus;* from the family Simulidae, for example, *Prosimulium yezoensis* and *Simulium ornatum;* from the family Tabanidae, for example, *Tabanus* trigonus;

from the family Muscidae, for example, house fly (*Musca domestica*), false stable fly (*Muscina stabulans*), biting house fly (*Stomoxys calcitrans*), and buffalo fly (*Haematobia irritans*);

from the family Calliphoridae;

from the family Sarcophagidae;

from the family Chironomidae, for example, Chironomus plumosus, Chironomus yoshimatsui, and Glyptotendipes tokunagai;

from the family Fannidae;

and the others.

Coleoptera:

from the family Chrysomelidae, for example, *Diabrotica* spp. including bean leaf beetle (*Cerotoma trifurcata*) such as western corn rootworm (*Diabrotica virgifera virgifera*), southern corn rootworm (*Diabrotica* undecimpunctata howardi), northern corn rootworm (*Diabrotica barberi*), Mexican corn rootworm (*Diabrotica virgifera zeae*), banded cucumber beetle (*Diabrotica* balteata) and Cucurbit Beetle(*Diabrotica speciosa*), barley leaf beetle (*Oulema melanopus*), cucurbit leaf beetle (Aulacophora *femoralis*), striped flea beetle (*Phyllotreta striolata*), Cabbage flea beetle (*Phyllotreta* cruciferae), Western black flea beetle (*Phyllotreta pusilla*), Cabbage stem flea beetle (Psylliodes *chrysocephala*), Hop free beetle (Psylliodes *punctulata*), Colorado potato beetle (*Leptinotarsa decemlineata*), rice leaf beetle (*Oulema oryzae*), grape *colaspis* (*Colaspis brunnea*), corn flea beetle (*Chaetocnema pulicaria*), sweet-potato flea beetle (*Chaetocnema confinis*), potato flea beetle (*Epitrix cucumeris*), rice leaf beetle (Dicladispa *armigera*), southern corn leaf beetle (Myochrous denticollis), Laccoptera quadrimaculata, and tobacco flea beetle (*Epitrix hirtipennis*);

from the family Carabidae, for example, Seedcorn beetle (Stenolophus *lecontei*) and slender seed-corn ground beetle (Clivina impressifrons);

from the family Scarabaeidae, for example, cupreus chafer (*Anomala cuprea*), soybean beetle (*Anomala* rufocuprea), *Anomala albopilosa*, Japanese beetle (*Popillia japonica*), yellowish elongate chafer (Heptophylla *picea*), European Chafer (*Rhizotrogus majalis*), Tomarus gibbosus, Holotrichia spp., Phyllophaga spp. (such as June beetle (Phyllophaga *crinita*)), and Diloboderus spp. (such as Diloboderus abderus);

from the family Anthriibidae, for example, coffee bean weevil (Araecerus coffeae);

from the family Aponidae, for example, sweet-potato weevil (Cylas formicarius);

from the family Bruchidae, for example, Mexican bean weevil (Zabrotes *subfasciatus*);

from the family Scolytidae, for example, pine beetle (Tomicus piniperda) and Coffee Berry Borer (Hypothenemus *hampei*);

from the family Curculionidae, for example, West Indian sweet-potato weevil (Euscepes postfasciatus), alfalfa weevil (*Hypera postica*), maize wevil (*Sitophilus* zeamais), rice weevil (*Sitophilus oryzae*), granary weevil (*Sitophilus granarius*), rice plant weevil (Echinocnemus squameus), rice water weevil (*Lissorhoptrus oryzophilus*), Asiatic palm weevil (Rhabdoscelus lineaticollis), boll weevil (*Anthonomus grandis*), nunting billbug (Sphenophorus venatus), Southern Corn Billbug (Sphenophorus callosus), Soybean stalk weevil (Sternechus subsignatus), Sugarcane weevil (Sphenophorus *levis*), rusty gourd-shaped weevil (Scepticus *griseus*), brown gourd-shaped weevil (Scepticus *uniformis*), Aracanthus spp. (such as Aracanthus mourei), and cotton root borer (*Eutinobothrus brasiliensis*);

from the family Tenebrionidae, for example, red meal beetle (Tribolium castaneum) and mason beetle (Tribolium *confusum*);

from the family Coccinellidae, for example, twenty-eight-spotted ladybird (*Epilachna* vigintioctopunctata);

from the family Bostrychidae, for example, common powder-post beetle (Lyctus *brunneus*), lesser grain borer (Rhizopertha dominica);

from the family Ptinidae;

from the family Cerambycidae, for example, citrus long-horned beetle (*Anoplophora* malasiaca), Migdolus fryanus, and red-necked longhorn (Aromia bungii);

from the family Elateridae, for example, Melanotus okinawensis, barley wireworm (*Agriotes* fuscicollis), Melanotus legatus, Anchastus spp., Conoderus spp., *Ctenicera* spp., *Limonius* spp., and Aeolus spp.;

from the family Staphylinidae, for example, Paederus *fuscipes;* from the family Dermestidae, for example, varied carpet beetle (Anthrenus *verbasci*) and hide beetle (Dermestes maculates);

from the family Anobiidae, for example, tobacco beetle (Lasioderma serricorne) and biscuit beetle (Stegobium paniceum);

from the family Laemophloeidae, for example, flat grain beetle (Cryptolestes *ferrugineus*);

from the family Silvanidae, for example, sawtoothed grain beetle (Oryzaephilus surinamensis);

from the family Nitidulidae, for example, blossom beetle (Brassicogethes *aeneus*);

and the others.

Orthoptera:

from the family Acrididae, for example, oriental migratory locust (*Locusta migratoria*), Moroccan locust (*Dociostaurus maroccanus*), Australian plague locust (*Chortoicetes terminifera*), red locust (*Nomadacris septemfasciata*), Brown Locust (*Locustana pardalina*), Tree Locust (Anacridium melanorhodon), Italian Locust (*Calliptamus italicus*), Differential grasshopper (*Melanoplus differentialis*), Two striped grasshopper (*Melanoplus bivittatus*), Migratory grasshopper (*Melanoplus sanguinipes*), Red-Legged grasshopper (*Melanoplus femurrubrum*), Clearwinged grasshopper (Camnula pellucida), desert locust (*Schistocerca gregaria*), Yellow-winged locust(Gastrimargus musicus), Spur-throated locust (Austracris guttulosa), Japanese grasshopper (Oxya *yezoensis*), rice grasshopper (Oxya *japonica*), and Bombay locust (Patanga succincta);

from the family Gryllotalpidae, for example, oriental mole cricket (*Gryllotalpa orientalis*);

from the family Gryllidae, for example, house cricket (*Acheta domestica*) and emma field cricket (Teleogryllus emma);

from the family Tettigoniidae, for example, Mormon cricket (Anabrus simplex);

and the others.

Hymenoptera:

from the family Tenthredinidae, for example, beet sawfly (*Athalia rosae*) and Nippon cabbage sawfly (*Athalia japonica*);

from the family Formicidae, for example, *Solenopsis* spp. (such as red imported fire ant (*Solenopsis invicta*), tropical fire ant (*Solenopsis geminata*)), *Atta* spp. (such as Brown leaf-cutting ant (*Atta capiguara*)), Acromyrmex spp., Paraponera *clavata*, black house ant (Ochetellus glaber), little red ant (*Monomorium pharaonis*), Argentine ant (*Linepithema humile*), Formica *fusca japonica, Pristomyrmex punctutus, Pheidole* noda, big-headed ant (*Pheidole megacephala*), *Camponotus* spp. (such as *Camponotus japonicus, Camponotus obscuripes*), *Pogonomyrmex* spp. (such as western harvester ant (*Pogonomyrmex occidentalis*)), Wasmania spp. (such as Wasmania *auropunctata*), and long-legged ant (Anoplolepis gracilipes);

from the family Vespidae, for example, Asian giant hornet (*Vespa* mandarinia *japonica*), *Vespa* simillima, *Vespa* analis Fabriciusi, Asian hornet (*Vespa velutina*), and *Polistes* jokahamae;

from the family Siricidae, for example, pine wood wasp (Urocerus *gigas*);

from the family Bethylidae;

and the others.

Blattodea:

from the family Blattellidae, for example, German cockroach (*Blattella germanica*);

from the family Blattidae, for example, smoky-brown cockroach (*Periplaneta fuliginosa*), American cockroach (*Periplaneta americana*), brown cockroach (*Periplaneta brunnea*), and black cockroach (*Blatta orientalis*); from the family Termitidae, for example, Japanese termite (*Reticulitermes speratus*), Formosan termite (*Coptotermes formosanus*), western drywood termite (*Incisitermes minor*), Cryptotermes *domesticus, Odontotermes formosanus*, Neotermes koshunensis, Glyptotermes satsumensis, Glyptotermes nakajimai, Glyptotermes *fuscus, Hodotermopsis sjostedti, Coptotermes guangzhouensis, Reticulitermes amamianus, Reticulitermes miyatakei, Reticulitermes kanmonensis,*

*Nasutitermes* takasagoensis, Pericapritermes nitobei, Sinocapritermes mushae, and Cornitermes cumulans; and the others.

Siphonaptera:

from the family *Pulex* spp. (such as *Pulex irritans*), *Ctenocephalides* spp. (such as *Ctenocephalides felis* and *Ctenocephalides canis*), *Xenopsylla* spp. (such as *Xenopsylla cheopis*), *Tunga* spp. (such as *Tunga penetrans*), *Echidnophaga* spp. (such as *Echidnophaga gallinacea*), and *Nosopsyllus* spp. (such as *Nosopsyllus fasciatus*).

Psocodae:

from the family Liposcelidae or Liposcelididae, for example, *Pediculus* spp. (such as *Pediculus humanus* capitis); Phtirus spp. (such as *Pthirus pubis*); *Haematopinus* spp. (such as cattle louse (*Haematopinus eurysternus*) and pig louse (*Haematopinus suis*)); *Bovicola* spp. (such as *Bovicola bovis, Bovicola ovis* and *Bovicola* breviceps); *Damalinia* spp. (such as *Damalinia forficula*); *Linognathus* spp. (such as *Linognathus vituli* and sheep trunk parasitic white lice (such as *Linognathus ovillus*)); *Solenopotes* spp. (such as *Solenopotes capillatus*); *Menopon* spp. (such as *Menopon gallinae*); Cummingsia spp.; *Trinoton* spp.; *Trichodectes* spp. (such as *Trichodectes canis*); Felicola spp. (such as Felicola subrostratus); *Menacanthus* spp. (such as *Menacanthus stramineus*); Werneckiella spp.; Trogiidae such as Trogium pulsatorium; Liposcelis corrodens, Liposcelis bostrychophila, Liposcelis pearmani, Liposcelis *entomophila.*

Lepismatidae:

from the family Lepismatidae, for exmaple, Ctenolepisma *villosa* and *Lepisma saccharina.*

Acari:

from the family Tetranychidae, for example, common red spider mite (*Tetranychus urticae*), kanzawa spider mite (*Tetranychus kanzawai*), red spider mite (*Tetranychus evansi*), citrus red mite (*Panonychus citri*), fruit-tree red spider mite (*Panonychus ulmi*), and *Oligonychus* spp.;

from the family Eriophyidae, for example, Japanese citrus rust mite (Aculops pelekassi), Phyllocoptruta *citri*, tomato mite (Aculops *lycopersici*), purple mite (Calacarus *carinatus*), tea rust mite (Acaphylla theavagrans), *Eriophyes chibaensis*, apple bud mite (*Aculus schlechtendali*), Aceria *diospyri*, Aceria tosichella, and Shevtchenkella sp.; from the family Tarsonemidae, for example, broad mite (*Polyphagotarsonemus latus*);

from the family Tenuipalpidae, for example, *Brevipalpus phoenicis;* from the family Tuckerellidae;

from the family Ixodidae, for example, *Haemaphysalis longicornis, Haemaphysalis flava, Haemaphysalis japonica, Haemaphysalis campanulata*, American dog tick (*Dermacentor variabilis*), *Dermacentor taiwanensis*, Rocky Mountain wood tick (*Dermacentor andersoni*), netted tick (*Dermacentor reticulatus*), *Ixodes ovatus, Ixodes persulcatus*, black-legged tick (*Ixodes scapularis*), *Ixodes pacificus, Ixodes holocyclus, Ixodes ricinus*, lone star tick (*Amblyomma americanum*), gulf coast tick(*Amblyomma maculatum*), *Rhipicephalus microplus*, cattle tick (*Rhipicephalus annulatus*), brown dog tick (*Rhipicephalus sanguineus*), *Rhipicephalus appendiculatus*, and *Rhipicephalus decoloratus*;

from the family Argasidae, for example, *Argas persicus, Ornithodoros hermsi, Ornithodoros turicata;* from the family Acaridae, for exmaple, Tyrophagus putrescentiae, and Tyrophagus *similis;* from the family Pyroglyphidae, for exmaple, *Dermatophagoides farinae* and *Dermatophagoides pteronyssinus*;

from the family Cheyletidae, for example, Cheyletus eruditus, Cheyletus *malaccensis, Chelacaropsis moorei*, and *Cheyletiella yasguri;* from the family Psoroptidae, for example, *Psoroptes ovis, Psoroptes equi, Knemidocoptes mutans*, Otodectes cynotis, and Chorioptes spp.;

from the family Sarcoptidae, for example, Notoedres cati, Notoedres *muris*, and *Sarcoptes scabiei;* from the family Listrophoridae, for example, Listrophorus gibbus;

from the family Dermanyssidae, for example, *Dermanyssus gallinae;* from the family Macronyssidae, for example, *Ornithonyssus* sylviarum, and *Ornithonyssus bacoti*);

from the family Varroidae, for example, Macronyssidae and *Varroa jacobsoni;* from the family Demodicidae, for example, *Demodex canis* and *Demodex cati;* from the family Trombiculidae, for example, Leptotrombidium akamushi, Leptotrombidium *pallidum*, and Leptotrombidium scutellare.

Araneae:

from the family Eutichuridae, for example, Cheiracanthium *japonicum;* from the family Theridiidae, for example, red-back spider (*Latrodectus* hasseltii);

and the others.

Polydesmida:

from the family Paradoxosomatidae, for example, flat-backed millipede (Oxidus gracilis) and Nedyopus tambanus; and the others.

Isopoda:

from the family Armadillidiidae, common pill bug (Armadillidium *vulgare*);

and the others.

Chilopoda:

from the family Scutigeridae, for example, Thereuonema hilgendorfi;

from the family Scolopendridae, giant tropical centipede (Scolopendra subspinipes);

from the family Ethopolyidae, Bothropolys rugosus; and the others.

Gastropoda:

from the family Limacidae, for example, tree slug (Limax *marginatus*) and garden tawny slug (Limax *flavus*);

from the family Philomycidae, for example, Meghimatium bilineatum;

from the family Ampullariidae, for example, golden apple snail (*Pomacea canaliculata*);

from the family Lymnaeidae, for example, Austropeplea ollula;

and the others.

Nematoda:

from the family Aphelenchoididae, for example, rice white-tip nematode (*Aphelenchoides besseyi*);

from the family Pratylenchidae, for example, root lesion nematode (*Pratylenchus* coffeae), *Pratylenchus* brachyurus, California meadow nematode (*Pratylenchus neglectus*), and *Radopholus similis;* from the family Heteroderidae, for example, javanese root-knot nematode (*Meloidogyne javanica*), southern root-knot nematode (*Meloidogyne incognita*), guava root-knot nematodes (*Meloidogyne* enterolobii), northern root-knot nematode (*Meloidogyne hapla*), soybean cyst nematode (*Heterodera glycines*), potato cyst nematode (*Globodera rostochiensis*), and white potato cyst nematode (*Globodera pallida*);

from the family Hoplolaimidae, for example, *Rotylenchulus reniformis;* from the family Anguinidae, for example, strawberry bud nematode (Nothotylenchus *acris*) and stem nematode (*Ditylenchus dipsaci*);

from the family Tylenchulidae, for example, citrus nematode (*Tylenchulus semipenetrans*);

from the family Longidoridae, for example, dagger nematode (*Xiphinema index*);

from the family Trichodoridae;

from the family Parasitaphelenchidae, for example, pine wilt disease (*Bursaphelenchus xylophilus*);

and the others.

The harmful arthropods such as harmful insects and harmful mites, harmful mollusks and harmful nematodes may be those having a reduced agent-sensitivity to or a developed agent-resistance to an insecticide, a mitecide, a molluscicide or a nematicide.

The method for controlling pests of the present invention is conducted by applying an effective amount of the present compound or the composition A to a harmful pest directly and/or a habitat where the harmful pest lives (for example, plant, soil, an interior of a house, and animal). Examples of a method for controlling pests of the present invention include foliar application, soil application, root application, shower application, smoking application, water-surface application, and seed application.

The present compound or the composition A is usually prepared by mixing them with an inert carrier such as solid carrier, liquid carrier or gaseous carrier, and if necessary, adding surfactants and the other auxiliary agents for formulation, to formulate into emulsifiable concentrates, oil solutions, dust formulations, granules, wettable powders, flowables, dry flowables, microcapsules, aerosols, smoking agents, poison baits, resin formulations, paste-like formulations, foams, and carbon dioxide formulations, and the others. Such formulations may be processed into mosquito repellent coils, electric mosquito repellent mats, liquid mosquito formulations, smoking agents, fumigants, sheet formulations, and which may be used. These formulations comprises usually 0.01 to 95% by weight of the present compound or the composition A.

Examples of the solid carrier to be used in the formulation include fine powders or granules of clays (for example, kaolin clay, diatomaceous earth, bentonite, Fubasami clay, or acid white clay), dry silica, wet silica, hydrated silica, talcs, ceramics, other inorganic minerals (for example, sericite, quartz, sulfur, active carbon, or calcium carbonate) or chemical fertilizers (for example, ammonium sulfate, ammonium phosphate, ammonium nitrate, urea, or ammonium chloride) and the others; as well as synthetic resins (for example, polyester resins such as polypropylene, polyacrylonitrile, polymethyl methacrylate or polyethylene terephthalate; nylon resins (for example, nylon-6, nylon-11, or nylon-66); polyamide resins; polyvinyl chloride, polyvinylidene chloride, vinyl chloride-propylene copolymers, and the others).

Examples of the liquid carriers include water; alcohols (for example, methanol, ethanol, isopropyl alcohol, butanol, hexanol, benzyl alcohol, ethylene glycol, propylene glycol, or phenoxy ethanol); ketones (for example, acetone, methyl ethyl ketone, or cyclohexanone); aromatic hydrocarbons (for example, toluene, xylene, ethyl benzene, dodecyl benzene, phenyl xylyl ethane, or methylnaphthalene); aliphatic hydrocarbons (for example, hexane, cyclohexane, kerosene, or light oil); esters (for example, ethyl acetate, butyl acetate, isopropyl myristate, ethyl oleate, diisopropyl adipate, diisobutyl adipate, or propylene glycol monomethyl ether acetate); nitriles (for example, acetonitrile, or isobutyronitrile); ethers (for example, diisopropyl etheR14-dioxane, 1,2-dimethoxyethane, diethyleneglycol dimethyl ether, diethylene glycol monomethyl ether, propylene glycol monomethyl ether, dipropylene glycol monomethyl ether, or 3-methoxy-3-methyl-1-butanol); amides (for example, DMF, or N,N-dimethylacetamide); sulfoxides (for example, dimethyl sulfoxide); propylene carbonate; and vegetable oils (for example, soybean oil or cottonseed oil).

Examples of gaseous carrier include fluorocarbon, butane gas, liquefied petroleum gas (LPG), dimethyl ether, and carbon dioxide gas.

Examples of the surfactants include nonionic surfactants such as polyoxyethylenated alkyl ethers, polyoxyethylenated alkyl aryl ethers, and polyethylene glycol fatty acid esters; and anionic surfactants such as alkyl sulfonates, alkylbenzene sulfonates and alkyl sulfates.

Examples of the other auxiliary agents for formulation include a binder, a dispersant, a colorant and a stabilizer. Specific examples include casein, gelatin, polysaccharides (for example, starch, gum arabic, cellulose derivatives and alginic acid), lignin derivatives, bentonite, water-soluble synthetic polymers (for example, polyvinyl alcohol, polyvinyl pyrrolidone and polyacrylic acids), acidic isopropyl phosphate, 2,6-di-tert-butyl-4-methylphenol, and a mixture of 2-tert-butyl-4-methoxyphenol and 3-tert-butyl-4-methoxyphenol. Specific examples thereof include Nimbus (registered trademark), Assist (registered trademark), Aureo (registered trademark), Iharol (registered trademark), Silwet L-77 (registered trademark), BreakThru (registered trademark), SundanceII (registered trademark), Induce (registered trademark), Penetrator (registered trademark), Agri-Dex (registered trademark), Lutensol A8 (registered trademark), NP-7 (registered trademark), Triton (registered trademark), Nufilm (registered trademark), Emulgator NP7 (registered trademark), Emulad (registered trademark), TRITON X 45 (registered trademark), AGRAL 90 (registered trademark), AGROTIN (registered trademark), ARPON (registered trademark), EnSpray N (registered trademark), and BANOLE (registered trademark) and the others.

Examples of a base material of the resin formulation include polyvinyl chloride polymers, polyurethane, and the others, and a plasticizer such as phthalate esters (for example, dimethyl phthalate, and dioctyl phthalate), adipic acid esters and stearic acid may be added to the base material, if necessary. The resin formulation can be prepared by kneading the present compound in the base material with a conventional kneading machine, and then molding it by injection molding, extrusion molding, or pressure molding and the like. The resultant resin formulation can be subjected to further molding or cutting procedure, if necessary, to be processed into shapes such as a plate, film, tape, net and string shape. The resin formulation can be processed into animal collars, animal ear tags, sheet products, trap strings, gardening supports, and other products.

Examples of a base material for the poison bait include bait ingredients such as grain powder, vegetable oil, saccharide and crystalline cellulose, and if necessary, with an addition of antioxidants such as dibutylhydroxytoluene and nordihydroguaiaretic acid, preservatives such as dehydroacetic acid, accidental ingestion inhibitors for children and pets such as a chili powder, and insect attraction fragrances such as cheese flavor, onion flavor and peanut oil.

As used herein, examples of the plant include whole plant, stem and leaf, flower, ear, fruit, tree stem, branch, crown, seed, vegetative reproductive organ, and seedling.

The vegetative reproductive organ represents a part of plant such as root, stem and leaf, which has a growth capacity if the part is cut off from its plant and then placed in the soil. Examples of the vegetative reproductive organ include tuberous root, creeping root, bulb, corm or solid bulb, tuber, rhizome, stolon, rhizophore, cane cuttings, propagule, and vine cutting. The "stolon" is often referred to as "runner", and the "propagule" is often referred to as "brood bud", which is divided into broad bud and bulbil. The vine cutting represents a shoot (which is a generic name of leaf and stem) of sweet potato (*Ipomoea batatas*) and Japanese yam (*Dioscorea japonica*), etc. The bulb, corm or solid bulb, tuber, rhizome, cane cuttings, rhizophore, and tuberous root are also collectively referred to as "bulb". For example, when the cultivation of potato starts with planting tubers in the soil, the used tuber is generally referred to as "seed potato".

Examples of a method for controlling harmful arthropods by applying an effective amount of the present compound or the composition A to soils include a method of applying an effective amount of the present compound or the composition A to soils before planting plants or after planting plants, a method of applying an effective amount of the present compound or the composition A to a root part of a crop to be protected from damage such as ingestion by harmful arthropods, and a method of controlling harmful arthropods that ingest a plant by permeating and transferring an effective amount of the present compound or the composition A from a root into the interior of the plant body. Specifically, examples of the application method include planting hole treatment (spraying into planting holes, soil mixing after planting hole treatment), plant foot treatment (plant foot spraying, soil mixing after plant foot treatment, irrigation at plant foot, plant foot treatment at a later seeding raising stage), planting furrow treatment (planting furrow spraying, soil mixing after planting furrow treatment), planting row treatment (planting row spraying, soil mixing after planting row treatment, planting row spraying at a growing stage), planting row treatment at the time of sowing (planting row spraying at the time of sowing, soil mixing after planting row treatment at the time of sowing), broadcast treatment (overall soil surface spraying, soil mixing after broadcast treatment), side-article treatment, treatment of water surface (application to water surface, application to water surface after flooding), other soil spraying treatment (spraying of a granular formulation on leaves at a growing stage, spraying under a canopy or around a tree stem, spraying on the soil surface, mixing with surface soil, spraying into seed holes, spraying on the ground surfaces of furrows, spraying between plants), other irrigation treatment (soil irrigation, irrigation at a seedling raising stage, drug solution injection treatment, irrigation of a plant part just above the ground, drug solution drip irrigation, chemigation), seedling raising box treatment (spraying into a seedling raising box, irrigation of a seedling raising box, flooding into a seedling raising box with drug solution), seedling raising tray treatment (spraying on a seedling raising tray, irrigation of a seedling raising tray, flooding into a seedling raising tray with drug solution), seedbed treatment (spraying on a seedbed, irrigation of a seedbed, spraying on a lowland rice nursery, immersion of seedlings), seedbed soil incorporation treatment (mixing with seedbed soil, mixing with seedbed soil before sowing, spraying at sowing before covering with soils, spraying at sowing after covering with soils, mixing with covering with soils), and other treatment (mixing with culture soil, plowing under, mixing with surface soil, mixing with soil at the place where raindrops fall from a canopy, treatment at a planting position, spraying of a granule formulation on flower clusters, mixing with a paste fertilizer).

Examples of the application to seeds (or seed treatments) include an application of the present compound or the composition A to seeds or vegetative reproductive organs, and specific examples thereof include spraying treatment in which a suspension of the present compound or the composition A is sprayed onto seed surface or the vegetative reproductive organ surface in the form of mist; smearing treatment in which the present compound or the composition A is coated a surface of seeds or the vegetative reproductive organ; a soaking treatment in which the seeds are soaked into the solution of the present compound or the composition A for a certain time; and a method for coating the seeds or the vegetative reproductive organ with a carrier containing the present compound or the composition A (film coating treatment, pellet coating treatment). Examples of the above-described vegetative reproductive organ include particularly seed potato.

When the composition A is applied to seeds or vegetative reproductive organs, the composition A may be also applied to seeds or vegetative reproductive organs as a single formulation, or the composition A may be applied to seeds or vegetative reproductive organs as a divided plurality of formulation by a plurality of time. Examples of the method in which the composition A is applied as a divided plurality of formulation by a plurality of time include, for exmaple, a method in which the formulations comprising as an active component the present compound only are applied, and seeds or vegetative reproductive organs are air dried, followed by applying the formulations comprising the present ingredient; and a method in which the formulations comprising as an active component the present compound X and the present ingredients are applied, and seeds or vegetative reproductive organs are air dried, followed by applying the formulations comprising the present ingredients other than the already-applied present ingredients, are included.

As used herein, seeds or vegetative reproductive organs carrying the present compound or the composition A means seeds or vegetative reproductive organs in the state where the present compound or the composition A is adhered to a surface of the seeds or the vegetative reproductive organ. The above-described seeds or vegetative reproductive organs carrying the present compound or the composition A may be adhered by any other materials that are different from the present compound or the composition A before or after being adhered the present compound or the composition A to the seeds or vegetative reproductive organs.

Also, when the composition A is adhered in a form of layer(s) to a surface of seeds or vegetative reproductive organ, the layer(s) is/are composed of one layer or a plurality of layer. Also, when a plurality layer are formed, each of the layer may be composed of a layer comprising one or more active ingredients, or a combination of a layer comprising one or more active ingredients and a layer not comprising an active ingredient.

Seeds or vegetative reproductive organs carrying the present compound or the composition A can be obtained, for example, by applying the formulations comprising the present compound or the composition A by the above-described application method to seeds to seeds or vegetative reproductive organs.

When the present compound or the composition A is applied for harmful arthropods control in agricultural fields, the application dose thereof is usually within a range of 1 to 10,000 g g of the present compound per 10,000 $m^2$. In the case of being applied to seeds or vegetative reproductive organs, the dose of application dose thereof is usually within a range of 0.001 to 100 g of the present compound per 1 Kg of seeds. When the present compound or the composition A is formulated into an emulsifiable concentrate, a wettable powder or a flowable etc., they are usually applied by diluting them with water so as to make an effective concentration of the active ingredients 0.01 to 10,000 ppm, and the dust formulation or the granular formulation, etc., is usually applied as itself without diluting them.

Also, the resin preparation which is processed into a sheet or a string may be applied by winding a plant with a sheet or a string of the resin preparation, putting a string of the resin preparation around a crop so that the plant is surrounded by the string, or laying a sheet of the resin preparation on the soil surface near the root of a plant.

When the present compound or the composition A is used to control harmful arthropods that live inside a house, the application dose as an amount of the present compound is usually within a range from 0.01 to 1,000 mg per 1 $m^2$ of an area to be treated, in the case of using it on a planar area. In the case of using it spatially, the application dose as an amount of the present compound is usually within a range from 0.01 to 500 mg per 1 $m^3$ of the space to be treated. When the present compound or the composition A is formulated into emulsifiable concentrates, wettable powders, flowables or the others, such formulations are usually applied after diluting it with water in such a way that a concentration of the active ingredient is within a range from 0.1 to 10,000 ppm. In the case of being formulated into oil solutions, aerosols, smoking agents, poison baits and the others, such formulations are used as itself without diluting it.

Also, the composition of the present compound or the composition A may be used as an agent for controlling harmful arthropods in agricultural lands such as paddy fields, fields, turfs, and orchards. Examples of the plants to be applied include the followings.

corn, rice, wheat, barley, rye, oat, sorghum, cotton, soybean, peanut, buckwheat, beet, rapeseed, sunflower, sugar cane, tobacco, solanaceous vegetables (for example, eggplant, tomato, pimento, pepper, or potato), cucurbitaceous vegetables (for example, cucumber, pumpkin, zucchini, water melon, or melon), cruciferous vegetables (for example, Japanese radish, white turnip, horseradish, kohlrabi, Chinese cabbage, cabbage, leaf mustard, broccoli, or cauliflower), asteraceous vegetables (for example, burdock, crown daisy, artichoke, or lettuce), liliaceous vegetables (for example, green onion, onion, garlic, or asparagus), ammiaceous vegetables (for example, carrot, parsley, celery, or parsnip), chenopodiaceous vegetables (for example, spinach, or Swiss chard), lamiaceous vegetables (for example, *Perilla frutescens*, mint, or basil), strawberry, sweet potato, *Dioscorea japonica, colocasia*, pomaceous fruits (for example, apple, pear, Japanese pear, Chinese quince, or quince), stone fleshy fruits (for example, peach, plum, nectarine, *Prunus* mume, cherry fruit, apricot, or prune), citrus fruits (for example, Citrus unshiu, orange, lemon, lime, or grapefruit), nuts (for example, chestnut, walnuts, hazelnuts, almond, pistachio, cashew nuts, or macadamia nuts), berry fruits (for example, blueberry, cranberry, blackberry or raspberry), grape, kaki persimmon, olive, Japanese plum, banana, coffee, date palm, coconuts, tea, mulberry, ornamental foliage plants, woodland plants, lawns, pastures.

The above-mentioned plants include also genetically modified crops.

EXAMPLES

Hereinafter, the present invention is explained in more detail by using Preparation Examples, Reference Preparation Examples, and Formulation Examples, and Test Examples, however, the present invention should not be limited to these examples.

As used herein, "Me" represents a methyl group, "Et" represents an ethyl group, "Pr" represents a propyl group, "Bu" represents a butyl group, "Pen" represents a pentyl group, "i-Pr" represents an isopropyl group, "i-Bu" represents an isobutyl group, "c-Pr" represents a cyclopropyl group, "c-Bu" represents a cyclobutyl group, "c-Pen" represents a cyclopentyl group, "c-Hex" represents a cyclohexyl group, and "Ph" represents a phenyl group.

Firstly, a preparation example of the compound of the present invention is shown.

When the physical property value of a compound is measured by liquid chromatography/mass spectrometry (hereinafter, referred to as LCMS), the measured molecular ion value ($[M+H]+$ or $[M-H]^-$ and relation time (hereinafter, referred to as RT) is described. Each condition of liquid chromatography (hereinafter, referred to as "LC") and mass spectrometry (hereinafter, referred to as "MS") is described below.

[Lc Condition]

Column: L-column2ODS, inner diameter 4.6 mm, length 30 mm, particle size 3 μm (Chemical Evaluation and Research Institute, Japan)

UV measurement wavelength: 254 nm

Mobile phase: A solution: 0.1% aqueous formic acid, solution B solution: 0.1% formic acid in acetonitrile, Flow rate: 2.0 mL/minute Pump: LC-20AD (manufactured by Shimazu) two machines (high pressure gradient)

Gradient condition: A solution is send under the concentration gradient described in [Table LC1].

TABLE LC1

| Time (min) | A solution (%) | B solution (%) |
|---|---|---|
| 0.01 | 90 | 10 |
| 2.00 | 0 | 100 |

TABLE LC1-continued

| Time (min) | A solution (%) | B solution (%) |
|---|---|---|
| 4.00 | 0 | 100 |
| 4.01 | 90 | 10 |

[MS condition]

Detector: LCMS-2020 (manufactured by Shimazu)

Ionization method: DUIS

Reference Preparation Example 1

A mixture of methyl (Z)-2-(5-bromo-2-methylphenoxy)-3-methoxyacrylate (prepared according to a method described in WO 2001/000562 A1) 20.0 g, bis(pinacolato) diboron 20.2 g, and [1,1'-bis(diphenylphosphino)ferrocene] palladium (II) dichloride 2.43 g, potassium acetate 19.5 g, and DMSO 250 mL was stirred at 80° C. for 10 hours. Water was added to the resulting mixture, and the resulting mixture was extracted with ethyl acetate. The resulting organic layers were washed with water and saturated brine successively, dried over anhydrous magnesium sulfate, and concentrated under reduced pressure. The resulting residues were subjected to silica gel column chromatography (ethyl acetate: hexane=1:4) to obtain an intermediate compound 1 represented by the following formula 11.8 g.

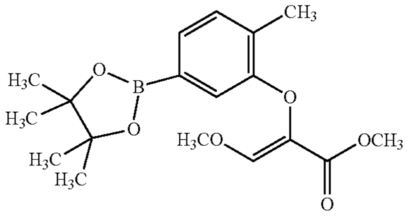 [SMILES: CO/C=C(\Oc1cc(B2OC(C)(C)C(C)(C)O2)ccc1C)C(=O)OC]

Intermediate compound 1:1H-NMR ($CDCl_3$) δ: 7.37 (1H, d), 7.32 (1H, s), 7.16 (1H, d), 7.10 (1H, s), 3.87 (3H, s), 3.69 (3H, s), 2.37 (3H, s), 1.31 (12H, s)

Reference Preparation Example 1-1

An intermediate compound 2 represented by the following formula was prepared by using methyl (Z)-2-(5-bromo-2-methylbenzyl)-3-methoxyacrylate (which was prepared according to the method described in WO 2001/000562 A1) in the place of methyl (Z)-2-(5-bromo-2-methylphenoxy)-3-methoxyacrylate according to the Reference Preparation Example 1.

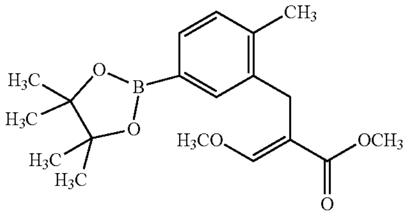 [SMILES: CO/C=C(\Cc1cc(B2OC(C)(C)C(C)(C)O2)ccc1C)C(=O)OC]

Intermediate compound 2:1H-NMR ($CDCl_3$) δ: 7.56-7.51 (2H, m), 7.47 (1H, s), 7.12 (1H, d), 3.85 (3H, s), 3.66 (3H, s), 3.57 (2H, s), 2.36 (3H, s), 1.32 (12H, s)

Reference Preparation Exmaple 1-2

An intermediate compound 3 represented by the following formula was prepared by using methyl (Z)-2-(5-bromo-2-chlorophenoxy)-3-methoxyacrylate (which was prepared according to the method described in WO 98/03464 A1) in the place of methyl (Z)-2-(5-bromo-2-methylphenoxy)-3-methoxyacrylate according to the Reference Preparation Example 1.

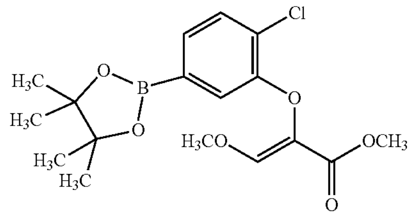 [SMILES: CO/C=C(\Oc1cc(B2OC(C)(C)C(C)(C)O2)ccc1Cl)C(=O)OC]

Intermediate compound 3: 1H-NMR ($CDCl_3$) δ: 7.38-7.37 (2H, m), 7.36 (1H, s), 7.19-7.17 (1H, m), 3.88 (3H, s), 3.72 (3H, s), 1.32 (12H, s)

Reference Preparation Example 2

To a mixture of the intermediate compound 1 0.50 g, ethanol 20 mL, acetonitrile 20 mL and water 20 mL was added meta-chloroperoxybenzoic acid (purity 70%, containing 30% water) 0.43 g at room temperature, and the mixture was stirred for 3 hours. To the resulting mixture were added saturated sodium thiosulfate aqueous solution and saturated ammonium chloride aqueous solution successively, and the mixture was stirred for 1 hour. The resulting mixture was concentrated under reduced pressure and extracted with ethyl acetate. The resulting organic layer was washed with water and saturated brine successively, and dried over anhydrous magnesium sulfate, and concentrated under reduced pressure. The resulting residue was subjected to a silica gel column chromatography to obtain an intermediate compound A1 represented by the following formula 0.29 g.

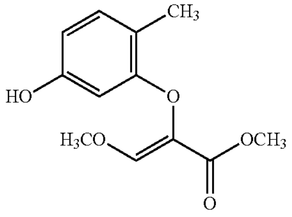 [SMILES: CO/C=C(\Oc1cc(O)ccc1C)C(=O)OC]

Intermediate compound A1:1H-NMR ($CDCl_3$) δ: 7.31 (1H, s), 6.98 (1H, d), 6.37 (1H, dd), 6.28 (1H, d), 4.75 (1H, s), 3.86 (3H, s), 3.71 (3H, s), 2.25 (3H, s)

Reference Preparation Example 2-1

The compound which was prepared according to the Reference Preparation Example 2 and its physical property value are shown below.

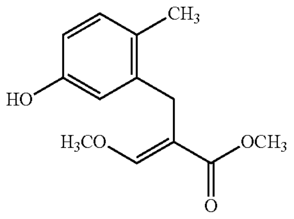

Intermediate compound A2:1H-NMR ($CDCl_3$) δ: 7.48 (1H, s), 6.97 (1H, d), 6.61-6.54 (2H, m), 4.67 (1H, br s), 3.84 (3H, s), 3.68 (3H, s), 3.50 (2H, s), 2.27 (3H, s)

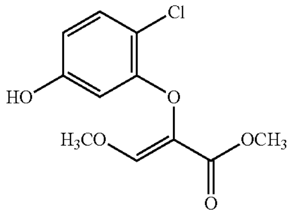 [SMILES: CO/C=C(\Oc1cc(O)ccc1Cl)C(=O)OC]

Intermediate compound A3: 1H-NMR (DMSO-$D_6$) 5: 9.69 (1H, br s), 7.61 (1H, s), 7.19 (1H, d), 6.40 (1H, dd), 6.26 (1H, d), 3.88 (3H, s), 3.66 (3H, s)

Reference Preparation Example 3

To a mixture of methyl 2-(5-hydroxy-2-methylphenoxy) acetate 0.50 g, triphenylphosphine 0.82 g, benzyl alcohol 0.39 mL and chloroform 10 mL was added bis(2-methoxyethyl) azodicarboxylate 0.78 g at 0° C., and the mixture was stirred at room temperature for 22 hours. To the resulting mixture was added saturated sodium bicarbonate aqueous solution, and the mixture was extracted with ethyl acetate. The resulting organic layer was washed with water and saturated brine successively, and dried over anhydrous magnesium sulfate, and concentrated under reduced pressure. The resulting residue was subjected to a silica gel column chromatography to obtain an intermediate compound C1 represented by the following formula 0.55 g.

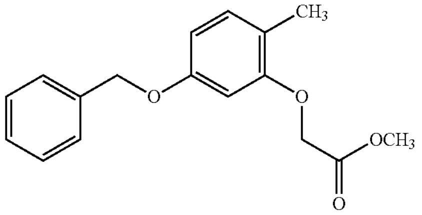 [SMILES: COC(=O)COc1cc(OCc2ccccc2)ccc1C]

Intermediate compound C1:1H-NMR ($CDCl_3$) δ: 7.45-7.30 (5H, m), 7.05 (1H, d), 6.52 (1H, dd), 6.38 (1H, d), 5.02 (2H, s), 4.62 (2H, s), 3.79 (3H, s), 2.22 (3H, s)

Reference Preparation Example 3-1

The compound which was prepared according to the Reference Preparation Example 3 and its physical property value are shown below A compound represented by formula (1b1):

(1b1)

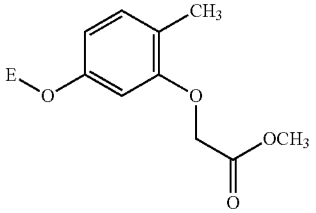

wherein E represents the below-mentioned groups.

Intermediate compound C3 (E: Pr)

1H-NMR ($CDCl_3$) δ: 7.03 (1H, d), 6.43 (1H, dd), 6.31 (1H, d), 4.62 (2H, s), 3.87 (2H, t), 3.80 (3H, s), 2.21 (3H, s), 1.84-1.73 (2H, m), 1.02 (3H, t).

Intermediate compound C4 (E: Bu)

$^1$H-NMR ($CDCl_3$) δ: 7.03 (1H, d), 6.43 (1H, dd), 6.30 (1H, d), 4.62 (2H, s), 3.91 (2H, t), 3.80 (3H, s), 2.21 (3H, s), 1.78-1.70 (2H, m), 1.53-1.42 (2H, m), 0.97 (3H, t).

Intermediate compound C5 (E: i-Bu)

$^1$H-NMR ($CDCl_3$) δ: 7.02 (1H, d), 6.43 (1H, dd), 6.31 (1H, d), 4.63 (2H, s), 3.80 (3H, s), 3.66 (2H, d), 2.21 (3H, s), 2.11-1.99 (1H, m), 1.01 (6H, d).

Intermediate compound C6 (E: Pen)

1H-NMR ($CDCl_3$) δ: 7.03 (1H, d), 6.43 (1H, dd), 6.31 (1H, d), 4.62 (2H, s), 3.90 (2H, t), 3.80 (3H, s), 2.21 (3H, s), 1.82-1.70 (2H, m), 1.46-1.31 (4H, m), 0.93 (3H, t).

Intermediate compound C7 (E: $CH_2$c-Pr)

1H-NMR ($CDCl_3$) δ: 7.02 (1H, d), 6.41 (1H, dd), 6.34 (1H, d), 4.62 (2H, s), 3.80 (3H, s), 3.74 (2H, d), 2.21 (3H, s), 1.31-1.18 (1H, m), 0.68-0.60 (2H, m), 0.37-0.29 (2H, m).

Intermediate compound C8 (E: $CH_2$c-Pen)

1H-NMR ($CDCl_3$) δ: 7.02 (1H, d), 6.44 (1H, dd), 6.31 (1H, d), 4.63 (2H, s), 3.80 (3H, s), 3.77 (2H, d), 2.39-2.27 (1H, m), 2.21 (3H, s), 1.88-1.76 (2H, m), 1.67-1.53 (4H, m), 1.40-1.28 (2H, m).

Intermediate compound C9 (E: $CH_2$c-Hex)

$^1$H-NMR ($CDCl_3$) δ: 7.02 (1H, d), 6.43 (1H, dd), 6.30 (1H, d), 4.62 (2H, s), 3.80 (3H, s), 3.70 (2H, d), 2.20 (3H, s), 1.90-1.80 (2H, m), 1.80-1.66 (4H, m), 1.35-1.14 (3H, m), 1.10-0.97 (2H, m).

Intermediate compound C10 (E: $CH_2CH_2Ph$)

1H-NMR ($CDCl_3$) δ: 7.36-7.21 (5H, m), 7.03 (1H, d), 6.44 (1H, dd), 6.30 (1H, d), 4.62 (2H, s), 4.13 (2H, t), 3.80 (3H, s), 3.08 (2H, t), 2.21 (3H, s).

Intermediate compound C11 (E: $CH_2C{\equiv}CH$)

1H-NMR ($CDCl_3$) δ:7.06 (1H, d), 6.52 (1H, dd), 6.38 (1H, d), 4.64 (2H, d), 4.62 (2H, s), 3.80 (3H, s), 2.52 (1H, t), 2.22 (3H, s).

Reference Preparation Example 4

To a mixture of methyl 2-(5-hydroxy-2-methylphenoxy) acetate 0.30 g, potassium carbonate 0.28 g and DMF 10 mL was added N-methyl-N-phenyl carbamoyl chloride 0.29 g at room temperature, and the mixture was stirred for 3 hours. To the resulting mixture was added saturated ammonium chloride aqueous solution, and the mixture was extracted with ethyl acetate. The resulting organic layer was washed with water and saturated brine successively, dried over anhydrous magnesium sulfate, and concentrated under reduced pressure. The resulting residue was subjected to a silica gel column chromatography to obtain the intermediate compound C2 represented by the following formula 0.47 g.

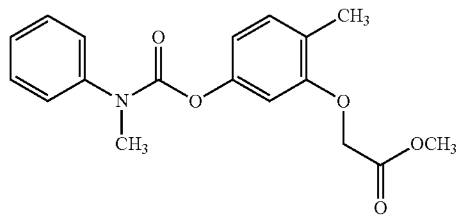 [SMILES: COC(=O)COc1cc(OC(=O)N(C)c2ccccc2)ccc1C]

Intermediate compound C2:1H-NMR ($CDCl_3$) δ: 7.44-7.32 (4H, m), 7.30-7.23 (1H, m), 7.10 (1H, d), 6.72-6.45 (2H, m), 4.62 (2H, s), 3.80 (3H, s), 3.42 (3H, s), 2.25 (3H, s)

Reference Preparation Example 4-1

The compound which was prepared according to the Reference Preparation Example 4 and its physical property value are shown below.

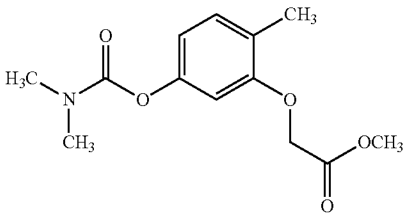 [SMILES: COC(=O)COc1cc(OC(=O)N(C)C)ccc1C]

Intermediate compound C12: $^1$H-NMR ($CDCl_3$) δ: 7.11 (1H, d), 6.66 (1H, dd), 6.50 (1H, d), 4.63 (2H, s), 3.80 (3H, s), 3.08 (3H, s), 3.00 (3H, s), 2.25 (3H, s)

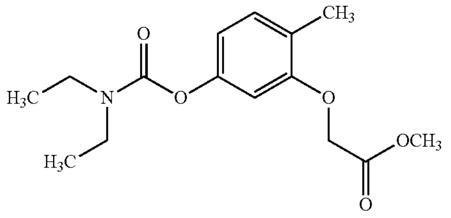 [SMILES: CCN(CC)C(=O)Oc1ccc(C)c(OCC(=O)OC)c1]

Intermediate compound C13: $^1$H-NMR ($CDCl_3$) δ: 7.10 (1H, d), 6.66 (1H, dd), 6.51 (1H, d), 4.62 (2H, s), 3.80 (3H, s), 3.47-3.32 (4H, m), 2.25 (3H, s), 1.28-1.16 (6H, m)

Reference Preparation Example 5

To a mixture of the intermediate compound C1 0.24 g, methyl formate 0.15 g, and dimethoxyethane 5 mL was added potassium tert-butoxide 0.21 g under ice-cooling, and the mixture was stirred at room temperature for 1 hour. 1N hydrochloric acid was added to the resulting mixture, and the mixture was extracted with ethyl acetate. The resulting organic layer was dried over anhydrous magnesium sulfate, and concentrated under reduced pressure to obtain the intermediate compound B1 represented by below-mentioned formula 0.19 g.

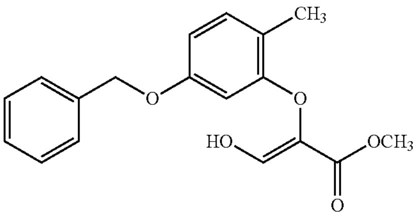 [SMILES: COC(=O)/C(=C/O)Oc1cc(OCc2ccccc2)ccc1C]

Intermediate compound B1: LCMS: 315 $[M+H]^+$, RT=1.90 min

Reference Preparation Example 5-1

The compound which was prepared according to the Reference Preparation Example 5 and its physical property value are shown below.

A compound represented by formula (1d1): $CH_3$ (1d1)

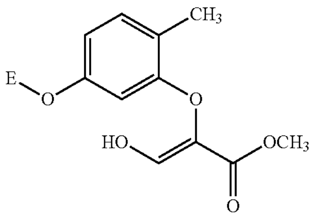

wherein E represents the following groups.

Intermediate compound B2 (E: Pen): LCMS: 295 $[M+H]^+$, RT=2.05 min.

Intermediate compound B3 (E: $CH_2$c-Pr): LCMS: 279 $[M+H]^+$, RT=1.82 min.

Intermediate compound B4 (E: $CH_2$c-Pen) LCMS: 307 $[M+H]^+$, RT=2.07 min.

Intermediate compound B5 (E: $CH_2$c-Hex) LCMS: 321 $[M+H]^+$, RT=2.16 min.

Reference Preparation Example 6

To a mixture of 5-bromo-2-methylbenzaldehyde 4.58 g THF 185 mL was added sodium hydride (60%, oily) 1.00 g under ice-cooling, and the mixture was stirred under ice-cooling for 20 minutes. Methyl dimethylphosphonoacetate 5.00 g was added to the resulting mixture, and the mixture was stirred at room temperature for 4 hours. To the resulting mixture was added saturated sodium bicarbonate aqueous solution, and the mixture was extracted with ethyl acetate. The resulting organic layer was washed with water and saturated brine successively, dried over anhydrous sodium sulfate, and concentrated under reduced pressure. The resulting residue was subjected to a silica gel column chromatography to obtain the intermediate compound 4 represented by the following formula 5.80 g.

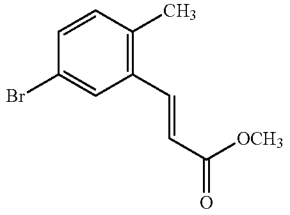

Intermediate compound 4: $^1$H-NMR ($CDCl_3$) δ: 7.87 (1H, d), 7.66 (1H, d), 7.38 (1H, dd), 7.08 (1H, d), 6.35 (1H, d), 3.82 (3H, s), 2.37 (3H, s)

Reference Preparation Example 7

A mixture of the intermediate compound 4 108.43 g, cobalt(II) chloride 5.52 g, and methanol 1084 mL was cooled to −54° C., and thereto was added sodium borohydride 40.35 g, and the mixture was stirred at −24° C. for 6 hours. To the resulting mixture was added 10% aqueous ammonium chloride solution, and the mixture was extracted with ethyl acetate. The resulting organic layer was washed with water, dried over anhydrous sodium sulfate, and concentrated under reduced pressure to obtain the intermediate compound 5 represented by the below-mentioned formula 93.91 g.

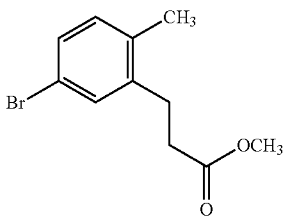

Intermediate compound 5: $^1$H-NMR ($CDCl_3$) δ: 7.27-7.22 (2H, m), 7.01 (1H, d), 3.69 (3H, s), 2.90 (2H, t), 2.58 (2H, t), 2.26 (3H, s)

Reference Preparation Example 8

A mixture of the intermediate compound 5 3.80 g and THF 137 mL was cooled to −72° C., and thereto was added lithium diisopropylamide (1.08 M hexane-THF solution) 27 mL, and the mixture was stirred at −66° C. for 30 minutes. To the resulting mixture was added methyl formate 7.10 g, and the mixture was stirred at −63° C. for 1 hour. To the resulting mixture was added 10% aqueous sodium hydrogen sulfate solution, and the mixture was extracted with ethyl acetate. The resulting organic layer was washed with water, dried over anhydrous sodium sulfate, and concentrated under reduced pressure to obtain the crude methyl 2-(5-bromo-2-methylbenzyl)-3-hydroxyacrylate. To the obtained crude methyl 2-(5-bromo-2-methylbenzyl)-3-hydroxyacrylate was added DMF 137 mL, and thereto were added potassium carbonate 6.13 g and dimethyl sulfate 4.66 g successively, and the mixture was stirred at room temperature for 4 hours. Water was added to the resulting mixture, and the mixture was extracted with MTBE. The resulting organic layer was washed with water, dried over anhydrous sodium sulfate, and concentrated under reduced pressure to obtain the intermediate compound E1 represented by the below-mentioned formula 3.61 g.

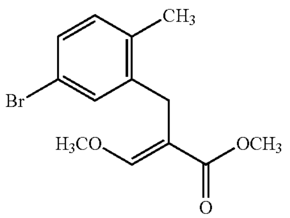 [SMILES: CO/C=C(\Cc1cc(Br)ccc1C)C(=O)OC]

Intermediate compound E1

Reference Preparation Example 8-1

The compound which was prepared according to the Reference Preparation Example 8 and its physical property value are shown below.

A compound represented by formula (II-A):

(II-A)

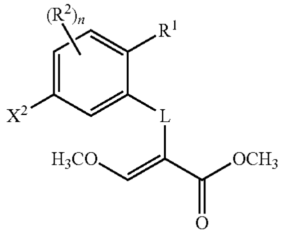

wherein n is 0, and a combination of $R^1$, $X^2$ and L represents any combinations indicated in [Table II-A].

TABLE II-A

| Intermediate compound | $R^1$ | $R^2$ | $R^3$ |
|---|---|---|---|
| E1 | Me | Br | $CH_2$ |
| E2 | Me | Br | O |
| E3 | Cl | Br | $CH_2$ |
| E4 | Cl | Br | O |

Intermediate compound E1:1H-NMR ($CDCl_3$) δ: 7.49 (1H, s), 7.20 (2H, m), 6.97 (1H, d), 3.86 (3H, s), 2.68 (3H, s), 3.50 (2H, m), 2.28 (3H, s)

Reference Preparation Example 9

To a mixture of 5-chloro-2-methylphenol 2.00 g, potassium carbonate 2.33 g, and DMF 20 mL was added methyl 2-bromoacetate 2.58 g, and the mixture was stirred at room temperature for 3 hours. Water was added to the resulting mixture, and the mixture was extracted with ethyl acetate. The resulting organic layer was washed with water and saturated brine successively, dried over anhydrous magnesium sulfate, and concentrated under reduced pressure. The resulting residue was subjected to a silica gel column chromatography (ethyl acetate: hexane=1 4) to obtain the intermediate compound 6 represented by the following formula 2.94 g.

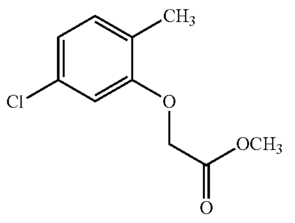

Intermediate compound 6: 1H-NMR ($CDCl_3$) δ: 7.07 (1H, dd), 6.89 (1H, dd), 6.68 (1H, d), 4.64 (2H, s), 3.81 (3H, s), 2.24 (3H, s)

Reference Preparation Example 10

To a mixture of the intermediate compound 6 3.00 g, methyl formate 2.3 mL and 1,2-dimethoxyethane 20 mL was added potassium tert-butoxide 3.15 g under ice-cooling. The mixture was stirred at room temperature for 2 hours. To the resulting mixture was 1N hydrochloric acid, and the mixture was extracted with ethyl acetate. The resulting organic layer was washed with water, dried over anhydrous sodium sulfate, and concentrated under reduced pressure to obtain the intermediate compound 7 represented by the following formula 2.44 g.

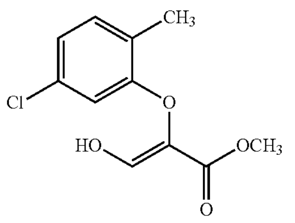 [SMILES: COC(=O)/C(=C/O)Oc1cc(Cl)ccc1C]

Intermediate compound 7: $^1$H-NMR ($CDCl_3$) δ: 7.53 (1H, d), 7.11 (1H, dt), 6.94 (1H, dd), 6.73 (1H, d), 5.76 (1H, d), 3.71 (3H, t), 2.32 (3H, s)

Reference Preparation Example 11

To a mixture of the intermediate 7 1.09 g, potassium carbonate 0.70 g, and DMF 10 mL was added iodomethane 0.62 mL under ice-cooling, and the mixture was stirred at room temperature for 2 hours. Water was added to the resulting mixture, and the mixture was extracted with MTBE. The resulting organic layer was washed with water and saturated brine successively, dried over anhydrous magnesium sulfate, and concentrated under reduced pressure. The resulting residue was subjected to a silica gel column chromatography (ethyl acetate; hexane=1:4) to obtain the intermediate compound D2 represented by the following formula 1.00 g.

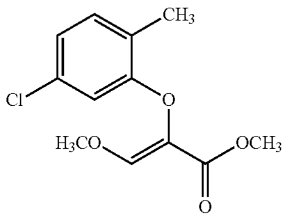 [SMILES: CO/C=C(\Oc1cc(Cl)ccc1C)C(=O)OC]

Intermediate compound D2

Reference Preparation Example 11-1

The compound which was prepared according to the Reference Preparation Example 11 and its physical property value are shown below.

A compound represented by formula (VI): C11~ L (VIQ (VI)

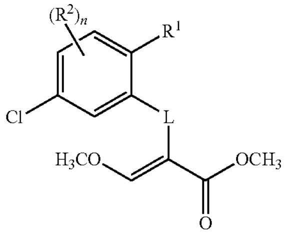

wherein n is 0, and a combination of $R^1$ and L represents any combinations indicated in [Table VI].

TABLE VI

| Intermediate compound | $R^1$ | L |
|---|---|---|
| Intermediate compound D1 | Me | $CH_2$ |
| Intermediate compound D2 | Me | O |
| Intermediate compound D3 | Cl | $CH_2$ |
| Intermediate compound D4 | Cl | O |

Intermediate compound D1:1H-NMR ($CDCl_3$) δ: 7.49 (1H, s), 7.06-7.01 (3H, m), 3.86 (3H, s), 3.68 (3H, s), 3.50 (2H, s), 2.31 (3H, s)

Intermediate compound D2:1H-NMR ($CDCl_3$) δ: 7.33 (1H, s), 7.07 (1H, dd), 6.88 (1H, dd), 6.70 (1H, d), 3.89 (3H, s), 3.72 (3H, s), 2.30 (3H, s)

Preparation Example 1

To a mixture of the intermediate compound A1 0.25 g, triphenylphosphine 0.33 g, ethanol 0.06 mL and chloroform 5 mL was added bis(2-methoxyethyl) azodicarboxylate 0.32 g at 0° C., and the mixture was stirred at room temperature for 16 hours. To the resulting mixture was added saturated sodium bicarbonate aqueous solution, and the mixture was extracted with ethyl acetate. The resulting organic layer was washed with water and saturated brine, dried over anhydrous magnesium sulfate, and concentrated under reduced pressure. The resulting residue was subjected to a silica gel column chromatography (ethyl acetate:hexane=1:4) to obtain the present compound 1 represented by the following formula 0.23 g.

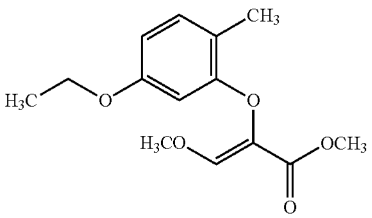 [SMILES: CCOc1ccc(C)c(O/C(=C\OC)C(=O)OC)c1]

Present compound 1:1H-NMR ($CDCl_3$) δ: 7.30 (1H, s), 7.03 (1H, d), 6.44 (1H, dd), 6.33 (1H, d), 3.95 (2H, q), 3.86 (3H, s), 3.70 (3H, s), 2.27 (3H, s), 1.37 (3H, t).

Preparation Example 1-1

The compound which was prepared according to the Preparation Example 1 and its physical property value are shown below.

A compound represented by formula (1a1):

(1a1)

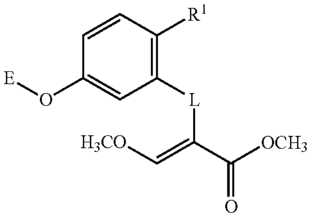

wherein a combination of E, $R^1$ and L represents any combinations indicated in [Table 1-1] to [Table 1-6].

TABLE 1-1

| Present compound | E | $R^1$ | L |
|---|---|---|---|
| 2 | 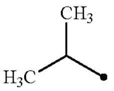 | Me | O |

TABLE 1-1-continued

| Present compound | E | $R^1$ | L |
|---|---|---|---|
| 3 | 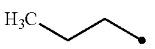 | Me | O |
| 4 | 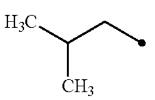 | Me | O |
| 5 | 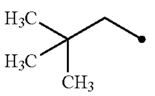 | Me | O |
| 6 | 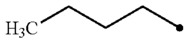 | Me | O |
| 7 | 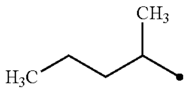 | Me | O |
| 8 | 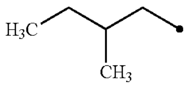 | Me | O |
| 9 | 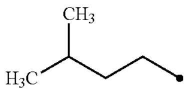 | Me | O |
| 10 | 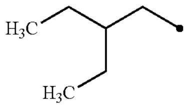 | Me | O |

TABLE 1-2

| Present compound | E | $R^1$ | L |
|---|---|---|---|
| 11 | 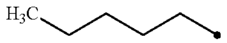 | Me | O |
| 12 | 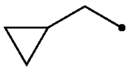 | Me | O |
| 13 | 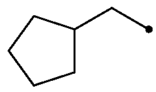 | Me | O |
| 14 | 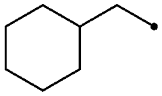 | Me | O |
| 15 | 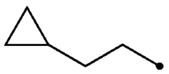 | Me | O |
| 16 | 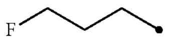 | Me | O |
| 17 | 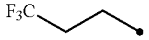 | Me | O |
| 18 | 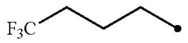 | Me | O |
| 19 | 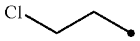 | Me | O |

TABLE 1-2-continued
| Present compound | E | $R^1$ | L |
|---|---|---|---|
| 20 | 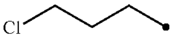 | Me | O |
TABLE 1-3
| Present compound | E | $R^1$ | L |
|---|---|---|---|
| 21 | 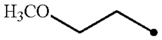 | Me | O |
| 22 | 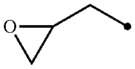 | Me | O |
| 23 | 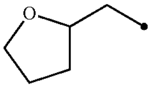 | Me | O |
| 24 | 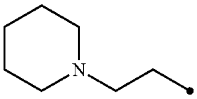 | Me | O |
| 25 | 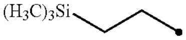 | Me | O |
| 26 | 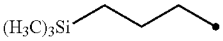 | Me | O |
| 27 | 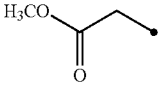 | Me | O |
| 28 | 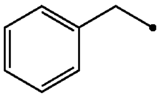 | Me | $CH_2$ |
| 29 | 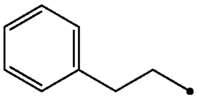 | Me | O |
| 30 | 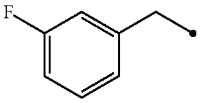 | Me | O |
TABLE 1-4
| Present compound | E | $R^1$ | L |
|---|---|---|---|
| 31 | 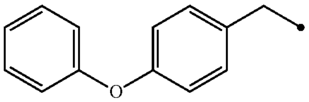 | Me | O |
| 32 | 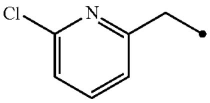 | Me | O |
| 33 | 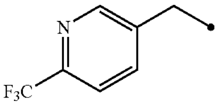 | Me | O |
TABLE 1-4-continued
| Present compound | E | $R^1$ | L |
|---|---|---|---|
| 34 | 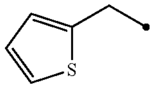 | Me | O |
| 35 | 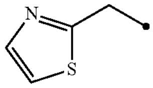 | Me | O |
| 36 | 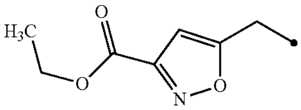 | Me | O |
| 37 | 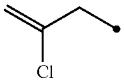 | Me | O |
| 38 | 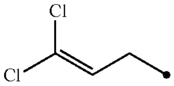 | Me | O |
| 39 | 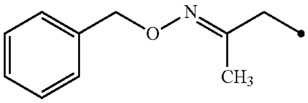 | Me | O |
TABLE 1-5
| Present compound | E | $R^1$ | L |
|---|---|---|---|
| 71 | 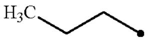 | Me | $CH_2$ |
| 72 | 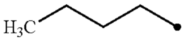 | Cl | O |
| 73 | 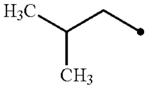 | Me | $CH_2$ |
| 74 | 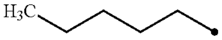 | Me | $CH_2$ |
| 75 | 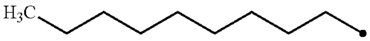 | Me | O |
| 76 | 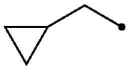 | Me | $CH_2$ |
| 77 | 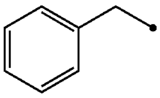 | Cl | O |
| 78 | 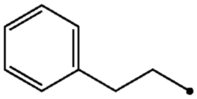 | Me | $CH_2$ |
| 79 | 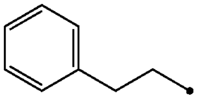 | Cl | O |

TABLE 1-5-continued

| Present compound | E | $R^1$ | L |
|---|---|---|---|
| 80 | 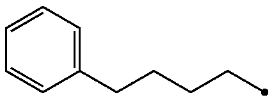 | Me | O |

TABLE 1-6

| Present compound | E | $R^1$ | L |
|---|---|---|---|
| 81 | 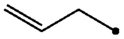 | Me | $CH_2$ |
| 82 | 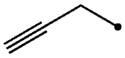 | Me | $CH_2$ |
| 83 | 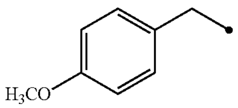 | Me | $CH_2$ |
| 84 | 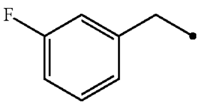 | Me | $CH_2$ |
| 85 | 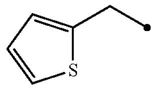 | Me | $CH_2$ |
| 86 | 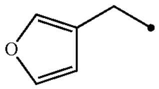 | Me | O |
| 87 | 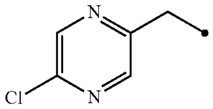 | Me | O |
| 88 | 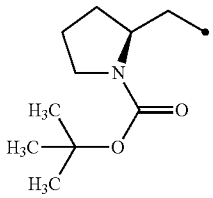 | Me | O |

Present compound 2:1H-NMR ($CDCl_3$) δ:7.30 (1H, s), 7.02 (1H, d), 6.45 (1H, dd), 6.31 (1H, d), 4.50-4.40 (1H, m), 3.86 (3H, s), 3.70 (3H, s), 2.27 (3H, s), 1.29 (6H, d).

Present compound 3: $^1$H-NMR ($CDCl_3$) δ: 7.31 (1H, s), 7.03 (1H, d), 6.45 (1H, dd), 6.33 (1H, d), 3.86 (3H, s), 3.84 (2H, t), 3.70 (3H, s), 2.27 (3H, s), 1.82-1.71 (2H, m), 1.01 (3H, t).

Present compound 4: $^1$H-NMR ($CDCl_3$) δ: 7.31 (1H, s), 7.03 (1H, d), 6.44 (1H, dd), 6.32 (1H, d), 3.87 (3H, s), 3.71 (3H, s), 3.63 (2H, d), 2.27 (3H, s), 2.09-1.97 (1H, m), 1.00 (6H, d).

Present compound 5: 1H-NMR ($CDCl_3$) δ: 7.33 (1H, s), 7.02 (1H, d), 6.44 (1H, dd), 6.31 (1H, d), 3.88 (3H, s), 3.71 (3H, s), 3.50 (2H, s), 2.26 (3H, s), 1.00 (9H, s).

Present compound 6: $^1$H-NMR ($CDCl_3$) δ: 7.30 (1H, s), 7.03 (1H, d), 6.44 (1H, dd), 6.32 (1H, d), 3.88 (2H, t), 3.86 (3H, s), 3.70 (3H, s), 2.27 (3H, s), 1.76-1.67 (2H, m), 1.52-1.40 (2H, m), 0.96 (3H, t).

Present compound 7: $^1$H-NMR ($CDCl_3$) δ: 7.30 (1H, s), 7.02 (1H, d), 6.44 (1H, dd), 6.31 (1H, d), 4.30-4.22 (1H, m), 3.86 (3H, s), 3.70 (3H, s), 2.26 (3H, s), 1.74-1.62 (1H, m), 1.53-1.33 (3H, m), 1.24 (3H, d), 0.92 (3H, t).

Present compound 8: $^1$H-NMR ($CDCl_3$) δ: 7.31 (1H, s), 7.02 (1H, d), 6.44 (1H, dd), 6.32 (1H, d), 3.86 (3H, s), 3.76-3.62 (2H, m), 3.70 (3H, s), 2.26 (3H, s), 1.86-1.76 (1H, m), 1.59-1.48 (1H, m), 1.29-1.17 (1H, m), 0.98 (3H, d), 0.93 (3H, t).

Present compound 9: $^1$H-NMR ($CDCl_3$) δ: 7.31 (1H, s), 7.03 (1H, d), 6.45 (1H, dd), 6.32 (1H, d), 3.90 (2H, t), 3.86 (3H, s), 3.70 (3H, s), 2.27 (3H, s), 1.84-1.75 (1H, m), 1.63 (2H, q), 0.94 (6H, d).

Present compound 10: $^1$H-NMR ($CDCl_3$) δ: 7.32 (1H, s), 7.03 (1H, d), 6.46 (1H, dd), 6.32 (1H, d), 3.87 (3H, s), 3.77 (2H, d), 3.71 (3H, s), 2.27 (3H, s), 1.66-1.58 (1H, m), 1.52-1.36 (4H, m), 0.91 (6H, t).

Present compound 11:1H-NMR ($CDCl_3$) δ: 7.30 (1H, s), 7.03 (1H, d), 6.44 (1H, dd), 6.32 (1H, d), 3.87 (2H, t), 3.86 (3H, s), 3.70 (3H, s), 2.26 (3H, s), 1.78-1.69 (2H, m), 1.46-1.31 (4H, m), 0.92 (3H, t).

Present compound 12:1H-NMR ($CDCl_3$) δ: 7.30 (1H, s), 7.03 (1H, d), 6.43 (1H, dd), 6.37 (1H, d), 3.86 (3H, s), 3.72 (2H, d), 3.70 (3H, s), 2.27 (3H, s), 1.29-1.19 (1H, m), 0.63 (2H, q), 0.32 (2H, q).

Present compound 13: 1H-NMR ($CDCl_3$) δ: 7.31 (1H, s), 7.02 (1H, d), 6.44 (1H, dd), 6.32 (1H, d), 3.86 (3H, s), 3.74 (2H, d), 3.70 (3H, s), 2.36-2.26 (1H, m), 2.26 (3H, s), 1.87-1.75 (2H, m), 1.66-1.53 (4H, m), 1.38-1.27 (2H, m).

Present compound 14: 1H-NMR ($CDCl_3$) δ: 7.31 (1H, s), 7.02 (1H, d), 6.43 (1H, dd), 6.31 (1H, d), 3.86 (3H, s), 3.70 (3H, s), 3.66 (2H, d), 2.26 (3H, s), 1.89-1.64 (6H, m), 1.34-1.15 (3H, m), 1.07-0.94 (2H, m).

Present compound 15: 1H-NMR ($CDCl_3$) δ: 7.31 (1H, s), 7.03 (1H, d), 6.46 (1H, dd), 6.33 (1H, d), 3.95 (2H, t), 3.86 (3H, s), 3.70 (3H, s), 2.27 (3H, s), 1.63 (2H, q), 0.87-0.76 (1H, m), 0.50-0.43 (2H, m), 0.12-0.06 (2H, m).

Present compound 16: 1H-NMR ($CDCl_3$) δ: 7.32 (1H, s), 7.04 (1H, d), 6.46 (1H, dd), 6.33 (1H, d), 4.69 (1H, t), 4.57 (1H, t), 4.02 (2H, t), 3.87 (3H, s), 3.71 (3H, s), 2.28 (3H, s), 2.20-2.06 (2H, m).

Present compound 17: $^1$H-NMR ($CDCl_3$) δ: 7.32 (1H, s), 7.05 (1H, d), 6.44 (1H, dd), 6.32 (1H, d), 4.12 (2H, t), 3.87 (3H, s), 3.71 (3H, s), 2.63-2.51 (2H, m), 2.27 (3H, s).

Present compound 18: 1H-NMR ($CDCl_3$) δ: 7.32 (1H, s), 7.04 (1H, d), 6.43 (1H, dd), 6.31 (1H, d), 3.93 (2H, t), 3.87 (3H, s), 3.71 (3H, s), 2.33-2.22 (2H, m), 2.27 (3H, s), 2.04-1.96 (2H, m).

Present compound 19: 1H-NMR ($CDCl_3$) δ: 7.31 (1H, s), 7.05 (1H, d), 6.45 (1H, dd), 6.36 (1H, d), 4.16 (2H, t), 3.87 (3H, s), 3.77 (2H, t), 3.71 (3H, s), 2.28 (3H, s).

Present compound 20: $^1$H-NMR ($CDCl_3$) δ: 7.31 (1H, s), 7.04 (1H, d), 6.46 (1H, dd), 6.32 (1H, d), 4.03 (2H, t), 3.87 (3H, s), 3.72 (2H, t), 3.71 (3H, s), 2.27 (3H, s), 2.23-2.15 (2H, m).

Present compound 21: $^1$H-NMR ($CDCl_3$) δ: 7.29 (1H, s), 7.03 (1H, d), 6.46 (1H, dd), 6.40 (1H, d), 4.04 (2H, t), 3.86 (3H, s), 3.71 (2H, t), 3.69 (3H, s), 3.44 (3H, s), 2.27 (3H, s). Present compound 22:1H-NMR ($CDCl_3$) δ: 7.31 (1H, s), 7.04 (1H, d), 6.45 (1H, dd), 6.38 (1H, d), 4.14 (1H, dd), 3.91-3.85 (1H, m), 3.87 (3H, s), 3.71 (3H, s), 3.34-3.29 (1H, m), 2.91-2.87 (1H, m), 2.74 (1H, dd), 2.27 (3H, s). Present compound 23: 1H-NMR ($CDCl_3$) δ: 7.30 (1H, s), 7.02 (1H, d), 6.45 (1H, dd), 6.38 (1H, d), 4.27-4.19 (1H, m), 3.96-3.78 (4H, m), 3.86 (3H, s), 3.70 (3H, s), 2.26 (3H, s), 2.10-1.88 (3H, m), 1.77-1.67 (1H, m).

Present compound 24: $^1$H-NMR ($CDCl_3$) δ: 7.30 (1H, s), 7.03 (1H, d), 6.45 (1H, dd), 6.35 (1H, d), 4.02 (2H, t), 3.86 (3H, s), 3.70 (3H, s), 2.72 (2H, t), 2.53-2.43 (4H, m), 2.26 (3H, s), 1.64-1.56 (4H, m), 1.48-1.40 (2H, m).

Present compound 25: $^1$H-NMR ($CDCl_3$) δ: 7.30 (1H, s), 7.03 (1H, d), 6.43 (1H, dd), 6.31 (1H, d), 3.99 (2H, t), 3.86 (3H, s), 3.70 (3H, s), 2.27 (3H, s), 1.09 (2H, t), 0.06 (9H, s).

Present compound 26: 1H-NMR ($CDCl_3$) δ: 7.30 (1H, s), 7.03 (1H, d), 6.44 (1H, dd), 6.33 (1H, d), 3.86 (3H, s), 3.83 (2H, t), 3.70 (3H, s), 2.27 (3H, s), 1.79-1.69 (2H, m), 0.60-0.54 (2H, m), 0.01 (9H, s).

Present compound 27: 1H-NMR ($CDCl_3$) δ: 7.31 (1H, s), 7.05 (1H, d), 6.44-6.38 (2H, m), 4.56 (2H, s), 3.87 (3H, s), 3.80 (3H, s), 3.71 (3H, s), 2.28 (3H, s).

Present compound 28: $^1$H-NMR ($CDCl_3$) δ: 7.46 (1H, s), 7.44-7.28 (5H, m), 7.02 (1H, d), 6.75 (1H, d), 6.69 (1H, dd), 4.99 (2H, s), 3.81 (3H, s), 3.66 (3H, s), 3.51 (2H, s), 2.28 (3H, s).

Present compound 29: $^1$H-NMR ($CDCl_3$) δ: 7.35-7.21 (6H, m), 7.03 (1H, d), 6.45 (1H, dd), 6.32 (1H, d), 4.09 (2H, t), 3.85 (3H, s), 3.70 (3H, s), 3.06 (2H, t), 2.27 (3H, s).

Present compound 30: 1H-NMR ($CDCl_3$) δ: 7.40-7.34 (2H, m), 7.29 (1H, s), 7.09-7.01 (3H, m), 6.51 (1H, dd), 6.38 (1H, d), 4.93 (2H, s), 3.84 (3H, s), 3.69 (3H, s), 2.27 (3H, s).

Present compound 31:1H-NMR ($CDCl_3$) δ: 7.39-7.30 (4H, m), 7.29 (1H, s), 7.14-6.98 (6H, m), 6.54 (1H, dd), 6.41 (1H, d), 4.94 (2H, s), 3.85 (3H, s), 3.69 (3H, s), 2.28 (3H, s).

Present compound 32: $^1$H-NMR ($CDCl_3$) δ: 7.66 (1H, t), 7.45 (1H, d), 7.31 (1H, s), 7.25 (1H, d), 7.04 (1H, d), 6.50 (1H, dd), 6.40 (1H, d), 5.09 (2H, s), 3.86 (3H, s), 3.70 (3H, s), 2.27 (3H, s).

Present compound 33: $^1$H-NMR ($CDCl_3$) δ: 8.76 (1H, s), 7.94 (1H, d), 7.70 (1H, d), 7.31 (1H, s), 7.07 (1H, d), 6.51 (1H, dd), 6.38 (1H, d), 5.08 (2H, s), 3.86 (3H, s), 3.70 (3H, s), 2.28 (3H, s).

Present compound 34: $^1$H-NMR ($CDCl_3$) δ: 7.33-7.29 (2H, m), 7.10-6.98 (3H, m), 6.54 (1H, dd), 6.41 (1H, d), 5.13 (2H, s), 3.85 (3H, s), 3.69 (3H, s), 2.28 (3H, s).

Present compound 35: 1H-NMR ($CDCl_3$) δ: 7.78 (1H, d), 7.35 (1H, d), 7.31 (1H, s), 7.06 (1H, d), 6.55 (1H, dd), 6.44 (1H, d), 5.30 (2H, s), 3.86 (3H, s), 3.70 (3H, s), 2.28 (3H, s).

Present compound 36: $^1$H-NMR ($CDCl_3$) δ: 7.32 (1H, s), 7.07 (1H, d), 6.72 (1H, s), 6.49 (1H, dd), 6.38 (1H, d), 5.12 (2H, s), 4.44 (2H, q), 3.87 (3H, s), 3.71 (3H, s), 2.28 (3H, s), 1.41 (3H, t).

Present compound 37: $^1$H-NMR ($CDCl_3$) δ: 7.32 (1H, s), 7.05 (1H, d), 6.46 (1H, dd), 6.37 (1H, d), 5.54-5.52 (1H, m), 5.42-5.40 (1H, m), 4.50 (2H, t), 3.87 (3H, s), 3.71 (3H, s), 2.27 (3H, s).

Present compound 38: 1H-NMR ($CDCl_3$) δ: 7.32 (1H, s), 7.05 (1H, d), 6.43 (1H, dd), 6.32 (1H, d), 6.11 (1H, t), 4.59 (2H, d), 3.87 (3H, s), 3.71 (3H, s), 2.28 (3H, s).

Present compound 39: $^1$H-NMR ($CDCl_3$) δ: 7.38-7.28 (6H, m), 7.01 (1H, d), 6.46 (1H, dd), 6.36 (1H, d), 5.12 (2H, s), 4.45 (2H, s), 3.85 (3H, s), 3.70 (3H, s), 2.27 (3H, s), 1.97 (3H, s).

Present compound 71: $^1$H-NMR ($CDCl_3$) δ: 7.47 (1H, s), 7.00 (1H, d), 6.67 (1H, d), 6.61 (1H, dd), 3.85 (2H, t), 3.83 (3H, s), 3.66 (3H, s), 3.51 (2H, s), 2.27 (3H, s), 1.82-1.71 (2H, m), 1.01 (3H, t).

Present compound 72: $^1$H-NMR ($CDCl_3$) δ: 7.33 (1H, s), 7.24 (1H, d), 6.48 (1H, dd), 6.39 (1H, d), 3.90-3.85 (5H, m), 3.72 (3H, s), 1.77-1.68 (2H, m), 1.52-1.41 (2H, m), 0.96 (3H, t).

Present compound 73: $^1$H-NMR ($CDCl_3$) δ: 7.48 (1H, s), 7.00 (1H, d), 6.67 (1H, d), 6.61 (1H, dd), 3.83 (3H, s), 3.67 (3H, s), 3.65 (2H, d), 3.51 (2H, s), 2.27 (3H, s), 2.09-1.98 (1H, m), 0.99 (6H, d).

Present compound 74: $^1$H-NMR ($CDCl_3$) δ: 7.47 (1H, s), 7.00 (1H, d), 6.69-6.58 (2H, m), 3.88 (2H, t), 3.83 (3H, s), 3.67 (3H, s), 3.51 (2H, s), 2.27 (3H, s), 1.78-1.71 (2H, m), 1.47-1.30 (4H, m), 0.92 (3H, t).

Present compound 75: $^1$H-NMR ($CDCl_3$) δ: 7.30 (1H, s), 7.02 (1H, d), 6.44 (1H, dd), 6.32 (1H, d), 3.87 (2H, t), 3.86 (3H, s), 3.70 (3H, s), 2.26 (3H, s), 1.77-1.69 (2H, m), 1.46-1.24 (12H, m), 0.88 (3H, t).

Present compound 76: 1H-NMR ($CDCl_3$) δ: 7.47 (1H, s), 7.00 (1H, d), 6.68 (1H, d), 6.60 (1H, dd), 3.83 (3H, s), 3.72 (2H, d), 3.66 (3H, s), 3.50 (2H, s), 2.26 (3H, s), 1.28-1.19 (1H, m), 0.64-0.58 (2H, m), 0.34-0.29 (2H, m).

Present compound 77: 1H-NMR ($CDCl_3$) δ: 7.42-7.24 (7H, m), 6.57 (1H, dd), 6.48 (1H, d), 4.98 (2H, s), 3.84 (3H, s), 3.70 (3H, s).

Present compound 78: $^1$H-NMR ($CDCl_3$) δ: 7.47 (1H, s), 7.34-7.19 (5H, m), 7.00 (1H, d), 6.69 (1H, d), 6.62 (1H, dd), 4.11 (2H, t), 3.81 (3H, s), 3.66 (3H, s), 3.51 (2H, s), 3.06 (2H, t), 2.27 (3H, s).

Present compound 79: $^1$H-NMR ($CDCl_3$) δ: 7.36-7.21 (7H, m), 6.48 (1H, dd), 6.39 (1H, d), 4.09 (2H, t), 3.86 (3H, s), 3.71 (3H, s), 3.06 (2H, t).

Present compound 80: 1H-NMR ($CDCl_3$) δ: 7.30 (1H, s), 7.29-7.25 (2H, m), 7.21-7.15 (3H, m), 7.02 (1H, d), 6.43 (1H, dd), 6.31 (1H, d), 3.91-3.87 (2H, m), 3.85 (3H, s), 3.69 (3H, s), 2.70-2.63 (2H, m), 2.26 (3H, s), 1.80-1.75 (4H, m).

Present compound 81:1H-NMR ($CDCl_3$) δ: 7.48 (1H, s), 7.01 (1H, d), 6.70 (1H, d), 6.63 (1H, dd), 6.10-5.98 (1H, m), 5.42-5.34 (1H, m), 5.28-5.23 (1H, m), 4.49-4.45 (2H, m), 3.83 (3H, s), 3.67 (3H, s), 3.51 (2H, s), 2.28 (3H, s).

Present compound 82:1H-NMR ($CDCl_3$) δ: 7.48 (1H, s), 7.03 (1H, d), 6.75 (1H, d), 6.69 (1H, dd), 4.62 (2H, d), 3.83 (3H, s), 3.67 (3H, s), 3.51 (2H, s), 2.49 (1H, t), 2.29 (3H, s).

Present compound 83: 1H-NMR ($CDCl_3$) δ: 7.46 (1H, s), 7.34 (2H, d), 7.02 (1H, d), 6.90 (2H, d), 6.74 (1H, d), 6.69 (1H, dd), 4.91 (2H, s), 3.82 (3H, s), 3.81 (3H, s), 3.66 (3H, s), 3.51 (2H, s), 2.28 (3H, s).

Present compound 84: 1H-NMR ($CDCl_3$) δ: 7.46 (1H, s), 7.36-7.28 (1H, m), 7.20-7.12 (2H, m), 7.04-6.95 (2H, m), 6.73 (1H, d), 6.67 (1H, dd), 4.99 (2H, s), 3.82 (3H, s), 3.66 (3H, s), 3.51 (2H, s), 2.28 (3H, s).

Present compound 85: 1H-NMR ($CDCl_3$) δ: 7.47 (1H, s), 7.31-7.27 (1H, m), 7.10-6.96 (3H, m), 6.75 (1H, d), 6.70 (1H, dd), 5.14 (2H, s), 3.81 (3H, s), 3.66 (3H, s), 3.51 (2H, s), 2.28 (3H, s).

Present compound 86: 1H-NMR ($CDCl_3$) δ: 7.49-7.46 (1H, m), 7.42-7.40 (1H, m), 7.29 (1H, s), 7.05 (1H, d), 6.52 (1H, dd), 6.47-6.45 (1H, m), 6.39 (1H, d), 4.85 (2H, s), 3.85 (3H, s), 3.69 (3H, s), 2.28 (3H, s).

Present compound 87: 1H-NMR ($CDCl_3$) δ: 8.58-8.55 (2H, m), 7.32 (1H, s), 7.07 (1H, d), 6.52 (1H, dd), 6.42 (1H, d), 5.14 (2H, s), 3.87 (3H, s), 3.71 (3H, s), 2.28 (3H, s).

Present compound 88: $^1$H-NMR ($CDCl_3$) δ: 7.31 (1H, s), 7.02 (1H, d), 6.52-6.46 (1H, m), 6.36-6.27 (1H, m), 4.17-3.98 (2H, m), 3.87 (3H, s), 3.85-3.65 (1H, m), 3.71 (3H, s), 3.43-3.27 (2H, m), 2.26 (3H, s), 2.06-1.77 (4H, m), 1.47 (9H, s).

Preparation Example 2

To a mixture of the intermediate compound A1 0.29 g, potassium carbonate 0.25 g, and DMF 10 mL was added benzyl bromide 0.16 mL at room temperature, and the mixture was stirred for 3 hours. Water was added to the resulting mixture, and the mixture was extracted with ethyl acetate. The resulting organic layer was washed with water and saturated brie, dried over anhydrous magnesium sulfate, and concentrated under reduced pressure. The resulting residue was subjected to a silica gel column chromatography (ethyl acetate: hexane=1:4) to obtain the present compound 40 represented by the following formula 0.31 g.

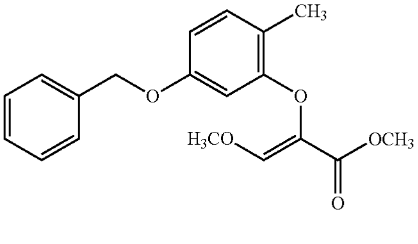 [SMILES: CO/C=C(\Oc1cc(OCc2ccccc2)ccc1C)C(=O)OC]

Present compound 40: $^1$H-NMR ($CDCl_3$) δ: 7.44-7.29 (5H, m), 7.29 (1H, s), 7.05 (1H, d), 6.53 (1H, dd), 6.41 (1H, d), 4.98 (2H, s), 3.84 (3H, s), 3.69 (3H, s), 2.27 (3H, s).

Preparation Example 2-1

The compound which was prepared according to the Preparation Example 2 and its physical property value are shown below.

A compound represented by formula (1a1) wherein a combination of E, $R^1$ and L represents any combinations indicated in [Table 2-1].

TABLE 2-1

| Present compound | E | $R^1$ | L |
|---|---|---|---|
| 41 | 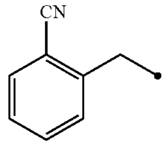 | Me | O |
| 42 | 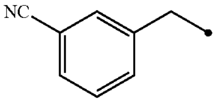 | Me | O |
| 43 | 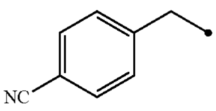 | Me | O |
| 44 | 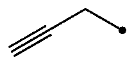 | Me | O |
| 45 | 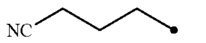 | Me | O |

Present compound 41:1H-NMR ($CDCl_3$) δ: 7.70-7.64 (2H, m), 7.61 (1H, t), 7.41 (1H, t), 7.32 (1H, s), 7.06 (1H, d), 6.55 (1H, dd), 6.42 (1H, d), 5.19 (2H, s), 3.87 (3H, s), 3.69 (3H, s), 2.28 (3H, s).

Present compound 42:1H-NMR ($CDCl_3$) δ: 7.74 (1H, s), 7.66-7.58 (2H, m), 7.48 (1H, t), 7.32 (1H, s), 7.06 (1H, d), 6.49 (1H, dd), 6.39 (1H, d), 5.00 (2H, s), 3.87 (3H, s), 3.70 (3H, s), 2.28 (3H, s).

Present compound 43: $^1$H-NMR ($CDCl_3$) δ: 7.67 (2H, d), 7.52 (2H, d), 7.30 (1H, s), 7.06 (1H, d), 6.48 (1H, dd), 6.38 (1H, d), 5.04 (2H, s), 3.86 (3H, s), 3.70 (3H, s), 2.28 (3H, s).

Present compound 44: 1H-NMR ($CDCl_3$) δ: 7.31 (1H, s), 7.06 (1H, d), 6.52 (1H, dd), 6.41 (1H, d), 4.61 (2H, d), 3.86 (3H, s), 3.70 (3H, s), 2.50 (1H, t), 2.28 (3H, s).

Present compound 45: $^1$H-NMR ($CDCl_3$) δ: 7.33 (1H, s), 7.05 (1H, d), 6.44 (1H, dd), 6.32 (1H, d), 4.00 (2H, t), 3.88 (3H, s), 3.72 (3H, s), 2.57 (2H, t), 2.28 (3H, s), 2.14-2.05 (2H, m).

Preparation Example 3

To a mixture of the intermediate compound A1 0.20 g, potassium carbonate 0.15 g, and DMF 5 mL was added dimethyl carbamoyl chloride 0.09 mL at room temperature, and the mixture was stirred for 19 hours. To the resulting mixture was added saturated ammonium chloride aqueous solution, and the mixture was extracted with ethyl acetate. The resulting organic layer was washed with water and saturated brine, dried over anhydrous magnesium sulfate, and concentrated under reduced pressure. The resulting residue was subjected to a silica gel column chromatography (ethyl acetate:hexane=1:3) to obtain the present compound 46 represented by the following formula 0.08 g.

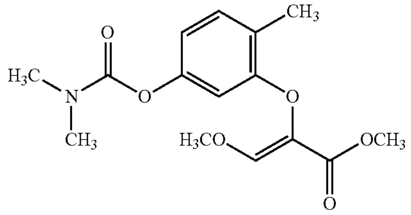 [SMILES: CO/C=C(\Oc1cc(OC(=O)N(C)C)ccc1C)C(=O)OC]

Present compound 46: 1H-NMR ($CDCl_3$) δ: 7.30 (1H, s), 7.10 (1H, d), 6.68 (1H, dd), 6.50 (1H, d), 3.86 (3H, s), 3.70 (3H, s), 3.06 (3H, s), 2.98 (3H, s), 2.31 (3H, s).

Preparation Example 3-1

The compound which was prepared according to the Preparation Example 3 and its physical property value are shown below.

A compound represented by formula (1a1) wherein a combination of E, $R^1$ and L represents any combinations indicated in [Table 3-1].

TABLE 3-1

| Present compound | E | $R^1$ | L |
|---|---|---|---|
| 47 | 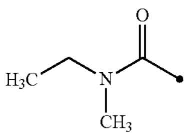 | Me | O |
| 48 | 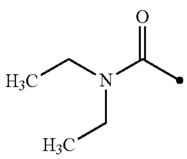 | Me | O |

TABLE 3-1-continued

| Present compound | E | $R^1$ | L |
|---|---|---|---|
| 49 | 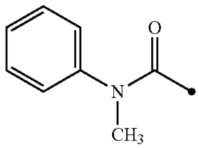 | Me | O |
| 50 | 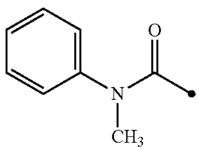 | Me | $CH_2$ |
| 51 | 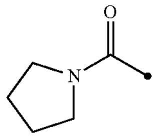 | Me | O |
| 52 | 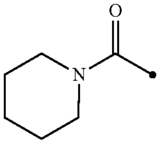 | Me | O |
| 89 | 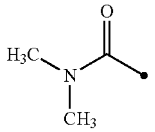 | Me | $CH_2$ |
| 90 | 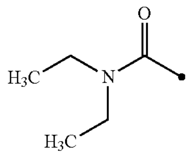 | Me | $CH_2$ |

Present compound 47: $^1$H-NMR ($CDCl_3$) δ: 7.30 (1H, s), 7.10 (1H, d), 6.71-6.65 (1H, m), 6.52-6.49 (1H, m), 3.86 (3H, s), 3.70 (3H, s), 3.47-3.34 (2H, m), 3.03 (1.5H, s), 2.96 (1.5H, s), 2.31 (3H, s), 1.24-1.13 (3H, m).

Present compound 48: $^1$H-NMR ($CDCl_3$) δ: 7.30 (1H, s), 7.10 (1H, d), 6.68 (1H, dd), 6.51 (1H, d), 3.86 (3H, s), 3.71 (3H, s), 3.44-3.32 (4H, m), 2.31 (3H, s), 1.25-1.14 (6H, m).

Present compound 49: $^1$H-NMR ($CDCl_3$) δ: 7.42-7.30 (4H, m), 7.29 (1H, s), 7.27-7.22 (1H, m), 7.09 (1H, d), 6.75-6.61 (1H, br m), 6.51 (1H, br s), 3.85 (3H, s), 3.69 (3H, s), 3.40 (3H, s), 2.30 (3H, s).

Present compound 50: $^1$H-NMR ($CDCl_3$) δ: 7.45 (1H, s), 7.41-7.32 (4H, m), 7.25-7.21 (1H, m), 7.06 (1H, d), 6.86-6.77 (2H, m), 3.83 (3H, s), 3.65 (3H, s), 3.51 (2H, s), 3.41 (3H, s), 2.30 (3H, s).

Present compound 51: $^1$H-NMR ($CDCl_3$) δ: 7.30 (1H, s), 7.10 (1H, d), 6.71 (1H, dd), 6.54 (1H, d), 3.86 (3H, s), 3.70 (3H, s), 3.52 (2H, t), 3.45 (2H, t), 2.31 (3H, s), 1.98-1.85 (4H, m).

Present compound 52: $^1$H-NMR ($CDCl_3$) δ: 7.30 (1H, s), 7.10 (1H, d), 6.67 (1H, dd), 6.50 (1H, d), 3.86 (3H, s), 3.70 (3H, s), 3.62-3.43 (4H, br m), 2.30 (3H, s), 1.69-1.52 (6H, m).

Present compound 89: 1H-NMR ($CDCl_3$) δ: 7.46 (1H, s), 7.07 (1H, d), 6.85-6.80 (2H, m), 3.83 (3H, s), 3.66 (3H, s), 3.52 (2H, s), 3.07 (3H, s), 2.99 (3H, s), 2.31 (3H, s).

Present compound 90: $^1$H-NMR ($CDCl_3$) δ: 7.46 (1H, s), 7.07 (1H, d), 6.87-6.80 (2H, m), 3.83 (3H, s), 3.67 (3H, s), 3.53 (2H, s), 3.46-3.32 (4H, m), 2.31 (3H, s), 1.27-1.15 (6H, m).

Preparation Example 4

To a mixture of the intermediate compound A1 0.25 g, triphosgene 0.10 g, and chloroform 5 mL was added N,N-diisopropylethylamine 0.18 mL at room temperature, and the mixture was stirred for 2 hours. To the resulting mixture were added propyl amine 0.11 mL and N,N-diisopropylethylamine 0.27 mL successively, and the mixture was stirred for 16 hours. Water was added to the resulting mixture, and the mixture was extracted with ethyl acetate. The resulting organic layer was washed with water and saturated brine successively, dried over anhydrous magnesium sulfate, and concentrated under reduced pressure. The resulting residue was subjected to a silica gel column chromatography (ethyl acetate: hexane=1:4) to obtain the present compound 53 represented by the following formula 0.18 g.

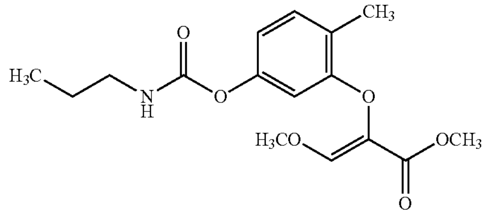 [SMILES: CCCNC(=O)Oc1ccc(C)c(O/C(=C\OC)C(=O)OC)c1]

Present compound 53: $^1$H-NMR ($CDCl_3$) δ: 7.29 (1H, s), 7.10 (1H, d), 6.69 (1H, dd), 6.52 (1H, d), 4.97-4.88 (1H, br m), 3.85 (3H, s), 3.70 (3H, s), 3.20 (2H, q), 2.30 (3H, s), 1.63-1.52 (2H, m), 0.95 (3H, t).

Preparation Example 4-1

The compound which was prepared according to the Preparation Example 4 and its physical property value are shown below.

A compound represented by formula (1a1) wherein a combination of E, $R^1$ and L represents any combinations indicated in [Table 4-1].

TABLE 4-1

| Present compound | E | $R^1$ | L |
|---|---|---|---|
| 54 | 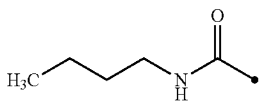 | Me | O |
| 55 | 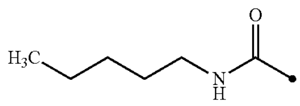 | Me | O |
| 56 | 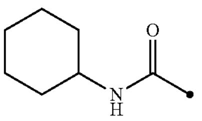 | Me | O |

TABLE 4-1-continued

| Present compound | E | $R^1$ | L |
|---|---|---|---|
| 57 | 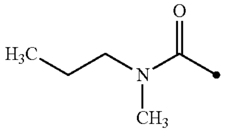 | Me | O |
| 58 | 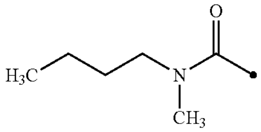 | Me | O |
| 59 | 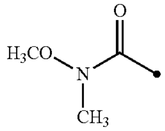 | Me | O |

Present compound 54: $^1$H-NMR ($CDCl_3$) δ: 7.29 (1H, s), 7.10 (1H, d), 6.69 (1H, dd), 6.52 (1H, d), 4.94-4.83 (1H, br m), 3.85 (3H, s), 3.70 (3H, s), 3.24 (2H, q), 2.30 (3H, s), 1.58-1.48 (2H, m), 1.43-1.32 (2H, m), 0.94 (3H, t).

Present compound 55: 1H-NMR ($CDCl_3$) δ: 7.29 (1H, s), 7.10 (1H, d), 6.69 (1H, dd), 6.52 (1H, d), 4.93-4.85 (1H, br m), 3.85 (3H, s), 3.70 (3H, s), 3.23 (2H, q), 2.30 (3H, s), 1.59-1.50 (2H, m), 1.38-1.28 (4H, m), 0.91 (3H, t).

Present compound 56: 1H-NMR ($CDCl_3$) δ: 7.29 (1H, s), 7.09 (1H, d), 6.69 (1H, dd), 6.52 (1H, d), 4.83-4.76 (1H, br m), 3.85 (3H, s), 3.70 (3H, s), 3.58-3.47 (1H, m), 2.30 (3H, s), 2.02-1.94 (2H, m), 1.77-1.66 (2H, m), 1.65-1.57 (1H, m), 1.42-1.29 (2H, m), 1.26-1.12 (3H, m).

Present compound 57: $^1$H-NMR ($CDCl_3$) δ: 7.30 (1H, s), 7.10 (1H, d), 6.71-6.63 (1H, m), 6.52-6.47 (1H, m), 3.86 (3H, s), 3.70 (3H, s), 3.38-3.25 (2H, m), 3.03 (1.4H, s), 2.97 (1.6H, s), 2.31 (3H, s), 1.68-1.58 (2H, m), 0.98-0.90 (3H, m).

Present compound 58: $^1$H-NMR ($CDCl_3$) δ: 7.30 (1H, s), 7.10 (1H, d), 6.71-6.64 (1H, m), 6.51-6.49 (1H, m), 3.86 (3H, s), 3.70 (3H, s), 3.41-3.28 (2H, m), 3.03 (1.4H, s), 2.96 (1.6H, s), 2.30 (3H, s), 1.64-1.52 (2H, m), 1.41-1.30 (2H, m), 0.98-0.92 (3H, m).

Present compound 59: 1H-NMR ($CDCl_3$) δ: 7.30 (1H, s), 7.13 (1H, d), 6.71 (1H, dd), 6.55 (1H, d), 3.86 (3H, s), 3.78 (3H, s), 3.70 (3H, s), 3.26 (3H, s), 2.32 (3H, s).

Preparation Example 5

To a mixture of the intermediate compound A1 0.20 g, propionyl chloride 0.09 mL, and chloroform 5 mL was added triethylamine 0.17 mL, and the mixture was stirred for 16 hours. To the resulting mixture was added water, and the mixture was extracted with ethyl acetate. The resulting organic layer was washed with water and saturated brine successively, dried over anhydrous magnesium sulfate, and concentrated under reduced pressure. The resulting residue was subjected to a silica gel column chromatography (ethyl acetate:hexane=1:4) to obtain the present compound 60 represented by the following formula 0.18 g.

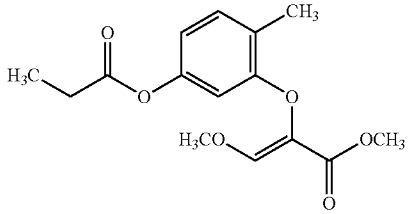 [SMILES: CCC(=O)Oc1ccc(C)c(O/C(=C\OC)C(=O)OC)c1]

Present compound 60: $^1$H-NMR ($CDCl_3$) δ: 7.31 (1H, s), 7.13 (1H, d), 6.66 (1H, dd), 6.48 (1H, d), 3.86 (3H, s), 3.71 (3H, s), 2.54 (2H, q), 2.32 (3H, s), 1.24 (3H, t).

Preparation Example 5-1

The compound which was prepared according to the Preparation Example 5 and its physical property value are shown below.

A compound represented by formula (1a1) wherein a combination of E, $R^1$ and L represents any combinations indicated in [Table 5-1].

TABLE 5-1

| Present compound | E | $R^1$ | L |
|---|---|---|---|
| 61 | 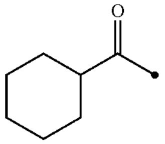 | Me | O |
| 62 | 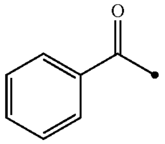 | Me | O |
| 63 | 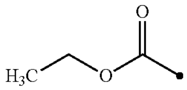 | Me | O |
| 64 | 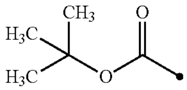 | Me | O |
| 65 | 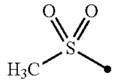 | Me | O |
| 66 | 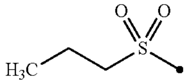 | Me | O |
| 67 | 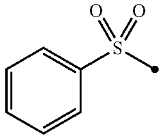 | Me | O |

Present compound 61: $^1$H-NMR ($CDCl_3$) δ: 7.30 (1H, s), 7.11 (1H, d), 6.63 (1H, dd), 6.44 (1H, d), 3.85 (3H, s), 3.70 (3H, s), 2.49 (1H, tt), 2.31 (3H, s), 2.07-1.98 (2H, m), 1.85-1.75 (2H, m), 1.71-1.63 (1H, m), 1.61-1.47 (2H, m), 1.39-1.20 (3H, m).

Present compound 62: ${}^{1}$H-NMR ($CDCl_3$) δ: 8.17 (2H, d), 7.62 (1H, t), 7.49 (2H, t), 7.31 (1H, s), 7.18 (1H, d), 6.79 (1H, dd), 6.60 (1H, d), 3.87 (3H, s), 3.71 (3H, s), 2.35 (3H, s).

Present compound 63: 1H-NMR ($CDCl_3$) δ: 7.31 (1H, s), 7.14 (1H, d), 6.76 (1H, dd), 6.57 (1H, d), 4.29 (2H, q), 3.87 (3H, s), 3.71 (3H, s), 2.32 (3H, s), 1.37 (3H, t).

Present compound 64: ${}^{1}$H-NMR ($CDCl_3$) δ: 7.31 (1H, s), 7.12 (1H, d), 6.77 (1H, dd), 6.55 (1H, d), 3.86 (3H, s), 3.70 (3H, s), 2.31 (3H, s), 1.54 (9H, s).

Present compound 65: 1H-NMR ($CDCl_3$) δ: 7.33 (1H, s), 7.17 (1H, d), 6.83 (1H, dd), 6.68 (1H, d), 3.88 (3H, s), 3.72 (3H, s), 3.07 (3H, s), 2.34 (3H, s).

Present compound 66: ${}^{1}$H-NMR ($CDCl_3$) δ: 7.33 (1H, s), 7.16 (1H, d), 6.81 (1H, dd), 6.66 (1H, d), 3.88 (3H, s), 3.72 (3H, s), 3.18-3.12 (2H, m), 2.33 (3H, s), 2.03-1.91 (2H, m), 1.09 (3H, t).

Present compound 67: ${}^{1}$H-NMR ($CDCl_3$) δ: 7.80 (2H, t), 7.64 (1H, t), 7.50 (2H, t), 7.25 (1H, s), 7.01 (1H, d), 6.46 (1H, dd), 6.42 (1H, d), 3.85 (3H, s), 3.70 (3H, s), 2.28 (3H, s).

Preparation Example 6

To a mixture of the intermediate compound A1 0.18 g, dimethyl carbamoyl chloride 0.11 g and DMF 5 mL was added sodium hydride (60%, oily) 0.05 g at room temperature, and the mixture was stirred for 4 hours. To the resulting mixture was added saturated ammonium chloride aqueous solution, and the mixture was extracted with ethyl acetate. The resulting organic layer was washed with water and saturated brine successively, dried over anhydrous magnesium sulfate, and concentrated under reduced pressure. The resulting residue was subjected to a silica gel column chromatography (ethyl acetate:hexane=1:3) to obtain the present compound 68 represented by the following formula 0.12 g.

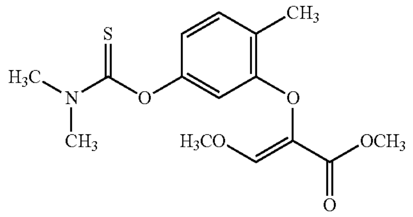 [SMILES: CO/C=C(\Oc1cc(OC(=S)N(C)C)ccc1C)C(=O)OC]

Present compound 68: 1H-NMR ($CDCl_3$) δ: 7.30 (1H, s), 7.15 (1H, d), 6.63 (1H, dd), 6.48 (1H, d), 3.86 (3H, s), 3.71 (3H, s), 3.44 (3H, s), 3.31 (3H, s), 2.33 (3H, s).

Preparation Example 6-1

The compound which was prepared according to the Reference Preparation Example 6 and its physical property value are shown below.

A compound represented by formula (1a1) wherein a combination of E, $R^1$ and L represents any combinations indicated in [Table 6-1].

TABLE 6-1

| Present compound | E | $R^1$ | L |
|---|---|---|---|
| 69 | 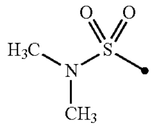 | Me | O |
| 70 | 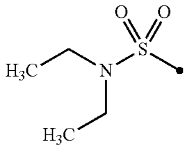 | Me | O |

Present compound 69: ${}^{1}$H-NMR ($CDCl_3$) δ: 7.33 (1H, s), 7.14 (1H, d), 6.83 (1H, dd), 6.69 (1H, d), 3.88 (3H, s), 3.71 (3H, s), 2.90 (6H, s), 2.32 (3H, s).

Present compound 70: 1H-NMR ($CDCl_3$) δ: 7.33 (1H, s), 7.13 (1H, d), 6.81 (1H, dd), 6.67 (1H, d), 3.87 (3H, s), 3.71 (3H, s), 3.30 (4H, q), 2.32 (3H, s), 1.16 (6H, t).

Preparation Example 7

To a mixture of the intermediate compound B1 0.19 g, potassium carbonate 0.10 g and DMF 5 mL was added iodomethane 0.10 mL at 0° C., and the mixture was stirred for 1 hour. To the resulting mixture was added water, and the mixture was extracted with MTBE. The resulting organic layer was washed with water and saturated brine successively, dried over anhydrous magnesium sulfate, and concentrated under reduced pressure. The resulting residue was subjected to a silica gel column chromatography (ethyl acetate: hexane=1:4) to obtain the present compound 40 represented by the following formula 0.09 g.

Preparation Example 8

A mixture of the intermediate compound D2 0.03 g, benzyl alcohol 0.02 g, palladium(II) acetate 0.001 g, 2-(di-t-butylphosphino)-1,1'-binaphtyl 0.002 g, cesium carbonate 0.08 g and toluene 2 mL was stirred at 40° C. for 15 hours. Water was added to the resulting mixture, and the mixture was extracted with ethyl acetate. The resulting organic layer was dried over anhydrous sodium sulfate, and concentrated under reduced pressure to obtain a crude product 0.03 g containing the present compound 40.

Present compound 40: LCMS: 329 $[M+H]^+$, RT=2.08 min.

Preparation Example 9

A mixture of the intermediate compound D1 0.05 g, benzyl alcohol 0.04 g and tBuBrettPhos Pd G3 0.01 g, sodium tert-butoxide 0.03 g, and dioxane 2 mL was stirred at 80° C. for 4 hours. Water was added to the reaction mixture, and the mixture was extracted with ethyl acetate. The resulting organic layer was dried over anhydrous sodium sulfate, and concentrated under reduced pressure to obtain a crude product 0.05 g containing the present compound 28.

Present compound 28: LCMS: 327 $[M+H]^+$, RT=2.22 min.

Next, the present compounds which were prepared according to the Preparation Examples described in the Examples, and the processes described in the Detailed Description, and their intermediate compounds are shown below.

A compound represented by formula (1A):

(1A)

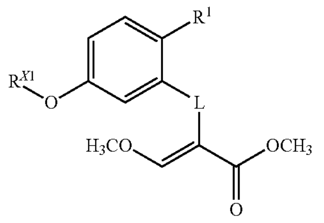

wherein $R^1$ represents a methyl group, L represents an oxygen atom, and $R^{X1}$ represents any substituents selected from Group X (hereinafter, referred to as Compound Class SX1).

Group X: a group consisting of Et,Pr,i-Pr, $(CH_2)_3CH_3$, $CH_2CH(CH_3)_2$,$CH(CH_3)CH_2CH_3$,$C(CH_3)_3$,$CH_2$c-Pr, $(CH_2)_4CH_3$, $(CH_2)_2CH(CH_3)_2$,$CH(CH_3)(CH_2)_2CH_3$,$CH(CH_2CH_3)CH_2CH_3$, $CH_2CH(CH_3)CH_2CH_3$, $C(CH_3)_2CH_2CH_3$, $CH_2C(CH_3)_3$, $CH_2$ c-Bu, $CH_2$ c-Pen, $CH_2$ c-Hex, $(CH_2)_2$c-Pr, (1-methylcyclopropyl)methyl, (2-methylcyclopropyl)methyl, 1-cyclopropylethyl, $(CH_2)_3$c-Pr, $(CH_2)_5CH_3$, $(CH_2)_3CH(CH_3)_2$, $(CH_2)_2CH(CH_3)CH_2CH_3$,$CH_2CH(CH_3)(CH_2)_2CH_3$,$CH(CH_3)(CH_2)_3CH_3$,$CH_2CH(CH_2CH_3)_2$,heptyl,octyl,nonyl ,decyl, $CH_2CH{=}CH_2$, $CH_2CH{=}CHCH_3$, $CH_2CH{=}C(CH_3)_2$, $CH_2CH{=}CF_2$, $CH_2CH{=}CCl_2$, $CH_2CH{=}CHCH_2CH_3$, $CH_2CH{=}CH(CH_2)_2CH_3$, $CH_2C(CH_3){=}CH_2$, $CH_2C(CH\ 3){=}CHCH_3$, $CH_2C(CH_3){=}C(CH_3)_2$, $CH_2C(CH_3){=}CHCH_2CH_3$, $CH_2C(CH_3){=}CH(CH_2)_2CH_3$, $CH_2CF{=}CH_2$, $CH_2CF{=}CHCH_3$, $CH_2CF{=}C(CH_3)_2$, $CH_2CF{=}CF_2$, $CH_2CF{=}CHCH_2CH_3$, $CH_2CF{=}CH(CH_2)_2CH_3$, $CH_2CCl{=}CH_2$, $CH_2CCl{=}CHCH_3$, $CH_2CCl{=}C(CH_3)_2$,$CH_2CCl{=}CCl_2$, $CH_2CCl{=}CHCH_2CH_3$,$CH_2CCl{=}CH(CH_2)_2CH_3$, $(CH_2)_2CH{=}CH_2$, $(CH_2)_2CH{=}CHCH_3$, $(CH_2)_2CH{=}CHCH_2CH_3$, $(CH_2)_2CH{=}C(CH_3)_2$, $(CH_2)_2C(CH_3){=}CH_2$, $(CH_2)_2C(CH_3){=}CHCH_3$, $(CH_2)_2C(CH_3){=}CHCH_2CH_3$, $(CH_2)_2C(CH_3){=}C(CH_3)_2$, $(CH_2)_3CH{=}CH_2$, $(CH_2)_3C(CH_3){=}CH_2$, $(CH_2)_4CH{=}CH_2$, $(CH_2)_4C(CH_3){=}CH_2$, $CH_2C{=}CH$, $CH_2C{=}CCH_3$, $CH_2C{=}CCH_2CH_3$, $CH_2C{=}C$ C-Pr, $CH_2C{=}CPh$, $(CH_2)_2C{=}CH$, $(CH_2)_2C{=}CCH_3$, $(CH_2)_2C{=}CCH_2CH_3$, $(CH_2)_2C \equiv Cc$—Pr, $(CH_2)_2{\equiv}CcPh$, $(CH_2)_3C{=}CH$, $(CH_2)_3C{=}CCH_3$, $(CH_2)_3C{=}CCH_2CH_3$, $(CH_2)_3C{=}Cc$—Pr, $(CH_2)_3C{=}CPh$, $CH_2Cl$, $CH_2Br$, $CH_2CN$, $CH_2OCH_3$, $CH_2OCH_2CH_3$, $CH_2O(CH\ 2)_2CH_3$, $CH_2OPh$, $CH_2SCH_3$, $CH_2S(O)CH_3$, $CH_2S(O)_2CH_3$, $CH_2SCH_2CH_3$, $CH_2S(O)CH_2CH_3$,$CH_2S(O)_2CH_2CH_3$, $CH_2S(CH_2)_2CH_3$,$CH_2S(O)(CH_2)_2CH_3$,$CH_2S(O)_2(CH_2)_2CH_3$,$CH_2SPh$,$CH_2S(O)Ph$,$CH_2S(O)_2Ph$,$CH_2C(O)CH_3$,$CH_2C(O)CH_2CH_3$, $CH_2C(O)\ Ph$, $CH_2C(O)NH_2$, $CH_2C(O)NHCH_3$, $CH_2C(O)N(CH_3)_2$, $CH_2C(O)NHPh$, $CH_2C(O)N(CH_3)\ Ph$, $CH_2C(O)\ OCH_3$, $CH_2C(O)\ OCH_2CH_3$, $CH_2OC(O)\ Ph$, $CH_2OC(O)\ OCH_3$, $CH_2OC(O)\ OCH_2CH_3$, $CH_2OC(O)\ OPh$, $CH_2OC(O)NHCH_3$,$CH_2OC(O)NHCH_2CH_3$,$CH_2OC(O)NHPh$,$CH_2OC(O)N(CH_3)_2$, $CH_2OC(O)N(CH_3)CH_2CH_3$,$CH_2OC(O)N(CH_3)\ Ph$, $CH_2OC(O)N(CH_2CH_3)_2$,$CH_2$ (2-oxiranyl),$CH_2$ (2-tetrahydrofuranyl),$CH_2$ (2-tetrahydropyranyl), $CH_2CH{=}NOCH_3$, $CH_2CH{=}NOCH_2CH_3$, $CH_2CH{=}NOCH_2Ph$ ,$CH_2C(CH_3){=}NOCH_3$, $CH_2C(CH_3){=}NOCH_2CH_3$, $CH_2C(CH_3){=}NOCH_2Ph$, $(CH_2)_2F$,$CH_2CF_3$, $(CH_2)_2C1$,$CH_2CCl_3$, $(CH_2)_2Br$, $(CH_2)_{21}$,$CH_2Si(CH_3)_3$, $(CH_2)_2CF_3$, $(CH_2)_2CN$, $(CH_2)_2NO_2$, $(CH_2)_2Si(CH_3)_3$, $(CH_2)_2OCH_3$, $(CH_2)_2OCH_2CH_3$, $(CH_2)_2SCH_3$, $(CH_2)_2SCH_2CH_3$, $(CH_2)_2SPh$, $(CH_2)_2S(O)CH_3$, $(CH_2)_2S(O)CH_2CH_3$, $(CH_2)_2S(O)Ph$, $(CH_2)_2S(O)_2CH_3$, $(CH_2)_2S(O)_2CH_2CH_3$, $(CH_2)_2S(O)_2Ph$, $(CH_2)_2NHCH_3$, $(CH_2)_2N(CH_3)_2$, $(CH_2)_2NHPh$, $(CH_2)_2NHCH_2Ph$, $(CH_2)_2N(CH_3)CH_2Ph$, $(CH_2)_2C(O)CH_3$, $(CH_2)_2C(O)CH_2CH_3$, $(CH\ 2)_2C(O)Ph$, $(CH_2)_2S(O)_2NHCH_3$, $(CH_2)_2S(O)_2N(CH_3)_2$, $(CH_2)_2S(O)_2NH\ Ph$, $(CH_2)_2S(O)_2N(CH_3)Ph$, $(CH_2)_2C(O)NH_2$, $(CH_2)_2C(O)NHCH_3$, $(CH_2)_2$, $C(O)N(CH_3)_2$, $(CH_2)_2C(O)NHPh$, $(CH_2)_2C(O)N(CH_3)Ph$, $(CH_2)_2C(O)OCH_3$, $(CH_2)_2C(O)OCH_2CH_3$, $(CH_2)_2NHC(O)CH_3$, $(CH_2)_2NHC(O)CH_2CH_3$, $(CH_2)_2NHC(O)Ph$, $(CH_2)_2NCH_3C(O)CH_3$, $(CH_2)_2NCH_3C(O)CH_2CH_3$, $(CH_2)_2NCH_3C(O)Ph$, $(CH_2)_2NHC(O)OCH_3$, $(CH_2)_2NHC(O)OCH_2CH_3$, $(CH_2)_2NHC(O)OP\ h$, $(CH_2)_2NCH_3C(O)OCH_3$, $(CH_2)_2NCH_3C(O)\ OCH_2CH_3$, $(CH_2)_2NCH_3C(O)OP\ h$, $(CH_2)_2NHC(O)NHCH_3$, $(CH_2)_2NHC(O)NHCH_2CH_3$, $(CH_2)_2NHC(O)NHPh$, $(CH_2)_2NHC(O)N(CH_3)_2$, $(CH_2)_2NHC(O)N(CH_3)CH_2CH_3$, $(CH_2)_2NHC(O)N(CH_3)Ph$, $(CH_2)_2NHC(O)N(CH_2CH_3)_2$, $(CH_2)_2NCH_3C(O)NHCH_3$, $(CH_2)_2NCH_3C(O)NHCH_2CH_3$, $(CH_2)_2NCH_3C(O)NHPh$, $(CH_2)_2NCH_3C(O)N(CH_3)_2$, $(CH_2)_2NCH_3C(O)N(CH_3)CH_2CH_3$, $(CH_2)_2NCH_3C(O)N(CH_3)$ Ph, $(CH_2)_2NCH_3C(O)\ N(CH_2CH_3)_2$, $(CH_2)_2OC(O)CH_3$, $(CH_2)_2OC(O)CH_2CH_3$, $(CH_2)_2OC(O)Ph$, $CH_2)_2OC(O)OCH_3$, $(CH_2)_2C(O)OCH_2CH_3$, $(CH_2)_2OC(O)OPh$, $(CH_2)_2OC(O\ )NHCH_3$, $(CH_2)_2OC(O)NHCH_2CH_3$, $(CH_2)_2OC(O)NHPh$, $(CH_2)_2OC(O)N(CH_3)_2$, $(CH_2)_2OC(O)N(CH_3)CH_2CH_3$, $(CH_2)_2OC(O)N(CH_3)$ Ph, $(CH_2)_2OC(O)N(CH_2CH_3)_2$, $(CH_2)_2S(O)_2NHCH_3$, $(CH_2)_2S(O)_2NHCH_2CH_3$, $(CH_2)_2S(O)_2N\ HPh$, $(CH_2)_2S(O)_2N(CH_3)_2$, $(CH_2)_2S(O)_2N(CH_3)CH_2CH_3$, $(CH_2)_2S(O)_2N(CH_3)Ph$, $(CH_2)_2S(O)_2N(CH_2CH_3)_2$, $(CH_2)_3F$, $(CH_2)_3Cl$, $(CH_2)_3Br$, $(CH_2)_3I$, $(CH_2)_3CF_3$, $(CH_2)_3CN$, $(CH_2)_3NO_2$, $(CH_2)_3Si(CH_3)_3$, $(CH_2)_3OCH_3$, $(CH_2)_3OCH_2CH_3$, $(CH_2)_3SCH_3$, $(CH_2)_3SCH_2CH_3$, $(CH_2)_3NHCH_3$, $(CH_2)_3N(CH_3)_2$, $(CH_2)_4F$, $(CH_2)_4Cl$, $(CH_2)_4CF_3$, $(CH_2)_4CN$, $(CH_2)_4NO_2$, $(CH_2)_4Ph$, $(CH_2)_4OCH_3$, $(CH_2)_4SCH_3$, $(CH_2)_4NHCH_3$, $(CH_2)_4N(CH_3)_2$, $(CH_2)_5F$, $(CH_2)_5Cl$, $(CH_2)_5CF_3$, $(CH_2)_5CN$, $(CH_2)_5NO_2$, $(CH_2)_5Ph$, $(CH_2)OCH_3$, $(CH_2)_5SCH_3$, $(CH_2)_5NHCH_3$, $(CH_2)_5N(CH_3)_2$, $(CH_2)_6F$, $(CH_2)_6Cl$, $(CH_2)_6CF_3$, $(CH_2)_6CN$, $(CH_2)_6NO_2$, $(CH_2)_6Ph$, $(CH_2)_6OCH_3$, $(CH_2)_6SCH_3$, $(CH_2)_6NHCH_3$, $(CH_2)_6N(CH_3)_2$,$CH_2CF_2CF_3$, $(CH_2)_2CF_2CF_3$,$CH_2(CF_2)_2CF_3$, $(CH_2)_2CF(CF_3)_2$, $(CH_2)_2(CF_2)_5CF_3$,$CF_3$,$CF_2CHF(CF_3)$, and $CF_2CHF(OCF_3)$,$CH_2CF_2CF_2H$.

The compound represented by formula (A1) wherein $R^1$ represents a chlorine atom, L represents an oxygen atom, and $R^{X1}$ represents any substituents selected from Group X (hereinafter, referred to as Compound Class SX2).

The compound represented by formula (1A) wherein $R^1$ represents a methyl group, L represents $CH_2$, and $R^{X1}$represents any substituents selected from Group X (hereinafter, referred to Compound Class SX3).

The compound represented by formula (1A) wherein $R^1$ represents a chlorine atom, L represents $CH_2$, and $R^{X1}$represents any substituents selected from Group X (hereinafter, referred to Compound Class SX4).

A compound represented by formula (1B):

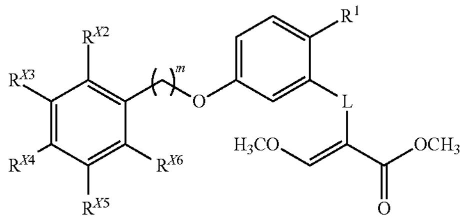

(1B)

wherein, $R^1$ represents a methyl group, L represents an oxygen atom, m is 1, and a combination of $R^{X2}$, $R^{X3}$, $R^{X4}$, $R^{X5}$, and $R^{X6}$ represents any combinations described in a combination A below (hereinafter, referred to as Compound Class SX5).

The combination A consists of Substituent Nos. ZA1 to ZA311. The Substituents Nos. ZA1 to ZA311 represent any combinations of $R^{X2}$, $R^{X3}$, $R^{X4}$, $R^{X5}$, and $R^{X6}$ respectively in the compound represented by formula (1B), the compound represented by formula (2B), and the compound represented by formula (3B), which are described below as [Substituent No. $R^{X2}$, $R^{X3}$, $R^{X4}$, $R^{X5}$, $R^{X6}$]. For example, Substituent No. ZA2 represents a combination wherein $R^{X2}$ represents a methyl group, and a combination of $R^{X3}$, $R^{X4}$, $R^{X5}$, and $R^{X6}$ represents a hydrogen atom.

Combination A

[ZA1;H,H,H,H,H], [ZA2;Me,H,H,H,H], [ZA3;F,H,H,H,H], [ZA4;C1,H, H,H,H], [ZA5;OMe,H,H,H,H], [ZA6;$CF_3$,H,H,H,H], [ZA7;H,Me,H,H,H], [ZA8;H,Et,H,H,H], [ZA9;H,Pr,H,H,H], [ZA10;H,i-Pr,H,H,H], [ZA11;H,t-Bu,H,H,H], [ZA12;H,OMe,H,H,H],[ZA13;H,OEt,H,H,H],[ZA14;H,OPr ,H,H,H], [ZA15;H,Oi-Pr,H,H,H], [ZA16;H,$CF_3$,H,H,H], [ZA17;H,$CF_2$H,H,H,H], [ZA18;H,CF $H_2$,H,H,H], [ZA19;H,F,H,H,H], [ZA20;H,C1,H,H,H], [ZA21;H,Br,H,H ,H], [ZA22;H,CN,H,H,H], [ZA23;H,Ph,H,H,H], [ZA24;H,OPh,H,H,H], [ZA25;H,c-Pr,H,H,H],[ZA26;H,c-Pen,H,H,H],[ZA27;H,c-Hex,H,H,H], [ZA28;H,H,Me,H,H], [ZA29;H,H,Et,H,H], [ZA30;H,H,Pr ,H,H],[ZA31;H,H,i-Pr,H,H],[ZA32;H,H,t-Bu,H,H],[ZA33;H,H,OMe,H,H],[ZA34;H,H,OEt,H,H],[ZA35;H,H,OPr ,H,H], [ZA36;H,H,Oi-Pr,H,H], [ZA37;H,H,$CF_3$,H,H], [ZA38;H,H,$CF_2$H,H,H], [ZA39;H,H,CF $H_2$,H,H], [ZA40;H,H,F,H,H], [ZA41;H,H,C1,H,H], [ZA42;H,H,Br,H,H], [ZA43;H,H,CN,H,H], [ZA44;H,H,Ph,H,H], [ZA45;H,H,OPh,H,H], [Z A46;H,H,c-Pr,H,H], [ZA47;H,H,c-Pen,H,H], [ZA48;H,H,c-Hex,H,H], [ZA49;H,H,H,H,F], [ZA50;Me,H,H,H,F], [ZA51;F,H,H,H,F], [ZA52;C1,H,H,H,F], [ZA53;H,Me,H,H,F], [ZA54;H,Et,H,H,F], [ZA 55;H,Pr,H,H,F], [ZA56;H,i-Pr,H,H,F], [ZA57;H,t-Bu,H,H,F], [ZA58;H,OMe,H,H,F], [ZA59;H,OEt,H,H,F], [ZA60;H,OPr,H,H,F], [ZA61;H,Oi-Pr,H,H,F], [ZA62;H,$CF_3$,H,H,F], [ZA63;H,$CF_2$H,H,H,F], [ZA64;H,CF $H_2$,H,H,F], [ZA65;H,F,H,H,F], [ZA66;H,C1,H,H,F], [ZA67;H,Br,H,H ,F], [ZA68;H,CN,H,H,F], [ZA69;H,Ph,H,H,F], [ZA70;H,OPh,H,H,F], [ZA71;H,c-Pr,H,H,F], [ZA72;H,c-Pen,H,H,F], [ZA73;H,c-Hex,H,H,F], [ZA74;H,H,Me,H,F], [ZA75;H,H,Et,H,F], [ZA76;H,H,Pr ,H,F], [ZA77;H,H,i-Pr,H,F], [ZA78;H,H,t-Bu,H,F], [ZA79;H,H,OMe,H,F], [ZA80;H,H,OEt,H,F], [ZA81;H,H,OPr ,H,F], [ZA82;H,H,Oi-Pr,H,F], [ZA83;H,H,$CF_3$,H,F], [ZA84;H,H,$CF_2$H,H,F], [ZA85;H,H,CF $H_2$,H,F], [ZA86;H,H,F,H,F], [ZA87;H,H,C1,H,F], [ZA88;H,H,Br,H,F], [ZA89;H,H,CN,H,F], [ZA90;H,H,Ph,H,F], [ZA91;H,H,OPh,H,F], [Z A92;H,H,c-Pr,H,F], [ZA93;H,H,c-Pen,H,F], [ZA94;H,H,c-Hex,H,F], [ZA95;H,H,H,H,C1], [ZA96;Me,H,H,H,C1], [ZA97;F,H,H,H ,C1], [ZA98;C1,H,H,H,C1], [ZA99;H,Me,H,H,C1], [ZA100;H,Et,H,H,C1]

[ZA101;H,Pr,H,H,C1],[ZA102;H,i-Pr,H,H,C1],[ZA103;H,t-Bu,H,H,C1],[ZA104;H,OMe,H,H,C1],[ZA105;H,OEt,H,H,C1],[ZA106;H,OPr,H,H,C1], [ZA107;H,Oi-Pr,H,H,C1],[ZA108;H,$CF_3$,H,H,C1],[ZA109;H,$CF_2$H,H,H,C1], [ZA11 0;H,$CFH_2$,H,H,C1], [ZA111;H,F,H,H,C1], [ZA112;H,C1,H,H,C1], [ZA 113;H,Br,H,H,C1], [ZA114;H,CN,H,H,C1], [ZA115;H,Ph,H,H,C1], [Z A116;H,OPh,H,H,C1], [ZA117;H,c-Pr,H,H,C1],[ZA118;H,c-Pen,H,H,C1], [ZA119;H,c-Hex,H,H,C1], [ZA120;H,H,Me,H,C1], [ZA121;H,H,Et,H,C1], [ZA122; H,H,Pr,H,C1], [ZA123;H,H,i-Pr,H,C1], [ZA124;H,H,t-Bu,H,C1],[ZA125;H,H,OMe,H,C1],[ZA126;H,H,OEt,H,C1],[ZA127;H ,H,OPr,H,C1], [ZA128;H,H,Oi-Pr,H,C1],[ZA129;H,H,$CF_3$,H,C1],[ZA130;H,H,$CF_2$H,H,C1],[ZA131; H,H,$CFH_2$,H,C1],[ZA132;H,H,F,H,C1],[ZA133;H,H,C1,H,C1],[ZA13 4;H,H,Br,H,C1], [ZA135;H,H,CN,H,C1], [ZA136;H,H,Ph,H,C1], [ZA1 37;H,H,OPh,H,C1], [ZA138;H,H,c-Pr,H,C1], [ZA139;H,H,c-Pen,H,C1], [ZA140;H,H,c-Hex,H,C1], [ZA141;H,H,H,H,Me], [ZA142;Me,H,H,H,Me], [ZA143;F,H ,H,H,Me], [ZA144;C1,H,H,H,Me],[ZA145;H,Me,H,H,Me],[ZA146;H,E t,H,H,Me],[ZA147;H,Pr,H,H,Me],[ZA148;H,i-Pr,H,H,Me], [ZA149;H,t-Bu,H,H,Me],[ZA150;H,OMe,H,H,Me], [ZA151;H,OEt,H,H,Me], [ZA152;H,OPr,H,H,Me], [ZA153;H,Oi-Pr,H,H,Me],[ZA154;H,$CF_3$,H,H,Me], [ZA155;H,$CF_2$H,H,H,Me],[ZA15 6;H,$CFH_2$,H,H,Me], [ZA157;H,F,H,H,Me],[ZA158;H,C1,H,H,Me],[ZA 159;H,Br,H,H,Me], [ZA160;H,CN,H,H,Me], [ZA161;H,Ph,H,H,Me], [Z A162;H,OPh,H,H,Me],[ZA163;H,c-Pr,H,H,Me], [ZA164;H,c-Pen,H,H,Me], [ZA165;H,c-Hex,H,H,Me], [ZA166;H,H,Me,H,Me],[ZA167;H,H,Et,H,Me],[ZA168;H,H,Pr,H,Me], [ZA169;H,H,i-Pr,H,Me], [ZA170;H,H,t-Bu,H,Me], [ZA171;H,H,OMe,H,Me],[ZA172;H,H,OEt,H,Me], [ZA173;H ,H,OPr,H,Me], [ZA174;H,H,Oi-Pr,H,Me], [ZA175;H,H,$CF_3$,H,Me],[ZA176;H,H,$CF_2$H,H,Me], [ZA177; H,H,$CFH_2$,H,Me],[ZA178;H,H,F,H,Me],[ZA179;H,H,C1,H,Me],[ZA18 0;H,H,Br,H,Me], [ZA181;H,H,CN,H,Me], [ZA182;H,H,Ph,H,Me], [ZA1 83;H,H,OPh,H,Me], [ZA184;H,H,c-Pr,H,Me],[ZA185;H,H,c-Pen,H,Me], [ZA186;H,H,c-Hex,H,Me],[ZA187;H,H,H,H,OMe], [ZA188;Me,H,H,H,OMe],[ZA189;F ,H,H,H,OMe], [ZA190;C1,H,H,H,OMe],[ZA191;H,Me,H,H,OMe],[ZA19 2;H,Et,H,H,OMe],[ZA193;H,Pr,H,H,OMe],[ZA194;H,i-Pr,H,H,OMe], [ZA195;H,t-Bu,H,H,OMe], [ZA196;H,OMe,H,H,OMe], [ZA197;H,OEt,H,H,OMe], [ZA 198;H,OPr,H,H,OMe],[ZA199;H,Oi-Pr,H,H,OMe], [ZA200;H,$CF_3$,H,H,OMe]

[ZA201;H,$CF_2$H,H,H,OMe], [ZA202;H,$CFH_2$,H,H,OMe], [ZA203;H,F,H, H,OMe],[ZA204;H,C1,H,H,OMe], [ZA205;H,Br,H,H,OMe],[ZA206;H,C N,H,H,OMe], [ZA207;H,Ph,H,H,OMe],[ZA208;H,OPh,H,H,OMe],[ZA20 9;H,c-Pr,H,H,OMe],[ZA210;H,c-Pen,H,H,OMe],[ZA211;H,c-Hex,H,H,OMe],[ZA212;H,H,Me,H,OMe],[ZA213;H,H,Et,H,OMe],[ZA2 14;H,H,Pr,H,OMe],[ZA215;H,H,i-Pr,H,OMe],[ZA216;H,H,t-Bu,H,OMe],

[ZA217;H,H,OMe,H,OMe], [ZA218;H,H,OEt,H,OMe], [ZA21 9;H,H,OPr,H,OMe], [ZA220;H,H,Oi-Pr,H,OMe], [ZA221;H,H,$CF_3$,H,OMe], [ZA222;H,H,$CF_2$H,H,OMe], [ZA2 23;H,H,$CFH_2$,H,OMe], [ZA224;H,H,F,H,OMe], [ZA225;H,H,C1,H,OMe], [ZA226;H,H,Br,H,OMe], [ZA227;H,H,CN,H,OMe], [ZA228;H,H,Ph,H, OMe], [ZA229;H,H,OPh,H,OMe],[ZA230;H,H,c-Pr,H,OMe], [ZA231;H,H,c-Pen,H,OMe],[ZA232;H,H,c-Hex,H,0Me], [ZA233;H,H,H,H,$CF_3$],[ZA234;Me,H,H,H,$CF_3$],[ZA235;F,H,H,H,$CF_3$], [ZA236;C1,H,H,H,$CF_3$], [ZA237;H, Me,H,

H,$CF_3$], [ZA2 38;H,Et,H,H,$CF_3$], [ZA239;H,Pr,H,H,$CF_3$], [ZA240;H,i-Pr,H,H,$CF_3$], [ZA241;H,t-Bu,H,H,$CF_3$], [ZA242;H,OMe,H,H,$CF_3$], [ZA243;H,OEt,H,H,$CF_3$], [ZA 244;H,OPr,H,H,$CF_3$], [ZA245;H,Oi-Pr,H,H,$CF_3$], [ZA246; H,$CF_3$,H,H,$CF_3$], [ZA247;H,$CF_2$H,H,H,$CF_3$], [Z A248;H, $CFH_2$,H,H,$CF_3$], [ZA249;H,F,H,H,$CF_3$], [ZA250;H,C1,H, H,CF 3],[ZA251;H,Br,H,H,$CF_3$],[ZA252;H,CN,H,H,$CF_3$], [ZA253;H,Ph,H, H,$CF_3$],[ZA254;H,OPh,H,H,$CF_3$], [ZA255;H,c-Pr,H,H,$CF_3$], [ZA256;H,c-Pen,H,H,$CF_3$], [ZA257;H,c-Hex,H,H,$CF_3$],[ZA258;H,H,Me,H,$CF_3$], [ZA259;H,H,Et,H,$CF_3$],[ZA2 60;H,H,Pr,H,$CF_3$], [ZA261; H,H,i-Pr,H,$CF_3$], [ZA262;H,H,t-Bu,H,$CF_3$], [ZA263;H,H, OMe,H,$CF_3$], [ZA264;H,H,OEt,H,$CF_3$], [ZA26 5;H,H,OPr, H,$CF_3$], [ZA266;H,H,Oi-Pr,H,$CF_3$], [ZA267;H,H,$CF_3$,H, $CF_3$], [ZA268;H,H,$CF_2$H,H,$CF_3$], [ZA2 69;H,H,$CFH_2$,H, $CF_3$], [ZA270;H,H,F,H,$CF_3$], [ZA271;H,H,C1,H,$CF_3$], [ZA272;H,H,Br,H,$CF_3$], [ZA273;H,H,CN,H,$CF_3$], [ZA274; H,H,Ph,H, $CF_3$],[ZA275;H,H,OPh,H,$CF_3$],[ZA276;H,H,c-Pr,H,$CF_3$],[ZA277;H,H,c-Pen,H,$CF_3$],[ZA278;H,H,c-Hex, H,$CF_3$], [ZA279;H,F,F,H,H], [ZA280;H,F,H,F,H], [ZA281; H,F,F ,F,H], [ZA282;F,F,F,H,H], [ZA283;F,F,H,F,H], [ZA284;F,H,F,H,F], [ZA285;F,F,F,F,F], [ZA286;H,C1,H, C1,H], [ZA287;H,OMe,H,OMe,H], [ZA288;H,F,C1,H,H], [ZA289;H,F,Me,H,H], [ZA290;H,F,OMe,H,H], [ZA291;H, F,$CF_3$,H,H], [ZA292;H,C1,F,H,H], [ZA293;H,C1,C1,H,H], [ZA294;H,C1,Me,H,H], [ZA295;H,C1,OMe,H,H], [ZA296; H,C1,$CF_3$,H ,H], [ZA297;H,Me,F,H,H], [ZA298;H,Me,C1, H,H], [ZA299;H,Me,Me,H ,H], [ZA300;H,Me,OMe,H,H], [ZA301;H,Me,$CF_3$,H,H], [ZA302;H,OMe,F,H,H], [ZA303;H,OMe,C1,H, H],[ZA304;H,OMe,Me,H,H], [ZA305;H,OMe,OMe,H,H],[ZA306;H,OMe, $CF_3$,H,H], [ZA307;H,$CF_3$,F,H,H], [ZA308;H,$CF_3$,C1,H,H], [ZA309; H, $CF_3$,F,H,H], [ZA310;H,$CF_3$,C1,H,H], [ZA311;H,$CF_3$,F, H,H]

The compound represented by formula (1B) wherein $R^1$ represents a chlorine atom, L represents an oxygen atom, m is 1, and a combination of $R^{X2}$, $R^{X3}$, $R^{X4}$, $R^{X5}$ and $R^{X6}$ represents any combinations described in the Combination A (hereinafter, referred to as Compound Class SX6).

The compound represented by formula (1B) wherein $R^1$ represents a methyl group, L represents $CH_2$, m is 1, and a combination of $R^{X2}$, $R^{X3}$, $R^{X4}$, $R^{X5}$ and $R^{X6}$ represents any combinations described in the Combination A (hereinafter, referred to as Compound Class SX7).

The compound represented by formula (1B) wherein $R^1$ represents a chlorine atom, L represents $CH_2$, m is 1, and a combination of $R^{X2}$, $R^{X3}$, $R^{X4}$, $R^{X5}$ and $R^{X6}$ represents any combinations described in the Combination A (hereinafter, referred to as Compound Class SX8).

The compound represented by formula (1B) wherein $R^1$ represents a methyl group, L represents an oxygen atom, m is 2, and a combination of $R^{X2}$, $R^{X3}$, $R^{X4}$, $R^{X5}$ and $R^{X6}$ represents any combinations descried in the Combination A (hereinafter, referred to as Compound Class SX9).

The compound represented by formula (1B) wherein $R^1$ represents a chlorine atom, L represents an oxygen atom, m is 2, and a combination of $R^{X2}$, $R^{X3}$, $R^{X4}$, $R^{X5}$ and $R^{X6}$ represents any combinations descried in the Combination A (hereinafter, referred to as Compound Class SX10).

The compound represented by formula (1B) wherein $R^1$ represents a methyl group, L represents $CH_2$, m is 2, and a combination of $R^{X2}$, $R^{X3}$, $R^{X4}$, $R^{X5}$ and $R^{X6}$ represents any combinations descried in the Combination A (hereinafter, referred to as Compound Class SX11).

The compound represented by formula (1B) wherein $R^1$ represents a chlorine atom, L represents $CH_2$, m is 2, and a combination of $R^{X2}$, $R^{X3}$, $R^{X4}$, $R^{X5}$ and $R^{X6}$ represents any combinations descried in the Combination A (hereinafter, referred to as Compound Class SX12).

The compound represented by formula (1B) wherein $R^1$ represents a methyl group, L represents an oxygen atom, m is 3, and a combination of $R^{X2}$, $R^{X3}$, $R^{X4}$, $R^{X5}$ and $R^{X6}$ represents any combinations descried in the Combination A (hereinafter, referred to as Compound Class SX13).

The compound represented by formula (1B) wherein $R^1$ represents a chlorine atom, L represents an oxygen atom, m is 3, and a combination of $R^{X2}$, $R^{X3}$, $R^{X4}$, $R^{X5}$ and $R^{X6}$ represents any combinations descried in the Combination A (hereinafter, referred to as Compound Class SX14).

The compound represented by formula (1B) wherein $R^1$ represents a methyl group, L represents $CH_2$, m is 3, and a combination of $R^{X2}$, $R^{X3}$, $R^{X4}$, $R^{X5}$ and $R^{X6}$ represents any combinations descried in the Combination A (hereinafter, referred to as Compound Class SX15).

The compound represented by formula (1B) wherein $R^1$ represents a chlorine atom, L represents $CH_2$, m is 3, and a combination of $R^{X2}$, $R^{X3}$, $R^{X4}$, $R^{X5}$ and $R^{X6}$ represents any combinations descried in the Combination A (hereinafter, referred to as Compound Class SX16).

A compound represented by formula (1C):

(1C)

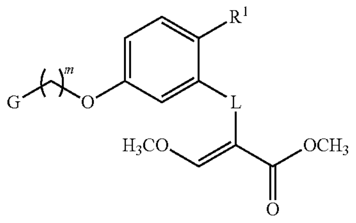

[wherein

G represents any one of the following formulae G1 to G28:

G1

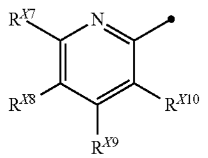

G2

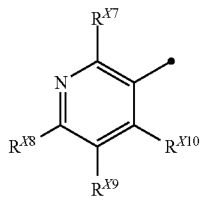

G3

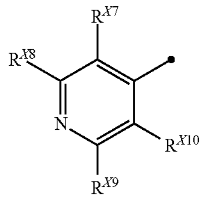

-continued
G4
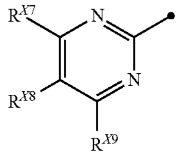
G5
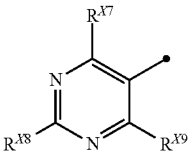
G6
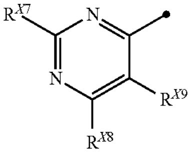
G7
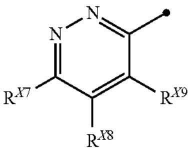
G8
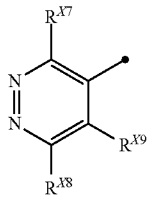
G9
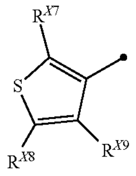
G10
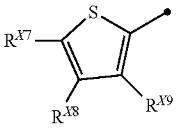
G11
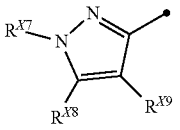
G12
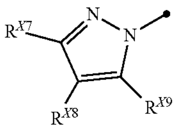
-continued
G13
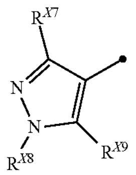
G14
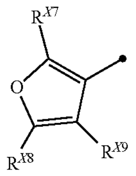
G15
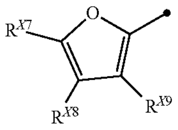
G16
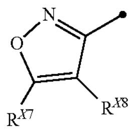
G17
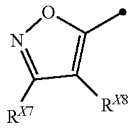
G18
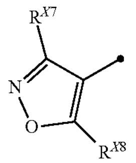
G19
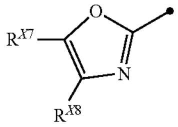
G20
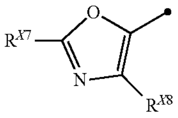
G21
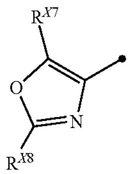
G22
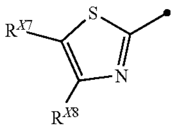

-continued

G23

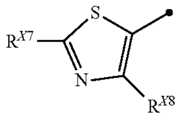

G24

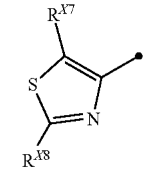

G25

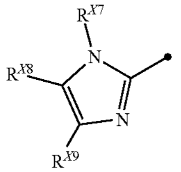

G26

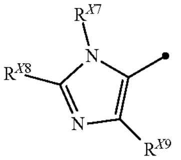

G27

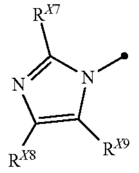

G28

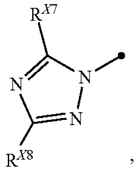

, $R^1$ represents a methyl group, L represents an oxygen atom, m is 1, and a combination of a structure of G and the substituents of $R^{X7}$, $R^{X8}$, $R^{X9}$, and $RX^{10}$ which depend on the structure of G represent any combinations described in the Combination B (hereinafter, referred to as Compound Class SX17).

The Combination B consists of Substituent Nos. ZB1 to ZB1145. The Substituent Nos. ZB1 to ZB1145 represents a combination of a structure of G and the substituents of $R^{X7}$, $R^{X8}$, $R^{X9}$, and $RX^{10}$ which depend on the structure of G in the compound represented by formula (1C), the compound represented by formula (2C), and the compound represented by formula (3C), which are described below as [Substituent No.: G, $R^{X7}$, $R^{X8}$, $R^{X9}$, $R^{X10}$]. For example, Substituent No. ZB2 represents a combination wherein G represents G1, $R^{X7}$ represents a methyl group, and a combination of $R^{X8}$, $R^{X9}$, and $R^{X10}$ represents a hydrogen atom.

Combination B

[ZB1;G1,H,H,H,H], [ZB2;G1,Me,H,H,H], [ZB3;G1,Et, H,H,H], [ZB4;G 1,Pr,H,H,H], [ZB5;G1,i-Pr,H,H,H], [ZB6; G1,c-Pr,H,H,H], [ZB7;G1,Ph,H,H,H], [ZB8;G1,OMe,H,H, H], [ZB9;G1,OEt, H,H,H],[ZB10;G1,OPh,H,H,H],[ZB11; G1,$CF_3$,H,H,H],[ZB12;G1,F,H ,H,H], [ZB13;G1,C1,H,H, H], [ZB14;G1,Br,H,H,H], [ZB15;G1,CN,H,H ,H],[ZB16; G1,H,Me,H,H],[ZB17;G1,H,Et,H,H],[ZB18;G1,H,Pr,H,H], [ZB19;G1,H,i-Pr,H,H],[ZB20;G1,H,c-Pr,H,H], [ZB21;G1, H,Ph,H,H], [ZB22;G1,H,OMe,H,H], [ZB23;G1,H,0 Et,H, H],[ZB24;G1,H,OPh,H,H],[ZB25;G1,H,$CF_3$,H,H],[ZB26; G1,H, F,H,H], [ZB27;G1,H,C1,H,H], [ZB28;G1,H,Br,H,H], [ZB29;G1,H,CN, H,H], [ZB30;G1,H,H,Me,H], [ZB31;G1, H,H,Et,H], [ZB32;G1,H,H,Pr, H], [ZB33;G1,H,H,i-Pr,H], [ZB34;G1,H,H,c-Pr,H], [ZB35;G1,H,H,Ph,H], [ZB36;G1, H,H,OMe,H], [ZB37;G1,H,H,0 Et,H], [ZB38;G1,H,H,OPh, H], [ZB39;G1,H,H,$CF_3$,H], [ZB40;G1,H,H, F,H], [ZB41; G1,H,H,C1,H], [ZB42;G1,H,H,Br,H], [ZB43;G1,H,H,CN, H], [ZB44;G1,H,H,H,Me], [ZB45;G1,H,H,H,Et], [ZB46; G1,H,H,H,Pr],[ZB47;G1,H,H,H,i-Pr],[ZB48;G1,H,H,H,c-Pr], [ZB49;G1,H,H,H,Ph], [ZB50;G1,H,H,H,OMe], [ZB51; G1,H,H,H,O Et], [ZB52;G1,H,H,H,OPh], [ZB53;G1,H,H, H,$CF_3$], [ZB54;G1,H,H,H, F], [ZB55;G1,H,H,H,C1], [ZB56;G1,H,H,H,Br], [ZB57;G1,H,H,H,CN], [ZB58;G2,H, H,H,H], [ZB59;G2,Me,H,H,H], [ZB60;G2,Et,H,H,H], [Z B61;G2,Pr,H,H,H], [ZB62;G2,i-Pr,H,H,H], [ZB63;G2,c-Pr, H,H,H], [ZB64;G2,Ph,H,H,H], [ZB65;G2,OMe,H,H,H], [ZB66;G2,0 Et,H,H,H], [ZB67;G2,OPh,H,H,H], [ZB68;G2, $CF_3$,H,H,H], [ZB69;G2, F,H,H,H], [ZB7;0G2,C1,H,H,H], [ZB71;G2,Br,H,H,H], [ZB72;G2,CN, H,H,H], [ZB73;G2,H, Me,H,H], [ZB74;G2,H,Et,H,H], [ZB75;G2,H,Pr, H,H], [ZB76;G2,H,i-Pr,H,H],[ZB77;G2,H,c-Pr,H,H], [ZB78;G2, H,Ph,H,H], [ZB79;G2,H,OMe,H,H], [ZB80;G2,H,0 Et,H, H],[ZB81;G2,H,OPh,H,H],[ZB82;G2,H,$CF_3$,H,H],[ZB83; G2,H, F,H,H], [ZB84;G2,H,C1,H,H], [ZB85;G2,H,Br,H,H], [ZB86;G2,H,CN, H,H], [ZB87;G2,H,H,Me,H], [ZB88;G2, H,H,Et,H], [ZB89;G2,H,H,Pr, H], [ZB90;G2,H,H,i-Pr,H], [ZB91;G2,H,H,c-Pr,H], [ZB92;G2,H,H,Ph,H], [ZB93;G2, H,H,OMe,H], [ZB94;G2,H,H,O Et,H], [ZB95;G2,H,H,OPh, H], [ZB96;G2,H,H,$CF_3$,H], [ZB97;G2,H,H, F,H], [ZB98; G2,H,H,C1,H], [ZB99;G2,H,H,Br,H], [ZB100;G2, H,H,CN ,H]

[ZB101;G2,H,H,H,Me], [ZB102;G2,H,H,H,Et], [ZB103; G2,H,H,H,Pr],[ZB104;G2,H,H,H,i-Pr],[ZB105;G2,H,H,H, c-Pr],[ZB106;G2,H,H,H,Ph],[ZB107;G2,H,H,H,OMe], [ZB108;G2,H,H, H,OEt],[ZB109;G2,H,H,H,OPh],[ZB110; G2,H,H,H,$CF_3$], [ZB111;G2, H,H,H,F],[ZB112;G2,H,H,H, C1],[ZB113;G2,H,H,H,Br],[ZB114;G2, H,H,H,CN], [ZB115;G3,H,H,H,H], [ZB116;G3,Me,H,H,H], [ZB117;G3, Et,H,H,H],[ZB118;G3,Pr,H,H,H],[ZB119;G3,i-Pr,H,H,H], [ZB120;G3,c-Pr,H,H,H],[ZB121;G3,Ph,H,H,H],[ZB122; G3,OMe,H,H,H],[ZB123;G 3,OEt,H,H,H],[ZB124;G3, OPh,H,H,H],[ZB125;G3,$CF_3$,H,H,H],[ZB1 26;G3,F,H,H, H],[ZB127;G3,C1,H,H,H],[ZB128;G3,Br,H,H,H],[ZB1 29;G3,CN,H,H,H], [ZB130;G3,H,Me,H,H], [ZB131;G3,H, Et,H,H], [ZB 132;G3,H,Pr,H,H], [ZB133;G3,H,i-Pr,H,H], [ZB134;G3,H,c-Pr,H,H],[ZB135;G3,H,Ph,H,H],[ZB136; G3,H,OMe,H,H],[ZB137;G3, H,OEt,H,H],[ZB138;G3,H, OPh,H,H],[ZB139;G3,H,$CF_3$,H,H],[ZB140;G3,H,F,H,H], [ZB141;G3,H,C1,H,H],[ZB142;G3,H,Br,H,H],[ZB143;G3, H,CN,H,H],[ZB144;G3,H,H,Me,H],[ZB145;G3,H,H,Et,H], [ZB14 6;G3,H,H,Pr,H], [ZB147;G3,H,H,i-Pr,H], [ZB148; G3,H,H,c-Pr,H], [ZB149;G3,H,H,Ph,H], [ZB150;G3,H,H, OMe,H], [ZB151;G3,H, H,OEt,H],[ZB152;G3,H,H,OPh, H],[ZB153;G3,H,H,$CF_3$,H],[ZB154;G 3,H,H,F,H], [ZB155; G3,H,H,C1,H], [ZB156;G3,H,H,Br,H], [ZB157;G 3,H,H, CN,H], [ZB158;G3,H,H,H,Me], [ZB159;G3,H,H,H,Et], [ZB160; G3,H,H,H,Pr], [ZB161;G3,H,H,H,i-Pr], [ZB162; G3,H,H,H,c-Pr], [ZB163;G3,H,H,H,Ph], [ZB164;G3,H,H, H,OMe], [ZB165;G3,H,H, H,OEt],[ZB166;G3,H,H,H, OPh],[ZB167;G3,H,H,H,$CF_3$], [ZB168;G3, H,H,H,F], [ZB169;G3,H,H,H,C1],[ZB170;G3,H,H,H,Br],[ZB171;G3, H,H,H,CN],[ZB172;G4,H,H,H,-],[ZB173;G4,Me,H,H,-],

[ZB174;G4, Et,H,H,-],[ZB175;G4,Pr,H,H,-],[ZB176;G4,i-Pr,H,H,-],[ZB177;G4,c-Pr,H,H,-],[ZB178;G4,Ph,H,H,-],[ZB179;G4,OMe,H,H,-],[ZB180;G 4,OEt,H,H,-],[ZB181;G4,OPh,H,H,-],[ZB182;G4,$CF_3$,H,H,-],[ZB1 83;G4,F,H,H,-],[ZB184;G4,C1,H,H,-],[ZB185;G4,Br,H,H,-],[ZB1 86;G4,CN,H,H,-],[ZB187;G4,H,Me,H,-],[ZB188;G4,H,Et,H,-],[ZB 189;G4,H,Pr,H,-],[ZB190;G4,H,i-Pr,H,-],[ZB191;G4,H,c-Pr,H,-],[ZB192;G4,H,Ph,H,-],[ZB193;G4,H,OMe,H,-],[ZB194;G4, H,OEt,H,-],[ZB195;G4,H,OPh,H,-],[ZB196;G4,H,$CF_3$,H,-],[ZB197;G4,H,F,H,-],[ZB198;G4,H,C1,H,-],[ZB199;G4,H,Br,H,-],[ZB200;G4,H,CN,H,-]

[ZB201;G4,H,H,Me,-],[ZB202;G4,H,H,Et,-],[ZB203;G4,H,H,Pr,-],[ZB204;G4,H,H,i-Pr,-],[ZB205;G4,H,H,c-Pr,-],[ZB206;G4,H,H,Ph,-],[ZB207;G4,H,H,OMe,-],[ZB208;G4,H, H,OEt,-],[ZB209;G4,H,H,OPh,-],[ZB210;G4,H,H,$CF_3$,-],[ZB211;G 4,H,H,F,-],[ZB212;G4,H,H,C1,-],[ZB213;G4,H,H,Br,-],[ZB214;G 4,H,H,CN,-], [ZB215;G5,H,H,H,-], [ZB216;G5,Me,H,H,-], [ZB217;G 5,Et,H,H,-],[ZB218;G5,Pr,H,H,-],[ZB219;G5,i-Pr,H,H,-],[ZB220;G5,c-Pr,H,H,-],[ZB221;G5,Ph,H,H,-],[ZB222;G5,OMe,H,H,-],[ZB223;G 5,OEt,H,H,-],[ZB224;G5,OPh,H,H,-],[ZB225;G5,$CF_3$,H,H,-],[ZB2 26;G5,F,H,H,-],[ZB227;G5,C1,H,H,-],[ZB228;G5,Br,H,H,-],[ZB2 29;G5,CN,H,H,-],[ZB230;G5,H,Me,H,-],[ZB231;G5,H,Et,H,-],[ZB 232;G5,H,Pr,H,-],[ZB233;G5,H,i-Pr,H,-],[ZB234;G5,H,c-Pr,H,-], [ZB235;G5,H,Ph,H,-], [ZB236;G5,H,OMe,H,-], [ZB237;G5, H,OEt,H,-],[ZB238;G5,H,OPh,H,-],[ZB239;G5,H,$CF_3$,H,-],[ZB240;G5,H,F,H,-],[ZB241;G5,H,C1,H,-],[ZB242;G5,H,Br,H,-],[ZB243;G5,H,CN,H,-],[ZB244;G5,H,H,Me,-],[ZB245;G5,H,H,Et,-],[ZB24 6;G5,H,H,Pr,-], [ZB247;G5,H,H,i-Pr,-], [ZB248;G5,H,H,c-Pr,-],[ZB249;G5,H,H,Ph,-],[ZB250;G5,H,H,OMe,-],[ZB251;G5,H, H,OEt,-],[ZB252;G5,H,H,OPh,-],[ZB253;G5,H,H,$CF_3$,-],[ZB254;G 5,H,H,F,-], [ZB255;G5,H,H,C1,-], [ZB256;G5,H,H,Br,-],[ZB257;G 5,H,H,CN,-], [ZB258;G6,H,H,H,-], [ZB259;G6,Me,H,H,-], [ZB260;G 6,Et,H,H,-], [ZB261;G6,Pr,H,H,-],[ZB262;G6,i-Pr,H,H,-],[ZB263;G6,c-Pr,H,H,-], [ZB264;G6,Ph,H,H,-], [ZB265;G6,OMe,H,H,-], [ZB266;G 6,OEt,H,H,-], [ZB267;G6,OPh,H,H,-], [ZB268;G6,$CF_3$,H,H,-], [ZB2 69;G6,F,H,H,-], [ZB270;G6,C1,H,H,-], [ZB271;G6,Br,H,H,-], [ZB2 72;G6,CN,H,H,-], [ZB273;G6,H,Me,H,-],[ZB274;G6,H,Et,H,-], [ZB 275;G6,H,Pr,H,-], [ZB276;G6,H,i-Pr,H,-], [ZB277;G6,H,c-Pr,H,-], [ZB278;G6,H,Ph,H,-],[ZB279;G6,H,OMe,H,-], [ZB280;G6, H,OEt,H,-], [ZB281;G6,H,OPh,H,-], [ZB282;G6,H,$CF_3$,H,-], [ZB283;G6,H,F,H,-], [ZB284;G6,H,C1,H,-], [ZB285;G6,H,Br,H,-], [ZB286;G6,H,CN,H,-], [ZB287;G6,H,H,Me,-], [ZB288;G6,H,H,Et,-], [ZB28 9;G6,H,H,Pr,-], [ZB290;G6,H,H,i-Pr,-],[ZB291;G6,H,H,c-Pr,-], [ZB292;G6,H,H,Ph,-], [ZB293;G6,H,H,OMe,-], [ZB294;G6,H, H,OEt,-],[ZB295;G6,H,H,OPh,-],[ZB296;G6,H,H,$CF_3$,-],[ZB297;G 6,H,H,F,-],[ZB298;G6,H,H,C1,-], [ZB299;G6,H,H,Br,-], [ZB300;G 6,H,H,CN,-]

[ZB301;G7,H,H,H,-],[ZB302;G7,Me,H,H,-],[ZB303;G7,Et,H,H,-], [ZB304;G7,Pr,H,H,-],[ZB305;G7,i-Pr,H,H,-],[ZB306;G7,c-Pr,H,H,-],[ZB307;G7,Ph,H,H,-],[ZB308;G7,OMe,H,H,-],[ZB309;G 7,OEt,H,H,-],[ZB310;G7,OPh,H,H,-],[ZB311;G7,$CF_3$,H,H,-],[ZB3 12;G7,F,H,H,-],[ZB313;G7,C1,H,H,-],[ZB314;G7,Br,H,H,-],[ZB3 15;G7,CN,H,H,-], [ZB316;G7,H,Me,H,-], [ZB317;G7,H,Et,H,-], [ZB 318;G7,H,Pr,H,-],[ZB319;G7,H,i-Pr,H,-],[ZB320;G7,H,c-Pr,H,-],[ZB321;G7,H,Ph,H,-],[ZB322;G7,H,OMe,H,-],[ZB323;G7, H,OEt,H,-],[ZB324;G7,H,OPh,H,-],[ZB325;G7,H,$CF_3$,H,-],[ZB326;G7,H,F,H,-],[ZB327;G7,H,C1,H,-],[ZB328;G7,H,Br,H,-],[ZB329;G7,H,CN,H,-], [ZB330;G7,H,H,Me,-], [ZB331;G7,H,H,Et,-], [ZB33 2;G7,H,H,Pr,-],[ZB333;G7,H,H,i-Pr,-], [ZB334;G7,H,H,c-Pr,-],[ZB335;G7,H,H,Ph,-],[ZB336;G7,H,H,OMe,-],[ZB337;G7,H,H,OEt,-],[ZB338;G7,H,H,OPh,-],[ZB339;G7,H,H,$CF_3$,-],[ZB340;G 7,H,H,F,-],[ZB341;G7,H,H,C1,-],[ZB342;G7,H,H,Br,-],[ZB343;G 7,H,H,CN,-], [ZB344;G8,H,H,H,-],[ZB345;G8,Me,H,H,-], [ZB346;G 8,Et,H,H,-],[ZB347;G8,Pr,H,H,-],[ZB348;G8,i-Pr,H,H,-],[ZB349;G8,c-Pr,H,H,-],[ZB350;G8,Ph,H,H,-],[ZB351;G8,OMe,H,H,-],[ZB352;G 8,OEt,H,H,-],[ZB353;G8,OPh,H,H,-],[ZB354;G8,$CF_3$,H,H,-],[ZB3 55;G8,F,H,H,-],[ZB356;G8,C1,H,H,-],[ZB357;G8,Br,H,H,-],[ZB3 58;G8,CN,H,H,-], [ZB359;G8,H,Me,H,-], [ZB360;G8,H,Et,H,-], [ZB 361;G8,H,Pr,H,-],[ZB362;G8,H,i-Pr,H,-],[ZB363;G8,H,c-Pr,H,-],[ZB364;G8,H,Ph,H,-],[ZB365;G8,H,OMe,H,-],[ZB366;G8, H,OEt,H,-],[ZB367;G8,H,OPh,H,-], [ZB368;G8,H,$CF_3$,H,-], [ZB369;G8,H,F,H,-],[ZB370;G8,H,C1,H,-],[ZB371;G8,H,Br,H,-],[ZB372;G8,H,CN,H,-],[ZB373;G8,H,H,Me,-],[ZB374;G8,H,H,Et,-],[ZB37 5;G8,H,H,Pr,-],[ZB376;G8,H,H,i-Pr,-],[ZB377;G8,H,H,c-Pr,-],[ZB378;G8,H,H,Ph,-],[ZB379;G8,H,H,OMe,-],[ZB380;G8,H, H,OEt,-],[ZB381;G8,H,H,OPh,-],[ZB382;G8,H,H,$CF_3$,-],[ZB383;G 8,H,H,F,-],[ZB384;G8,H,H,C1,-], [ZB385;G8,H,H,Br,-], [ZB386;G 8,H,H,CN,-],[ZB387;G9,H,H,H,-],[ZB388;G9,Me,H,H,-],[ZB389;G 9,Et,H,H,-], [ZB390;G9,Pr,H,H,-], [ZB391;G9,i-Pr,H,H,-],[ZB392;G9,c-Pr,H,H,-],[ZB393;G9,Ph,H,H,-],[ZB394;G9,OMe,H,H,-],[ZB395;G 9,OEt,H,H,-], [ZB396;G9,OPh,H,H,-], [ZB397;G9,$CF_3$,H,H,-], [ZB3 98;G9,F,H,H,-], [ZB399;G9,C1,H,H,-], [ZB400;G9,Br,H,H,-]

[ZB401;G9,CN,H,H,-], [ZB402;G9,H,Me,H,-], [ZB403;G9,H,Et,H,-], [ZB404;G9,H,Pr,H,-], [ZB405;G9,H,i-Pr,H,-], [ZB406;G9,H,c-Pr,H,-], [ZB407;G9,H,Ph,H,-],[ZB408;G9,H,OMe,H,-], [ZB409;G9, H,OEt,H,-], [ZB410;G9,H,OPh,H,-], [ZB411;G9,H,$CF_3$,H,-], [ZB412;G9,H,F,H,-], [ZB413;G9,H,C1,H,-], [ZB414;G9,H,Br,H,-], [ZB415;G9,H,CN,H,-], [ZB416;G9,H,H,Me,-], [ZB417;G9,H,H,Et,-], [ZB41 8;G9,H,H,Pr,-], [ZB419;G9,H,H,i-Pr,-],[ZB420;G9,H,H,c-Pr,-], [ZB421;G9,H,H,Ph,-], [ZB422;G9,H,H,OMe,-], [ZB423;G9,H, H,OEt,-],[ZB424;G9,H,H,OPh,-],[ZB425;G9,H,H,$CF_3$,-],[ZB426;G 9,H,H,F,-],[ZB427;G9,H,H,C1,-], [ZB428;G9,H,H,Br,-], [ZB429;G 9,H,H,CN,-], [ZB430;G10,H,H,H,-], [ZB431;G10,Me,H,H,-], [ZB432;G10,Et,H,H,-], [ZB433;G10,Pr,H,H,-],[ZB434;G10,i-Pr,H,H,-],[ZB435;G10,c-Pr,H,H,-],[ZB436;G10,Ph,H,H,-],[ZB437;G10,OMe,H,H,-],[ZB438;G10,OEt,H,H,-],[ZB439;G10,OPh,H,H,-],[ZB440;G10,$CF_3$,H,H,-],[ZB441;G10,F,H,H,-], [ZB442;G10,C1,H,H,-], [ZB443;G10,Br,H,H ,-],[ZB444;G10,CN,H,H,-],[ZB445;G1O,H,Me,H,-],[ZB446;G1O,H, Et,H,-],[ZB447;G10,H,Pr,H,-],[ZB448;G10,H,i-Pr,H,-],[ZB449;G10,H,c-Pr,H,-],[ZB450;G10,H,Ph,H,-],[ZB451;G10,H,OMe,H,-],[ZB452;G 10,H,OEt,H,-],[ZB453;G10,H,OPh,H,-],[ZB454;G10,H,$CF_3$,H,-],[ZB455;G10,H,F,H,-], [ZB456;G10,H,C1,H,-],[ZB457;G10,H,Br,H,-], [ZB458;G10,H,CN,H,-], [ZB459;G10,H,H,Me,-], [ZB460;G10,H,H, Et,-],[ZB461;G10,H,H,Pr,-],[ZB462;G10,H,H,i-Pr,-], [ZB463;G10,H,H,c-Pr,-],[ZB464;G10,H,H,Ph,-],[ZB465;G10,H,H,OMe,-],[ZB466;G10,H,H,OEt,-],[ZB467;G10,H,H,OPh,-],[ZB468;G1O,H,H,$CF_3$,-],[ZB 469;G10,H,H,F,-],[ZB470;G10,H,H,C1,-],[ZB471;G10,H,H,Br,-], [ZB472;G10,H,H,CN,-],[ZB473;G11,H,H,H,-],[ZB474;G11,H,Me,H,-],[ZB475;G11,HEt,H,-],[ZB476;G11,HPr,H,-],[ZB477;G11,Hi-Pr,H,-],[ZB478;G11,Hc-Pr,H,-],[ZB479;G11,HPh,H,-],[ZB480;G11,HOMe,H,-],[ZB481;G11,HOEt,H,-],[ZB482;G11,HOPh,H,-],[ZB483;G11,H$CF_3$,H,-],[ZB484;G11,HF,H,-],[ZB485;G11,HCl,H,-],[ZB486;G11,HBr,H,-],[ZB487;G11,HCN,H,-],[ZB488;G11,H,H,Me,-],[ZB489;G11,H,H,Et,-],[ZB 490;G11,H,H,Pr,-],[ZB491;G11,H,H,i-Pr,-],[ZB492;G11,H,H,c-Pr,-],[ZB493;G11,H,H,Ph,-],[ZB494;G11,H,H,OMe,-],

[ZB495;G11,H,H,OEt,-], [ZB496;G11,H,H,OPh,-], [ZB497;G11,H,H,$CF_3$,-], [ZB 498;G11,H,H,F,-], [ZB499; G11,H,H,C1,-], [ZB500;G11,H,H,Br,-]

[ZB501;G11,H,H,CN,-],[ZB502;G11,Me,H,H,-],[ZB503; G11,Me,Me, H,-],[ZB504;G11,MeEt,H,-],[ZB505;G11, MePr,H,-],[ZB506;G11,M ei-Pr,H,-], [ZB507;G11,Mec-Pr, H,-],[ZB508;G11,MePh,H,-],[ZB509;G11,MeOMe,H,-], [ZB510;G 11,MeOEt,H,-],[ZB511;G11,MeOPh,H,-], [ZB512;G11,Me$CF_3$,H,-],[ZB513;G11,MeF,H,-],[ZB514; G11,MeCl,H,-],[ZB515;G11,MeBr,H,-],[ZB516;G11, MeCN,H,-],[ZB517;G11,Me,H,Me,-],[ZB518;G11,Me, H,Et,-],[ZB519;G11,Me,H,Pr,-],[ZB520;G11,Me,H,i-Pr,-], [ZB521;G11,Me,H,c-Pr,-],[ZB522;G11,Me,H,Ph,-], [ZB523;G11,Me,H,OMe,-],[ZB524;G 11,Me,H,OEt,-], [ZB525;G11,Me,H,OPh,-],[ZB526;G11,Me,H,$CF_3$,-], [ZB527;G11,Me,H,F,-],[ZB528;G11,Me,H,C1,-],[ZB529; G11,Me, H,Br,-],[ZB530;G11,Me,H,CN,-],[ZB531;G12,H, H,H,-],[ZB532;G1 2,Me,H,H,-],[ZB533;G12,Et,H,H,-], [ZB534;G12,Pr,H,H,-],[ZB53 5;G12,i-Pr,H,H,-],[ZB536; G12,c-Pr,H,H,-],[ZB537;G12,Ph,H,H,-],[ZB538;G12,OMe, H,H,-],[ZB539;G12,OEt,H,H,-],[ZB540;G12,OPh,H,H,-], [ZB541;G12,$CF_3$,H,H,-],[ZB542;G12,F,H,H,-],[ZB543; G12,C1,H,H,-],[ZB544;G12,Br,H,H ,-],[ZB545;G12,CN,H, H,-],[ZB546;G12,H,Me,H,-],[ZB547;G12,H, Et,H,-], [ZB548;G12,H,Pr,H,-],[ZB549;G12,H,i-Pr,H,-], [ZB550; G12,H,c-Pr,H,-],[ZB551;G12,H,Ph,H,-],[ZB552;G12,H, OMe,H,-],[ZB553;G 12,H,OEt,H,-],[ZB554;G12,H,OPh, H,-],[ZB555;G12,H,$CF_3$,H,-],[ZB556;G12,H,F,H,-], [ZB557;G12,H,C1,H,-],[ZB558;G12,H,Br,H,-], [ZB559; G12,H,CN,H,-], [ZB560;G12,H,H,Me,-], [ZB561;G12,H,H, Et,-],[ZB562;G12,H,H,Pr,-],[ZB563;G12,H,H,i-Pr,-], [ZB564;G12,H,H,c-Pr,-],[ZB565;G12,H,H,Ph,-],[ZB566; G12,H,H,OMe,-],[ZB567;G12,H,H,OEt,-],[ZB568;G12,H, H,OPh,-],[ZB569;G12,H,H,$CF_3$,-],[ZB 570;G12,H,H,F,-], [ZB571;G12,H,H,C1,-],[ZB572;G12,H,H,Br,-], [ZB573; G12,H,H,CN,-],[ZB574;G13,H,H,H,-],[ZB575;G13,Me,H, H,-],[ZB576;G13,Et,H,H,-],[ZB577;G13,Pr,H,H,-],[ZB578; G13,i-Pr,H,H,-],[ZB579;G13,c-Pr,H,H,-],[ZB580;G13,Ph, H,H,-],[ZB581;G13,OMe,H,H,-],[ZB582;G13,OEt,H,H,-], [ZB583;G13,OPh,H,H,-],[ZB584;G13,$CF_3$,H,H,-],[ZB585; G13,F,H,H,-],[ZB586;G13,C1,H,H,-],[ZB587;G13, Br,H,H ,-],[ZB588;G13,CN,H,H,-],[ZB589;G13,H,H,Me,-], [ZB590;G13,H, H,Et,-],[ZB591;G13,H,H,Pr,-],[ZB592; G13,H,H,i-Pr,-], [ZB593;G13,H,H,c-Pr,-],[ZB594;G13,H, H,Ph,-],[ZB595;G13,H,H,OMe,-],[ZB596;G13,H,H,OEt,-], [ZB597;G13,H,H,OPh,-],[ZB598;G13,H,H,$CF_3$,-],[ZB 599; G13,H,H,F,-], [ZB600;G13,H,H,C1,-]

[ZB601;G13,H,H,Br,-],[ZB602;G13,H,H,CN,-],[ZB603; G13,H,Me,H ,-],[ZB604;G13,Me,Me,H,-],[ZB605;G13,Et, Me,H,-],[ZB606;G13, Pr,Me,H,-],[ZB607;G13,i-Pr,Me, H,-],[ZB608;G13,c-Pr,Me,H,-],[ZB609;G13,Ph,Me,H,-], [ZB610;G13,OMe,Me,H,-],[ZB 611;G13,OEt,Me,H,-], [ZB612;G13,OPh,Me,H,-],[ZB613;G13,$CF_3$,M e,H,-], [ZB614;G13,F,Me,H,-],[ZB615;G13,C1,Me,H,-],[ZB616; G1 3,Br,Me,H,-],[ZB617;G13,CN,Me,H,-],[ZB618;G13,H, Me,Me,-],[Z B619;G13,H,Me,Et,-],[ZB620;G13,H,Me, Pr,-],[ZB621;G13,H,Me,i-Pr,-],[ZB622;G13,H,Me,c-Pr,-], [ZB623;G13,H,Me,Ph,-], [ZB624;G13,H,Me,OMe,-], [ZB625;G 13,H,Me,OEt,-],[ZB626;G13,H,Me,OPh,-], [ZB627;G13,H,Me,$CF_3$,-], [ZB628;G13,H,Me,F,-], [ZB629;G13,H,Me,C1,-], [ZB630;G13,H,M e,Br,-], [ZB631;G13,H,Me,CN,-],[ZB632;G14,H,H,H,-],[ZB633; G1 4,Me,H,H,-], [ZB634;G14,Et,H,H,-], [ZB635;G14,Pr,H, H,-], [ZB63 6;G14,i-Pr,H,H,-],[ZB637;G14,c-Pr,H,H,-], [ZB638;G14,Ph,H,H,-], [ZB639;G14,OMe,H,H,-], [ZB640; G14,OEt,H,H,-],[ZB641;G14,OPh,H,H,-],[ZB642;G14, $CF_3$,H,H,-], [ZB643;G14,F,H,H,-], [ZB644;G14,C1,H,H,-], [ZB645;G14,Br,H,H ,-], [ZB646;G14,CN,H,H,-], [ZB647; G14,H,Me,H,-], [ZB648;G14,H, Et,H,-], [ZB649;G14,H,Pr, H,-], [ZB650;G14,H,i-Pr,H,-], [ZB651;G14,H,c-Pr,H,-], [ZB652;G14,H,Ph,H,-],[ZB653;G14,H,OMe,H,-], [ZB654;G 14,H,OEt,H,-],[ZB655;G14,H,OPh,H,-],[ZB656; G14,H,$CF_3$,H,-],[ZB657;G14,H,F,H,-],[ZB658;G14,H,C1, H,-],[ZB659;G14,H,Br,H,-], [ZB660;G14,H,CN,H,-], [ZB661;G14,H,H,Me,-], [ZB662;G14,H,H, Et,-],[ZB663; G14,H,H,Pr,-],[ZB664;G14,H,H,i-Pr,-], [ZB665;G14,H,H, c-Pr,-],[ZB666;G14,H,H,Ph,-],[ZB667;G14,H,H,OMe,-], [ZB668;G14,H,H,OEt,-], [ZB669;G14,H,H,OPh,-], [ZB670;G14,H,H,$CF_3$,-], [ZB 671;G14,H,H,F,-], [ZB672; G14,H,H,C1,-], [ZB673;G14,H,H,Br,-], [ZB674;G14,H,H, CN,-], [ZB675;G15,H,H,H,-], [ZB676;G15,Me,H,H,-], [ZB677;G15,Et,H,H,-], [ZB678;G15,Pr,H,H,-], [ZB679; G15,i-Pr,H,H,-],[ZB680;G15,c-Pr,H,H,-],[ZB681;G15,Ph, H,H,-],[ZB682;G15,OMe,H,H,-],[ZB683;G15,OEt,H,H,-], [ZB684;G15,OPh,H,H,-],[ZB685;G15,$CF_3$,H,H,-],[ZB686; G15,F,H,H,-],[ZB687;G15,C1,H,H,-],[ZB688; G15,Br,H,H ,-], [ZB689;G15,CN,H,H,-], [ZB690;G15,H, Me,H,-], [ZB691;G15,H, Et,H,-],[ZB692;G15,H,Pr,H,-], [ZB693;G15,H,i-Pr,H,-],[ZB694;G15,H,c-Pr,H,-], [ZB695; G15,H,Ph,H,-], [ZB696;G15,H,OMe,H,-], [ZB697;G 15,H, OEt,H,-],[ZB698;G15,H,OPh,H,-],[ZB699;G15,H,$CF_3$, H,-],[ZB700;G15,H, F,H,-]

[ZB701;G15,H,C1,H,-],[ZB702;G15,H,Br,H,-],[ZB703; G15,H,CN,H ,-],[ZB704;G15,H,H,Me,-],[ZB705;G15,H,H, Et,-],[ZB706;G15,H, H,Pr,-],[ZB707;G15,H,H,i-Pr,-], [ZB708;G15,H,H,c-Pr,-],[ZB709;G15,H,H,Ph,-],[ZB710; G15,H,H,OMe,-],[ZB711;G15,H,H,OEt,-],[ZB712;G15,H, H,OPh,-],[ZB713;G15,H,H,$CF_3$,-],[ZB 714;G15,H,H,F,-], [ZB715;G15,H,H,C1,-],[ZB716;G15,H,H,Br,-], [ZB717; G15,H,H,CN,-],[ZB718;G16,H,H,-,-],[ZB719;G16,Me, H,-,-],[ZB720;G16,Et,H,-,-],[ZB721;G16,Pr,H,-,-],[ZB722; G16,i-Pr,H,-,-],[ZB723;G16,c-Pr,H,-,-],[ZB724;G16,Ph, H,-,-],[ZB725;G16,OMe,H,-,-],[ZB726;G16,OEt,H,-,-], [ZB727;G16,OPh,H,-,-],[ZB728;G16,$CF_3$,H,-,-], [ZB729; G16,F,H,-,-], [ZB730;G16,C1,H,-,-], [ZB731;G16,Br,H,-,-], [ZB732;G16,CN,H,-,-],[ZB733;G16,H,Me,-,-],[ZB734; G16,H, Et,-,-],[ZB735;G16,H,Pr,-,-],[ZB736;G16,H,i-Pr,-,-],[ZB737;G16,H,c-Pr,-,-],[ZB738;G16,H,Ph,-,-], [ZB739;G16,H,OMe,-,-],[ZB740;G 16,H,OEt,-,-],[ZB741; G16,H,OPh,-,-],[ZB742;G16,H,$CF_3$,-,-],[ZB743;G16,H, F,-,-],[ZB744;G16,H,C1,-,-],[ZB745;G16,H,Br,-,-],[ZB746; G16,H,CN,-,-],[ZB747;G17,H,H,-,-],[ZB748;G17,Me, H,-,-],[ZB749;G17,Et,H,-,-],[ZB750;G17,Pr,H,-,-],[ZB751; G17,i-Pr,H,-,-],[ZB752;G17,c-Pr,H,-,-],[ZB753;G17,Ph, H,-,-],[ZB754;G17,OMe,H,-,-],[ZB755;G17,OEt,H,-,-], [ZB756;G17,OPh,H,-,-],[ZB757;G17,$CF_3$,H,-,-],[ZB758; G17,F,H,-,-],[ZB759;G17,C1,H,-,-],[ZB760;G17,Br,H,-,-], [ZB761;G17,CN,H,-,-],[ZB762;G17,H,Me,-,-],[ZB763; G17,H, Et,-,-],[ZB764;G17,H,Pr,-,-],[ZB765;G17,H,i-Pr,-,-],[ZB766;G17,H,c-Pr,-,-],[ZB767;G17,H,Ph,-,-], [ZB768;G17,H,OMe,-,-],[ZB769;G 17,H,OEt,-,-],[ZB770; G17,H,OPh,-,-],[ZB771;G17,H,$CF_3$,-,-],[ZB772;G17,H, F,-,-],[ZB773;G17,H,C1,-,-],[ZB774;G17,H,Br,-,-],[ZB775; G17,H,CN,-,-],[ZB776;G18,H,H,-,-],[ZB777;G18,Me, H,-,-],[ZB778;G18,Et,H,-,-],[ZB779;G18,Pr,H,-,-],[ZB780; G18,i-Pr,H,-,-],[ZB781;G18,c-Pr,H,-,-],[ZB782;G18,Ph, H,-,-],[ZB783;G18,OMe,H,-,-],[ZB784;G18,OEt,H,-,-], [ZB785;G18,OPh,H,-,-],[ZB786;G18,$CF_3$,H,-,-],[ZB787; G18,F,H,-,-],[ZB788;G18,C1,H,-,-],[ZB789;G18,Br,H,-,-], [ZB790;G18,CN,H,-,-],[ZB791;G18,H,Me,-,-],[ZB792; G18,H, Et,-,-],[ZB793;G18,H,Pr,-,-],[ZB794;G18,H,i-Pr,-,-],[ZB795;G18,H,c-Pr,-,-],[ZB796;G18,H,Ph,-,-], [ZB797;G18,H,OMe,-,-],[ZB798;G 18,H,OEt,-,-],[ZB799; G18,H,OPh,-,-],[ZB800;G18,H,$CF_3$,-,-]

[ZB801;G18,H,F,-,-],[ZB802;G18,H,C1,-,-],[ZB803;G18,H,Br,-,-],[ZB804;G18,H,CN,-,-],[ZB805;G19,H,H,-,-],[ZB806;G19,Me,H ,-,-],[ZB807;G19,Et,H,-,-],[ZB808;G19,Pr,H,-,-],[ZB809;G19, i-Pr,H,-,-],[ZB810;G19,c-Pr,H,-,-],[ZB811;G19,Ph,H,-,-],[ZB812;G19,OMe,H,-,-],[ZB813;G19,OEt,H,-,-],[ZB814;G19,OPh,H,-,-],[ZB815;G19,$CF_3$,H,-,-], [ZB816;G19,F,H,-,-], [ZB817;G19,C1,H,-,-],[ZB818;G19,Br,H,-,-],[ZB819;G19,CN,H,-,-],[ZB820;G19,H,Me,-,-],[ZB821;G19,H, Et,-,-],[ZB822;G19,H,Pr,-,-],[ZB823;G19,H,i-Pr,-,-],[ZB824;G19,H,c-Pr,-,-],[ZB825;G19,H,Ph,-,-],[ZB826;G19,H,OMe,-,-],[ZB827;G 19,H,OEt,-,-],[ZB828;G19,H,OPh,-,-],[ZB829;G19,H,$CF_3$,-,-],[ZB830;G19,H,F,-,-],[ZB831;G19,H,C1,-,-],[ZB832;G19,H,Br,-,-],[ZB833;G19,H,CN,-,-],[ZB834;G20,H,H,-,-],[ZB835;G20,Me,H,-,-],[ZB836;G20,Et,H,-,-],[ZB837;G20,Pr,H,-,-],[ZB838;G20,i-Pr,H,-,-],[ZB839;G20,c-Pr,H,-,-],[ZB840;G20,Ph,H,-,-],[ZB841;G20,OMe,H,-,-],[ZB842;G20,OEt,H,-,-],[ZB843;G20,OPh,H,-,-],[ZB844;G20,$CF_3$,H,-,-], [ZB845;G20,F,H,-,-], [ZB846;G20,C1,H,-,-],[ZB847;G20,Br,H,-,-],[ZB848;G20,CN,H,-,-],[ZB849;G20,H,Me,-,-],[ZB850;G20,H, Et,-,-],[ZB851;G20,H,Pr,-,-],[ZB852;G20,H,i-Pr,-,-],[ZB853;G20,H,c-Pr,-,-],[ZB854;G20,H,Ph,-,-],[ZB855;G20,H,OMe,-,-],[ZB856;G 20,H,OEt,-,-],[ZB857;G20,H,OPh,-,-],[ZB858;G20,H,$CF_3$,-,-],[ZB859;G20,H,F,-,-],[ZB860;G20,H,C1,-,-],[ZB861;G20,H,Br,-,-],[ZB862;G20,H,CN,-,-],[ZB863;G21,H,H,-,-],[ZB864;G21,Me,H,-,-],[ZB865;G21,Et,H,-,-],[ZB866;G21,Pr,H,-,-],[ZB867;G21,i-Pr,H,-,-],[ZB868;G21,c-Pr,H,-,-],[ZB869;G21,Ph,H,-,-],[ZB870;G21,OMe,H,-,-],[ZB871;G21,OEt,H,-,-],[ZB872;G21,OPh,H,-,-],[ZB873;G21,$CF_3$,H,-,-],[ZB874;G21,F,H,-,-], [ZB875;G21,C1,H,-,-],[ZB876;G21,Br,H,-,-],[ZB877;G21,CN,H,-,-],[ZB878;G21,H,Me,-,-],[ZB879;G21,H, Et,-,-],[ZB880;G21,H,Pr,-,-],[ZB881;G21,H,i-Pr,-,-],[ZB882;G21,H,c-Pr,-,-],[ZB883;G21,H,Ph,-,-],[ZB884;G21,H,OMe,-,-],[ZB885;G 21,H,OEt,-,-],[ZB886;G21,H,OPh,-,-],[ZB887;G21,H,$CF_3$,-,-],[ZB888;G21,H,F,-,-], [ZB889;G21,H,C1,-,-], [ZB890;G21,H,Br,-,-],[ZB891;G21,H,CN,-,-],[ZB892;G22,H,H,-,-],[ZB893;G22,Me,H,-,-],[ZB894;G22,Et,H,-,-],[ZB895;G22,Pr,H,-,-],[ZB896;G22,i-Pr,H,-,-],[ZB897;G22,c-Pr,H,-,-],[ZB898;G22,Ph,H,-,-],[ZB899;G22,OMe,H,-,-],[ZB900;G22,0Et,H,-,-]

[ZB901;G22,OPh,H,-,-], [ZB902;G22,$CF_3$,H,-,-],[ZB903;G22,F,H,-,-],[ZB904;G22,C1,H,-,-],[ZB905;G22,Br,H,-,-],[ZB906;G22,C N,H,-,-], [ZB907;G22,H,Me,-,-],[ZB908;G22,H,Et,-,-], [ZB909;G 22,H,Pr,-,-],[ZB910;G22,H,i-Pr,-,-],[ZB911;G22,H,c-Pr,-,-],[ZB912;G22,H,Ph,-,-],[ZB913;G22,H,OMe,-,-],[ZB914;G 22,H,OEt,-,-],[ZB915;G22,H,OPh,-,-],[ZB916;G22,H,$CF_3$,-,-],[ZB917;G22,H,F,-,-],[ZB918;G22,H,C1,-,-],[ZB919;G22,H,Br,-,-],[ZB920;G22,H,CN,-,-], [ZB921;G23,H,H,-,-], [ZB922;G23,Me,H,-,-],[ZB923;G23,Et,H,-,-],[ZB924;G23,Pr,H,-,-],[ZB925;G23,i-Pr,H,-,-], [ZB926;G23,c-Pr,H,-,-],[ZB927;G23,Ph,H,-,-],[ZB928;G23,OMe,H,-,-],[ZB929;G23,OEt,H,-,-],[ZB930;G23,OPh,H,-,-],[ZB931;G23,$CF_3$,H,-,-],[ZB932;G23,F,H,-,-],[ZB933;G23,C1,H,-,-],[ZB934;G23,Br,H,-,-],[ZB935;G23,CN,H,-,-],[ZB936;G23,H,Me,-,-],[ZB937;G23,H, Et,-,-],[ZB938;G23,H,Pr,-,-],[ZB939;G23,H,i-Pr,-,-],[ZB940;G23,H,c-Pr,-,-],[ZB941;G23,H,Ph,-,-],[ZB942;G23,H,OMe,-,-],[ZB943;G 23,H,OEt,-,-], [ZB944;G23,H,OPh,-,-], [ZB945;G23,H,$CF_3$,-,-], [ZB946;G23,H,F,-,-], [ZB947;G23,H,C1,-,-], [ZB948;G23,H,Br,-,-],[ZB949;G23,H,CN,-,-], [ZB950;G24,H,H,-,-], [ZB951;G24,Me,H,-,-],[ZB952;G24,Et,H,-,-],[ZB953;G24,Pr,H,-,-],[ZB954;G24,i-Pr,H,-,-],[ZB955;G24,c-Pr,H,-,-],[ZB956;G24,Ph,H,-,-],[ZB957;G24,OMe,H,-,-],[ZB958;G24,OEt,H,-,-],[ZB959;G24,OPh,H,-,-],[ZB960;G24,$CF_3$,H,-,-],[ZB961;G24,F,H,-,-],[ZB962;G24,C1,H,-,-],[ZB963;G24,Br,H,-,-],[ZB964;G24,CN,H,-,-],[ZB965;G24,H,Me,-,-],[ZB966;G24,H, Et,-,-],[ZB967;G24,H,Pr,-,-],[ZB968;G24,H,i-Pr,-,-],[ZB969;G24,H,c-Pr,-,-],[ZB970;G24,H,Ph,-,-],[ZB971;G24,H,OMe,-,-],[ZB972;G 24,H,OEt,-,-], [ZB973;G24,H,OPh,-,-], [ZB974;G24,H,$CF_3$,-,-], [ZB975;G24,H,F,-,-], [ZB976;G24,H,C1,-,-], [ZB977;G24,H,Br,-,-],[ZB978;G24,H,CN,-,-], [ZB979;G25,H,H,H,-], [ZB980;G25,H,Me, H,-],[ZB981;G25,H,Et,H,-],[ZB982;G25,H,Pr,H,-],[ZB983;G25,H ,i-Pr,H,-],[ZB984;G25,H,c-Pr,H,-],[ZB985;G25,H,Ph,H,-], [ZB986;G25,H,OMe,H,-],[ZB987;G 25,H,OEt,H,-],[ZB988;G25,H,OPh,H,-],[ZB989;G25,H,$CF_3$,H,-],[ZB990;G25,H,F,H,-],[ZB991;G25,H,C1,H,-],[ZB992;G25,H,Br,H,-], [ZB993;G25,H,CN,H,-],[ZB994;G25,H,H,Me,-], [ZB995;G25,H,H, Et,-],[ZB996;G25,H,H,Pr,-],[ZB997;G25,H,H,i-Pr,-], [ZB998;G25,H,H,c-Pr,-],[ZB999;G25,H,H,Ph,-],[ZB1000;G25,H,H,OMe,-]

[ZB1001;G25,H,H,OEt,-],[ZB1002;G25,H,H,OPh,-],[ZB1003;G25,H ,H,$CF_3$,-],[ZB1004;G25,H,H,F,-],[ZB1005;G25,H,H,C1,-],[ZB100 6;G25,H,H,Br,-],[ZB1007;G25,H,H,CN,-],[ZB1008;G25,Me,H,H,-],[ZB1009;G25,Me,Me,H,-],[ZB1010;G25,Me,Et,H,-],[ZB1011;G25, Me,Pr,H,-],[ZB1012;G25,Me,i-Pr,H,-],[ZB1013;G25,Me,c-Pr,H,-],[ZB1014;G25,Me,Ph,H,-],[ZB1015;G25,Me,OMe,H,-],[ZB1 016;G25,Me,OEt,H,-],[ZB1017;G25,Me,OPh,H,-],[ZB1018;G25,Me, $CF_3$,H,-],[ZB1019;G25,Me,F,H,-],[ZB1020;G25,Me,C1,H,-],[ZB10 21;G25,Me,Br,H,-],[ZB1022;G25,Me,CN,H,-],[ZB1023;G25,Me,H,M e,-],[ZB1024;G25,Me,H,Et,-],[ZB1025;G25,Me,H,Pr,-],[ZB1026; G25,Me,H,i-Pr,-], [ZB1027;G25,Me,H,c-Pr,-],[ZB1028;G25,Me,H,Ph,-],[ZB1029;G25,Me,H,OMe,-],[ZB103 0;G25,Me,H,OEt,-],[ZB1031;G25,Me,H,OPh,-],[ZB1032;G25,Me,H, $CF_3$,-],[ZB1033;G25,Me,H,F,-],[ZB1034;G25,Me,H,C1,-],[ZB1035;G25,Me,H,Br,-],[ZB1036;G25,Me,H,CN,-],[ZB1037;G26,H,H,H,-],[ZB1038;G26,H,Me,H,-],[ZB1039;G26,H,Et,H,-],[ZB1040;G26,H, Pr,H,-],[ZB1041;G26,H,i-Pr,H,-],[ZB1042;G26,H,c-Pr,H,-],[ZB1043;G26,H,Ph,H,-],[ZB1044;G26,H,OMe,H,-],[ZB104 5;G26,H,OEt,H,-],[ZB1046;G26,H,OPh,H,-], [ZB1047;G26,H,$CF_3$,H,-],[ZB1048;G26,H,F,H,-],[ZB1049;G26,H,C1,H,-],[ZB1050;G26, H,Br,H,-], [ZB1051;G26,H,CN,H,-], [ZB1052;G26,H,H,Me,-], [ZB10 53;G26,H,H,Et,-], [ZB1054;G26,H,H,Pr,-],[ZB1055;G26,H,H,i-Pr,-], [ZB1056;G26,H,H,c-Pr,-],[ZB1057;G26,H,H,Ph,-],[ZB1058;G26,H,H,OMe,-],[ZB1059; G26,H,H,OEt,-],[ZB1060;G26,H,H,OPh,-],[ZB1061;G26,H,H,$CF_3$,-], [ZB1062;G26,H,H,F,-],[ZB1063;G26,H,H,C1,-], [ZB1064;G26,H, H,Br,-],[ZB1065;G26,H,H,CN,-],[ZB1066;G26,Me,H,H,-],[ZB1067;G26,Me,Me,H,-],[ZB1068;G26,Me,Et,H,-],[ZB1069;G26,Me,Pr,H,-],[ZB1070;G26,Me,i-Pr,H,-],[ZB1071;G26,Me,c-Pr,H,-],[ZB1072;G26,Me,Ph,H,-],[ZB1073;G26,Me,OMe,H,-],[ZB1 074;G26,Me,OEt,H,-],[ZB1075;G26,Me,OPh,H,-],[ZB1076;G26,Me, $CF_3$,H,-],[ZB1077;G26,Me,F,H,-],[ZB1078;G26,Me,C1,H,-],[ZB10 79;G26,Me,Br,H,-],[ZB1080;G26,Me,CN,H,-],[ZB1081;G26,Me,H,M e,-],[ZB1082;G26,Me,H,Et,-],[ZB1083;G26,Me,H,Pr,-],[ZB1084; G26,Me,H,i-Pr,-], [ZB1085;G26,Me,H,c-Pr,-],[ZB1086;G26,Me,H,Ph,-],[ZB1087;G26,Me,H,OMe,-],[ZB108 8;G26,Me,H,OEt,-],[ZB1089;G26,Me,H,OPh,-],[ZB1090;G26,Me,H, $CF_3$,-], [ZB1091;G26,Me,H,F,-], [ZB1092;G26,Me,H,C1,-], [ZB1093;G26,Me,H,Br,-],[ZB1094;G26,Me,H,CN,-],[ZB1095;G27,H,H,H,-],[ZB1096;G27,Me,H,H,-],[ZB1097;G27,Et,H,H,-],[ZB1098;G27,Pr ,H,H,-],[ZB1099;G27,i-Pr,H,H,-],[ZB1100;G27,c-Pr,H,H,-]

[ZB1101;G27,Ph,H,H,-],[ZB1102;G27,OMe,H,H,-], [ZB1103;G27,OE t,H,H,-],[ZB1104;G27,OPh,H,H,-], [ZB1105;G27,$CF_3$,H,H,-],[ZB1 106;G27,F,H,H,-], [ZB1107;G27,C1,H,H,-],[ZB1108;G27,Br,H,H,-],[ZB1109; G27,CN,H,H,-],[ZB1110;G27,H,Me,H,-],[ZB1111; G27,H ,Et,H,-],[ZB1112;G27,H,Pr,H,-],[ZB1113;G27,H,i-Pr,H,-],[ZB1114;G27,H,c-Pr,H,-],[ZB1115;G27,H,Ph,H,-], [ZB1116;G27,H,OMe,H,-],[ZB111 7;G27,H,OEt,H,-], [ZB1118;G27,H,OPh,H,-],[ZB1119;G27,H,$CF_3$,H ,-], [ZB1120;G27,H,F,H,-],[ZB1121;G27,H,C1,H,-],[ZB1122; G27, H,Br,H,-],[ZB1123;G27,H,CN,H,-],[ZB1124;G27,H, H,Me,-],[ZB11 25;G27,H,H,Et,-],[ZB1126;G27,H,H,Pr,-], [ZB1127;G27,H,H,i-Pr,-],[ZB1128;G27,H,H,c-Pr,-], [ZB1129;G27,H,H,Ph,-],[ZB1130;G27,H,H,OMe,-], [ZB1131; G27,H,H,OEt,-],[ZB1132;G27,H,H,OPh,-], [ZB1133;G27,H,H,$CF_3$,-],[ZB1134;G27,H,H,F,-],[ZB1135; G27,H,H,C1,-],[ZB1136;G27,H, H,Br,-],[ZB1137;G27,H, H,CN,-],[ZB1138;G28,H,H,-,-],[ZB1139; G28,Me,H,-,-], [ZB1140;G28,C1,H,-,-],[ZB1141;G28,$CF_3$,H,-,-], [ZB1142; G28,H,Me,-,-],[ZB1143;G28,H,C1,-,-],[ZB1144;G28,H,C $F_3$,-,-],[ZB1145;G28,H,SH,-,-]

The compound represented by formula (1C) wherein $R^1$ represents a chlorine atom, L represents an oxygen atom, m is 1, and a combination of a structure of G and the substituents of $R^{X7}$, $R^{X3}$, $R^{X9}$, and $R^{X10}$ which depend on a structure of G represents any combinations descried in the Combination B (hereinafter, referred to as Compound Class SX18).

The compound represented by formula (1C) wherein $R^1$ represents a methyl group, L represents $CH_2$, m is 1, and a combination of a structure of G and the substituents of $R^{X7}$, $R^{X8}$, $R^{X9}$, and $R^{X10}$ which depend on a structure of G represents any combinations descried in the Combination B (hereinafter, referred to as Compound Class SX19).

The compound represented by formula (1C) wherein $R^1$ represents a chlorine atom, L represents $CH_2$, m is 1, and a combination of a structure of G and the substituents of $R^{X7}$, $R^{X8}$, $R^{X9}$, and $R^{X10}$ which depend on a structure of G represents any combinations descried in the Combination B (hereinafter, referred to as Compound Class SX20).

The compound represented by formula (1C) wherein $R^1$ represents a methyl group, L represents an oxygen atom, m is 2, and a combination of a structure of G and the substituents of $R^{X7}$, $R^{X8}$, $R^{X9}$, and $R^{X10}$ which depend on a structure of G represents any combinations descried in the Combination B (hereinafter, referred to as Compound Class SX21).

The compound represented by formula (1C) wherein $R^1$ represents a chlorine atom, L represents an oxygen atom, m is 2, and a combination of a structure of G and the substituents of $R^{X7}$, $R^{X8}$, $R^{X9}$, and $R^{X10}$ which depend on a structure of G represents any combinations descried in the Combination B (hereinafter, referred to as Compound Class SX22).

The compound represented by formula (1C) wherein $R^1$ represents a methyl group, L represents $CH_2$, m is 2, and a combination of a structure of G and the substituents of $R^{X7}$, $R^{X8}$, $R^{X9}$, and $R^{X10}$ which depend on a structure of G represents any combinations descried in the Combination B (hereinafter, referred to as Compound Class SX23).

The compound represented by formula (1C) wherein $R^1$ represents a chlorine atom, L represents $CH_2$, m is 2, and a combination of a structure of G and the substituents of $R^{X7}$, $R^{X8}$, $R^{X9}$, and $R^{X10}$ which depend on a structure of G represents any combinations descried in the Combination B (hereinafter, referred to as Compound Class SX24).

The compound represented by formula (1C) wherein $R^1$ represents a methyl group, L represents an oxygen atom, m is 3, and a combination of a structure of G and the substituents of $R^{X7}$, $R^{X8}$, $R^{X9}$, and $R^{X10}$ which depend on a structure of G represents any combinations descried in the Combination B (hereinafter, referred to as Compound Class SX25).

The compound represented by formula (1C) wherein $R^1$ represents a chlorine atom, L represents an oxygen atom, m is 3, and a combination of a structure of G and the substituents of $R^{X7}$, $R^{X8}$, $R^{X9}$, and $R^{X10}$ which depend on a structure of G represents any combinations descried in the Combination B (hereinafter, referred to as Compound Class SX26).

The compound represented by formula (1C) wherein $R^1$ represents a methyl group, L represents $CH_2$, m is 3, and a combination of a structure of G and the substituents of $R^{X7}$, $R^{X8}$, $R^{X9}$, and $R^{X10}$ which depend on a structure of G represents any combinations descried in the Combination B (hereinafter, referred to as Compound Class SX27).

The compound represented by formula (1C) wherein $R^1$ represents a chlorine atom, L represents $CH_2$, m is 3, and a combination of a structure of G and the substituents of $R^{X7}$, $R^{X8}$, $R^{X9}$, and $R^{X10}$ which depend on a structure of G represents any combinations descried in the Combination B (hereinafter, referred to as Compound Class SX28).

A compound represented by formula (1D):

(1D)

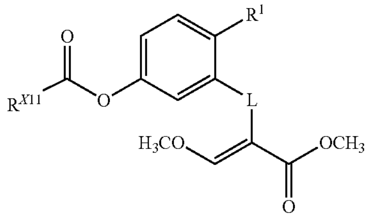

wherein $R^1$ represents a methyl group, L represents an oxygen atom, and $R^{X11}$ represents any substituents selected from Group X, Group Y and Group Z (hereinafter, referred to as Compound Class SX29).

Group Y: a group consisting of Me, Ph, $CH_2Ph$, $(CH_2)_2Ph$, $(CH_2)_3Ph$, 2-pyridyl, 3-pyridyl, 4-pyridyl, 2-thienyl, and 3-thienyl.

Group Z: a group consisting of 1-pyrrolidinyl, 1-piperidinyl, and 4-morpholinyl.

The compound represented by formula (1D) wherein $R^1$ represents a chlorine atom, L represents an oxygen atom, and $R^{X11}$ represents any substituents selected from Group X, Group Y and Group Z (hereinafter, referred to as Compound Class SX30).

The compound represented by formula (1D) wherein $R^1$ represents a methyl group, L represents $CH_2$, and $R^{X11}$ represents any substituents selected from Group X, Group Y and Group Z (hereinafter, referred to as Compound Class SX31)

The compound represented by formula (1D) wherein $R^1$ represents a chlorine atom, L represents $CH_2$, and $R^{X11}$ represents any substituents selected from Group X, Group Y and Group Z (hereinafter, referred to as Compound Class SX32)

A compound represented by formula (1E):

(1E)

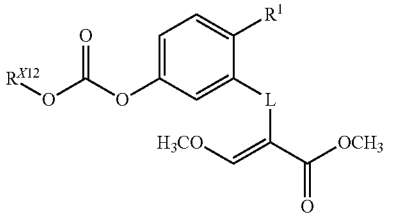

wherein $R^1$ represents a methyl group, L represents an oxygen atom, and $R^{X12}$ represents any substituents selected from Group X and Group Y (hereinafter, referred to as Compound Class SX33).

The compound represented by formula (1E) wherein $R^1$ represents a chlorine atom, L represents an oxygen atom, and $R^{X12}$ represents any substituents selected from Group X and Group Y (hereinafter, referred to as Compound Class SX34).

The compound represented by formula (1E) wherein $R^1$ represents a methyl group, L represents $CH_2$, and $R^{X12}$ represents any substituents selected from Group X and Group Y (hereinafter, referred to as Compound Class SX35).

The compound represented by formula (1E) wherein $R^1$ represents a chlorine atom, L represents $CH_2$, and $R^{X12}$ represents any substituents selected from Group X and Group Y (hereinafter, referred to as Compound Class SX36).

A compound represented by formula (1F):

(1F)

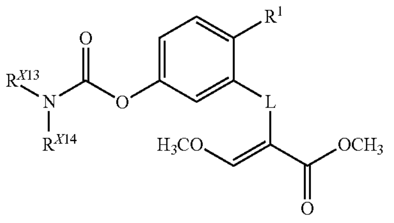

wherein $R^1$ represents a methyl group, L represents an oxygen atom, and $R^{X13}$ represents a hydrogen atom, and $R^{X14}$ represents any substituents selected from Group X and Group Y (hereinafter, referred to as Compound Class SX37).

The compound represented by formula (1F) wherein $R^1$ represents a chlorine atom, L represents an oxygen atom, and $R^{X13}$ represents a hydrogen atom, and $R^{X14}$ represents any substituents selected from Group X and Group Y (hereinafter, referred to as Compound Class SX38).

The compound represented by formula (1F) wherein $R^1$ represents a methyl group, L represents $CH_2$, and $R^{X13}$ represents a hydrogen atom, and $R^{X14}$ represents any substituents selected from Group X and Group Y (hereinafter, referred to as Compound Class SX39).

The compound represented by formula (1F) wherein $R^1$ represents a chlorine atom, L represents $CH_2$, and $R^{X13}$ represents a hydrogen atom, and $R^{X14}$ represents any substituents selected from Group X and Group Y (hereinafter, referred to as Compound Class SX40).

The compound represented by formula (1F) wherein $R^1$ represents a methyl group, L represents an oxygen atom, and $R^{X}1^{3}$ represents a methyl group, and $R^{X14}$ represents any substituents selected from Group X and Group Y (hereinafter, referred to as Compound Class SX41).

The compound represented by formula (1F) wherein $R^1$ represents a chlorine atom, L represents an oxygen atom, and $R^{X13}$ represents a methyl group, and $R^{X14}$ represents any substituents selected from Group X and Group Y (hereinafter, referred to as Compound Class SX42).

The compound represented by formula (1F) wherein $R^1$ represents a methyl group, L represents $CH_2$, and $R^{X13}$ represents a methyl group, and $R^{X14}$ represents any substituents selected from Group X and Group Y (hereinafter, referred to as Compound Class SX43).

The compound represented by formula (1F) wherein $R^1$ represents a chlorine atom, L represents $CH_2$, and $R^{X13}$ represents a methyl group, and $R^{X14}$ represents any substituents selected from Group X and Group Y (hereinafter, referred to as Compound Class SX44).

The compound represented by formula (1F) wherein $R^1$ represents a methyl group, L represents an oxygen atom, and $R^{X13}$ represents an ethyl group, and $R^{X14}$ represents any substituents selected from Group X and Group Y (hereinafter, referred to as Compound Class SX45).

The compound represented by formula (1F) wherein $R^1$ represents a chlorine atom, L represents an oxygen atom, and $R^{X13}$ represents an ethyl group, and $R^{X14}$ represents any substituents selected from Group X and Group Y (hereinafter, referred to as Compound Class SX46).

The compound represented by formula (1F) wherein $R^1$ represents a methyl group, L represents $CH_2$, and $R^{X13}$ represents an ethyl group, and $R^{X14}$ represents any substituents selected from Group X and Group Y (hereinafter, referred to as Compound Class SX47).

The compound represented by formula (1F) wherein $R^1$ represents a chlorine atom, L represents $CH_2$, and $R^{X13}$ represents an ethyl group, and $R^{X14}$ represents any substituents selected from Group X and Group Y (hereinafter, referred to as Compound Class SX48).

A compound represented by formula (1G):

(1G)

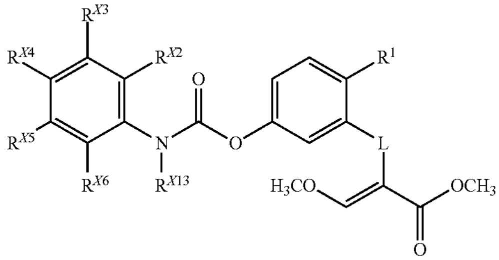

wherein $R^1$ represents a methyl group, L represents an oxygen atom, $R^{X13}$ represents a hydrogen atom, and a combination of $R^{X2}$, $R^{X3}$, $R^{X4}$, $R^{X5}$, and $R^{X6}$ represents any combinations described in the Combination A (hereinafter, referred to as Compound Class SX49).

The compound represented by formula (1G) wherein $R^1$ represents a chlorine atom, L represents an oxygen atom, and $R^{X13}$ represents a hydrogen atom, and a combination of $R^{X2}$, $R^{X3}$, $R^{X4}$, $R^{X5}$, and $R^{X6}$ represents any combinations described in the Combination A (hereinafter, referred to as Compound Class SX50).

The compound represented by formula (1G) wherein $R^1$ represents a methyl group, L represents $CH_2$, and $R^{X13}$ represents a hydrogen atom, and a combination of $R^{X2}$, $R^{X3}$, $R^{X4}$, $R^{X5}$, and $R^{X6}$ represents any combinations described in the Combination A (hereinafter, referred to as Compound Class SX51).

The compound represented by formula (1G) wherein $R^1$ represents a chlorine atom, L represents $CH_2$, and $R^{X13}$ represents a hydrogen atom, and a combination of $R^{X2}$, $R^{X3}$, $R^{X4}$, $R^{X5}$, and $R^{X6}$ represents any combinations described in the Combination A (hereinafter, referred to as Compound Class SX52).

The compound represented by formula (1G) wherein $R^1$ represents a methyl group, L represents an oxygen atom, and $R^{X13}$ represents a methyl group, and a combination of $R^{X2}$, $R^{X3}$, $R^{X4}$, $R^{X5}$, and $R^{X6}$ represents any combinations described in the Combination A (hereinafter, referred to as Compound Class SX53).

The compound represented by formula (1G) wherein $R^1$ represents a chlorine atom, L represents an oxygen atom, and $R^{X13}$ represents a methyl group, and a combination of $R^{X2}$, $R^{X3}$, $R^{X4}$, $R^{X5}$, and $R^{X6}$ represents any combinations described in the Combination A (hereinafter, referred to as Compound Class SX54).

The compound represented by formula (1G) wherein $R^1$ represents a methyl group, L represents $CH_2$, and $R^{X13}$ represents a methyl group, and a combination of $R^{X2}$, $R^{X3}$, $R^{X4}$, $R^{X5}$, and $R^{X6}$ represents any combinations described in the Combination A (hereinafter, referred to as Compound Class SX55).

The compound represented by formula (1G) wherein $R^1$ represents a chlorine atom, L represents $CH_2$, and $R^{X13}$ represents a methyl group, and a combination of $R^{X2}$, $R^{X3}$, $R^{X4}$, $R^{X5}$, and $R^{X6}$ represents any combinations described in the Combination A (hereinafter, referred to as Compound Class SX56).

The compound represented by formula (1G) wherein $R^1$ represents a methyl group, L represents an oxygen atom, and $R^{X13}$ represents an ethyl group, and a combination of $R^{X2}$, $R^{X3}$, $R^{X4}$, $R^{X5}$, and $R^{X6}$ represents any combinations described in the Combination A (hereinafter, referred to as Compound Class SX57).

The compound represented by formula (1G) wherein $R^1$ represents a chlorine atom, L represents an oxygen atom, and $R^{X13}$ represents an ethyl group, and a combination of $R^{X2}$, $R^{X3}$, $R^{X4}$, $R^{X5}$, and $R^{X6}$ represents any combinations described in the Combination A (hereinafter, referred to as Compound Class SX58).

The compound represented by formula (1G) wherein $R^1$ represents a methyl group, L represents $CH_2$, and $R^{X13}$ represents an ethyl group, and a combination of $R^{X2}$, $R^{X3}$, $R^{X4}$, $R^{X5}$, and $R^{X6}$ represents any combinations described in the Combination A (hereinafter, referred to as Compound Class SX59).

The compound represented by formula (1G) wherein $R^1$ represents a chlorine atom, L represents $CH_2$, and $R^{X13}$ represents an ethyl group, and a combination of $R^{X2}$, $R^{X3}$, $R^{X4}$, $R^{X5}$, and $R^{X6}$ represents any combinations described in the Combination A (hereinafter, referred to as Compound Class SX60).

A compound represented by formula (1H):

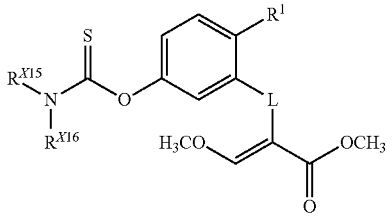

(1H)

wherein $R^1$ represents a methyl group, L represents an oxygen atom, $R^{X15}$ represents a hydrogen atom, and $R^{X16}$ represents any substituents selected from Group X and Group Y (hereinafter, referred to as Compound Class SX61).

The compound represented by formula (1H) wherein $R^1$ represents a chlorine atom, L represents an oxygen atom, and $R^{X15}$ represents a hydrogen atom, and $R^{X16}$ represents any substituents selected from Group X and Group Y (hereinafter, referred to as Compound Class SX62).

The compound represented by formula (1H) wherein $R^1$ represents a methyl group, L represents $CH_2$, and $R^{X15}$ represents a hydrogen atom, and $R^{X16}$ represents any substituents selected from Group X and Group Y (hereinafter, referred to as Compound Class SX63).

The compound represented by formula (1H) wherein $R^1$ represents a chlorine atom, L represents $CH_2$, and $R^{X15}$ represents a hydrogen atom, and $R^{X16}$ represents any substituents selected from Group X and Group Y (hereinafter, referred to as Compound Class SX64).

The compound represented by formula (1H) wherein $R^1$ represents a methyl group, L represents an oxygen atom, and $R^{X15}$ represents a methyl group, and $R^{X16}$ represents any substituents selected from Group X and Group Y (hereinafter, referred to as Compound Class SX65).

The compound represented by formula (1H) wherein $R^1$ represents a chlorine atom, L represents an oxygen atom, and $R^{X15}$ represents a methyl group, and $R^{X16}$ represents any substituents selected from Group X and Group Y (hereinafter, referred to as Compound Class SX66).

The compound represented by formula (1H) wherein $R^1$ represents a methyl group, L represents $CH_2$, and $R^{X15}$ represents a methyl group, and $R^{X16}$ represents any substituents selected from Group X and Group Y (hereinafter, referred to as Compound Class SX67).

The compound represented by formula (1H) wherein $R^1$ represents a chlorine atom, L represents $CH_2$, and $R^{X15}$ represents a methyl group, and $R^{X16}$ represents any substituents selected from Group X and Group Y (hereinafter, referred to as Compound Class SX68).

A compound represented by formula (1K):

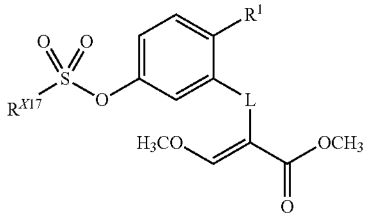

(1K)

wherein $R^1$ represents a methyl group, L represents an oxygen atom, and $R^{X27}$ represents any substituents selected from Group X and Group Y (hereinafter, referred to as Compound Class SX69).

The compound represented by formula (1K) wherein $R^1$ represents a chlorine atom, L represents an oxygen atom, and $R^{X27}$ represents any substituents selected from Group X and Group Y (hereinafter, referred to as Compound Class SX70).

The compound represented by formula (1K) wherein $R^1$ represents a methyl group, L represents $CH_2$, and $R^{X17}$ represents any substituents selected from Group X and Group Y (hereinafter, referred to as Compound Class SX71).

The compound represented by formula (1K) wherein $R^1$ represents a chlorine atom, L represents $CH_2$, and $R^{X17}$ represents any substituents selected from Group X and Group Y (hereinafter, referred to as Compound Class SX72).

A compound represented by formula (1J):

(1J)

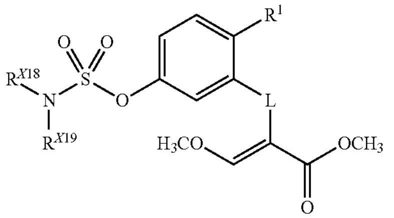

wherein $R^1$ represents a methyl group, L represents an oxygen atom, $R^{X18}$ represents a hydrogen atom, and $R^{X19}$ represents any substituents selected from Group X and Group Y (hereinafter, referred to as Compound Class SX73).

The compound represented by formula (1J) wherein $R^1$ represents a chlorine atom, L represents an oxygen atom, $R^{X18}$ represents a hydrogen atom, and $R^{X19}$ represents any substituents selected from Group X and Group Y (hereinafter, referred to as Compound Class SX74).

The compound represented by formula (1J) wherein $R^1$ represents a methyl group, L represents $CH_2$, $R^{X18}$ represents a hydrogen atom, and $R^{X19}$ represents any substituents selected from Group X and Group Y (hereinafter, referred to as Compound Class SX75).

The compound represented by formula (1J) wherein $R^1$ represents a chlorine atom, L represents $CH_2$, $R^{X18}$ represents a hydrogen atom, and $R^{X19}$ represents any substituents selected from Group X and Group Y (hereinafter, referred to as Compound Class SX76).

The compound represented by formula (1J) wherein $R^1$ represents a methyl group, L represents an oxygen atom, $R^{X18}$ represents a methyl group, and $R^{X19}$ represents any substituents selected from Group X and Group Y (hereinafter, referred to as Compound Class SX77).

The compound represented by formula (1J) wherein $R^1$ represents a chlorine atom, L represents an oxygen atom, $R^{X18}$ represents a methyl group, and $R^{X19}$ represents any substituents selected from Group X and Group Y (hereinafter, referred to as Compound Class SX78).

The compound represented by formula (1J) wherein $R^1$ represents a methyl group, L represents $CH_2$, $R^{X18}$ represents a methyl group, and $R^{X19}$ represents any substituents selected from Group X and Group Y (hereinafter, referred to as Compound Class SX79).

The compound represented by formula (1J) wherein $R^1$ represents a chlorine atom, L represents $CH_2$, $R^{X18}$ represents a methyl group, and $R^{X19}$ represents any substituents selected from Group X and Group Y (hereinafter, referred to as Compound Class SX80).

A compound represented by formula (2A):

(2A)

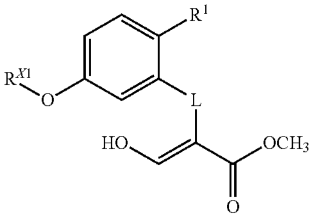

wherein $R^1$ represents a methyl group, L represents an oxygen atom, and $R^{X1}$ represents any substituents selected from Group X.

The compound represented by formula (2A) wherein $R^1$ represents a chlorine atom, L represents an oxygen atom, and $R^{X1}$ represents any substituents selected from Group X.

The compound represented by formula (2A) wherein $R^1$ represents a methyl group, L represents $CH_2$, and $R^{X1}$represents any substituents selected from Group X.

The compound represented by formula (2A) wherein $R^1$ represents a chlorine atom, L represents $CH_2$, and $R^{X1}$ represents any substituents selected from Group X.

A compound represented by formula (2B):

(2B)

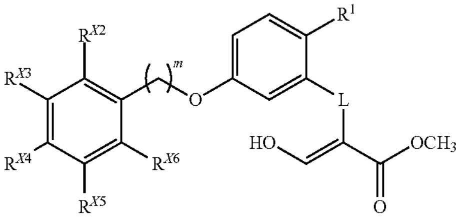

wherein $R^1$ represents a methyl group, L represents an oxygen atom, m is 1, and a combination of $R^{X2}$, $R^{X3}$, $R^{X4}$, $R^{X5}$, and $R^{X6}$represents any combinations described in Combination A.

The compound represented by formula (2B) wherein $R^1$ represents a chlorine atom, L represents an oxygen atom, m is 1, and a combination of $R^{X2}$, $R^{X}$S, $R^{X4}$, $R^{X5}$, and $R^{X6}$ represents any combinations described in Combination A.

The compound represented by formula (2B) wherein $R^1$ represents a methyl group, L represents $CH_2$, m is 1, and a combination of $R^{X2}$, $R^{X3}$, $R^{X4}$, $R^{X5}$, and $R^{X6}$ represents any combinations described in Combination A.

The compound represented by formula (2B) wherein $R^1$ represents a chlorine atom, L represents $CH_2$, m is 1, and a combination of $R^{X2}$, $R^{X}$S, $R^{X4}$, $R^{X5}$, and $R^{X6}$ represents any combinations described in Combination A.

The compound represented by formula (2B) wherein $R^1$ represents a methyl group, L represents an oxygen atom, m is 2, and a combination of $R^{X2}$, $R^{X3}$, $R^{X4}$, $R^{X5}$, and $R^{X6}$ represents any combinations described in Combination A.

The compound represented by formula (2B) wherein $R^1$ represents a chlorine atom, L represents an oxygen atom, m is 2, and a combination of $R^{X2}$, $R^{X3}$, $R^{X4}$, $R^{X5}$, and $R^{X6}$ represents any combinations described in Combination A.

The compound represented by formula (2B) wherein $R^1$ represents a methyl group, L represents $CH_2$, m is 2, and a combination of $R^{X2}$, $R^{X3}$, $R^{X4}$, $R^{X5}$, and $R^{X6}$ represents any combinations described in Combination A.

The compound represented by formula (2B) wherein $R^1$ represents a chlorine atom, L represents $CH_2$, m is 2, and a combination of $R^{X2}$, $R^{X3}$, $R^{X4}$, $R^{X5}$, and $R^{X6}$ represents any combinations described in Combination A.

The compound represented by formula (2B) wherein $R^1$ represents a methyl group, L represents an oxygen atom, m is 3, and a combination of $R^{X2}$, $R^{X3}$, $R^{X4}$, $R^{X5}$, and $R^{X6}$ represents any combinations described in Combination A.

The compound represented by formula (2B) wherein $R^1$ represents a chlorine atom, L represents an oxygen atom, m is 3, and a combination of $R^{X2}$, $R^{X3}$, $R^{X4}$, $R^{X5}$, and $R^{X6}$ represents any combinations described in Combination A.

The compound represented by formula (2B) wherein $R^1$ represents a methyl group, L represents $CH_2$, m is 3, and a combination of $R^{X2}$, $R^{X3}$, $R^{X4}$, $R^{X5}$, and $R^{X6}$ represents any combinations described in Combination A.

The compound represented by formula (2B) wherein $R^1$ represents a chlorine atom, L represents $CH_2$, m is 3, and a combination of $R^{X2}$, $R^{X3}$, $R^{X4}$, $R^{X5}$, and $R^{X6}$ represents any combinations described in Combination A.

A compound represented by formula (2C):

(2C)

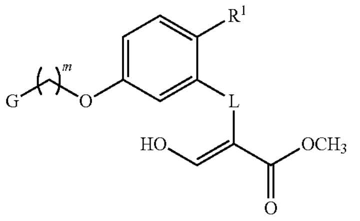

wherein $R^1$ represents a methyl group, L represents an oxygen atom, m is 1, and a combination of a structure of G and the substituents of $R^{X7}$, $R^{X3}$, $R^{X9}$, and $R^{X10}$ which depend on a structure of G represents any combinations descried in the Combination B.

A compound represented by formula (2C) wherein $R^1$ represents a chlorine atom, L represents an oxygen atom, m is 1, and a combination of a structure of G and the substituents of $R^{X7}$, $R^{X8}$, $R^{X9}$, and $R^{X10}$ which depend on a structure of G represents any combinations descried in the Combination B.

A compound represented by formula (2C) wherein $R^1$ represents a methyl group, L represents $CH_2$, m is 1, and a combination of a structure of G and the substituents of $R^{X7}$, $R^{X8}$, $R^{X9}$, and $R^{X10}$ which depend on a structure of G represents any combinations descried in the Combination B.

A compound represented by formula (2C) wherein $R^1$ represents a chlorine atom, L represents $CH_2$, m is 1, and a combination of a structure of G and $R^{X7}$, $R^{X8}$, $R^{X9}$, and $R^{X10}$ which depend on a structure of G represents any combinations descried in the Combination B.

A compound represented by formula (2C) wherein $R^1$ represents a methyl group, L represents an oxygen atom, m is 2, and a combination of a structure of G and $R^{X7}$, $R^{X8}$, $R^{X9}$, and $R^{X10}$ which depend on a structure of G represents any combinations descried in the Combination B.

A compound represented by formula (2C) wherein $R^1$ represents a chlorine atom, L represents an oxygen atom, m is 2, and a combination of a structure of G and $R^{X7}$, $R^{X8}$, $R^{X9}$, and $R^{X10}$ which depend on a structure of G represents any combinations descried in the Combination B.

A compound represented by formula (2C) wherein $R^1$ represents a methyl group, L represents $CH_2$, m is 2, and a combination of a structure of G and the substituents of $R^{X7}$, $R^{X8}$, $R^{X9}$, and $R^{X10}$ which depend on a structure of G represents any combinations descried in the Combination B.

A compound represented by formula (2C) wherein $R^1$ represents a chlorine atom, L represents $CH_2$, m is 2, and a combination of a structure of G and the substituents of $R^{X7}$, $R^{X8}$, $R^{X9}$, and $R^{X10}$ which depend on a structure of G represents any combinations descried in the Combination B.

A compound represented by formula (2C) wherein $R^1$ represents a methyl group, L represents an oxygen atom, m is 3, and a combination of a structure of G and the substituents of $R^{X7}$, $R^{X8}$, $R^{X9}$, and $R^{X10}$ which depend on a structure of G represents any combinations descried in the Combination B.

A compound represented by formula (2C) wherein $R^1$ represents a chlorine atom, L represents an oxygen atom, m is 3, and a combination of a structure of G and the substituents of $R^{X7}$, $R^{X8}$, $R^{X9}$, and $R^{X10}$ which depend on a structure of G represents any combinations descried in the Combination B.

A compound represented by formula (2C) wherein $R^1$ represents a methyl group, L represents $CH_2$, m is 3, and a combination of a structure of G and the substituents of $R^{X7}$, $R^{X8}$, $R^{X9}$, and $R^{X10}$ which depend on a structure of G represents any combinations descried in the Combination B.

A compound represented by formula (2C) wherein $R^1$ represents a chlorine atom, L represents $CH_2$, m is 3, and a combination of a structure of G and the substituents of $R^{X7}$, $R^{X8}$, $R^{X9}$, and $R^{X10}$ which depend on a structure of G represents any combinations descried in the Combination B.

A compound represented by formula (2D):

(2D)

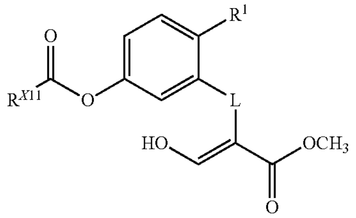

wherein $R^1$ represents a methyl group, L represents an oxygen atom, and $R^{X11}$ represents any substituents selected from Group X, Group Y and Group Z.

The compound represented by formula (2D) wherein $R^1$ represents a chlorine atom, L represents an oxygen atom, and $R^{X11}$ represents any substituents selected from Group X, Group Y and Group Z.

The compound represented by formula (2D) wherein $R^1$ represents a methyl group, L represents $CH_2$, and $R^{X11}$ represents any substituents selected from Group X, Group Y and Group Z.

The compound represented by formula (2D) wherein $R^1$ represents a chlorine atom, L represents $CH_2$, and $R^{X11}$ represents any substituents selected from Group X, Group Y and Group Z.

A compound represented by formula (2F):

(2F)

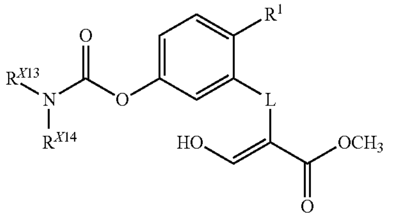

wherein $R^1$ represents a methyl group, L represents an oxygen atom, $R^{X13}$ represents a hydrogen atom, and $R^{X14}$ represents any substituents selected from Group X and Group Y.

A compound represented by formula (2F) wherein $R^1$ represents a chlorine atom, L represents an oxygen atom, $R^{X13}$represents a hydrogen atom, and $R^{X14}$ represents any substituents selected from Group X and Group Y.

A compound represented by formula (2F) wherein $R^1$ represents a methyl group, L represents $CH_2$, $R^{X13}$ represents a hydrogen atom, and $R^{X14}$ represents any substituents selected from Group X and Group Y.

A compound represented by formula (2F) wherein $R^1$ represents a chlorine atom, L represents $CH_2$, $R^{X13}$ represents a hydrogen atom, and $R^{X14}$ represents any substituents selected from Group X and Group Y.

A compound represented by formula (2F) wherein $R^1$ represents a methyl group, L represents an oxygen atom, $R^{X13}$represents a methyl group, and $R^{X14}$ represents any substituents selected from Group X and Group Y.

A compound represented by formula (2F) wherein $R^1$ represents a chlorine atom, L represents an oxygen atom, $R^{X13}$ represents a methyl group, and $R^{X14}$ represents any substituents selected from Group X and Group Y.

A compound represented by formula (2F) wherein $R^1$ represents a methyl group, L represents $CH_2$, $R^{X13}$ represents a methyl group, and $R^{X14}$ represents any substituents selected from Group X and Group Y.

A compound represented by formula (2F) wherein $R^1$ represents a chlorine atom, L represents $CH_2$, $R^{X13}$ represents a methyl group, and $R^{X14}$ represents any substituents selected from Group X and Group Y.

A compound represented by formula (2F) wherein $R^1$ represents a methyl group, L represents an oxygen atom, $R^{X13}$represents an ethyl group, and $R^{X14}$ represents any substituents selected from Group X and Group Y.

A compound represented by formula (2F) wherein $R^1$ represents a chlorine atom, L represents an oxygen atom, $R^{X13}$ represents an ethyl group, and $R^{X14}$ represents any substituents selected from Group X and Group Y.

A compound represented by formula (2F) wherein $R^1$ represents a methyl group, L represents $CH_2$, $R^{X13}$ represents an ethyl group, and $R^{X14}$ represents any substituents selected from Group X and Group Y.

A compound represented by formula (2F) wherein $R^1$ represents a chlorine atom, L represents $CH_2$, $R^{X13}$ represents an ethyl group, and $R^{X14}$ represents any substituents selected from Group X and Group Y.

A compound represented by formula (3A):

(3A)

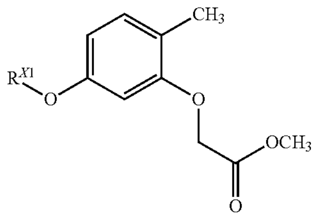

wherein $R^{X1}$ represents any substituents selected from Group X.

A compound represented by formula (3B):

(3B)

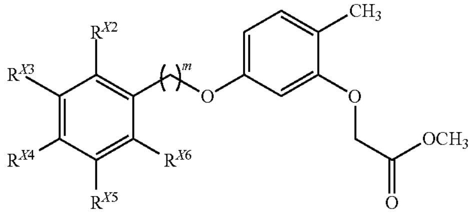

wherein m is 1, and a combination of $R^{X2}$, $R^{X3}$, $R^{X4}$, $R^{X5}$ and $R^{X6}$ represents any combinations described in the Combination A.

The compound represented by formula (3B) wherein m is 2, and a combination of $R^{X2}$, $R^{X3}$, $R^{X4}$, $R^{X5}$ and $R^{X6}$ represents any combinations described in the Combination A.

The compound represented by formula (3B) wherein m is 3, and a combination of $R^{X2}$, $R^{X3}$, $R^{X4}$, $R^{X5}$ and $R^{X6}$ represents any combinations described in the Combination A.

A compound represented by formula (3C):

(3C)

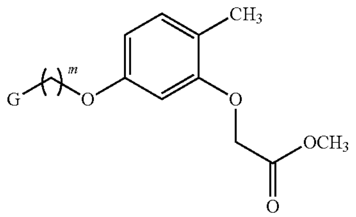

wherein m is 1, and a combination of a structure of G and the substituents of $R^{X7}$, $R^{X3}$, $R^{X9}$, and $R^{X10}$ which depend on a structure of G represents any combinations descried in the Combination B.

The compound represented by formula (3C) wherein m is 2, and a combination of a structure of G and the substituents of $R^{X7}$, $R^{X3}$, $R^{X9}$, and $R^{X10}$ which depend on a structure of G represents any combinations descried in the Combination B.

The compound represented by formula (3C) wherein m is 3, and a combination of a structure of G and the substituents of $R^{X7}$, $R^{X8}$, $R^{X9}$, and $R^{X10}$ which depend on a structure of G represents any combinations descried in the Combination B.

A compound represented by formula (3D):

(3D)

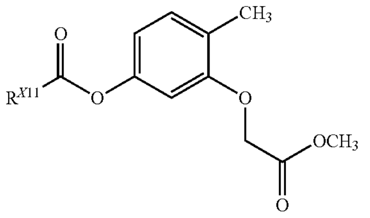

wherein $R^{X11}$ represents any substituents selected from Group X, Group Y and Group Z.

A compound represented by formula (3F):

(3F)

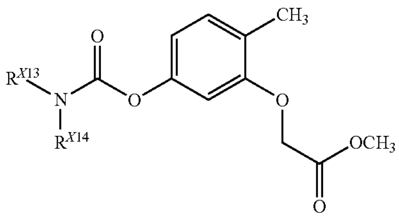

wherein $R^{X13}$ represents a hydrogen atom, and $R^{X14}$ represents any substituents selected from Group X and Group Y.

The compound represented by formula (3F) wherein $R^{X13}$represents a methyl group, and $R^{X14}$ represents any substituents selected from Group X and Group Y.

The compound represented by formula (3F) wherein $R^{X13}$represents an ethyl group, and $R^{X14}$ represents any substituents selected from Group X and Group Y.

A compound represented by formula (4A):

(4A)

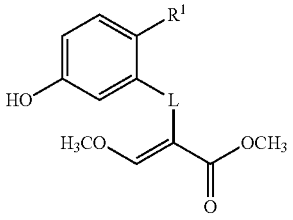

wherein L represents an oxygen atom, and $R^1$ represents any substituents selected from Group W.

Group W: a group consisting of Me, Et, Pr, c-Pr, $CF_3$, F, Cl, Br, and I.

The compound represented by formula (4A) wherein L represents $CH_2$, and $R^1$ represents any substituents selected from Group W.

A compound represented by formula (5A):

(5A)

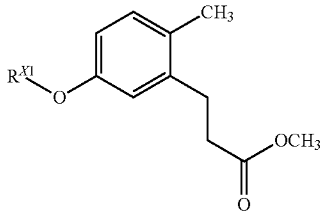

wherein $R^{X1}$ represents any substituents selected from Group X.

A compound represented by formula (5B):

(5B)

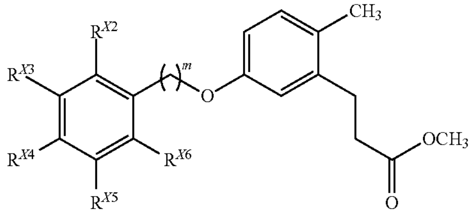

wherein m is 1, and a combination of $R^{X2}$, $R^{X3}$, $R^{X4}$, $R^{X5}$, and $R^{X6}$ represents any combinations described in Combination A.

The compound represented by formula (5B) wherein m is 2, and a combination of $R^{X2}$, $R^{X3}$, $R^{X4}$, $R^{X5}$, and $R^{X6}$ represents any combinations described in Combination A.

The compound represented by formula (5B) wherein m is 3, and a combination of $R^{X2}$, $R^{X3}$, $R^{X4}$, $R^{X5}$, and $R^{X6}$ represents any combinations described in Combination A.

A compound represented by formula (5C):

(5C)

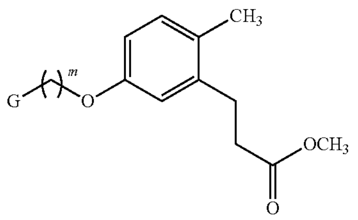

wherein m is 1, and a combination of a structure of G and the substituents of $R^{X7}$, $R^{X8}$, $R^{X9}$, and $R^{X10}$ which depend on a structure of G represents any combinations descried in the Combination B.

The compound represented by formula (5C) wherein m is 2, and a combination of a structure of G and the substituents of $R^{X7}$, $R^{X8}$, $R^{X9}$, and $R^{X10}$ which depend on a structure of G represents any combinations descried in the Combination B.

The compound represented by formula (5C) wherein m is 3, and a combination of a structure of G and the substituents of $R^{X7}$, $R^{X8}$, $R^{X9}$, and $R^{X10}$ which depend on a structure of G represents any combinations descried in the Combination B.

A compound represented by formula (5D):

(5D)

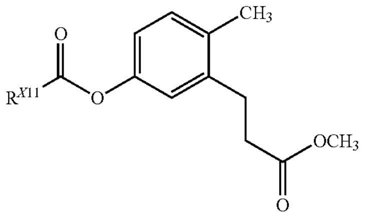

wherein $R^{X11}$ represents any substituents selected from Group X, Group Y and Group Z.

A compound represented by formula (5F):

(5F)

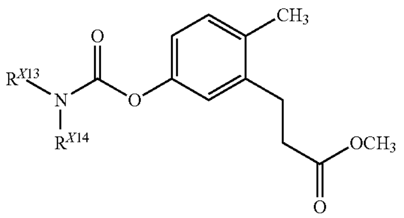

wherein $R^{X}13$ represents a hydrogen atom, and $R^{X14}$ represents any substituents selected from Group X and Group Y.

The compound represented by formula (5F) wherein $R^{X13}$represents a methyl group, and $R^{X14}$ represents any substituents selected from Group X and Group Y.

The compound represented by formula (5F) wherein $R^{X13}$represents an ethyl group, and $R^{X14}$ represents any substituents selected from Group X and Group Y.

Next, the formulation Examples of the Present compound is described. The "parts" represents "part by weight" unless otherwise specified. Also the present compound S represents any compounds described as Compound Class SX1 to SX80.

Formulation Example 1

Fifty(50) parts of any one of the present compound S, 3 parts of calcium lignin sulfonate, 2 parts of magnesium lauryl sulfate, and 45 parts of synthetic hydrated silicon dioxide are well mixed-grinding to obtain a formulation.

Formulation Example 2

Twenty(20) parts of any one of the present compound S, and 1.5 parts of sorbitan trioleate are mixed with 28.5 parts of an aqueous solution containing 2 parts of polyvinyl alcohol, and the mixture is then finely-ground by a wet grinding method. To the mixture is then added 40 parts of an aqueous solution containing 0.05 parts of xanthan gum and 0.1 parts of magnesium aluminum silicate, and 10 parts of propylene glycol is further added thereto, and the mixture is mixed with starring to obtain a formulation.

Formulation Example 3

Two(2) parts of any one of the present compound S, 88 parts of kaolin clay and 10 parts of talc are mixed-grinding thoroughly to obtain a formulation.

Formulation Example 4

Five(5) parts of any one of the present compound S, 14 parts of polyoxyethylene styryl phenyl ether, 6 parts of calcium dodecylbenzene sulfonate and 75 parts of xylene are mixed-grinding thoroughly to obtain a formulation.

Formulation Example 5

Two(2) parts of any one of the present compound S, 1 part of synthetic hydrated silicon dioxide, 2 parts of calcium lignosulfonate, 30 parts of bentonite and 65 parts of kaolin clay are mixed-grinding, and thereto is added water, and the mixture is well kneaded and is then granulated and dried to obtain a formulation.

Formulation Example 6

Twenty (20) parts of the present compound S, 35 parts of a mixture of white carbon and ammonium polyoxyethylene alkyl ether sulfate (weight ratio is 1:1) and appropriate amount of water is mixed to make the total amount thereof 100 parts, and the mixture is then finely-ground with a grinder to obtain a formulation.

Next, Test Examples are Described

The untreated groups in Test Example 1 to Test Exmaple 9 represent tested groups in which the same conditions as those of each of the Test Examples were conducted except that DMSO was dispensed in the place of a DMSO diluted solution comprising the present compound. Also the untreated groups in Test Exmaple 10 to Test Exmaple 22 represent tested groups in which an aqueous diluted solution of a formulation comprising the present compound is not applied.

Test Example 1: Control Test Against Wheat *Septoria* Leaf Blotch Fungus (*Septoria Tritici*)

The present compound 1 to 16, 18 to 23, 25, 26, 28 to 30, 33 to 35, 37, 38 to 40, 42 to 52, 54 to 87, 89, or 90 was diluted with DMSO so as to contain 150 ppm, and 1 μL of the dilution solutions were dispensed into titer plate (96 well), and thereafter, thereto was then dispensed 150 μL of a potato dextrose broth (PDB broth) to which conidia of *Septoria tritici* were inoculated in advance. This plate was cultured at 18° C. for 5 days, thereby allowing *Septoria tritici* to undergo proliferation, and the absorbance at 550 nm of each well of the titer plate was then measured to determine a degree of growth of *Septoria tritici*. As a result, every of the growth in the well in treated groups treated with each of the present compounds showed 50% or less compared to the growth in an untreated well.

Test Example 2: Control Test Against Soybean Anthracnose Fungus (*Colletotrichum Truncatum*)

The present compound 2 to 16, 18 to 20, 25, 26, 29, 38, 40, 42 to 44, 46 to 49, 51, 52, 55, 57 to 64, 71, or 76 was diluted with DMSO so as to contain 150 ppm, and 1 μL of the dilution solutions were dispensed into titer plate (96 well), and thereafter, thereto was then dispensed 150 μL of a potato dextrose broth (PDB broth) to which conidia of *Colletotrichum truncatum* were inoculated in advance. This plate was cultured at 18° C. for 4 days, thereby allowing *Colletotrichum truncatum* to undergo proliferation, and the absorbance at 550 nm of each well of the titer plate was then measured to determine a degree of growth of the *Colletotrichum truncatum*. As a result, every of the growth in the well in treated groups treated with each of the present compounds showed 50% or less compared to the growth in an untreated well.

Test Example 3: Control Test Against Cucurbitaceae *phytophthora* Rot Fungus (*Phytophthora Capsici*)

The present compound 1 to 20, 23, 25, 26, 29, 34, 37, 38, 40 to 49, 51, 52, 54 to 64, 68, 71, 73 to 76, 80, 89, or 90 was diluted with DMSO so as to contain 150 ppm, and 1 μL of the dilution solutions were dispensed into titer plate (96 well), and thereafter, thereto was then dispensed 150 μL of a potato dextrose broth (PDB broth) to which spores of *Phytophthora capsici* were inoculated in advance. This plate was cultured at 27° C. for 3 days, thereby allowing *Phytophthora capsici* to undergo proliferation, and the absorbance at 550 nm of each well of the titer plate was then measured to determine a degree of growth of the *Phytophthora capsici*. As a result, every of the growth in the well in treated groups treated with each of the present compounds showed 50% or less compared to the growth in an untreated well.

Test Example 4: Control Test Against Seedling Blight Fungus (*Pythium Ultimum*)

The present compound 1 to 20, 23, 25, 26, 29, 34, 37, 38, 40 to 49, 51, 52, 54 to 64, 66, 68, 71 to 76, 79 to 81, 84 to 86, 89, or 90 was diluted with DMSO so as to contain 150 ppm, and 1 μL of the dilution solutions were dispensed into titer plate (96 well), and thereafter, thereto was then dispensed 150 μL of a potato dextrose broth (PDB broth) to which spores of *Pythium ultimum* were inoculated in advance. This plate was cultured at 23° C. for 5 days, thereby allowing *Pythium ultimum* to undergo proliferation, and the absorbance at 550 nm of each well of the titer plate was then measured to determine a degree of growth of the *Pythium ultimum*. As a result, every of the growth in the well in treated groups treated with each of the present compounds showed 50% or less compared to the growth in an untreated well.

Test Example 5: Control Test Against Corn Smut Fungus (*Ustilago Maydis*)

The present compound 1 to 20, 23, 25, 26, 29, 30, 34, 37 to 49, 51, 52, 54 to 64, 68, 71 to 76, 78 to 87, 89, or 90 was diluted with DMSO so as to contain 150 ppm, and 1 μL of the dilution solutions were dispensed into titer plate (96 well), and thereafter, thereto was then dispensed 150 μL of a potato dextrose broth (PDB broth) to which conidia of *Ustilago maydis* were inoculated in advance. This plate was cultured at 18° C. for 4 days, thereby allowing *Ustilago maydis* to undergo proliferation, and the absorbance at 550 nm of each well of the titer plate was then measured to determine a degree of growth of the *Ustilago maydis*. As a result, every of the growth in the well in treated groups treated with each of the present compounds showed 50% or less compared to the growth in an untreated well.

Test Example 6: Control Test Against Barley Scald Fungus (Rhynchosporium Secalis)

The present compound 1 to 20, 23, 25, 26, 29 to 49, 51, 52, 54 to 64, 66 to 68, 71 to 87, 89, or 90 was diluted with DMSO so as to contain 150 ppm, and 1 μL of the dilution solutions were dispensed into titer plate (96 well), and thereafter, thereto was then dispensed 150 μL of a potato dextrose broth (PDB broth) to which conidia of Rhynchosporium secalis were inoculated in advance. This plate was cultured at 18° C. for 7 days, thereby allowing Rhynchosporium secalis to undergo proliferation, and the absorbance at 550 nm of each well of the titer plate was then measured to determine a degree of growth of the Rhynchosporium secalis. As a result, every of the growth in the well in treated groups treated with each of the present compounds showed 50% or less compared to the growth in an untreated well.

Test Example 7: Control Test Against Cucumber *Botrytis* Rot Fungus (*Botrytis Cinerea*)

The present compound 1 to 20, 23, 25, 26, 29 to 34, 36 to 49, 51, 52, 54 to 64, 66, 68, 71 to 85, 87, 89, or 90 was diluted with DMSO so as to contain 150 ppm, and 1 μL of the dilution solutions were dispensed into titer plate (96 well), and thereafter, thereto was then dispensed 150 μL of a potato dextrose broth (PDB broth) to which conidia of *Botrytis cinerea* were inoculated in advance. This plate was cultured at 18° C. for 4 days, thereby allowing *Botrytis cinerea* to undergo proliferation, and the absorbance at 550 nm of each well of the titer plate was then measured to determine a degree of growth of the *Botrytis cinerea*. As a result, every of the growth in the well in treated groups treated with each of the present compounds showed 50% or less compared to the growth in an untreated well.

Test Example 8: Control Test Against Peach Scab Fungus (*Cladosporium Carpophilum*)

The present compound 1 to 20, 23, 25, 26, 29 to 49, 51, 52, 54 to 64, 66 to 68, 71 to 87, 89, or 90 was diluted with DMSO so as to contain 150 ppm, and 1 μL of the dilution solutions were dispensed into titer plate (96 well), and thereafter, thereto was then dispensed 150 μL of a potato dextrose broth (PDB broth) to which conidia of *Cladosporium carpophilum* were inoculated in advance. This plate was cultured at 18° C. for 5 days, thereby allowing *Cladosporium carpophilum* to undergo proliferation, and the absorbance at 550 nm of each well of the titer plate was then measured to determine a degree of growth of the *Cladosporium carpophilum*. As a result, every of the growth in the well in treated groups treated with each of the present compounds showed 50% or less compared to the growth in an untreated well.

Test Example 9: Control Test Against Rice Brown Spot Fungus (*Cochliobolus Miyabeanus*)

The present compound 28, 30 to 33, 35, 37, 39, 50, 66, 67, 69, 70, 72 to 75, 77 to 89, or 90 was diluted with DMSO so as to contain 150 ppm, and 1 μL of the dilution solutions were dispensed into titer plate (96 well), and thereafter, thereto was then dispensed 150 μL of a potato dextrose broth (PDB broth) to which conidia of *Cochliobolus miyabeanus* were inoculated in advance. This plate was cultured at 23° C. for 3 days, thereby allowing *Cochliobolus miyabeanus* to undergo proliferation, and the absorbance at 550 nm of each well of the titer plate was then measured to determine a degree of growth of the *Cochliobolus miyabeanus*. As a result, every of the growth in the well in treated groups treated with each of the present compounds showed 50% or less compared to the growth in an untreated well.

Test Example 10: Control Test Against Soybean Rust (*Phakopsora Pachyrhizi*)

Soybean leaf (cv; Kurosengoku) was punched out to 1 cm diameter to prepare a leaf disk. Each 1 mL of an agar medium (agar concentration 1.2%) was dispensed in each well of 24 well microplate. A piece of the leaf disk was placed on agar medium on each well. To a mixture of 0.5 μL of Sorpol (registered trademark) 1200KX, 4.5 μL of DMSO, and 5 μL of xylene was added 20 μL of a solution containing 10000 ppm of the test compound in DMSO. The resulting mixture was diluted with ion exchange water to prepare a mixture containing a predetermined concentration of the test compound. The resulting mixture was sprayed in 10 μL per one leaf disk. After 1 day, an aqueous suspension of conidia of *Phakopsora pachyrhizi* having an amino acid substitution of F129L on mitochondrial cytochrome b protein ($1.0\times10^5$/mL) was inoculated onto the leaf disks. After the inoculation, the microplate was placed in a growth chamber (light on for 6 hours, light off for 18 hours, 23° C. temperature, 60% humidity). After 1 day, the leaf disks were air-dried to disappear water droplets on the surface of the leaf disk, and the microplate was placed again in the growth chamber for 12 days. Thereafter, a lesion area of soybean rust disease was assessed. As a result, lesion areas in the leaf disk treated with any one of the present compounds 1 to 10, 15 to 20, 23, 28 to 31, 33 to 35, 37, 39, 40, 50, 55, 56, 66 to 68, 70, 71 to 87, 89, or 90 as a tested compound at a prescribed concentration of 50 ppm showed 30% or more compared to the lesion areas in an untreated leaf disk.

Test Example 11: Control Test Against Rice Blast (Pyricularia *Oryzae*)

Each of plastic pots was filled with soil and thereto rice (cv; HINOHIKARI) seeds were sown and the plants were grown in a greenhouse for 20 days. Thereafter, the present compound 19, 44, or 80, each of which was made to a formulation according to the similar method to that of Formulation Example 6, was mixed with water so as to be 200 ppm. The mixtures were sprayed to foliar parts so as to adhere adequately on the leaves of the above-mentioned rice. After spraying the mixtures, the rices were air-dried and were placed at 24° C. during daytime and 20° C. during nighttime under a high humidity for 6 to 7 days while the above-mentioned spraying-treated rice were contacted rice seedlings (cv; Hinohikari) infected by Pyricularia *oryzae*, and a lesion area was observed. As a result, every of the lesion areas in rice treated with each of the present compounds showed 30% or less compared to the lesion are in an untreated rice.

Test Example 12: Control Test Against Barley Net Blotch (*Pyrenophora Teres*)

Each of plastic pots was filled with soil and thereto barley (cv; NISHINOHOSHI) seeds were sown and the barleys were grown in a greenhouse for 7 days. Thereafter, the present compound 2, 4 to 6, 13, 14, 16, 18 to 20, 26, 34, 39, 46 to 49, 51, 52, 54, 55, 57, 58, 64, 67, 68, 75 to 77, 80 to 83, 85 to 88, or 89, each of which was made to a formulation according to the similar method to that of Formulation Example 6, was mixed with water so as to be a prescribed concentration (200 ppm). The resulting mixtures were sprayed to foliar parts so as to adhere adequately on the leaves of the above-mentioned barley. After spraying the mixtures, the barleys were air-dried and after 1 day, an aqueous suspension of the conidia of *Pyrenophora teres* was spraying-inoculated. After the inoculation, the barleys were placed at 23° C. during daytime and 20° C. during nighttime under a high humidity for 3 day and then cultivated in a greenhouse for 7 days, and a lesion area was observed. As a result, every of the lesion areas in barleys treated with each of the present compounds showed 30% or less compared to the lesion area in an untreated barley.

Test Example 13: Control Test Against Cucumber Downy Mildew (*Pseudoperonospora Cubensis*)

Each of plastic pots was filled with soil and thereto cucumber (cv; SAGAMIHANJIRO) seeds were sown and the cucumbers were grown in a greenhouse for 12 days. Thereafter, the present compound 2, 47, or 61, each of which was made to a formulation according to the similar method to that of Formulation Example 6, was mixed with water so as to be 200 ppm. The mixtures were sprayed to foliar parts so as to adhere adequately on the leaves of the above-mentioned cucumber. After spraying the mixtures, the cucumbers were air-dried and after 1 day, an aqueous suspension of a spore of *Pseudoperonospora cubensis* was spraying-inoculated. After the inoculation, the cucumbers were placed firstly at 23° C. under a high humidity for 1 day and were then cultivated in a greenhouse for 10 days, and a lesion area was observed. As a result, every of the lesion areas in cucumbers treated with each of the present compounds showed 30% or less compared to the lesion area in an untreated cucumber.

Test Example 14: Control Test Against Wheat Brown Rust (*Puccinia Recondita*)

Each of plastic pots was filled with soil and thereto wheat (cv; SHIROGANE) seeds were sown and the wheats were grown in a greenhouse for 9 days. The present compound 2 to 6, 10 to 16, 18, 19, 20, 25, 26, 29, 31, 32, 34, 35, 39 to 42, 46, 47, 49, 52 to 64, 66 to 68, 73, 75 to 78, 80, 81, 83 to 89, or 90, each of which was made to a formulation according to the similar method to that of Formulation Example 6, was mixed with water so as to be 200 ppm, and the mixtures were sprayed to foliar parts so as to adhere adequately on the leaves of the above-mentioned wheat. After spraying the mixtures, the wheats were air-dried and were then cultivated at 20° C. under lighting for 5 to 7 days. The conidia of *Puccinia recondita* were sprinkling-inoculated. After the inoculation, the wheats were placed under a dark and humid condition at 23° C. for 1 day and were then cultivated at 20° C. under lighting for 8 days, and a lesion area was observed. As a result, every of the lesion areas in wheats treated with each of the present compounds showed 30% or less compared to the lesion area in an untreated wheat.

Test Example 15: Control Test Against *Septoria* Leaf Blotch (*Septoria Tritici*)

Each of plastic pots was filled with soil and thereto wheat (cv; Apogee) seeds were sown and the wheats were grown in a greenhouse for 10 days. Thereafter, the present compound 1, 3 to 6, 10, 11, 13 to 16, 18 to 21, 25, 26, 29 to 37, 39, 40, 46 to 49, 51, 53 to 55, 57, 58, 64, 72, 73, 75, 77 to 80, 82, 83, 85 to 88, or 89, each of which was made to a formulation according to the similar method to that of Formulation Example 6, was mixed with water so as to be 200 ppm. The mixtures were sprayed to foliar parts so as to adhere adequately on the leaves of the above-mentioned wheat. After spraying the mixtures, the wheats were air-dried and after 4 days, an aqueous suspension of the conidia of *Septoria tritici* was spraying-inoculated. After the inoculation, the wheats were placed at 18° C. under a high humidity for 3 days and then under lighting for 14 to 18 days, and a lesion area was observed. As a result, every of the lesion areas in wheats treated with each of the present compounds showed 30% or less compared to the lesion area in an untreated wheat.

Test Example 16: Control Test Against *Septoria* Leaf Blotch (*Septoria Tritici*)

Each of plastic pots was filled with soil and thereto wheat (cv; Apogee) seeds were sown and the wheats were grown in a greenhouse for 10 days. Thereafter, the present compound 3 to 5, 7 to 11, 15, 16, 21, 25, 26, 29, 31, 34, 37, 39, 44, 46, 47, 49, 57, 58, 71 to 75, 77 to 82, 84, 88, 89, or 90, each of which was made to a formulation according to the similar method to that of Formulation Example 6, was mixed with water so as to be 200 ppm. The mixtures were sprayed to foliar parts so as to adhere adequately on the leaves of the above-mentioned wheat. After spraying the mixtures, the wheats were air-dried and were placed under lighting for 14 to 18 days, and a lesion area was observed. As a result, every of the lesion areas in wheats treated with each of the present compounds showed 30% or less compared to the lesion area in an untreated wheat.

Test Example 17: Control Test Against Tomato Late Blight (*Phytophthora Infestans*)

Each of plastic pots was filled with soils and thereto tomato (cv; PATIO) seeds were sown and the tomatoes were grown in a greenhouse for 20 days. Thereafter, the present compound 2, 11 to 14, 16, 18 to 21, 29, 35, 39, 49, 51, 52, 55, 56, 60 to 64, 66, 76, 80, 85, or 86, each of which was made to a formulation according to the similar method to that of Formulation Example 6, was mixed with water so as to be 200 ppm. The mixtures were sprayed to foliar parts so as to adhere adequately on the leaves of the above-mentioned tomato. After spraying the mixtures, the tomatoes were air-dried and after 1 day, an aqueous suspension of the spores of *Phytophthora infestans* were spraying-inoculated. After the inoculation, the tomatoes were placed in a greenhouse of 23° C. during daytime and 20° C. during nighttime under a high humidity for 1 day, and a lesion area was observed. As a result, every of the lesion areas in tomatoes treated with each of the present compounds showed 30% or less compared to the lesion area in an untreated tomato.

Test Example 18: Control Test Against Soybean Rust (*Phakopsora Pachyrhizi*)

Each of plastic pots was filled with soil and thereto soybean (cv: Kurosengoku) seeds were sown and the soybeans were grown in a greenhouse for 10 to 14 days. Thereafter, the present compound 1 to 16, 18 to 23, 25, 26, 29 to 32, 34, 35, 37 to 40, 44 to 46, 48, 49, 51 to 59, 61 to 64, 68, 71 to 73, 75 to 77, 79 to 83, 85 to 89, or 90, each of which was made to a formulation according to the similar method to that of Formulation Example 6, was mixed with water so as to be 200 ppm. The resulting mixtures were sprayed to foliar parts so as to adhere adequately on the leaves of the above-mentioned soybean. After spraying the mixtures, the soybeans were air-dried and after 2 to 5 days, an aqueous suspension of the conidia of *Phakopsora pachyrhizi* was spraying-inoculated. After the inoculation, the soybeans were placed in a greenhouse of 23° C. during daytime and 20° C. during nighttime under a high humidity for 1 to 2 days, and were then cultivated in the greenhouse for 12 days, and a lesion area was observed. As a result, every of the lesion areas in soybean treated with each of the present compounds showed 30% or less compared to the lesion area in an untreated soybean.

Test Example 19: Control Test Against Soybean Rust (*Phakopsora Pachyrhizi*)

Each of plastic pots was filled with soil and thereto soybean (cv: Kurosengoku) seeds were sown and the soybeans were grown in a greenhouse for 10 days, and an aqueous suspension containing the conidia of *Phakopsora pachyrhizi* was spraying-inoculated. After the inoculation, the soybeans were placed in a greenhouse of 23° C. during daytime and 20° C. during nighttime under a high humidity for 1 day, and were then cultivated in the greenhouse for 1 to 2 days, and thereafter, the present compound 1 to 16, 18, 19, 21 to 23, 25, 26, 37, 40, 44, 46, 47 to 49, 57, 58, 68, 71 to 77, 80 to 82, 89, or 90, each of which was made to a formulation according to the similar method to that of Formulation Example 6, was mixed with water so as to be 200 ppm, and the resulting mixtures were sprayed to foliar parts so as to adhere adequately on the leaves of the above-mentioned soybean. After spraying the mixtures, the soybeans were air-dried and cultivated in a greenhouse for 8 days, and a lesion area was then observed. As a result, every of the lesion areas in soybean treated with each of the present compounds showed 30% or less compared to the lesion area in an untreated soybean.

Test Example 20: Control Test Against Soybean Leaf Spot (*Cercospora* Sojina)

Each of plastic pots was filled with soil and thereto soybean (cv: Tachinagawa) seeds were sown and the soybeans were grown in a greenhouse for 13 days. Thereafter, the present compound 1 to 16, 18 to 21, 25, 26, 29 to 35, 37, 39, 40, 44, 46 to 49, 54 to 58, 64, 71 to 89, or 90, each of which was made to a formulation according to the similar method to that of Formulation Example 6, was mixed with water so as to be 200 ppm. The resulting mixtures were sprayed to foliar parts so as to adhere adequately on the leaves of the above-mentioned soybean. After spraying the mixtures, the soybeans were air-dried and after 1 day, an aqueous suspension of the conidia of *Cercospora* sojina was spraying-inoculated. After the inoculation, the soybeans were placed in a greenhouse of 23° C. during daytime and 20° C. during nighttime under a high humidity for 3 days, and were then cultivated in the greenhouse for 16 days, and a lesion area was observed. As a result, every of the lesion areas in soybean treated with each of the present compounds showed 30% or less compared to the lesion area in an untreated soybean.

Test Example 21: Control Test Against Tomato Early Blight (*Alternaria Solani*)

Each of plastic pots was filled with soils and thereto tomato (cv; PATIO) seeds were sown and the tomatoes were grown in a greenhouse for 20 days. Thereafter, the present compound 3 to 6, 9, 11 to 16, 18 to 20, 29, 32, 35, 36, 44, 51, 57 to 59, 68, 71, 75, 76, 80, 86, or 87, each of which was made to a formulation according to the similar method to that of Formulation Example 6, was mixed with water so as to be 200 ppm. The resulting mixtures were sprayed to foliar parts so as to adhere adequately on the leaves of the above-mentioned tomato. After spraying the mixtures, the tomatoes were air-dried and after 1 day, an aqueous suspension of the conidia of *Alternaria solani* were spraying-inoculated. After the inoculation, the tomatoes were placed at 18° C. under a high humidity for 6 days, and a lesion area was observed. As a result, every of the lesion areas in tomatoes treated with each of the present compounds showed 30% or less compared to the lesion area in an untreated tomato.

Test Example 22: Control Test Against Kidney Bean Stem Rot (*Sclerotinia Sclerotiorum*)

Each of plastic pots was filled with soil and thereto Kidney bean (cv; NAGAUZURA SAITO) seeds were sown and the kidney beans were grown in a greenhouse for 8 days. Thereafter, the present compound 2 to 16, 18 to 20, 25, 26, 29, 48, 53, 55, 57, 58, 64, 71, 76, 77, or 89, each of which was made to a formulation according to the similar method to that of Formulation Example 6, was mixed with water so as to be 200 ppm. The resulting mixtures were sprayed to the foliar parts so as to adhere adequately on the leaves of the above-mentioned kidney bean. After spraying the mixtures, the kidney beans were air-dried and a PDA medium containing hyphae of *Sclerotinia sclerotiorum* was placed on the leaves of the kidney bean. After the inoculation, all kidney beans were placed under a high humidity during only night and after 4 days, a lesion area was observed. As a result, every of the lesion areas in kidney beans treated with each of the present compounds showed 30% or less compared to the lesion area in an untreated kidney beans.

Next, it is shown that the present compound is useful for control on harmful arthropod.

Test Method 23

The present compound is made to a formulation according to a similar method to that described in the Formulation Example 6, and thereto is added water containing 0.03 v/v % of a spreader to prepare a diluted solution containing a prescribed concentration of the test compound.

Cabbage (*Brassicae oleracea*) seedling (on the developmental stage of the second to third true leaf) is planted in a cup, and the diluted solutions are sprayed into the seedling at a ratio of 20 mL/seedling. Thereafter, the stem and leaf of the seedling is cut out and is then installed into the container that is covered with the filter paper. Five(5) cabbage moth (*Plutella xylostella*) at the second instar larval stages are released into the cup. After 5 days, the surviving insects are counted, and the mortality of insects is calculated by the following equation.

$$\text{Mortality } (\%) = \{1 - \text{the number of the surviving insects}/5\} \times 100$$

Test Example 23

The test was conducted at the prescribed concentration of 500 ppm by using the present compound 28 according to the Test method 23, and as a result, the present compound 28 showed 100% as a mortality.

INDUSTRIAL APPLICABILITY

The compound of the present invention has efficacies on controlling pests, and can be used to control pests.

The invention claimed is:

1. A compound of the formula (VI):

(VI)

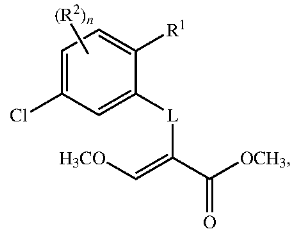

wherein

L represents an oxygen atom or $CH_2$, $R^1$ represents a methyl group, $R^2$ represents a C1-C3 chain hydrocarbon group optionally substituted with at least one halogen atom, a cyclopropyl group or a halogen atom, n is 0.

* * * * *